(12) United States Patent
Chen et al.

(10) Patent No.: US 7,641,915 B2
(45) Date of Patent: Jan. 5, 2010

(54) LIPID NANOPARTICLE BASED COMPOSITIONS AND METHODS FOR THE DELIVERY OF BIOLOGICALLY ACTIVE MOLECULES

(75) Inventors: TongQian Chen, Longmont, CO (US); Chandra Vargeese, Blue Bell, PA (US); Kurt Vagle, Longmont, CO (US); WeiMin Wang, Superior, CO (US); Ye Zhang, Broomfield, CO (US)

(73) Assignee: Sirna Therapeutics, Inc, San Francisco, CA (US)

( * ) Notice: Subject to any disclaimer, the term of this patent is extended or adjusted under 35 U.S.C. 154(b) by 100 days.

(21) Appl. No.: 12/048,023

(22) Filed: Mar. 13, 2008

(65) Prior Publication Data
US 2008/0188675 A1     Aug. 7, 2008

Related U.S. Application Data

(62) Division of application No. 11/353,630, filed on Feb. 14, 2006, now Pat. No. 7,514,099.

(60) Provisional application No. 60/652,787, filed on Feb. 14, 2005, provisional application No. 60/678,531, filed on May 6, 2005, provisional application No. 60/703,946, filed on Jul. 29, 2005, provisional application No. 60/737,024, filed on Nov. 15, 2005.

(51) Int. Cl.
 *A61K 9/127* (2006.01)
 *A61K 31/56* (2006.01)
(52) U.S. Cl. ........................... 424/450; 514/182
(58) Field of Classification Search .................. None
See application file for complete search history.

(56) References Cited

U.S. PATENT DOCUMENTS

| 4,946,787 | A  | 8/1990  | Eppstein et al. |
| 6,670,332 | B1 | 12/2003 | Wheeler |
| 7,404,969 | B2 | 7/2008  | Chen et al. |
| 7,514,099 | B2 | 4/2009  | Chen et al. |
| 2006/0211642 | A1 | 9/2006 | McSwiggen et al. |
| 2008/0020058 | A1 | 1/2008 | Chen et al. |

FOREIGN PATENT DOCUMENTS

| WO | WO9713743     | 4/1997  |
| WO | WO02072068    | * 9/2002 |
| WO | WO2005007196  | 1/2005  |
| WO | WO2005026372  | 3/2005  |
| WO | WO2005120152  | 12/2005 |
| WO | WO2007022030  | 2/2007  |
| WO | WO2007076328  | 7/2007  |

OTHER PUBLICATIONS

Koltover, et al., "An Inverted Hexagonal Phase of Cationic Liposome-DNA Complexes Related to DNA Release and Delivery", Science, 1998, vol. 281, pp. 78-81.

* cited by examiner

*Primary Examiner*—Richard Schnizer
(74) *Attorney, Agent, or Firm*—Matthew A. Leff; David A. Mathaet

(57) ABSTRACT

The present invention relates to novel cationic lipids, transfection agents, microparticles, nanoparticles, and short interfering nucleic acid (siNA) molecules. The invention also features compositions, and methods of use for the study, diagnosis, and treatment of traits, diseases and conditions that respond to the modulation of gene expression and/or activity in a subject or organism. Specifically, the invention relates to novel cationic lipids, microparticles, nanoparticles and transfection agents that effectively transfect or deliver biologically active molecules, such as antibodies (e.g., monoclonal, chimeric, humanized etc.), cholesterol, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, dsRNA, allozymes, aptamers, decoys and analogs thereof, and small nucleic acid molecules, such as short interfering nucleic acid (siNA), short interfering RNA (siRNA), double-stranded RNA (dsRNA), micro-RNA (miRNA), and short hairpin RNA (shRNA) molecules, to relevant cells and/or tissues, such as in a subject or organism. Such novel cationic lipids, microparticles, nanoparticles and transfection agents are useful, for example, in providing compositions to prevent, inhibit, or treat diseases, conditions, or traits in a cell, subject or organism. The compositions described herein are generally referred to as formulated molecular compositions (FMC) or lipid nanoparticles (LNP).

1 Claim, 45 Drawing Sheets

Cationic Lipids

FIGURE 7
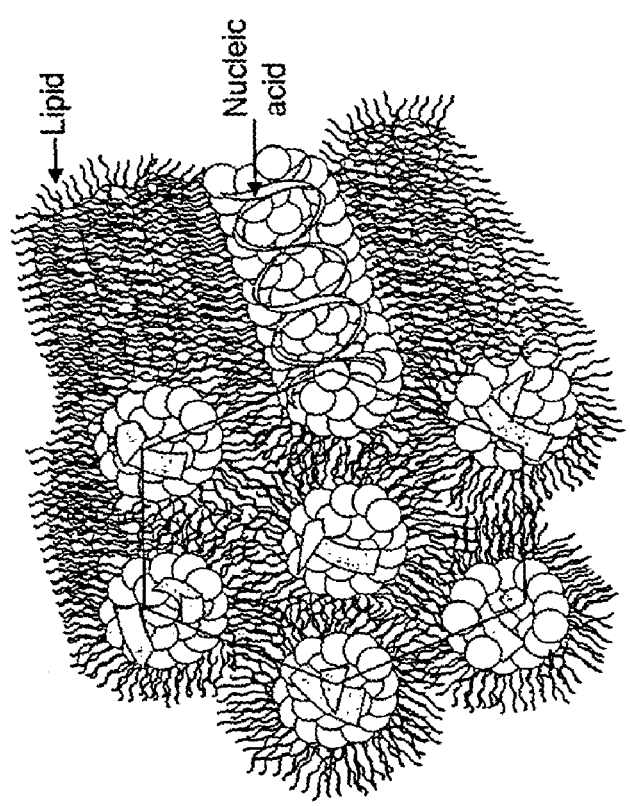
Inverted Hexagonal Structure
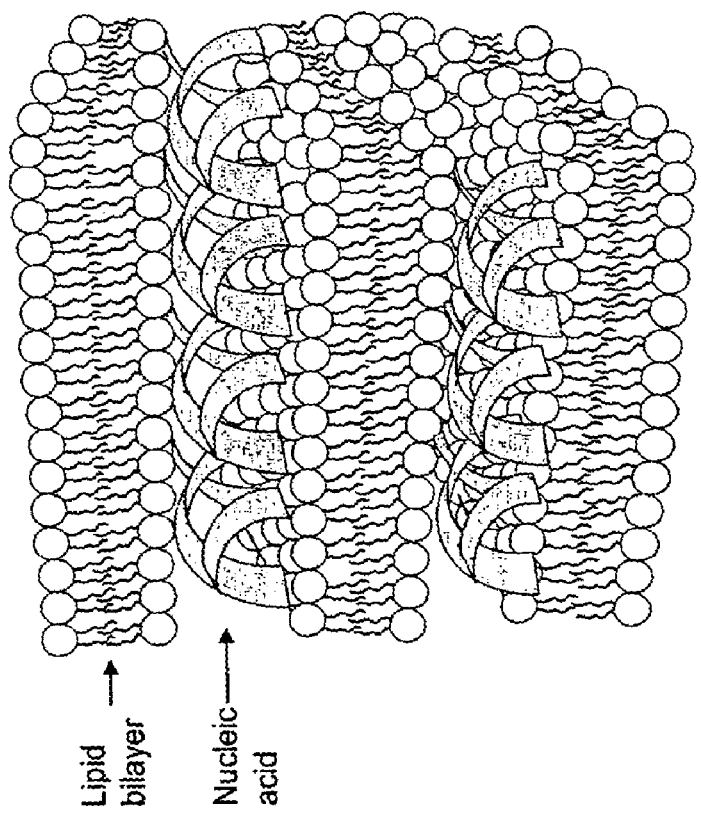
Lamella Structure

Lipid Composition in L051

Lipid Structures in L073

CLinDMA

DMOBA

DSPC

Cholesterol

2KPEG-DMG

FIGURE 14

HBV site 263 siRNA

5'- B GGAcucucuCAAuuuucuTT B -3'  Sense (SEQ ID NO: 6)
3'- T$_s$TccuGAAGAGAGuuAAAAGA -5'  Antisense (SEQ ID NO: 7)

HBV site 1583 siRNA

5'- B GcAcuucGcuuCAccucuGTT B -3'  Sense (SEQ ID NO: 8)
3'- T$_s$TcGuGAAGcGAAGuGGAGAC -5'  Antisense (SEQ ID NO: 9)

AGT = deoxy A, G & T
*AGCU* = ribo A, G, C, U
AG = 2'-O-methyl A & G
cu = 2'-fluoro C & U
B = 3',5' inverted deoxy abasic
s = phosphorothioate FIGURE 15: In vitro Analysis of siNA Formulation L051 Activity in HBV Expressing Hep G2 Cells FIGURE 16: In vitro Analysis of siNA Formulation L053 and L054 activity in HBV Expressing Hep G2 Cells FIGURE 18: Activity of siNA Formulation L051 compositions in HBV Mouse Model, Serum HBV DNA FIGURE 19: Activity of siNA siNA Formulation L051 compositions in HBV Mouse Model, Serum HBsAg FIGURE 20: In Vitro Analysis of siNA Formulation L051 Activity in HCV Replicon System FIGURE 21: In Vitro Analysis of siNA Formulation L053 and L054 Activity in HCV Replicon System Lipid Composition in LNP 083 pCLinDMA (48%)

DSPC (40%)

Cholesterol (10%)

2KPEG-Chol (2%)

Lipid Composition in LNP 077 eCLinDMA (48%)
DSPC (40%)
Cholesterol (10%)
2KPEG-Chol (2%)

Lipid Composition in LNP 080 eCLinDMA (48%)
DSPC (40%)
Cholesterol (10%)
2KPEG-DMG (2%)

Lipid Composition in LNP 082 pCLinDMA (48%)
DSPC (40%)
Cholesterol (10%)
2KPEG-DMG (2%)

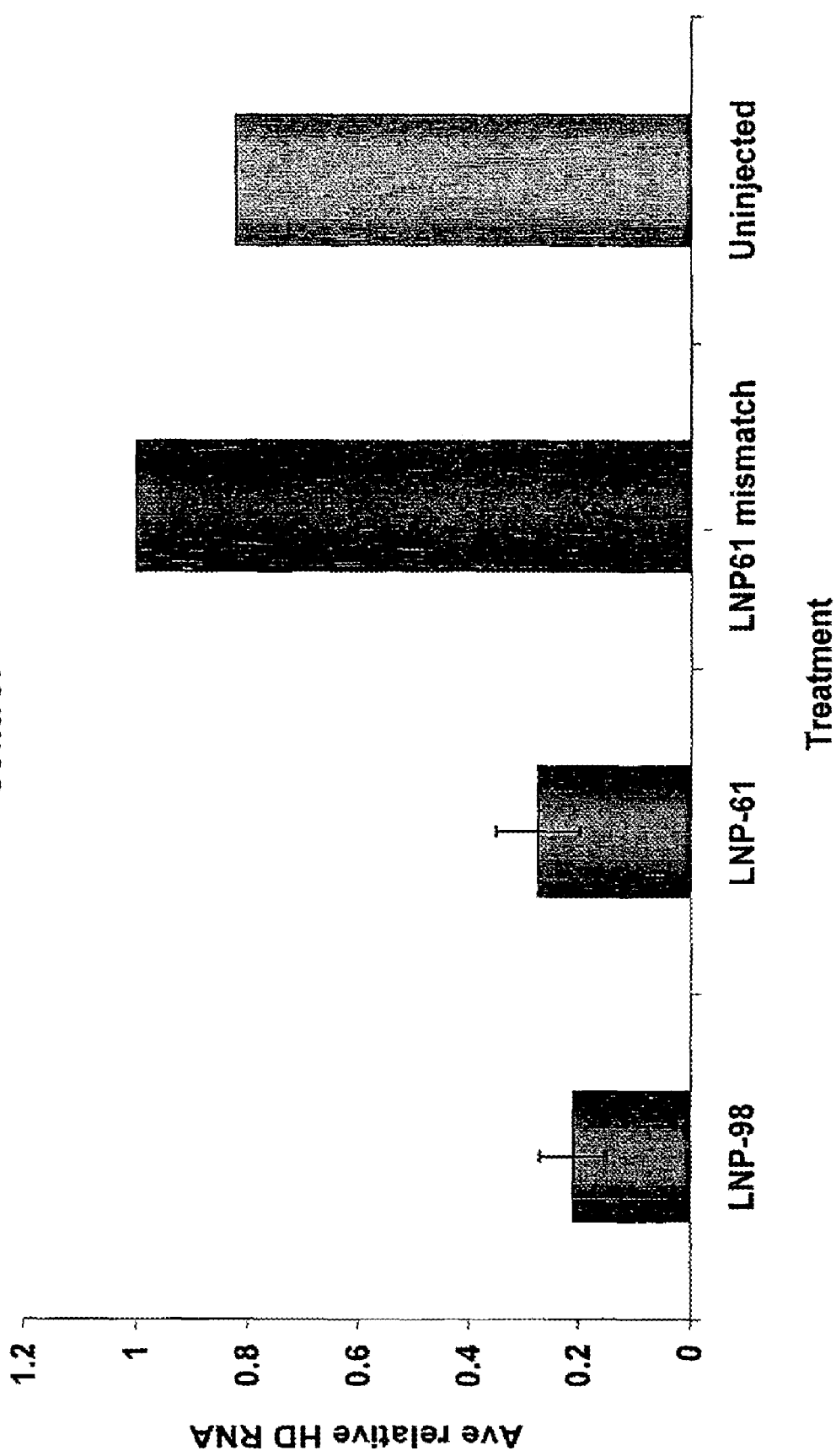
Figure 44: Relative expression of HD RNA with active LNP-98 and LNP-61 formulated active siNA compared to LNP-61 mismatch control

SEQUENCE LISTING

<160> NUMBER OF SEQ ID NOS: 11

<210> SEQ ID NO 1
<211> LENGTH: 21
<212> TYPE: DNA

```
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-5 attached inverted deoxyabasic moiety
<220> FEATURE:
<221> NAME/KEY: misc_feature
<222> LOCATION: (1)..(2)
<223> OTHER INFORMATION: 2'-deoxy-2'-fluoro
<220> FEATURE:
<221> NAME/KEY: misc_feature
<222> LOCATION: (3)..(4)
<223> OTHER INFORMATION: 2'-deoxy
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(9)
<223> OTHER INFORMATION: 2'-deoxy
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy
<220> FEATURE:
<221> NAME/KEY: misc_feature
<222> LOCATION: (12)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(19)
<223> OTHER INFORMATION: 2'-deoxy
<220> FEATURE:
<221> NAME/KEY: misc_feature
<222> LOCATION: (1)..(19)
<223> OTHER INFORMATION: Ribonucleotide modified or unmodified as
      described for this sequence
<220> FEATURE:
<221> NAME/KEY: misc_feature
<222> LOCATION: (21)..(21)
<223> OTHER INFORMATION: 3'-3 attached inverted deoxyabasic moiety

<400> SEQUENCE: 1
cugauagggu gcuugcgagt t                                           21

<210> SEQ ID NO 2
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(8)
```

```
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(17)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: 2'-O-methyl
<220> FEATURE:
<221> NAME/KEY: misc_feature
<222> LOCATION: (1)..(19)
<223> OTHER INFORMATION: Ribonucleotide modified or unmodified as
      described for this sequence
<220> FEATURE:
<221> NAME/KEY: misc_feature
<222> LOCATION: (20)..(21)
<223> OTHER INFORMATION: Phosphorothioate internucleotide linkage

<400> SEQUENCE: 2
cucgcaagca cccuaucagt t                                            21

<210> SEQ ID NO 3
<211> LENGTH: 21
<212> TYPE: DNA
<213> ORGANISM: Artificial
<220> FEATURE:
<223> OTHER INFORMATION: Synthetic

<400> SEQUENCE: 3
cctgtattcc catcccatcg t                                            21

<210> SEQ ID NO 4
<211> LENGTH: 21
<212> TYPE: DNA
<213> ORGANISM: Artificial
<220> FEATURE:
<223> OTHER INFORMATION: Synthetic

<400> SEQUENCE: 4
tgagccaaga gaaacggact g                                            21

<210> SEQ ID NO 5
<211> LENGTH: 27
<212> TYPE: DNA
<213> ORGANISM: Artificial
<220> FEATURE:
<223> OTHER INFORMATION: Synthetic

<400> SEQUENCE: 5
ttcgcaaaat acctatggga gtgggcc                                      27

<210> SEQ ID NO 6
<211> LENGTH: 21
<212> TYPE: DNA
```

```
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: 2'-deoxy-2'- fluoro
<220> FEATURE:
<221> NAME/KEY: misc_feature
<222> LOCATION: (1)..(1)
<223> OTHER INFORMATION: 5'-5 attached inverted deoxyabasic moiety
<220> FEATURE:
<221> NAME/KEY: misc_feature
<222> LOCATION: (3)..(4)
<223> OTHER INFORMATION: 2'-deoxy
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(10)
<223> OTHER INFORMATION: 2'-deoxy
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-deoxy
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy
<220> FEATURE:
<221> NAME/KEY: misc_feature
<222> LOCATION: (16)..(17)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: 2'-deoxy
<220> FEATURE:
<221> NAME/KEY: misc_feature
<222> LOCATION: (1)..(19)
<223> OTHER INFORMATION: Ribonucleotide modified or unmodified as
      described for this sequence
<220> FEATURE:
<221> NAME/KEY: misc_feature
<222> LOCATION: (21)..(21)
<223> OTHER INFORMATION: Inverted deoxyabasic

<400> SEQUENCE: 6
cugguacaga ccauauugat t                                              21

<210> SEQ ID NO 7
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (4)..(4)
```

<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'- fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(17)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: 2'-O-methyl
<220> FEATURE:
<221> NAME/KEY: misc_feature
<222> LOCATION: (1)..(19)
<223> OTHER INFORMATION: Ribonucleotide modified or unmodified as
    described for this sequence
<220> FEATURE:
<221> NAME/KEY: misc_feature
<222> LOCATION: (20)..(21)
<223> OTHER INFORMATION: Phosphorothioate internucleotide linker

<400> SEQUENCE: 7
ucaauauggu cuguaccagt t                                              21

<210> SEQ ID NO 8
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: 2'-deoxy-2'-fluoro
<220> FEATURE:
<221> NAME/KEY: misc_feature
<222> LOCATION: (1)..(1)
<223> OTHER INFORMATION: Inverted deoxyabasic
<220> FEATURE:
<221> NAME/KEY: misc_feature
<222> LOCATION: (3)..(4)
<223> OTHER INFORMATION: 2'-deoxy
<220> FEATURE:

-continued

```
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy
<220> FEATURE:
<221> NAME/KEY: misc_feature
<222> LOCATION: (7)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-deoxy
<220> FEATURE:
<221> NAME/KEY: misc_feature
<222> LOCATION: (10)..(11)
<223> OTHER INFORMATION: 2'-deoxy-2'-fluoro
<220> FEATURE:
<221> NAME/KEY: misc_feature
<222> LOCATION: (12)..(15)
<223> OTHER INFORMATION: 2'-deoxy
<220> FEATURE:
<221> NAME/KEY: misc_feature
<222> LOCATION: (16)..(17)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: 2'-deoxy
<220> FEATURE:
<221> NAME/KEY: misc_feature
<222> LOCATION: (1)..(19)
<223> OTHER INFORMATION: Ribonucleotide modified or unmodified as
      described for this sequence
<220> FEATURE:
<221> NAME/KEY: misc_feature
<222> LOCATION: (21)..(21)
<223> OTHER INFORMATION: 3'-3 attached inverted deoxyabasic moiety

<400> SEQUENCE: 8
ucagcauuac caagauuaat t                                           21

<210> SEQ ID NO 9
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(8)
<223> OTHER INFORMATION: 2'-deoxy-2'-flouro
<220> FEATURE:
<221> NAME/KEY: misc_feature
<222> LOCATION: (9)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
```

```
<223> OTHER INFORMATION: 2'-O-methyl
<220> FEATURE:
<221> NAME/KEY: misc_feature
<222> LOCATION: (16)..(17)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: 2'-O-methyl
<220> FEATURE:
<221> NAME/KEY: misc_feature
<222> LOCATION: (1)..(19)
<223> OTHER INFORMATION: Ribonucleotide modified or unmodified as
      described for this sequence
<220> FEATURE:
<221> NAME/KEY: misc_feature
<222> LOCATION: (20)..(21)
<223> OTHER INFORMATION: Phosphorothioate internucleotide linker

<400> SEQUENCE: 9
uuaaucuugg uaaugcugat t                                            21

<210> SEQ ID NO 10
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-5 attached inverted deoxyabasic moiety
<220> FEATURE:
<221> NAME/KEY: misc_feature
<222> LOCATION: (2)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (14)..(15)
<223> OTHER INFORMATION: 2'-deoxy-2'-fluoro
<220> FEATURE:
<221> NAME/KEY: misc_feature
<222> LOCATION: (17)..(19)
<223> OTHER INFORMATION: 2'-deoxy-2'-fluoro
<220> FEATURE:
<221> NAME/KEY: misc_feature
<222> LOCATION: (1)..(19)
<223> OTHER INFORMATION: Ribonucleotide modified or unmodified as
      described for this sequence
<220> FEATURE:
<221> NAME/KEY: misc_feature
<222> LOCATION: (20)..(21)
<223> OTHER INFORMATION: Thymidine
<220> FEATURE:
<221> NAME/KEY: misc_feature
<222> LOCATION: (21)..(21)
<223> OTHER INFORMATION: 3'-3 attached inverted deoxyabasic moiety

<400> SEQUENCE: 10
accgugugaa ucauugucut t                                            21

<210> SEQ ID NO 11
<211> LENGTH: 21
```

```
-continued

<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(9)
<223> OTHER INFORMATION: 2'-O-methyl
<220> FEATURE:
<221> NAME/KEY: misc_feature
<222> LOCATION: (10)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (1)..(19)
<223> OTHER INFORMATION: Ribonucleotide modified or unmodified as
      described for this sequence
<220> FEATURE:
<221> NAME/KEY: misc_feature
<222> LOCATION: (20)..(21)
<223> OTHER INFORMATION: Thymidine
<220> FEATURE:
<221> NAME/KEY: misc_feature
<222> LOCATION: (20)..(21)
<223> OTHER INFORMATION: Phosphorothioate internucleotide linkage

<400> SEQUENCE: 11
agacaaugau ucacacggut t                                            21
```

LIPID NANOPARTICLE BASED COMPOSITIONS AND METHODS FOR THE DELIVERY OF BIOLOGICALLY ACTIVE MOLECULES

This application is a divisional application of U.S. patent application Ser. No. 11/353,630, filed Feb. 14, 2006, and claims the benefit of U.S. Provisional patent application No. 60/652,787, filed Feb. 14, 2005, U.S. Provisional patent application No. 60/678,531, filed May 6, 2005, U.S. Provisional patent application No. 60/703,946, filed Jul. 29, 2005, and U.S. Provisional patent application No. 60/737,024, filed Nov. 15, 2005. These applications are incorporated by reference herein in their entirety including the drawings.

FIELD OF THE INVENTION

The present invention relates to novel particle forming delivery agents including cationic lipids, microparticles, and nanoparticles that are useful for delivering various molecules to cells. The invention also features compositions, and methods of use for the study, diagnosis, and treatment of traits, diseases and conditions that respond to the modulation of gene expression and/or activity in a subject or organism. Specifically, the invention relates to novel cationic lipids, microparticles, nanoparticles and transfection agents that effectively transfect or deliver biologically active molecules, such as antibodies (e.g., monoclonal, chimeric, humanized etc.), cholesterol, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, allozymes, aptamers, decoys and analogs thereof, and small nucleic acid molecules, such as short interfering nucleic acid (siNA), short interfering RNA (siRNA), double-stranded RNA (dsRNA), micro-RNA (miRNA), and short hairpin RNA (shRNA) molecules, to relevant cells and/or tissues, such as in a subject or organism. Such novel cationic lipids, microparticles, nanoparticles and transfection agents are useful, for example, in providing compositions to prevent, inhibit, or treat diseases, conditions, or traits in a cell, subject or organism.

BACKGROUND OF THE INVENTION

The present invention relates to the delivery of biologically active molecules to cells. Specifically, the invention relates to compounds, compositions and methods for delivering nucleic acids, polynucleotides, and oligonucleotides such RNA, DNA and analogs thereof, peptides, polypeptides, proteins, antibodies, hormones and small molecules, to cells by facilitating transport across cellular membranes in, for example, epithelial tissues and endothelial tissues. The compounds, compositions and methods of the invention are useful in therapeutic, research, and diagnostic applications that rely upon the efficient transfer of biologically active molecules into cells, tissues, and organs. The discussion is provided only for understanding of the invention that follows. This summary is not an admission that any of the work described below is prior art to the claimed invention.

The cellular delivery of various therapeutic compounds, such as antiviral and chemotherapeutic agents, is usually compromised by two limitations. First the selectivity of a number of therapeutic agents is often low, resulting in high toxicity to normal tissues. Secondly, the trafficking of many compounds into living cells is highly restricted by the complex membrane systems of the cell. Specific transporters allow the selective entry of nutrients or regulatory molecules, while excluding most exogenous molecules such as nucleic acids and proteins. Various strategies can be used to improve transport of compounds into cells, including the use of lipid carriers, biodegradable polymers, and various conjugate systems.

The most well studied approaches for improving the transport of foreign nucleic acids into cells involve the use of viral vectors or cationic lipids and related cytofectins. Viral vectors can be used to transfer genes efficiently into some cell types, but they generally cannot be used to introduce chemically synthesized molecules into cells. An alternative approach is to use delivery formulations incorporating cationic lipids, which interact with nucleic acids through one end and lipids or membrane systems through another (for a review see Felgner, 1990, *Advanced Drug Delivery Reviews*, 5, 162-187; Felgner 1993, *J. Liposome Res.*, 3, 3-16). Synthetic nucleic acids as well as plasmids can be delivered using the cytofectins, although the utility of such compounds is often limited by cell-type specificity, requirement for low serum during transfection, and toxicity.

Another approach to delivering biologically active molecules involves the use of conjugates. Conjugates are often selected based on the ability of certain molecules to be selectively transported into specific cells, for example via receptor-mediated endocytosis. By attaching a compound of interest to molecules that are actively transported across the cellular membranes, the effective transfer of that compound into cells or specific cellular organelles can be realized. Alternately, molecules that are able to penetrate cellular membranes without active transport mechanisms, for example, various lipophilic molecules, can be used to deliver compounds of interest. Examples of molecules that can be utilized as conjugates include but are not limited to peptides, hormones, fatty acids, vitamins, flavonoids, sugars, reporter molecules, reporter enzymes, chelators, porphyrins, intercalcators, and other molecules that are capable of penetrating cellular membranes, either by active transport or passive transport.

The delivery of compounds to specific cell types, for example, cancer cells or cells specific to particular tissues and organs, can be accomplished by utilizing receptors associated with specific cell types. Particular receptors are overexpressed in certain cancerous cells, including the high affinity folic acid receptor. For example, the high affinity folate receptor is a tumor marker that is overexpressed in a variety of neoplastic tissues, including breast, ovarian, cervical, colorectal, renal, and nasoparyngeal tumors, but is expressed to a very limited extent in normal tissues. The use of folic acid based conjugates to transport exogenous compounds across cell membranes can provide a targeted delivery approach to the treatment and diagnosis of disease and can provide a reduction in the required dose of therapeutic compounds. Furthermore, therapeutic bioavailability, pharmacodynamics, and pharmacokinetic parameters can be modulated through the use of bioconjugates, including folate bioconjugates. Godwin et al., 1972, *J. Biol. Chem.*, 247, 2266-2271, report the synthesis of biologically active pteroyloligo-L-glutamates. Habus et al., 1998, *Bioconjugate Chem.*, 9, 283-291, describe a method for the solid phase synthesis of certain oligonucleotide-folate conjugates. Cook, U.S. Pat. No. 6,721, 208, describes certain oligonucleotides modified with specific conjugate groups. The use of biotin and folate conjugates to enhance transmembrane transport of exogenous molecules, including specific oligonucleotides has been reported by Low et al., U.S. Pat. Nos. 5,416,016, 5,108,921, and International PCT publication No. WO 90/12096. Manoharan et al., International PCT publication No. WO 99/66063 describe certain folate conjugates, including specific nucleic acid folate conjugates with a phosphoramidite moiety attached to the nucleic acid component of the conjugate, and methods for the synthesis of these folate conjugates. Nomura et al., 2000, *J. Org. Chem.*, 65, 5016-5021, describe the synthesis of an intermediate, alpha-[2-(trimethylsilyl)ethoxycarbonyl]folic acid, useful in the synthesis of ceratin types of folate-nucleoside conjugates. Guzaev et al., U.S. Pat. No. 6,335,434, describes the synthesis of certain folate oligonucleotide conjugates. Vargeese et al., International PCT Publication No. WO 02/094185 and U.S. Patent Application Publication Nos. 20030130186 and 20040110296 describe certain nucleic acid conjugates.

The delivery of compounds to other cell types can be accomplished by utilizing receptors associated with a certain type of cell, such as hepatocytes. For example, drug delivery systems utilizing receptor-mediated endocytosis have been employed to achieve drug targeting as well as drug-uptake enhancement. The asialoglycoprotein receptor (ASGPr) (see for example Wu and Wu, 1987, *J. Biol. Chem.* 262, 4429-4432) is unique to hepatocytes and binds branched galactose-terminal glycoproteins, such as asialoorosomucoid (ASOR). Binding of such glycoproteins or synthetic glycoconjugates to the receptor takes place with an affinity that strongly depends on the degree of branching of the oligosaccharide chain, for example, triatennary structures are bound with greater affinity than biatenarry or monoatennary chains (Baenziger and Fiete, 1980, *Cell*, 22, 611-620; Connolly et al., 1982, *J. Biol. Chem.*, 257, 939-945). Lee and Lee, 1987, *Glycoconjugate J.*, 4, 317-328, obtained this high specificity through the use of N-acetyl-D-galactosamine as the carbohydrate moiety, which has higher affinity for the receptor, compared to galactose. This "clustering effect" has also been described for the binding and uptake of mannosyl-terminating glycoproteins or glycoconjugates (Ponpipom et al., 1981, *J. Med. Chem.*, 24, 1388-1395). The use of galactose and galactosamine based conjugates to transport exogenous compounds across cell membranes can provide a targeted delivery approach to the treatment of liver disease such as HBV and HCV infection or hepatocellular carcinoma. The use of bioconjugates can also provide a reduction in the required dose of therapeutic compounds required for treatment. Furthermore, therapeutic bioavailability, pharmacodynamics, and pharmacokinetic parameters can be modulated through the use of bioconjugates.

A number of peptide based cellular transporters have been developed by several research groups. These peptides are capable of crossing cellular membranes in vitro and in vivo with high efficiency. Examples of such fusogenic peptides include a 16-amino acid fragment of the homeodomain of ANTENNAPEDIA, a *Drosophila* transcription factor (Wang et al., 1995, *PNAS USA.*, 92, 3318-3322); a 17-mer fragment representing the hydrophobic region of the signal sequence of Kaposi fibroblast growth factor with or without NLS domain (Antopolsky et al., 1999, *Bioconj. Chem.*, 10, 598-606); a 17-mer signal peptide sequence of caiman crocodylus Ig(5) light chain (Chaloin et al., 1997, *Biochem. Biophys. Res. Comm.*, 243, 601-608); a 17-amino acid fusion sequence of HIV envelope glycoprotein gp4114, (Morris et al., 1997, *Nucleic Acids Res.*, 25, 2730-2736); the HIV-1 Tat49-57 fragment (Schwarze et al., 1999, *Science*, 285, 1569-1572); a transportan A—achimeric 27-mer consisting of N-terminal fragment of neuropeptide galanine and membrane interacting wasp venom peptide mastoporan (Lindgren et al., 2000, *Bioconjugate Chem.*, 11, 619-626); and a 24-mer derived from influenza virus hemagglutinin envelop glycoprotein (Bongartz et al., 1994, *Nucleic Acids Res.*, 22, 4681-4688). These peptides were successfully used as part of an antisense oligodeoxyribonucleotide-peptide conjugate for cell culture transfection without lipids. In a number of cases, such conjugates demonstrated better cell culture efficacy then parent oligonucleotides transfected using lipid delivery. In addition, use of phage display techniques has identified several organ targeting and tumor targeting peptides in vivo (Ruoslahti, 1996, *Ann. Rev. Cell Dev. Biol.*, 12, 697-715). Conjugation of tumor targeting peptides to doxorubicin has been shown to significantly improve the toxicity profile and has demonstrated enhanced efficacy of doxorubicin in the in vivo murine cancer model MDA-MB-435 breast carcinoma (Arap et al., 1998, *Science*, 279, 377-380).

Another approach to the intracellular delivery of biologically active molecules involves the use of cationic polymers. For example, Ryser et al., International PCT Publication No. WO 79/00515 describes the use of high molecular weight lysine polymers for increasing the transport of various molecules across cellular membranes. Rothbard et al., International PCT Publication No. WO 98/52614, describes certain methods and compositions for transporting drugs and macromolecules across biological membranes in which the drug or macromolecule is covalently attached to a transport polymer consisting of from 6 to 25 subunits, at least 50% of which contain a guanidino or amidino side chain. The transport polymers are preferably polyarginine peptides composed of all D-, all L- or mixtures of D- and L-arginine. Rothbard et al., U.S. Patent Application Publication No. 20030082356, describes certain poly-lysine and poly-arginine compounds for the delivery of drugs and other agents across epithelial tissues, including the skin, gastrointestinal tract, pulmonary epithelium and blood brain barrier. Wendel et al., U.S. Patent Application Publication No. 20030032593, describes certain polyarginine compounds. Rothbard et al., U.S. Patent Application Publication No. 20030022831, describes certain poly-lysine and poly-arginine compounds for intra-ocular delivery of drugs. Kosak, U.S. Patent Application Publication No. 20010034333, describes certain cyclodextran polymers compositions that include a cross-linked cationic polymer component. Beigelman et al., U.S. Pat. No. 6,395,713; Reynolds et al., International PCT Publication No. WO 99/04819; Beigelman et al., International PCT Publication No. WO 99/05094; and Beigelman et al., U.S. Patent Application Publication No. 20030073640 describe certain lipid based formulations.

Another approach to the intracellular delivery of biologically active molecules involves the use of liposomes or other particle forming compositions. Since the first description of liposomes in 1965, by Bangham (*J. Mol. Biol.* 13, 238-252), there has been a sustained interest and effort in the area of developing lipid-based carrier systems for the delivery of pharmaceutically active compounds. Liposomes are attractive drug carriers since they protect biological molecules from degradation while improving their cellular uptake. One of the most commonly used classes of liposome formulations for delivering polyanions (e.g., DNA) is that which contains cationic lipids. Lipid aggregates can be formed with macromolecules using cationic lipids alone or including other lipids and amphiphiles such as phosphatidylethanolamine. It is well known in the art that both the composition of the lipid formulation as well as its method of preparation have effect on the structure and size of the resultant anionic macromolecule-cationic lipid aggregate. These factors can be modulated to optimize delivery of polyanions to specific cell types in vitro and in vivo. The use of cationic lipids for cellular delivery of biologically active molecules has several advantages. The encapsulation of anionic compounds using cationic lipids is essentially quantitative due to electrostatic interaction. In addition, it is believed that the cationic lipids interact with the negatively charged cell membranes initiating cellular membrane transport (Akhtar et al., 1992, *Trends Cell Bio.*, 2, 139; Xu et al., 1996, *Biochemistry* 35, 5616).

Experiments have shown that plasmid DNA can be encapsulated in small particles that consist of a single plasmid encapsulated within a bilayer lipid vesicle (Wheeler, et al., 1999, Gene Therapy 6, 271-281). These particles typically contain the fusogenic lipid dioleoylphosphatidylethanolamine (DOPE), low levels of a cationic lipid, and can be stabilized in aqueous media by the presence of a poly(ethylene glycol) (PEG) coating. These particles have systemic applications as they exhibit extended circulation lifetimes following intravenous (i.v.) injection, can accumulate preferentially in various tissues and organs or tumors due to the enhanced vascular permeability in such regions, and can be designed to escape the lyosomic pathway of endocytosis by disruption of endosomal membranes. These properties can be useful in delivering biologically active molecules to various cell types for experimental and therapeutic applications. For example, the effective use of nucleic acid technologies such as short interfering RNA (siRNA), antisense, ribozymes, decoys, triplex forming oligonucleotides, 2-5A oligonucleotides, and aptamers in vitro and in vivo may benefit from efficient delivery of these compounds across cellular membranes. Lewis et al., U.S. Patent Application Publication No. 20030125281, describes certain compositions consisting of the combination of siRNA, certain amphipathic compounds, and certain polycations. MacLachlan, U.S. Patent Application Publication No. 20030077829, describes certain lipid based formulations. MacLachlan, International PCT Publication No. WO 05/007196, describes certain lipid encapsulated interfering RNA formulations. Vargeese et al., International PCT Publication No. WO2005007854 describes certain polycationic compositions for the cellular delivery of polynucleotides. McSwiggen et al., International PCT Publication Nos. WO 05/019453, WO 03/70918, WO 03/74654 and U.S. Patent Application Publication Nos. 20050020525 and 20050032733, describes short interfering nucleic acid molecules (siNA) and various technologies for the delivery of siNA molecules and other polynucleotides.

In addition, recent work involving cationic lipid particles demonstrated the formation of two structurally different complexes comprising nucleic acid (or other polyanionic compound) and cationic lipid (Safinya et al., Science, 281: 78-81 (1998). One structure comprises a multilamellar structure with nucleic acid monolayers sandwiched between cationic lipid bilayers ("lamellar structure") (FIG. 7). A second structure comprises a two dimensional hexagonal columnar phase structure ("inverted hexagonal structure") in which nucleic acid molecules are encircled by cationic lipid in the formation of a hexagonal structure (FIG. 7). Safinya et al. demonstrated that the inverted hexagonal structure transfects mammalian cells more efficiently than the lamellar structure. Further, optical microscopy studies showed that the complexes comprising the lamellar structure bind stably to anionic vesicles without fusing to the vesicles, whereas the complexes comprising the inverted hexagonal structure are unstable and rapidly fuse to the anionic vesicles, releasing the nucleic acid upon fusion.

The structural transformation from lamellar phase to inverted hexagonal phase complexes is achieved either by incorporating a suitable helper lipid that assists in the adoption of an inverted hexagonal structure or by using a co-surfactant, such as hexanol. However, neither of these transformation conditions are suitable for delivery in biological systems. Furthermore, while the inverted hexagonal complex exhibits greater transfection efficiency, it has very poor serum stability compared to the lamellar complex. Thus, there remains a need to design delivery agents that are serum stable, i.e. stable in circulation, that can undergo structural transformation, for example from lamellar phase to inverse hexagonal phase, under biological conditions.

The present application provides compounds, compositions and methods for significantly improving the efficiency of systemic and local delivery of biologically active molecules. Among other things, the present application provides compounds, compositions and methods for making and using novel delivery agents that are stable in circulation and undergo structural changes under appropriate physiological conditions (e.g., pH) which increase the efficiency of delivery of biologically active molecules.

SUMMARY OF THE INVENTION

The present invention features compounds, compositions, and methods to facilitate delivery of various molecules into a biological system, such as cells. The compounds, compositions, and methods provided by the instant invention can impart therapeutic activity by transferring therapeutic compounds across cellular membranes or across one or more layers of epithelial or endothelial tissue. The present invention encompasses the design and synthesis of novel agents for the delivery of molecules, including but not limited to small molecules, lipids, nucleosides, nucleotides, nucleic acids, polynucleotides, oligonucleotides, antibodies, toxins, negatively charged polymers and other polymers, for example proteins, peptides, hormones, carbohydrates, or polyamines, across cellular membranes. Non-limiting examples of polynucleotides that can be delivered across cellular membranes using the compounds and methods of the invention include short interfering nucleic acids (siNA) (which includes siRNAs), antisense oligonucleotides, enzymatic nucleic acid molecules, 2',5'-oligoadenylates, triplex forming oligonucleotides, aptamers, and decoys. In general, the transporters described are designed to be used either individually or as part of a multi-component system, with or without degradable linkers. The compounds of the invention (generally shown in the Formulae below), when formulated into compositions, are expected to improve delivery of molecules into a number of cell types originating from different tissues, in the presence or absence of serum.

The compounds, compositions, and methods of the invention are useful for delivering biologically active molecules (e.g., siNAs, siRNAs, nucleic acids, polynucleotides, oligonucleotides, peptides, polypeptides, proteins, hormones, antibodies, and small molecules) to cells or across epithelial and endothelial tissues, such as skin, mucous membranes, vasculature tissues, gastrointestinal tissues, blood brain barrier tissues, opthamological tissues, pulmonary tissues, liver tissues, cardiac tissues, kidney tissues etc. The compounds, compositions, and methods of the invention can be used both for delivery to a particular site of administration or for systemic delivery.

The compounds, compositions, and methods of the invention can increase delivery or availability of biologically active molecules (e.g., siNAs, siRNAs, nucleic acids, polynucleotides, oligonucleotides, peptides, polypeptides, proteins, hormones, antibodies, and small molecules) to cells or tissues compared to delivery of the molecules in the absence of the compounds, compositions, and methods of the invention. As such, the level of a biologically active molecule inside a cell, tissue, or organism is increased in the presence of the compounds and compositions of the invention compared to when the compounds and compositions of the invention are absent.

In one aspect, the invention features novel cationic lipids, transfection agents, microparticles, nanoparticles, and formulations thereof with biologically active molecules. In another embodiment, the invention features compositions, and methods of use for the study, diagnosis, and treatment of traits, diseases, and conditions that respond to the modulation of gene expression and/or activity in a subject or organism. In another embodiment, the invention features novel cationic lipids, microparticles, nanoparticles transfection agents, and formulations that effectively transfect or deliver small nucleic acid molecules, such as short interfering nucleic acid (siNA), short interfering RNA (siRNA), double-stranded RNA (dsRNA), micro-RNA (miRNA), and short hairpin RNA (shRNA) molecules, to relevant cells and/or tissues, such as in a subject or organism. Such novel cationic lipids, microparticles, nanoparticles, transfection agents, and formulations are useful, for example, in providing compositions to prevent, inhibit, or treat diseases, conditions, or traits in a cell, subject or organism as described herein.

In one aspect, the instant invention features various cationic lipids, microparticles, nanoparticles, transfection agents, and formulations for the delivery of chemically-modified synthetic short interfering nucleic acid (siNA) molecules that modulate target gene expression or activity in cells, tissues, such as in a subject or organism, by RNA interference (RNAi). The use of chemically-modified siNA improves various properties of native siRNA molecules through increased resistance to nuclease degradation in vivo, improved cellular uptake, and improved pharmacokinetic properties in vivo. The cationic lipids, microparticles, nanoparticles, transfection agents, formulations, and siNA molecules of the instant invention provide useful reagents and methods for a variety of therapeutic, veterinary, diagnostic, target validation, genomic discovery, genetic engineering, and pharmacogenomic applications.

In one aspect, the invention features compositions and methods that independently or in combination modulate the expression of target genes encoding proteins, such as proteins associated with the maintenance and/or development of a disease, trait, or condition, such as a liver disease, trait, or condition. These genes are referred to herein generally as target genes. Such target genes are generally known in the art and transcripts of such genes are commonly referenced by Genbank Accession Number, see for example International PCT Publication No. WO 03/74654, serial No. PCT/US03/05028, and U.S. patent application Ser. No. 10/923,536 both incorporated by reference herein). The description below of the various aspects and embodiments of the invention is provided with reference to exemplary target genes and target gene transcripts. However, the various aspects and embodiments are also directed to other target genes, such as gene homologs, gene transcript variants, and gene polymorphisms (e.g., single nucleotide polymorphism, (SNPs)) that are associated with certain target genes. As such, the various aspects and embodiments are also directed to other genes that are involved in pathways of signal transduction or gene expression that are involved, for example, in the maintenance and/or development of a disease, trait, or condition. These additional genes can be analyzed for target sites using the methods described for target genes herein. Thus, the modulation of other genes and the effects of such modulation of the other genes can be performed, determined, and measured as described herein.

In one embodiment, the invention features a compound having Formula CLI:

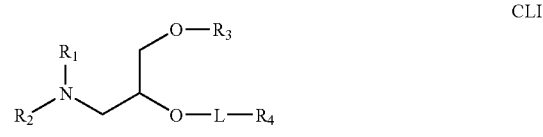

CLI wherein each R1 and R2 is independently a C1 to C10 alkyl, alkynyl, or aryl hydrocarbon; R3 is a C9-C24 aliphatic saturated or unsaturated hydrocarbon, L is a linker, and R4 is cholesterol, a cholesterol derivative, a steroid hormone, or a bile acid. In one embodiment, R1 and R2 each independently is methyl, ethyl, propyl, isopropyl, or butyl. In one embodiment, R3 is linoyl, isostearyl, oleyl, elaidyl, petroselinyl, linolenyl, elaeostearyl, arachidyl, myristoyl, palmitoyl, or lauroyl. In one embodiment, R4 is cholesterol. In one embodiment, L is a C1 to C10 alkyl, alkyl ether, polyether, or polyethylene glycol linker. In another embodiment, L is an acetal, amide, carbonyl, carbamide, carbamate, carbonate, ester (for example, monoester, diester), or succinyl linker. In one embodiment, R1 and R2 are methyl, R3 is linoyl, L is butyl, and R4 is cholesterol, which compound is generally referred to herein as CLinDMA or 3-Dimethylamino-2-(Cholest-5-en-3β-oxybutan-4-oxy)-1-(cis,cis-9,12-octadecadienoxy)propane.

In one embodiment, the invention features a compound having Formula CLII:

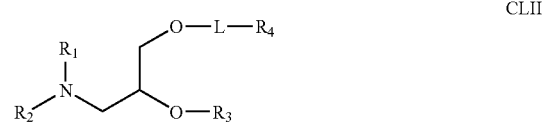

CLII wherein each R1 and R2 is independently a C1 to C10 alkyl, alkynyl, or aryl hydrocarbon; R3 is a C9-C24 aliphatic saturated or unsaturated hydrocarbon, L is a linker, and R4 is cholesterol, a cholesterol derivative, a steroid hormone, or a bile acid. In one embodiment, R1 and R2 each independently is methyl, ethyl, propyl, isopropyl, or butyl. In one embodiment, R3 is linoyl, isostearyl, oleyl, elaidyl, petroselinyl, linolenyl, elaeostearyl, arachidyl, myristoyl, palmitoyl, or lauroyl. In one embodiment, R4 is cholesterol. In one embodiment, L is a C1 to C10 alkyl, alkyl ether, polyether, or polyethylene glycol linker. In another embodiment, L is an acetal, amide, carbonyl, carbamide, carbamate, carbonate, ester (i.e., monoester, diester) or succinyl linker. In one embodiment, R1 and R2 are methyl, R3 is linoyl, L is butyl, and R4 is cholesterol.

In one embodiment, the invention features a compound having Formula CLIII:

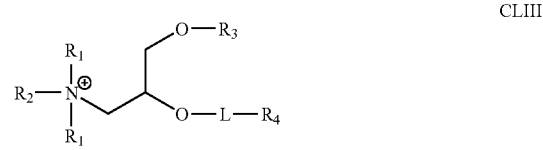

CLIII wherein each R1 and R2 is independently a C1 to C10 alkyl, alkynyl, or aryl hydrocarbon; R3 is a C9-C24 aliphatic saturated or unsaturated hydrocarbon, L is a linker, and R4 is cholesterol, a cholesterol derivative, a steroid hormone, or a bile acid. In one embodiment, R1 and R2 each independently is methyl, ethyl, propyl, isopropyl, or butyl. In one embodiment, R3 is linoyl, isostearyl, oleyl, elaidyl, petroselinyl, linolenyl, elaeostearyl, arachidyl, myristoyl, palmitoyl, or lauroyl. In one embodiment, R4 is cholesterol. In one embodiment, L is a C1 to C10 alkyl, alkyl ether, polyether, or polyethylene glycol linker. In one embodiment, L is an acetal, amide, carbonyl, carbamide, carbamate, carbonate, ester (i.e., monoester, diester), or succinyl linker. In one embodiment, each R1 and R2 are methyl, R3 is linoyl, L is butyl, and R4 is cholesterol.

In one embodiment, the invention features a compound having Formula CLIV:

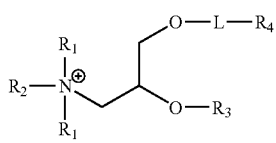

CLIV wherein each R1 and R2 is independently a C1 to C10 alkyl, alkynyl, or aryl hydrocarbon; R3 is a C9-C24 aliphatic saturated or unsaturated hydrocarbon, L is a linker, and R4 is cholesterol, a cholesterol derivative, a steroid hormone, or a bile acid. In one embodiment, R1 and R2 each independently is methyl, ethyl, propyl, isopropyl, or butyl. In one embodiment, R3 is linoyl, isostearyl, oleyl, elaidyl, petroselinyl, linolenyl, elaeostearyl, arachidyl, myristoyl, palmitoyl, or lauroyl. In one embodiment, R4 is cholesterol. In one embodiment, L is a C1 to C10 alkyl, alkyl ether, polyether, or polyethylene glycol linker. In another embodiment, L is an acetal, amide, carbonyl, carbamide, carbamate, carbonate, ester (i.e., monoester, diester), or succinyl linker. In one embodiment, each R1 and R2 are methyl, R3 is linoyl, L is butyl, and R4 is cholesterol.

In one embodiment, the invention features a compound having Formula CLV:

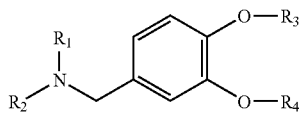

CLV wherein each R1 and R2 is independently a C1 to C10 alkyl, alkynyl, or aryl hydrocarbon; and each R3 and R4 is independently a C12-C24 aliphatic hydrocarbon, which can be the same or different. In one embodiment, R1 and R2 each independently is methyl, ethyl, propyl, isopropyl, or butyl. In one embodiment, R3 and R4 each independently is linoyl, isostearyl, oleyl, elaidyl, petroselinyl, linolenyl, elaeostearyl, arachidyl, myristoyl, palmitoyl, or lauroyl. In one embodiment, R1 and R2 are methyl, and R3 and R4 are oleyl, this compound is generally referred to herein as DMOBA or N,N-Dimethyl-3,4-dioleyloxybenzylamine.

In one embodiment, the invention features a compound having Formula CLVI:

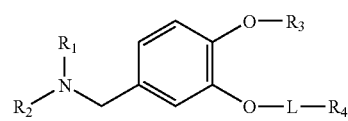

CLVI wherein each R1 and R2 is independently a C1 to C10 alkyl, alkynyl, or aryl hydrocarbon; R3 is a C9-C24 aliphatic saturated or unsaturated hydrocarbon, L is a linker, and R4 is cholesterol, a cholesterol derivative, a steroid hormone, or a bile acid. In one embodiment, R1 and R2 each independently is methyl, ethyl, propyl, isopropyl, or butyl. In one embodiment, R3 is linoyl, isostearyl, oleyl, elaidyl, petroselinyl, linolenyl, elaeostearyl, arachidyl, myristoyl, palmitoyl, or lauroyl. In one embodiment, R4 is cholesterol. In one embodiment, L is a C1 to C10 alkyl, alkyl ether, polyether, or polyethylene glycol linker. In another embodiment, L is an acetal, amide, carbonyl, carbamide, carbamate, carbonate, ester (i.e., monoester, diester), or succinyl linker. In one embodiment, R1 and R2 are methyl, R3 is linoyl, L is butyl, and R4 is cholesterol.

In one embodiment, the invention features a compound having Formula CLVII:

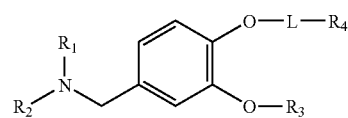

CLVII wherein each R1 and R2 is independently a C1 to C10 alkyl, alkynyl, or aryl hydrocarbon; R3 is a C9-C24 aliphatic saturated or unsaturated hydrocarbon, L is a linker, and R4 is cholesterol, a cholesterol derivative, a steroid hormone, or a bile acid. In one embodiment, R1 and R2 each independently is methyl, ethyl, propyl, isopropyl, or butyl. In one embodiment, R3 is linoyl, isostearyl, oleyl, elaidyl, petroselinyl, linolenyl, elaeostearyl, arachidyl, myristoyl, palmitoyl, or lauroyl. In one embodiment, R4 is cholesterol. In one embodiment, L is a C1 to C10 alkyl, alkyl ether, polyether, or polyethylene glycol linker. In another embodiment, L is an acetal, amide, carbonyl, carbamide, carbamate, carbonate, ester (i.e., monoester, diester), or succinyl linker. In one embodiment, R1 and R2 are methyl, R3 is linoyl, L is butyl, and R4 is cholesterol.

In one embodiment, the invention features a compound having Formula CLVIII:

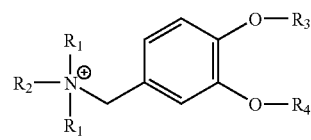

CLVIII wherein each R1 and R2 is independently a C1 to C10 alkyl, alkynyl, or aryl hydrocarbon; and each R3 and R4 is independently a C12-C24 aliphatic hydrocarbon which can be the same or different. In one embodiment, R1 and R2 each independently is methyl, ethyl, propyl, isopropyl, or butyl. In one embodiment, R3 and R4 each independently is linoyl, isostearyl, oleyl, elaidyl, petroselinyl, linolenyl, elaeostearyl, arachidyl, myristoyl, palmitoyl, or lauroyl. In one embodiment, each R1 and R2 are methyl, and R3 and R4 are linoyl.

In one embodiment, the invention features a compound having Formula CLIX:

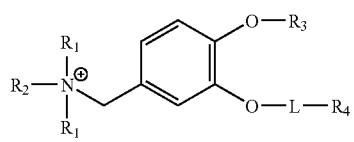

CLIX wherein each R1 and R2 is independently a C1 to C10 alkyl, alkynyl, or aryl hydrocarbon; R3 is a C9-C24 aliphatic saturated or unsaturated hydrocarbon, L is a linker, and R4 is cholesterol, a cholesterol derivative, a steroid hormone, or a bile acid. In one embodiment, R1 and R2 each independently is methyl, ethyl, propyl, isopropyl, or butyl. In one embodiment, R3 is linoyl, isostearyl, oleyl, elaidyl, petroselinyl, linolenyl, elaeostearyl, arachidyl, myristoyl, palmitoyl, or lauroyl. In one embodiment, R4 is cholesterol. In one embodiment, L is a C1 to C10 alkyl, alkyl ether, polyether, or polyethylene glycol linker. In another embodiment, L is an acetal, amide, carbonyl, carbamate carbamide, carbamate, carbonate, ester (i.e., monoester, diester), or succinyl linker. In one embodiment, each R1 and R2 are methyl, R3 is linoyl, L is butyl, and R4 is cholesterol.

In one embodiment, the invention features a compound having Formula CLX:

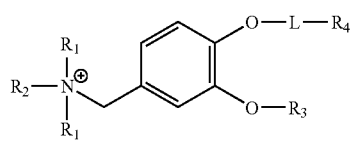

CLX wherein each R1 and R2 is independently a C1 to C10 alkyl, alkynyl, or aryl hydrocarbon; R3 is a C9-C24 aliphatic saturated or unsaturated hydrocarbon, L is a linker, and R4 is cholesterol, a cholesterol derivative, a steroid hormone, or a bile acid. In one embodiment, R1 and R2 each independently is methyl, ethyl, propyl, isopropyl, or butyl. In one embodiment, R3 is linoyl, isostearyl, oleyl, elaidyl, petroselinyl, linolenyl, elaeostearyl, arachidyl, myristoyl, palmitoyl, or lauroyl. In one embodiment, R4 is cholesterol. In one embodiment, L is a C1 to C10 alkyl, alkyl ether, polyether, or polyethylene glycol linker. In another embodiment, L is an acetal, amide, carbonyl, carbamide, carbamate, carbonate, ester (i.e., monoester, diester), or succinyl linker. In one embodiment, each R1 and R2 are methyl, R3 is linoyl, L is butyl, and R4 is cholesterol.

In one embodiment, the invention features a compound having Formula CLXI:

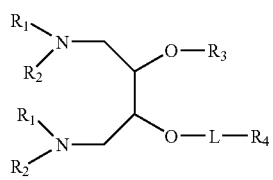

CLXI wherein each R1 and R2 is independently a C1 to C10 alkyl, alkynyl, or aryl hydrocarbon; R3 is a C9-C24 aliphatic saturated or unsaturated hydrocarbon, L is a linker, and R4 is cholesterol, a cholesterol derivative, a steroid hormone, or a bile acid. In one embodiment, R1 and R2 each independently is methyl, ethyl, propyl, isopropyl, or butyl. In one embodiment, R3 is linoyl, isostearyl, oleyl, elaidyl, petroselinyl, linolenyl, elaeostearyl, arachidyl, myristoyl, palmitoyl, or lauroyl. In one embodiment, R4 is cholesterol. In one embodiment, L is a C1 to C10 alkyl, alkyl ether, polyether, or polyethylene glycol linker. In another embodiment, L is an acetal, amide, carbonyl, carbamide, carbamate, carbonate, ester (i.e., monoester, diester), or succinyl linker. In one embodiment, each R1 and R2 are methyl, R3 is linoyl, L is butyl, and R4 is cholesterol.

In one embodiment, the invention features a compound having Formula CLXIIa or CLXIIb:

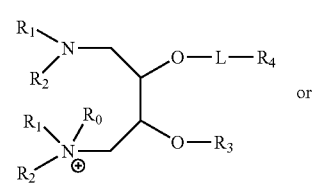

CLXIIa or

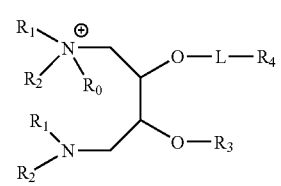

CLXIIb wherein R0 and each R1 and R2 is independently a C1 to C10 alkyl, alkynyl, or aryl hydrocarbon; R3 is a C9-C24 aliphatic saturated or unsaturated hydrocarbon, L is a linker, and R4 is cholesterol, a cholesterol derivative, a steroid hormone, or a bile acid. In one embodiment, R1 and R2 each independently is methyl, ethyl, propyl, isopropyl, or butyl. In one embodiment, R3 is linoyl, isostearyl, oleyl, elaidyl, petroselinyl, linolenyl, elaeostearyl, arachidyl, myristoyl, palmitoyl, or lauroyl. In one embodiment, R4 is cholesterol. In one embodiment, L is a C1 to C10 alkyl, alkyl ether, polyether, or polyethylene glycol linker. In another embodiment, L is an acetal, amide, carbonyl, carbamide, carbamate, carbonate, ester (i.e., monoester, diester), or succinyl linker. In one embodiment, each R1 and R2 are methyl, R3 is linoyl, L is butyl, and R4 is cholesterol.

In one embodiment, the invention features a compound having Formula CLXIII:

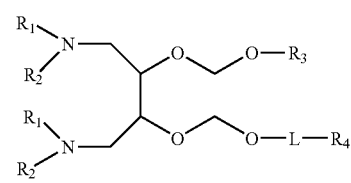

CLXIII wherein each R1 and R2 is independently a C1 to C10 alkyl, alkynyl, or aryl hydrocarbon; R3 is a C9-C24 aliphatic saturated or unsaturated hydrocarbon, L is a linker, and R4 is cholesterol, a cholesterol derivative, a steroid hormone, or a bile acid. In one embodiment, R1 and R2 each independently is methyl, ethyl, propyl, isopropyl, or butyl. In one embodiment, R3 is linoyl, isostearyl, oleyl, elaidyl, petroselinyl, linolenyl, elaeostearyl, arachidyl, myristoyl, palmitoyl, or lauroyl. In one embodiment, R4 is cholesterol. In one embodiment, L is a C1 to C10 alkyl, alkyl ether, polyether, or polyethylene glycol linker. In another embodiment, L is an acetal, amide, carbonyl, carbamide, carbamate, carbonate, ester (i.e., monoester, diester), or succinyl linker. In one embodiment, each R1 and R2 are methyl, R3 is linoyl, L is butyl, and R4 is cholesterol.

In one embodiment, the invention features a compound having Formula CLXIVa and CLXIVb:

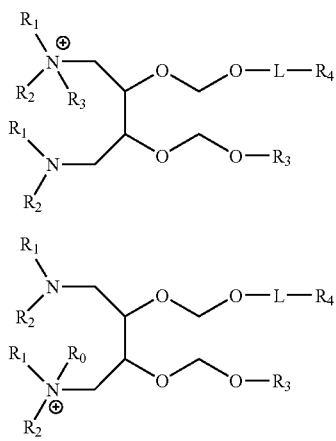

wherein R0 and each R1 and R2 is independently a C1 to C10 alkyl, alkynyl, or aryl hydrocarbon; R3 is a C9-C24 aliphatic saturated or unsaturated hydrocarbon, L is a linker, and R4 is cholesterol, a cholesterol derivative, a steroid hormone, or a bile acid. In one embodiment, R1 and R2 each independently is methyl, ethyl, propyl, isopropyl, or butyl. In one embodiment, R3 is linoyl, isostearyl, oleyl, elaidyl, petroselinyl, linolenyl, elaeostearyl, arachidyl, myristoyl, palmitoyl, or lauroyl. In one embodiment, R4 is cholesterol. In one embodiment, L is a C1 to C10 alkyl, alkyl ether, polyether, or polyethylene glycol linker. In another embodiment, L is an acetal, amide, carbonyl, carbamide, carbamate, carbonate, ester (i.e., monoester, diester), or succinyl linker. In one embodiment, each R1 and R2 are methyl, R3 is linoyl, L is butyl, and R4 is cholesterol.

In one embodiment, the invention features a compound having Formula CLXV:

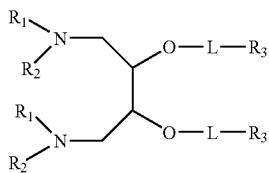

wherein each R1 and R2 is independently a C1 to C10 alkyl, alkynyl, or aryl hydrocarbon; L is a linker, and each R3 is independently cholesterol, a cholesterol derivative, a steroid hormone, or a bile acid. In one embodiment, R1 and R2 each independently is methyl, ethyl, propyl, isopropyl, or butyl. In one embodiment, R3 is cholesterol. In one embodiment, L is a C1 to C10 alkyl, alkyl ether, polyether, or polyethylene glycol linker. In another embodiment, L is an acetal, amide, carbonyl, carbamide, carbamate, carbonate, ester (i.e., monoester, diester), or succinyl linker. In one embodiment, each R1 and R2 are methyl, R3 is cholesterol, and L is butyl.

In one embodiment, the invention features a compound having Formula CLXVI:

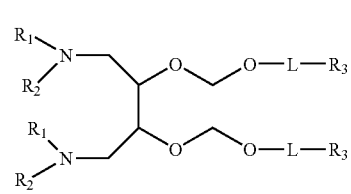

wherein each R1 and R2 is independently a C1 to C10 alkyl, alkynyl, or aryl hydrocarbon; each L is a linker whose structure is independent of the other L, and each R3 is independently cholesterol, a cholesterol derivative, a steroid hormone, or a bile acid. In one embodiment, R1 and R2 each independently is methyl, ethyl, propyl, isopropyl, or butyl. In one embodiment, R3 is cholesterol. In one embodiment, L is a C1 to C10 alkyl, alkyl ether, polyether, or polyethylene glycol linker. In another embodiment, L is an acetal, amide, carbonyl, carbamide, carbamate, carbonate, ester (i.e., monoester, diester), or succinyl linker. In one embodiment, each R1 and R2 are methyl, R3 is cholesterol, and L is butyl.

In one embodiment, the invention features a compound having Formula CLXVII:

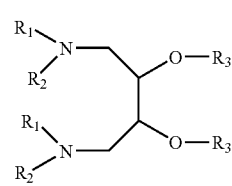

wherein each R1 and R2 is independently a C1 to C10 alkyl, alkynyl, or aryl hydrocarbon and R3 is a C9-C24 aliphatic saturated or unsaturated hydrocarbon. In one embodiment, R1 and R2 each independently is methyl, ethyl, propyl, isopropyl, or butyl. In one embodiment, R3 is linoyl, isostearyl, oleyl, elaidyl, petroselinyl, linolenyl, elaeostearyl, arachidyl, myristoyl, palmitoyl, or lauroyl. In one embodiment, each R1 and R2 are methyl and R3 is linoyl.

In one embodiment, the invention features a compound having Formula CLXVIII:

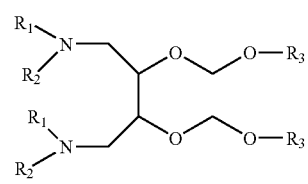

wherein each R1 and R2 is independently a C1 to C10 alkyl, alkynyl, or aryl hydrocarbon; R3 is a C9-C24 aliphatic saturated or unsaturated hydrocarbon. In one embodiment, R1 and R2 each independently is methyl, ethyl, propyl, isopropyl, or butyl. In one embodiment, R3 is linoyl, isostearyl, oleyl, elaidyl, petroselinyl, linolenyl, elaeostearyl, arachidyl, myristoyl, palmitoyl, or lauroyl. In one embodiment, each R1 and R2 are methyl and R3 is linoyl.

In one embodiment, the invention features a compound having Formula CLXIX:

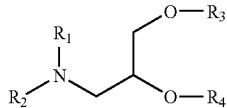

CLXIX wherein each R1 and R2 is independently a C1 to C10 alkyl, alkynyl, or aryl hydrocarbon; R3 and R4 are each individually a C9-C24 aliphatic saturated or unsaturated hydrocarbon, which can be the same or different. In one embodiment, R1 and R2 each independently is methyl, ethyl, propyl, isopropyl, or butyl. In one embodiment, R3 and R4 each individually is linoyl, isostearyl, oleyl, elaidyl, petroselinyl, linolenyl, elaeostearyl, arachidyl, myristoyl, palmitoyl, or lauroyl. In one embodiment, R3 or R4 is cholesterol, a cholesterol derivative, a steroid hormone, or a bile acid.

In one embodiment, the invention features a compound having Formula CLXX:

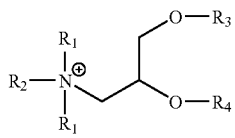

CLXX wherein each R1 and R2 is independently a C1 to C10 alkyl, alkynyl, or aryl hydrocarbon; R3 and R4 are each individually a C9-C24 aliphatic saturated or unsaturated hydrocarbon, which can be the same or different. In one embodiment, R1 and R2 each independently is methyl, ethyl, propyl, isopropyl, or butyl. In one embodiment, R3 and R4 each individually is linoyl, isostearyl, oleyl, elaidyl, petroselinyl, linolenyl, elaeostearyl, arachidyl, myristoyl, palmitoyl, or lauroyl. In one embodiment, R3 or R4 is cholesterol, a cholesterol derivative, a steroid hormone, or a bile acid.

In one embodiment, the invention features a compound having Formula CLXXI:

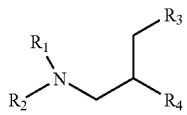

CLXXI wherein each R1 and R2 is independently a C1 to C10 alkyl, alkynyl, or aryl hydrocarbon; R3 and R4 are each individually a C9-C24 aliphatic saturated or unsaturated hydrocarbon, which can be the same or different. In one embodiment, R1 and R2 each independently is methyl, ethyl, propyl, isopropyl, or butyl. In one embodiment, R3 and R4 each individually is linoyl, isostearyl, oleyl, elaidyl, petroselinyl, linolenyl, elaeostearyl, arachidyl, myristoyl, palmitoyl, or lauroyl. In one embodiment, R3 or R4 is cholesterol, a cholesterol derivative, a steroid hormone, or a bile acid.

In one embodiment, the invention features a compound having Formula CLXXII:

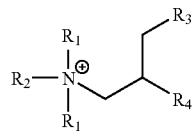

CLXXII wherein each R1 and R2 is independently a C1 to C10 alkyl, alkynyl, or aryl hydrocarbon; R3 and R4 are each individually a C9-C24 aliphatic saturated or unsaturated hydrocarbon, which can be the same or different. In one embodiment, R1 and R2 each independently is methyl, ethyl, propyl, isopropyl, or butyl. In one embodiment, R3 and R4 each individually is linoyl, isostearyl, oleyl, elaidyl, petroselinyl, linolenyl, elaeostearyl, arachidyl, myristoyl, palmitoyl, or lauroyl. In one embodiment, R3 or R4 is cholesterol, a cholesterol derivative, a steroid hormone, or a bile acid.

In one embodiment, the invention features a compound having Formula CLXXIII:

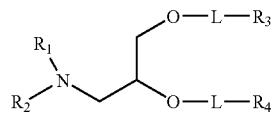

CLXXIII wherein each R1 and R2 is independently a C1 to C10 alkyl, alkynyl, or aryl hydrocarbon; R3 is a C9-C24 aliphatic saturated or unsaturated hydrocarbon, and L is a linker. In one embodiment, R1 and R2 each independently is methyl, ethyl, propyl, isopropyl, or butyl. In one embodiment, R3 and R4 each individually is linoyl, isostearyl, oleyl, elaidyl, petroselinyl, linolenyl, elaeostearyl, arachidyl, myristoyl, palmitoyl, or lauroyl. In one embodiment, R3 or R4 is cholesterol, a cholesterol derivative, a steroid hormone, or a bile acid. In one embodiment, L is a C1 to C10 alkyl, alkyl ether, polyether, or polyethylene glycol linker. In another embodiment, L is an acetal, amide, carbonyl, carbamide, carbamate, carbonate, ester (i.e., monoester, diester), or succinyl linker.

In one embodiment, the invention features a compound having Formula CLXXIV:

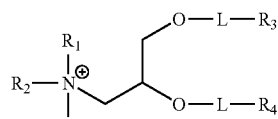

CLXXIV wherein each R1 and R2 is independently a C1 to C10 alkyl, alkynyl, or aryl hydrocarbon; R3 is a C9-C24 aliphatic saturated or unsaturated hydrocarbon, and L is a linker. In one embodiment, R1 and R2 each independently is methyl, ethyl, propyl, isopropyl, or butyl. In one embodiment, R3 and R4 each individually is linoyl, isostearyl, oleyl, elaidyl, petroselinyl, linolenyl, elaeostearyl, arachidyl, myristoyl, palmitoyl, or lauroyl. In one embodiment, R3 or R4 is cholesterol, a cholesterol derivative, a steroid hormone, or a bile acid. In one embodiment, L is a C1 to C10 alkyl, alkyl ether, polyether, or polyethylene glycol linker. In another embodiment, L is an acetal, amide, carbonyl, carbamide, carbamate, carbonate, ester (i.e., monoester, diester), or succinyl linker.

In one embodiment, the invention features a compound having Formula CLXXV:

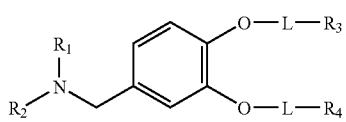

CLXXV wherein each R1 and R2 is independently a C1 to C10 alkyl, alkynyl, or aryl hydrocarbon; R3 is a C9-C24 aliphatic saturated or unsaturated hydrocarbon, and L is a linker. In one embodiment, R1 and R2 each independently is methyl, ethyl, propyl, isopropyl, or butyl. In one embodiment, R3 and R4 each individually is linoyl, isostearyl, oleyl, elaidyl, petroselinyl, linolenyl, elaeostearyl, arachidyl, myristoyl, palmitoyl, or lauroyl. In one embodiment, R3 or R4 is cholesterol, a cholesterol derivative, a steroid hormone, or a bile acid. In one embodiment, L is a C1 to C10 alkyl, alkyl ether, polyether, or polyethylene glycol linker. In another embodiment, L is an acetal, amide, carbonyl, carbamide, carbamate, carbonate, ester (i.e., monoester, diester), or succinyl linker.

In one embodiment, the invention features a compound having Formula CLXXVI:

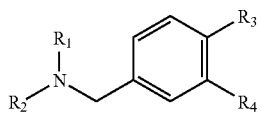

CLXXVI wherein each R1 and R2 is independently a C1 to C10 alkyl, alkynyl, or aryl hydrocarbon; R3 and R4 are each individually a C9-C24 aliphatic saturated or unsaturated hydrocarbon, which can be the same or different. In one embodiment, R1 and R2 each independently is methyl, ethyl, propyl, isopropyl, or butyl. In one embodiment, R3 and R4 each individually is linoyl, isostearyl, oleyl, elaidyl, petroselinyl, linolenyl, elaeostearyl, arachidyl, myristoyl, palmitoyl, or lauroyl. In one embodiment, R3 or R4 is cholesterol, a cholesterol derivative, a steroid hormone, or a bile acid.

In one embodiment, the invention features a compound having Formula CLXXVII:

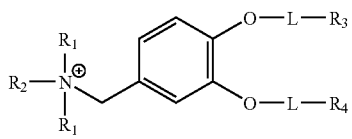

CLXXVII wherein each R1 and R2 is independently a C1 to C10 alkyl, alkynyl, or aryl hydrocarbon; R3 and R4 are each individually a C9-C24 aliphatic saturated or unsaturated hydrocarbon, and L is a linker. In one embodiment, R1 and R2 each independently is methyl, ethyl, propyl, isopropyl, or butyl. In one embodiment, R3 and R4 each individually is linoyl, isostearyl, oleyl, elaidyl, petroselinyl, linolenyl, elaeostearyl, arachidyl, myristoyl, palmitoyl, or lauroyl. In one embodiment, R3 or R4 is cholesterol, a cholesterol derivative, a steroid hormone, or a bile acid. In one embodiment, L is a C1 to C10 alkyl, alkyl ether, polyether, or polyethylene glycol linker. In another embodiment, L is an acetal, amide, carbonyl, carbamide, carbamate, carbonate, ester (i.e., monoester, diester), or succinyl linker.

In one embodiment, the invention features a compound having Formula CLXXVIII:

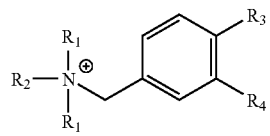

CLXXVIII wherein each R1 and R2 is independently a C1 to C10 alkyl, alkynyl, or aryl hydrocarbon; R3 and R4 are each individually a C9-C24 aliphatic saturated or unsaturated hydrocarbon, which can be the same or different. In one embodiment, R1 and R2 each independently is methyl, ethyl, propyl, isopropyl, or butyl. In one embodiment, R3 and R4 each individually is linoyl, isostearyl, oleyl, elaidyl, petroselinyl, linolenyl, elaeostearyl, arachidyl, myristoyl, palmitoyl, or lauroyl. In one embodiment, R3 or R4 is cholesterol, a cholesterol derivative, a steroid hormone, or a bile acid.

In one embodiment, the invention features a compound having Formula CLXXIX:

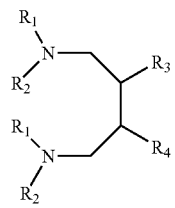

CLXXIX wherein each R1 and R2 is independently a C1 to C10 alkyl, alkynyl, or aryl hydrocarbon; R3 and R4 are each individually a C9-C24 aliphatic saturated or unsaturated hydrocarbon, which can be the same or different. In one embodiment, R1 and R2 each independently is methyl, ethyl, propyl, isopropyl, or butyl. In one embodiment, R3 and R4 each individually is linoyl, isostearyl, oleyl, elaidyl, petroselinyl, linolenyl, elaeostearyl, arachidyl, myristoyl, palmitoyl, or lauroyl. In one embodiment, R3 or R4 is cholesterol, a cholesterol derivative, a steroid hormone, or a bile acid.

In one embodiment, the invention features a compound having Formula NLI:

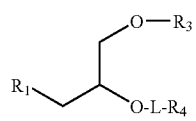

NLI wherein R1 is H, OH, or a C1 to C10 alkyl, alkynyl, or aryl hydrocarbon or alcohol; R3 is a C9-C24 aliphatic saturated or unsaturated hydrocarbon, L is a linker, and R4 is cholesterol, a cholesterol derivative, a steroid hormone, or a bile acid. In one embodiment, R1 is OH, methyl, ethyl, propyl, isopropyl, or butyl or its corresponding alcohol. In one embodiment, R3 is linoyl, isostearyl, oleyl, elaidyl, petroselinyl, linolenyl, elaeostearyl, arachidyl, myristoyl, palmitoyl, or lauroyl. In one embodiment, R4 is cholesterol. In one embodiment, L is a C1 to C10 alkyl, alkyl ether, polyether, or polyethylene glycol linker. In another embodiment, L is an acetal, amide, carbonyl, carbamide, carbamate, carbonate, ester (for example, monoester, diester), or succinyl linker. In one embodiment, R1 is OH, R3 is linoyl, L is butyl, and R4 is cholesterol.

In one embodiment, the invention features a compound having Formula NLII:

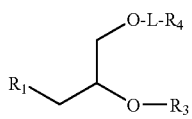

NLII wherein R1 is H, OH, or a C1 to C10 alkyl, alkynyl, or aryl hydrocarbon or alcohol; R3 is a C9-C24 aliphatic saturated or unsaturated hydrocarbon, L is a linker, and R4 is cholesterol, a cholesterol derivative, a steroid hormone, or a bile acid. In one embodiment, R1 is methyl, ethyl, propyl, isopropyl, or butyl or its corresponding alcohol. In one embodiment, R3 is linoyl, isostearyl, oleyl, elaidyl, petroselinyl, linolenyl, elaeostearyl, arachidyl, myristoyl, palmitoyl, or lauroyl. In one embodiment, R4 is cholesterol. In one embodiment, L is a C1 to C10 alkyl, alkyl ether, polyether, or polyethylene glycol linker. In another embodiment, L is an acetal, amide, carbonyl, carbamide, carbamate, carbonate, ester (i.e., monoester, diester) or succinyl linker. In one embodiment, R1 is OH, R3 is linoyl, L is butyl, and R4 is cholesterol.

In one embodiment, the invention features a compound having Formula NLIII:

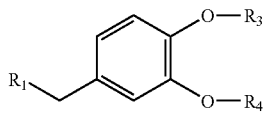

NLIII wherein R1 is H, OH, a C1 to C10 alkyl, alkynyl, or aryl hydrocarbon or alcohol; and each R3 and R4 is independently a C12-C24 aliphatic hydrocarbon, which can be the same or different. In one embodiment, R1 is methyl, ethyl, propyl, isopropyl, or butyl or its corresponding alcohol. In one embodiment, R3 and R4 each independently is linoyl, isostearyl, oleyl, elaidyl, petroselinyl, linolenyl, elaeostearyl, arachidyl, myristoyl, palmitoyl, or lauroyl. In one embodiment, R1 is OH, and R3 and R4 are oleyl, this compound is generally referred to herein as DOBA or dioleyloxybenzyl alcohol.

In one embodiment, the invention features a compound having Formula NLIV:

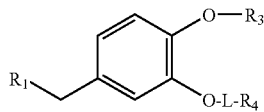

NLIV wherein R1 is H, OH a C1 to C10 alkyl, alkynyl, or aryl hydrocarbon or alcohol; R3 is a C9-C24 aliphatic saturated or unsaturated hydrocarbon, L is a linker, and R4 is cholesterol, a cholesterol derivative, a steroid hormone, or a bile acid. In one embodiment, R1 is methyl, ethyl, propyl, isopropyl, or butyl or its corresponding alcohol. In one embodiment, R3 is linoyl, isostearyl, oleyl, elaidyl, petroselinyl, linolenyl, elaeostearyl, arachidyl, myristoyl, palmitoyl, or lauroyl. In one embodiment, R4 is cholesterol. In one embodiment, L is a C1 to C10 alkyl, alkyl ether, polyether, or polyethylene glycol linker. In another embodiment, L is an acetal, amide, carbonyl, carbamide, carbamate, carbonate, ester (i.e., monoester, diester), or succinyl linker. In one embodiment, R1 is OH, R3 is linoyl, L is butyl, and R4 is cholesterol.

In one embodiment, the invention features a compound having Formula NLV:

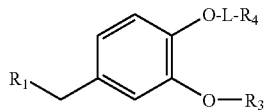

NLV wherein R1 is H, OH a C1 to C10 alkyl, alkynyl, or aryl hydrocarbon or alcohol; R3 is a C9-C24 aliphatic saturated or unsaturated hydrocarbon, L is a linker, and R4 is cholesterol, a cholesterol derivative, a steroid hormone, or a bile acid. In one embodiment, R1 is methyl, ethyl, propyl, isopropyl, or butyl or its corresponding alcohol. In one embodiment, R3 is linoyl, isostearyl, oleyl, elaidyl, petroselinyl, linolenyl, elaeostearyl, arachidyl, myristoyl, palmitoyl, or lauroyl. In one embodiment, R4 is cholesterol. In one embodiment, L is a C1 to C10 alkyl, alkyl ether, polyether, or polyethylene glycol linker. In another embodiment, L is an acetal, amide, carbonyl, carbamide, carbamate, carbonate, ester (i.e., monoester, diester), or succinyl linker. In one embodiment, R1 is OH, R3 is linoyl, L is butyl, and R4 is cholesterol.

In one embodiment, the invention features a compound having Formula NLVI:

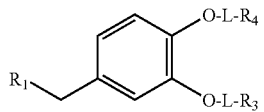

NLVI wherein R1 is H, OH, a C1 to C10 alkyl, alkynyl, or aryl hydrocarbon or alcohol; R3 is a C9-C24 aliphatic saturated or unsaturated hydrocarbon, and each L is a linker. In one embodiment, R1 is methyl, ethyl, propyl, isopropyl, or butyl or its corresponding alcohol. In one embodiment, R3 and R4 each individually is linoyl, isostearyl, oleyl, elaidyl, petroselinyl, linolenyl, elaeostearyl, arachidyl, myristoyl, palmitoyl, or lauroyl. In one embodiment, R3 or R4 is cholesterol, a cholesterol derivative, a steroid hormone, or a bile acid. In one embodiment, each L independently is a C1 to C10 alkyl, alkyl ether, polyether, or polyethylene glycol linker. In another embodiment, each L independently is an acetal, amide, carbonyl, carbamide, carbamate, carbonate, ester (i.e., monoester, diester), or succinyl linker.

In one embodiment, the invention features a compound having Formula NLVII:

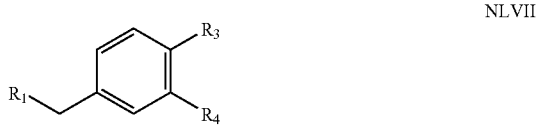

NLVII wherein R1 is independently H, OH, a C1 to C10 alkyl, alkynyl, or aryl hydrocarbon or alcohol; R3 and R4 are each individually a C9-C24 aliphatic saturated or unsaturated hydrocarbon, which can be the same or different. In one embodiment, R1 is methyl, ethyl, propyl, isopropyl, or butyl or its corresponding alcohol. In one embodiment, R3 and R4 each individually is linoyl, isostearyl, oleyl, elaidyl, petroselinyl, linolenyl, elaeostearyl, arachidyl, myristoyl, palmitoyl, or lauroyl. In one embodiment, R3 or R4 is cholesterol, a cholesterol derivative, a steroid hormone, or a bile acid.

In one embodiment, each O—R3 and/or O—R4 of any compound having Formulae CLI-CLXIV, CLXVII-CLXXII, CLXXVI, and CLXXVIII-CLXXIX further comprises a linker L (e.g., wherein —O—R3 and/or —O—R4 as shown above is —O-L-R3 and/or —O-L-R4), where L is a C1 to C10 alkyl, alkyl ether, polyether, polyethylene glycol, acetal, amide, succinyl, carbonyl, carbamide, carbamate, carbonate, ester (i.e., monoester, diester), or other linker as is generally known in the art.

In one embodiment, a formulation of the invention (e.g., a formulated molecular compositions (FMC) or lipid nanoparticle (LNP) of the invention) is a neutral lipid having any of formulae NLI-NLVII.

Examples of a steroid hormone include those comprising cholesterol, estrogen, testosterone, progesterone, glucocortisone, adrenaline, insulin, glucagon, cortisol, vitamin D, thyroid hormone, retinoic acid, and/or growth hormones.

In one embodiment, the invention features a composition comprising a biologically active molecule (e.g., a polynucleotide such as a siNA, antisense, aptamer, decoy, ribozyme, 2-5A, triplex forming oligonucleotide, other nucleic acid molecule or other biologically active molecule described herein), a cationic lipid, a neutral lipid, and a polyethyleneglycol conjugate, such as a PEG-diacylglycerol, PEG-diacylglycamide, PEG-cholesterol, or PEG-DMB conjugate. In another embodiment, the composition further comprises cholesterol or a cholesterol derivative. The compositions described herein are generally referred to as formulated molecular compositions (FMC) or lipid nanoparticles (LNP). In some embodiments of the invention, a formulated molecular composition (FMC) or lipid nanoparticle (LNP) composition further comprises cholesterol or a cholesterol derivative.

Suitable cationic lipid include those cationic lipids which carry a net negative charge at a selected pH, such as physiological pH. Particularly useful cationic lipids include those having a relatively small head group, such as a tertiary amine, quaternary amine or guanidine head group, and sterically hindered asymmetric lipid chains. In any of the embodiments described herein, the cationic lipid can be selected from those comprising Formulae CLI, CLII, CLIII, CLIV, CLV, CLVI, CLVII, CLVIII, CLIX, CLX, CLXI, CLXII, CLXIII, CLXIV, CLXV, CLXVI, CLXVII, CLXVIII, CLXIX, CLXX, CLXXI, CLXXII, CLXXIII, CLXXIV, CLXXV, CLXXVI, CLXXVII, CLXXVIII, CLXXIX; N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-Dioleoyl-3-Dimethylammonium-propane (DODAP), 1,2-Dioleoylcarbamyl-3-Dimethylammonium-propane (DOCDAP), 1,2-Dilineoyl-3-Dimethylammonium-propane (DLINDAP), Dioleoyloxy-N-[2-sperminecarboxamido)ethyl}-N,N-dimethyl-1-propanaminiumtrifluoroacetate (DOSPA), Dioctadecylamidoglycyl spermine (DOGS), DC-Chol, 1,2-Dimyristyloxypropyl-3-dimethyl-hydroxyethyl ammonium bromide (DMRIE), 3-Dimethylamino-2-(Cholest-5-en-3-beta-oxybutan-4-oxy)-1-(cis,cis-9,12-octadecadienoxy)propane (CLinDMA), 2-[5'-(cholest-5-en-3β-oxy)-3'-oxapentoxy)-3-dimethyl-1-(cis,cis-9', 12'-octadecadienoxy)propane (CpLinDMA), N,N-Dimethyl-3,4-dioleyloxybenzylamine (DMOBA), 1,2-N,N'-Dioleylcarbamyl-3-dimethylamino-propane (DOcarbDAP), and/or a mixture thereof, as well as other cationic lipids sharing similar properties. The above cationic lipids can include various differing salts as are known in the art. Non-limiting examples of these cationic lipid structures are shown in FIGS. 1-5 and FIG. 19.

In some embodiments, the head group of the cationic lipid can be attached to the lipid chain via a cleavable or non-cleavable linker, such as a linker described herein or otherwise known in the art. Non-limiting examples of suitable linkers include those comprising a C1 to C10 alkyl, alkyl ether, polyether, polyethylene glycol, acetal, amide, carbonyl, carbamide, carbamate, carbonate, ester (i.e., monoester, diester), or succinyl.

Suitable neutral lipids include those comprising any of a variety of neutral uncharged, zwitterionic or anionic lipids capable of producing a stable complex. They are preferably neutral, although they can alternatively be positively or negatively charged. In any of the embodiments described herein, suitable neutral lipids include those selected from compounds having formulae NLI-NLVII, dioleoylphosphatidylethanolamine (DOPE), palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), -phosphatidylet-hanolamine (POPE) and dioleoyl-phosphatidylethanolamine 4-(N-maleimidomethyl)-cyclohexane-1-carboxylate (DOPE-mal), cholesterol, as well as other neutral lipids described herein below, and/or a mixture thereof.

Suitable polyethyleneglycol-diacylglycerol or polyethyleneglycol-diacylglycamide (PEG-DAG) conjugates include those comprising a dialkylglycerol or dialkylglycamide group having alkyl chain length independently comprising from about C4 to about C40 saturated or unsaturated carbon atoms. The dialkylglycerol or dialkylglycamide group can further comprise one or more substituted alkyl groups. In any of the embodiments described herein, the PEG conjugate can be selected from PEG-dilaurylglycerol (C12), PEG-dimyristylglycerol (C14), PEG-dipalmitoylglycerol (C16), PEG-disterylglycerol (C18), PEG-dilaurylglycamide (C12), PEG-dimyristylglycamide (C14), PEG-dipalmitoylglycamide (C16), and PEG-disterylglycamide (C18), PEG-cholesterol (1-[8'-(Cholest-5-en-3β-oxy)carboxamido-3',6'-dioxaoctanyl]carbamoyl-ω-methyl-poly(ethylene glycol), and PEG-DMB (3,4-Ditetradecoxybenzyl-ω-methyl-poly(ethylene glycol) ether).

In one embodiment, the invention features a composition comprising a biologically active molecule (e.g., a polynucleotide such as a siNA, antisense, aptamer, decoy, ribozyme, 2-5A, triplex forming oligonucleotide, or other nucleic acid molecule) formulated as L051, L053, L054, L060, L061, L069, L073, L077, L080, L082, L083, L086, L097, L098, L099, L100, L101, L102, L103, and/or L104 (see Table IV).

Other suitable PEG conjugates include PEG-cholesterol or PEG-DMB conjugates (see for example FIG. 24). In one embodiment, PEG conjugates include PEGs attached to saturated or unsaturated lipid chains such as oleyl, linoleyl and similar lipid chains.

In one embodiment, the invention features a composition comprising a biologically active molecule (e.g., a polynucleotide such as a siNA, antisense, aptamer, decoy, ribozyme, 2-5A, triplex forming oligonucleotide, or other nucleic acid molecule), a cationic lipid having any of Formulae CLI-CLXXIX, a neutral lipid, and a PEG-DAG (i.e., polyethyleneglycol-diacylglycerol or polyethyleneglycol-diacylglycamide), PEG-cholesterol, or PEG-DMB conjugate. In another embodiment, the composition further comprises cholesterol or a cholesterol derivative. In another embodiment, the composition is formulated as L051, L053, L054, L060, L061, L069, L073, L077, L080, L082, L083, L086, L097, L098, L099, L100, L101, L102, L103, and/or L104 herein (see Table IV).

In one embodiment, the invention features a composition comprising a biologically active molecule (e.g., a polynucleotide such as a siNA, antisense, aptamer, decoy, ribozyme, 2-5A, triplex forming oligonucleotide, or other nucleic acid molecule), a cationic lipid comprising 3-Dimethylamino-2-(Cholest-5-en-3-beta-oxybutan-4-oxy)-1-(cis,cis-9,12-octadecadienoxy)propane (CLinDMA), a neutral lipid comprising distearoylphosphatidylcholine (DSPC), a PEG-DAG comprising PEG-n-dimyristylglycerol (PEG-DMG), and cholesterol. In one embodiment, the molar ratio of CLinDMA:DSPC:cholesterol:PEG-DMG are 48:40:10:2 respectively, this composition is generally referred to herein as formulation L051.

In one embodiment, the invention features a composition comprising a biologically active molecule (e.g., a polynucleotide such as a siNA, antisense, aptamer, decoy, ribozyme, 2-5A, triplex forming oligonucleotide, or other nucleic acid molecule), a cationic lipid comprising N,N-Dimethyl-3,4-dioleyloxybenzylamine (DMOBA), a neutral lipid comprising distearoylphosphatidylcholine (DSPC), a PEG-DAG comprising PEG-n-dimyristylglycerol (PEG-DMG), and cholesterol. In one embodiment, the molar ratio of DMOBA:DSPC:cholesterol:PEG-DMG are 30:20:48:2 respectively, this composition is generally referred to herein as formulation L053.

In one embodiment, the invention features a composition comprising a biologically active molecule (e.g., a polynucleotide such as a siNA, antisense, aptamer, decoy, ribozyme, 2-5A, triplex forming oligonucleotide, or other nucleic acid molecule), a cationic lipid comprising N,N-Dimethyl-3,4-dioleyloxybenzylamine (DMOBA), a neutral lipid comprising distearoylphosphatidylcholine (DSPC), a PEG-DAG comprising PEG-n-dimyristylglycerol (PEG-DMG), and cholesterol. In one embodiment, the molar ratio of DMOBA:DSPC:cholesterol:PEG-DMG are 50:20:28:2 respectively, this composition is generally referred to herein as formulation L054. In another embodiment, the composition further comprises a neutral lipid, such as dioleoylphosphatidylethanolamine (DOPE), palmitoyloleoylphosphatidylcholine (POPC), egg phosphatidylcholine (EPC), distearoylphosphatidylcholine (DSPC), cholesterol, and/or a mixture thereof.

In one embodiment, the invention features a composition comprising a biologically active molecule (e.g., a polynucleotide such as a siNA, antisense, aptamer, decoy, ribozyme, 2-5A, triplex forming oligonucleotide, or other nucleic acid molecule), a cationic lipid comprising 3-Dimethylamino-2-(Cholest-5-en-3-beta-oxybutan-4-oxy)-1-(cis,cis-9,12-octadecadienoxy)propane (CLinDMA), a cationic lipid comprising N,N-Dimethyl-3,4-dioleyloxybenzylamine (DMOBA), a neutral lipid comprising distearoylphosphatidylcholine (DSPC), a PEG-DAG comprising PEG-n-dimyristylglycerol (PEG-DMG), and cholesterol. In one embodiment, the molar ratio of CLinDMA:DMOBA:DSPC:cholesterol:PEG-DMG are 25:25:20:28:2 respectively, this composition is generally referred to herein as formulation L073.

In one embodiment, the invention features a composition comprising a biologically active molecule (e.g., a polynucleotide such as a siNA, antisense, aptamer, decoy, ribozyme, 2-5A, triplex forming oligonucleotide, or other nucleic acid molecule), a cationic lipid comprising 3-Dimethylamino-2-(Cholest-5-en-3-beta-oxybutan-4-oxy)-1-(cis,cis-9,12-octadecadienoxy)propane (CLinDMA), a neutral lipid comprising distearoylphosphatidylcholine (DSPC), a PEG comprising PEG-Cholesterol (PEG-Chol), and cholesterol. In one embodiment, the molar ratio of CLinDMA:DSPC:cholesterol:PEG-Chol are 48:40:10:2 respectively, this composition is generally referred to herein as formulation L069.

In one embodiment, the invention features a composition comprising a biologically active molecule (e.g., a polynucleotide such as a siNA, antisense, aptamer, decoy, ribozyme, 2-5A, triplex forming oligonucleotide, or other nucleic acid molecule), a cationic lipid comprising 1,2-N,N'-Dioleylcarbamyl-3-dimethylaminopropane (DOcarbDAP), a neutral lipid comprising distearoylphosphatidylcholine (DSPC), a PEG-DAG comprising PEG-n-dimyristylglycerol (PEG-DMG), and cholesterol. In one embodiment, the molar ratio of DOcarbDAP:DSPC:cholesterol:PEG-DMG are 30:20:48:2 respectively, this composition is generally referred to herein as formulation T018.1.

In one embodiment, the invention features a composition comprising a biologically active molecule (e.g., a polynucleotide such as a siNA, antisense, aptamer, decoy, ribozyme, 2-5A, triplex forming oligonucleotide, or other nucleic acid molecule), a cationic lipid comprising N,N-dimethyl-2,3-dioleyloxy)propylamine (DODMA), a neutral lipid comprising distearoylphosphatidylcholine (DSPC), a PEG-DAG comprising PEG-n-dimyristylglycerol (PEG-DMG), and cholesterol. In one embodiment, the molar ratio of DODMA:DSPC:cholesterol:PEG-DMG are 30:20:48:2 respectively, this composition is generally referred to herein as formulation T019.1.

In one embodiment, the invention features a composition comprising a biologically active molecule (e.g., a polynucleotide such as a siNA, antisense, aptamer, decoy, ribozyme, 2-5A, triplex forming oligonucleotide, or other nucleic acid molecule), and a cationic lipid comprising a compound having any of Formula CLI, CLII, CLIII, CLIV, CLV, CLVI, CLVII, CLVIII, CLIX, CLX, CLXI, CLXII, CLXIII, CLXIV, CLXV, CLXVI, CLXVII, CLXVIII, CLXIX, CLXX, CLXXI, CLXXII, CLXXIII, CLXXIV, CLXXV, CLXXVI, CLXXVII, CLXXVIII, CLXXIX. In another embodiment, the composition further comprises a neutral lipid, such as dioleoylphosphatidylethanolamine (DOPE), palmitoyloleoylphosphatidylcholine (POPC), egg phosphatidylcholine (EPC), distearoylphosphatidylcholine (DSPC), cholesterol, and/or a mixture thereof. In another embodiment, the composition further comprises a PEG conjugate. In yet another embodiment, the composition further comprises cholesterol or a cholesterol derivative.

In one embodiment, the invention features a composition comprising a biologically active molecule (e.g., a polynucleotide such as a siNA, antisense, aptamer, decoy, ribozyme, 2-5A, triplex forming oligonucleotide, or other nucleic acid molecule), and a cationic lipid comprising 3-Dimethylamino-2-(Cholest-5-en-3-beta -oxybutan-4-oxy)-1-(cis,cis-9,12-octadecadienoxy)propane (CLinDMA). In another embodiment, the composition further comprises a neutral lipid, such as dioleoylphosphatidylethanolamine (DOPE), palmitoyloleoylphosphatidylcholine (POPC), egg phosphatidylcholine (EPC), distearoylphosphatidylcholine (DSPC), cholesterol, and/or a mixture thereof. In another embodiment, the composition further comprises a PEG conjugate (i.e., polyethyleneglycol diacylglycerol (PEG-DAG), PEG-cholesterol, or PEG-DMB). In yet another embodiment, the composition further comprises cholesterol or a cholesterol derivative.

In one embodiment, the invention features a composition comprising a biologically active molecule (e.g., a polynucleotide such as a siNA, antisense, aptamer, decoy, ribozyme, 2-5A, triplex forming oligonucleotide, or other nucleic acid molecule), and a cationic lipid comprising N,N-Dimethyl-3,4-dioleyloxybenzylamine (DMOBA). In another embodiment, the composition further comprises a neutral lipid, such as dioleoylphosphatidylethanolamine (DOPE), palmitoyloleoylphosphatidylcholine (POPC), egg phosphatidylcholine (EPC), distearoylphosphatidylcholine (DSPC), cholesterol, and/or a mixture thereof. In yet another embodiment, the composition further comprises the cationic lipid CLinDMA. In another embodiment, the composition further comprises a PEG conjugate. In yet another embodiment, the composition further comprises cholesterol or a cholesterol derivative.

The term "biologically active molecule" as used herein refers to compounds or molecules that are capable of eliciting or modifying a biological response in a system. Non-limiting examples of biologically active molecules include antibodies (e.g., monoclonal, chimeric, humanized etc.), cholesterol, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, siNA, dsRNA, allozymes, aptamers, decoys and analogs thereof. Biologically active molecules of the invention also include molecules capable of modulating the pharmacokinetics and/or pharmacodynamics of other biologically active molecules, for example, lipids and polymers such as polyamines, polyamides, polyethylene glycol and other polyethers. In certain embodiments, the term biologically active molecule is used interchangeably with the term "molecule" or "molecule of interest" herein.

In one embodiment, the invention features a composition comprising a siNA molecule, a cationic lipid having any of Formulae CLI-CLXXIX, a neutral lipid, and a polyethyleneglycol-diacylglycerol or polyethyleneglycol-diacylglycamide (PEG-DAG) conjugate (i.e., polyethyleneglycol diacylglycerol (PEG-DAG), PEG-cholesterol, or PEG-DMB). These compositions are generally referred to herein as formulated siNA compositions. In another embodiment, a formulated siNA composition of the invention further comprises cholesterol or a cholesterol derivative.

In one embodiment, the siNA component of a formulated siNA composition of the invention is chemically modified so as not to stimulate an interferon response in a mammalian cell, subject, or organism. Such siNA molecules can be said to have improved toxicologic profiles, such as having attenuated or no immunostimulatory properties, having attenuated or no off-target effect, or otherwise as described herein.

In one embodiment, the invention features a composition comprising: (a) a cationic lipid having any of Formulae CLI-CLXXIX; (b) a neutral lipid; (c) a polyethyleneglycol -diacylglycerol (PEG-DAG) conjugate (i.e., polyethyleneglycol diacylglycerol (PEG-DAG), PEG-cholesterol, or PEG-DMB); and (d) a short interfering nucleic acid (siNA) molecule that mediates RNA interference (RNAi) against RNA of a target gene, wherein each strand of said siNA molecule is about 18 to about 28 nucleotides in length; and one strand of said siNA molecule comprises nucleotide sequence having sufficient complementarity to the target gene RNA for the siNA molecule to mediate RNA interference against the target gene RNA. In one embodiment, the target RNA comprises RNA sequence referred to by Genbank Accession numbers in International PCT Publication No. WO 03/74654, serial No. PCT/US03/05028, and U.S. patent application Ser. No. 10/923,536 both incorporated by reference herein. In another embodiment, the composition further comprises cholesterol or a cholesterol derivative.

In one embodiment, the invention features a composition comprising: (a) a cationic lipid having any of Formulae CLI-CLXXIX; (b) a neutral lipid; (c) a polyethyleneglycol -diacylglycerol (PEG-DAG) conjugate (i.e., polyethyleneglycol diacylglycerol (PEG-DAG), PEG-cholesterol, or PEG-DMB); and (d) a short interfering nucleic acid (siNA) molecule that mediates RNA interference (RNAi) against a Hepatitis Virus RNA, wherein each strand of said siNA molecule is about 18 to about 28 nucleotides in length; and one strand of said siNA molecule comprises nucleotide sequence having sufficient complementarity to the Hepatitis Virus RNA for the siNA molecule to mediate RNA interference against the Hepatitis Virus RNA. In one embodiment, the Hepatitis Virus RNA is Hepatitis B Virus (HBV). In one embodiment, the Hepatitis Virus RNA is Hepatitis C Virus (HCV). In one embodiment, the siNA comprises sequences described in U.S. Patent Application Nos. 60/401,104, 10/667,271, and 10/942,560, which are incorporated by reference in their entireties herein. In another embodiment, the composition further comprises cholesterol or a cholesterol derivative.

In one embodiment, the invention features a composition comprising: (a) a cationic lipid having any of Formulae CLI-CLXXIX; (b) a neutral lipid; (c) a polyethyleneglycol conjugate (i.e., polyethyleneglycol diacylglycerol (PEG-DAG), PEG-cholesterol, or PEG-DMB); and (d) a short interfering nucleic acid (siNA) molecule that mediates RNA interference (RNAi) against Protein Tyrosine Phosphatase 1B (PTP1B) RNA, wherein each strand of said siNA molecule is about 18 to about 28 nucleotides in length; and one strand of said siNA molecule comprises nucleotide sequence having sufficient complementarity to the PTP1B RNA for the siNA molecule to mediate RNA interference against the PTP1B RNA. In one embodiment, the siNA comprises sequences described in U.S. Patent Application Publication Nos. 20040019001 and 200500704978, which are incorporated by reference in their entireties herein. In another embodiment, the composition further comprises cholesterol or a cholesterol derivative.

In one embodiment, the invention features a composition comprising: (a) a cationic lipid having any of Formulae CLI-CLXXIX; (b) a neutral lipid; (c) a polyethyleneglycol conjugate (i.e., polyethyleneglycol diacylglycerol (PEG-DAG), PEG-cholesterol, or PEG-DMB); and (d) a short interfering nucleic acid (siNA) molecule that mediates RNA interference (RNAi) against Transforming Growth Factor beta (TGF-beta) and/or Transforming Growth Factor beta Receptor (TGF-betaR) RNA, wherein each strand of said siNA molecule is about 18 to about 28 nucleotides in length; and one strand of said siNA molecule comprises nucleotide sequence having sufficient complementarity to the TGF-beta and/or TGF-betaR RNA for the siNA molecule to mediate RNA interference against the TGF-beta and/or TGF-betaR RNA. In one embodiment, the siNA comprises sequences described in U.S. Ser. No. 11/054,047, which is incorporated by reference in their entireties herein. In another embodiment, the composition further comprises cholesterol or a cholesterol derivative.

In one embodiment, the invention features a composition comprising: (a) a cationic lipid having any of Formulae CLI-CLXXIX; (b) a neutral lipid; (c) a polyethyleneglycol conjugate (i.e., polyethyleneglycol diacylglycerol (PEG-DAG), PEG-cholesterol, or PEG-DMB); and (d) a short interfering nucleic acid (siNA) molecule that mediates RNA interference (RNAi) against cholesteryl ester transfer protein (CETP) RNA, wherein each strand of said siNA molecule is about 18 to about 28 nucleotides in length; and one strand of said siNA molecule comprises nucleotide sequence having sufficient complementarity to the CETP RNA for the siNA molecule to mediate RNA interference against the CETP RNA. In one embodiment, the siNA comprises sequences described in U.S. Ser. No. 10/921,554, which is incorporated by reference in its entirety herein. In another embodiment, the composition further comprises cholesterol or a cholesterol derivative.

In one embodiment, the invention features a composition comprising: (a) a cationic lipid having any of Formulae CLI-CLXXIX; (b) a neutral lipid; (c) a polyethyleneglycol conjugate (i.e., polyethyleneglycol diacylglycerol (PEG-DAG), PEG-cholesterol, or PEG-DMB); and (d) a short interfering nucleic acid (siNA) molecule that mediates RNA interference (RNAi) against Gastric Inhibitory Peptide (GIP) RNA, wherein each strand of said siNA molecule is about 18 to about 28 nucleotides in length; and one strand of said siNA molecule comprises nucleotide sequence having sufficient complementarity to the GIP RNA for the siNA molecule to mediate RNA interference against the GIP RNA. In one embodiment, the siNA comprises sequences described in U.S. Ser. No. 10/916,030, which is incorporated by reference in its entirety herein. In another embodiment, the composition further comprises cholesterol or a cholesterol derivative.

In one embodiment, the invention features a composition comprising: (a) a cationic lipid having any of Formulae CLI-CLXXIX; (b) a neutral lipid; (c) a polyethyleneglycol conjugate (i.e., polyethyleneglycol diacylglycerol (PEG-DAG), PEG-cholesterol, or PEG-DMB); and (d) a short interfering nucleic acid (siNA) molecule that mediates RNA interference (RNAi) against Stearoyl-CoA Desaturase (SCD) RNA, wherein each strand of said siNA molecule is about 18 to about 28 nucleotides in length; and one strand of said siNA molecule comprises nucleotide sequence having sufficient complementarity to the SCD RNA for the siNA molecule to mediate RNA interference against the SCD RNA. In one embodiment, the siNA comprises sequences described in U.S. Ser. No. 10/923,451, which is incorporated by reference in its entirety herein. In another embodiment, the composition further comprises cholesterol or a cholesterol derivative.

In one embodiment, the invention features a composition comprising: (a) a cationic lipid having any of Formulae CLI-CLXXIX; (b) a neutral lipid; (c) a polyethyleneglycol-diacylglycerol conjugate (i.e., polyethyleneglycol diacylglycerol (PEG-DAG), PEG-cholesterol, or PEG-DMB); and (d) a short interfering nucleic acid (siNA) molecule that mediates RNA interference (RNAi) against Acetyl-CoA carboxylase (ACACB) RNA, wherein each strand of said siNA molecule is about 18 to about 28 nucleotides in length; and one strand of said siNA molecule comprises nucleotide sequence having sufficient complementarity to the ACACB RNA for the siNA molecule to mediate RNA interference against the ACACB RNA. In one embodiment, the siNA comprises sequences described in U.S. Ser. No. 10/888,226, which is incorporated by reference in its entirety herein. In another embodiment, the composition further comprises cholesterol or a cholesterol derivative.

In one embodiment, the invention features a composition comprising: (a) a cationic lipid having any of Formulae CLI-CLXXIX; (b) a neutral lipid; (c) a polyethyleneglycol conjugate (i.e., polyethyleneglycol diacylglycerol (PEG-DAG), PEG-cholesterol, or PEG-DMB); and (d) a short interfering nucleic acid (siNA) molecule that mediates RNA interference (RNAi) against apolipoprotein RNA (e.g., apo AI, apo A-IV, apo B, apo C-III, and/or apo E RNA), wherein each strand of said siNA molecule is about 18 to about 28 nucleotides in length; and one strand of said siNA molecule comprises nucleotide sequence having sufficient complementarity to the apolipoprotein RNA for the siNA molecule to mediate RNA interference against the apolipoprotein RNA. In one embodiment, the siNA comprises sequences described in U.S. Ser. No. 11/054,047, which is incorporated by reference in their entireties herein. In another embodiment, the composition further comprises cholesterol or a cholesterol derivative.

In one embodiment, the invention features a composition comprising: (a) a cationic lipid having any of Formulae CLI-CLXXIX; (b) a neutral lipid; (c) a polyethyleneglycol conjugate (i.e., polyethyleneglycol diacylglycerol (PEG-DAG), PEG-cholesterol, or PEG-DMB); and (d) a short interfering nucleic acid (siNA) molecule that mediates RNA interference (RNAi) against VEGF and/or VEGF-receptor RNA (e.g., VEGF, VEGFR1, VEGFR2 and/or VEGFR3 RNA), wherein each strand of said siNA molecule is about 18 to about 28 nucleotides in length; and one strand of said siNA molecule comprises nucleotide sequence having sufficient complementarity to the VEGF and/or VEGF-receptor RNA for the siNA molecule to mediate RNA interference against the VEGF and/or VEGF-receptor RNA. In one embodiment, the siNA comprises sequences described in U.S. Ser. No. 10/962,898, which is incorporated by reference in their entireties herein. In another embodiment, the composition further comprises cholesterol or a cholesterol derivative.

In one embodiment, the invention features a composition comprising: (a) a cationic lipid having any of Formulae CLI-CLXXIX; (b) a neutral lipid; (c) a polyethyleneglycol conjugate (i.e., polyethyleneglycol diacylglycerol (PEG-DAG), PEG-cholesterol, or PEG_DMB); and (d) a short interfering nucleic acid (siNA) molecule that mediates RNA interference (RNAi) against IL4-receptor RNA, wherein each strand of said siNA molecule is about 18 to about 28 nucleotides in length; and one strand of said siNA molecule comprises nucleotide sequence having sufficient complementarity to the IL4-receptor RNA for the siNA molecule to mediate RNA interference against the IL4-receptor RNA. In one embodiment, the siNA comprises sequences described in U.S. Ser. No. 11/001,347, which is incorporated by reference in their entireties herein. In another embodiment, the composition further comprises cholesterol or a cholesterol derivative.

In one embodiment, the invention features a composition comprising: (a) a cationic lipid having any of Formulae CLI-CLXXIX; (b) a neutral lipid; (c) a polyethyleneglycol conjugate (i.e., polyethyleneglycol diacylglycerol (PEG-DAG), PEG-cholesterol, or PEG_DMB); and (d) a short interfering nucleic acid (siNA) molecule that mediates RNA interference (RNAi) against Hairless RNA, wherein each strand of said siNA molecule is about 18 to about 28 nucleotides in length; and one strand of said siNA molecule comprises nucleotide sequence having sufficient complementarity to the Hairless RNA for the siNA molecule to mediate RNA interference against the Hairless RNA. In one embodiment, the siNA comprises sequences described in U.S. Ser. No. 10/919,964, which is incorporated by reference in their entireties herein. In another embodiment, the composition further comprises cholesterol or a cholesterol derivative.

In one embodiment, the invention features a composition comprising: (a) a cationic lipid having any of Formulae CLI-CLXXIX; (b) a neutral lipid; (c) a polyethyleneglycol conjugate (i.e., polyethyleneglycol diacylglycerol (PEG-DAG), PEG-cholesterol, or PEG_DMB); and (d) a short interfering nucleic acid (siNA) molecule that mediates RNA interference (RNAi) against a target RNA, wherein each strand of said siNA molecule is about 18 to about 28 nucleotides in length; and one strand of said siNA molecule comprises nucleotide sequence having sufficient complementarity to the target RNA for the siNA molecule to mediate RNA interference against the target RNA. In one embodiment, the target RNA comprises RNA sequence referred to by Genbank Accession numbers in International PCT Publication No. WO 03/74654, serial No. PCT/US03/05028, and U.S. patent application Ser. No. 10/923,536 both incorporated by reference herein. In another embodiment, the composition further comprises cholesterol or a cholesterol derivative.

In one embodiment, the cationic lipid component (e.g., a compound having any of Formulae CLI-CLXXIX or as otherwise described herein) of a composition of invention comprises from about 2% to about 60%, from about 5% to about 45%, from about 5% to about 15%, or from about 40% to about 50% of the total lipid present in the formulation.

In one embodiment, the neutral lipid component of a composition of the invention comprises from about 5% to about 90%, or from about 20% to about 85% of the total lipid present in the formulation.

In one embodiment, the PEG conjugate (i.e., PEG_DAG, PEG-cholesterol, PEG-DMB) of a composition of the invention comprises from about 1% to about 20%, or from about 4% to about 15% of the total lipid present in the formulation.

In one embodiment, the cholesterol component of a composition of the invention comprises from about 10% to about 60%, or from about 20% to about 45% of the total lipid present in the formulation.

In one embodiment, a formulated siNA composition of the invention comprises a cationic lipid component comprising from about 30 to about 50% of the total lipid present in the formulation, a neutral lipid comprising from about 30 to about 50% of the total lipid present in the formulation, and a PEG conjugate (i.e., PEG_DAG, PEG-cholesterol, PEG-DMB) comprising about 0 to about 10% of the total lipid present in the formulation.

In one embodiment, a formulated molecular composition of the invention comprises a biologically active molecule (e.g., a polynucleotide such as a siNA, antisense, aptamer, decoy, ribozyme, 2-5A, triplex forming oligonucleotide, or other nucleic acid molecule), a compound having any of Formulae CLI-CLXXIX, DSPC, and a PEG conjugate (i.e., PEG-DAG, PEG-cholesterol, PEG-DMB). In one embodiment, the PEG conjugate is PEG-dilaurylglycerol (C12), PEG-dimyristylglycerol (C14), PEG -dipalmitoylglycerol (C16), or PEG-disterylglycerol (C18). In another embodiment, the PEG conjugate is PEG-dilaurylglycamide (C12), PEG-dimyristylglycamide (C14), PEG -dipalmitoylglycamide (C16), or PEG-disterylglycamide (C18). In another embodiment, the PEG conjugate is PEG-cholesterol or PEG-DMB. In another embodiment, the formulated molecular composition further comprises cholesterol or a cholesterol derivative.

In one embodiment, a formulated molecular composition of the invention comprises a biologically active molecule (e.g., a polynucleotide such as a siNA, antisense, aptamer, decoy, ribozyme, 2-5A, triplex forming oligonucleotide, or other nucleic acid molecule), a compound having Formula CLI, DSPC, and a PEG conjugate. In one embodiment, the PEG conjugate is PEG-dilaurylglycerol (C12), PEG-dimyristylglycerol (C14), PEG-dipalmitoylglycerol (C16), or PEG-disterylglycerol (C18). In another embodiment, the PEG conjugate is PEG-dilaurylglycamide (C12), PEG-dimyristylglycamide (C14), PEG-dipalmitoylglycamide (C16), or PEG -disterylglycamide (C18). In another embodiment, the PEG conjugate is PEG-cholesterol or PEG-DMB. In another embodiment, the formulated molecular composition further comprises cholesterol or a cholesterol derivative.

In one embodiment, a formulated molecular composition of the invention comprises a biologically active molecule (e.g., a polynucleotide such as a siNA, antisense, aptamer, decoy, ribozyme, 2-5A, triplex forming oligonucleotide, or other nucleic acid molecule), a compound having Formula CLV, DSPC, and a PEG conjugate. In one embodiment, the PEG conjugate is PEG-dilaurylglycerol (C12), PEG-dimyristylglycerol (C14), PEG-dipalmitoylglycerol (C16), or PEG-disterylglycerol (C18). In another embodiment, the PEG conjugate is PEG-dilaurylglycamide (C12), PEG-dimyristylglycamide (C14), PEG-dipalmitoylglycamide (C16), or PEG-disterylglycamide (C18). In another embodiment, the PEG conjugate is PEG-cholesterol or PEG-DMB. In another embodiment, the formulated molecular composition further comprises cholesterol or a cholesterol derivative.

In one embodiment, a composition of the invention (e.g., a formulated molecular composition) further comprises a targeting ligand for a specific cell of tissue type. Non -limiting examples of such ligands include sugars and carbohydrates such as galactose, galactosamine, and N-acetyl galactosamine; hormones such as estrogen, testosterone, progesterone, glucocortisone, adrenaline, insulin, glucagon, cortisol, vitamin D, thyroid hormone, retinoic acid, and growth hormones; growth factors such as VEGF, EGF, NGF, and PDGF; cholesterol; bile acids; neurotransmitters such as GABA, Glutamate, acetylcholine; NOGO; inositol triphosphate; diacylglycerol; epinephrine; norepinephrine; Nitric Oxide, peptides, vitamins such as folate and pyridoxine, drugs, antibodies and any other molecule that can interact with a receptor in vivo or in vitro. The ligand can be attached to any component of a formulated siNA composition of invention (e.g., cationic lipid component, neutral lipid component, PEG-DAG component, or siNA component etc.) using a linker molecule, such as an amide, amido, carbonyl, ester, peptide, disulphide, silane, nucleoside, abasic nucleoside, polyether, polyamine, polyamide, peptide, carbohydrate, lipid, polyhydrocarbon, phosphate ester, phosphoramidate, thiophosphate, alkylphosphate, or photolabile linker. In one embodiment, the linker is a biodegradable linker.

In one embodiment, the PEG conjugate of the invention, such as a PEG-DAG, PEG-cholesterol, PEG-DMB, comprises a 200 to 10,000 atom PEG molecule.

In one embodiment, the compositions of the present invention, e.g., a formulated molecular composition, comprise a diacylglycerol-polyethyleneglycol conjugate, i.e., a DAG-PEG conjugate. The term "diacylglycerol" refers to a compound having 2-fatty acyl chains, R1 and R2, both of which have independently between 2 and 30 carbons bonded to the 1- and 2-position of glycerol by ester linkages. The acyl groups can be saturated or have varying degrees of unsaturation. Diacylglycerols have the following general Formula VIII:

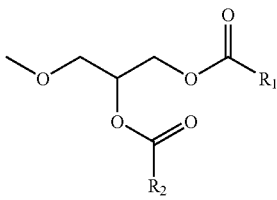

wherein R1 and R2 are each an alkyl, substituted alkyl, aryl, substituted aryl, lipid, or a ligand. In one embodiment, R1 and R2 are each independently a C2 to C30 alkyl group. In one embodiment, the DAG-PEG conjugate is a dilaurylglycerol (C12)-PEG conjugate, a dimyristylglycerol (C14)-PEG conjugate, a dipalmitoylglycerol (C16)-PEG conjugate, a disterylglycerol (C18)-PEG conjugate, PEG-dilaurylglycamide (C12), PEG-dimyristylglycamide (C14), PEG-dipalmitoylglycamide (C16), or PEG-disterylglycamide (C18). Those of skill in the art will readily appreciate that other diacylglycerols can be used in the DAG-PEG conjugates of the present invention.

In one embodiment, the compositions of the present invention, e.g., a formulated molecular composition, comprise a polyethyleneglycol-cholesterol conjugate, i.e., a PEG-chol conjugate. The PEG-chol conjugate can comprise a 200 to 10,000 atom PEG molecule linked to cholesterol or a cholesterol derivative. An exemplary PEG-chol and the synthesis thereof is shown in FIG. 24.

In one embodiment, the compositions of the present invention, e.g., a formulated molecular composition, comprise a polyethyleneglycol-DMB conjugate. The term "DMB" refers to the compound 3,4-Ditetradecoxylbenzyl-β-methyl-poly (ethylene glycol) ether. The PEG-DMB conjugate can comprise a 200 to 10,000 atom PEG molecule linked to DMB. An exemplary PEG-DMB and the synthesis thereof is shown in FIG. 24.

The term "ligand" refers to any compound or molecule, such as a drug, peptide, hormone, or neurotransmitter that is capable of interacting with another compound, such as a receptor, either directly or indirectly. The receptor that interacts with a ligand can be present on the surface of a cell or can alternately be an intercellular receptor. Interaction of the ligand with the receptor can result in a biochemical reaction, or can simply be a physical interaction or association. Non-limiting examples of ligands include sugars and carbohydrates such as galactose, galactosamine, and N-acetyl galactosamine; hormones such as estrogen, testosterone, progesterone, glucocortisone, adrenaline, insulin, glucagon, cortisol, vitamin D, thyroid hormone, retinoic acid, and growth hormones; growth factors such as VEGF, EGF, NGF, and PDGF; cholesterol; bile acids; neurotransmitters such as GABA, Glutamate, acetylcholine; NOGO; inostitol triphosphate; diacylglycerol; epinephrine; norepinephrine; Nitric Oxide, peptides, vitamins such as folate and pyridoxine, drugs, antibodies and any other molecule that can interact with a receptor in vivo or in vitro. The ligand can be attached to a compound of the invention using a linker molecule, such as an amide, amido, carbonyl, ester, peptide, disulphide, silane, nucleoside, abasic nucleoside, polyether, polyamine, polyamide, peptide, carbohydrate, lipid, polyhydrocarbon, phosphate ester, phosphoramidate, thiophosphate, alkylphosphate, or photolabile linker. In one embodiment, the linker is a biodegradable linker.

The term "degradable linker" as used herein, refers to linker moieties that are capable of cleavage under various conditions. Conditions suitable for cleavage can include but are not limited to pH, UV irradiation, enzymatic activity, temperature, hydrolysis, elimination, and substitution reactions, and thermodynamic properties of the linkage.

The term "photolabile linker" as used herein, refers to linker moieties as are known in the art that are selectively cleaved under particular UV wavelengths. Compounds of the invention containing photolabile linkers can be used to deliver compounds to a target cell or tissue of interest, and can be subsequently released in the presence of a UV source.

The term "lipid" as used herein, refers to any lipophilic compound. Non-limiting examples of lipid compounds include fatty acids and their derivatives, including straight chain, branched chain, saturated and unsaturated fatty acids, carotenoids, terpenes, bile acids, and steroids, including cholesterol and derivatives or analogs thereof.

In addition to the foregoing components, the compositions of the present invention can further comprise cationic poly (ethylene glycol) (PEG) lipids, or CPLs, that have been designed for insertion into lipid bilayers to impart a positive charge (see for example Chen, et al., 2000, *Bioconj. Chem.* 11, 433-437). Suitable formulations for use in the present invention, and methods of making and using such formulations are disclosed, for example in U.S. application Ser. No. 09/553,639, which was filed Apr. 20, 2000, and PCT Patent Application No. CA 00/00451, which was filed Apr. 20, 2000 and which published as WO 00/62813 on Oct. 26, 2000, the teachings of each of which is incorporated herein in its entirety by reference.

In one embodiment, the compositions of the present invention, i.e., those formulated molecular compositions containing PEG conjugates, are made using any of a number of different methods. In one embodiment, the present invention provides lipid-nucleic acid particles produced via hydrophobic polynucleotide-lipid intermediate complexes. The complexes are preferably charge-neutralized. Manipulation of these complexes in either detergent-based or organic solvent-based systems can lead to particle formation in which the nucleic acid is protected.

In one embodiment, the present invention provides a serum-stable formulated molecular composition (e.g., comprising a biologically active molecules such as polynucleotides including siNA, antisense, aptamer, decoy, ribozyme, 2-5A, triplex forming oligonucleotide, or other nucleic acid molecules) in which the biologically active molecule is encapsulated in a lipid bilayer and is protected from degradation (for example, where the composition adopts a lamellar structure). Additionally, the formulated particles formed in the present invention are preferably neutral or negatively-charged at physiological pH. In one embodiment, for in vivo applications, neutral particles can be advantageous, while for in vitro applications the particles can be negatively charged. This provides the further advantage of reduced aggregation over the positively-charged liposome formulations in which a biologically active molecule can be encapsulated in cationic lipids.

In addition, the present invention provides serum-stable formulated molecular compositions that undergo a rapid pH-dependent phase transition. The pH-dependent phase transition results in a structural change that increases the efficiency of delivery of a biologically active molecule, such as a polynucleotide, into a biological system, such as a cell. The structural change can increase the efficiency of delivery by, for example, increasing cell membrane fusion and release of a biologically active molecule into a biological system. Thus, in one embodiment, the serum-stable formulated molecular composition is stable in plasma or serum (i.e., in circulation) and stable at physiologic pH (i.e., about pH 7.4) and undergoes a rapid pH-dependent phase transition resulting in a structural change that increases the efficiency of delivery of a biologically active molecule into a biological system. In one embodiment, the pH dependent phase transition occurs at about pH 5.5-6.5. In one embodiment, the serum-stable formulated molecular composition undergoes a structural change to adopt an inverted hexagonal structure at about pH 5.5-6.5. For example, the serum-stable formulated molecular composition can transition from a stable lamellar structure adopted in circulation (i.e., in plasma or serum) at physiologic pH (about pH 7.4) to a less stable and more efficient delivery composition having an inverted hexagonal structure at pH 5.5-6.5, which is the pH found in the early endosome. The serum-stable formulated molecular compositions that undergo a rapid pH-dependent phase transition demonstrate increased efficiency in the delivery of biologically active molecules due to their stability in circulation at physiologic pH and their ability to undergo a pH dependent structural change that increases cell membrane fusion and release of a biologically active molecule into a biological system, such as a cell.

The serum-stable formulated molecular composition that undergoes a rapid pH-dependent phase transition comprises a biologically active molecule (e.g., a polynucleotide such as a siNA, antisense, aptamer, decoy, ribozyme, 2-5A, triplex forming oligonucleotide, other nucleic acid molecule or other biologically active molecule described herein), a cationic lipid, a neutral lipid, and a polyethylene conjugate such as a polyethyleneglycol-diacylglycerol, polyethyleneglycol-diacylglycamide, polyethyleneglycol-cholesterol or polyethylene-DMB conjugate. In another embodiment, the composition further comprises cholesterol or a cholesterol derivative. Examples of suitable cationic lipids, neutral lipids, and PEG conjugates are provided herein.

In one embodiment, the invention features a serum-stable formulated molecular composition comprising a biologically active molecule (e.g., a siNA molecule), a cationic lipid, a neutral lipid, and a PEG-conjugate, in which the cationic lipid is CLinDMA, the neutral lipid is distearoylphosphatidylcholine (DSPC), and the PEG conjugate is PEG-DMG. In another embodiment, the composition further comprises cholesterol or a cholesterol derivative. This is known as formulation L051 (see Table IV).

In one embodiment, the invention features a serum-stable formulated molecular composition comprising a biologically active molecule (e.g., a siNA molecule), a cationic lipid, a neutral lipid, and a PEG-conjugate, in which the cationic lipid is DMOBA, the neutral lipid is distearoylphosphatidylcholine (DSPC), and the PEG conjugate is PEG-DMG. In another embodiment, the composition further comprises cholesterol or a cholesterol derivative. This is known as formulation L053 or L054 (see Table IV).

In one embodiment, the invention features a serum-stable formulated molecular composition comprising a biologically active molecule (e.g., a siNA molecule), a cationic lipid, a neutral lipid, and a PEG-conjugate, in which the cationic lipid is CLinDMA, the neutral lipid is distearoylphosphatidylcholine (DSPC), and the PEG conjugate is 2KPEG-cholesterol. In another embodiment, the composition further comprises cholesterol or a cholesterol derivative. This is known as formulation L069 (see Table IV).

In one embodiment, the invention features a serum-stable formulated molecular composition comprising a biologically active molecule (e.g., a siNA molecule), a cationic lipid, a neutral lipid, and a PEG-conjugate, in which the cationic lipid is pCLinDMA or CLinDMA and DMOBA, the neutral lipid is distearoylphosphatidylcholine (DSPC), and the PEG conjugate is PEG-DMG. In another embodiment, the composition further comprises cholesterol or a cholesterol derivative. This is known as formulation L073 (see Table IV).

In one embodiment, the invention features a serum-stable formulated molecular composition comprising a biologically active molecule (e.g., a siNA molecule), a cationic lipid, a neutral lipid, and a PEG-conjugate, in which the cationic lipid is eCLinDMA, the neutral lipid is distearoylphosphatidylcholine (DSPC), and the PEG conjugate is 2KPEG-cholesterol. In another embodiment, the composition further comprises cholesterol or a cholesterol derivative. This is known as formulation L077 (see Table IV).

In one embodiment, the invention features a serum-stable formulated molecular composition comprising a biologically active molecule (e.g., a siNA molecule), a cationic lipid, a neutral lipid, and a PEG-conjugate, in which the cationic lipid is eCLinDMA, the neutral lipid is distearoylphosphatidylcholine (DSPC), and the PEG conjugate is 2KPEG-DMG. In another embodiment, the composition further comprises cholesterol or a cholesterol derivative. This is known as formulation L080 (see Table IV).

In one embodiment, the invention features a serum-stable formulated molecular composition comprising a biologically active molecule (e.g., a siNA molecule), a cationic lipid, a neutral lipid, and a PEG-conjugate, in which the cationic lipid is pCLinDMA, the neutral lipid is distearoylphosphatidylcholine (DSPC), and the PEG conjugate is 2KPEG-DMG. In another embodiment, the composition further comprises cholesterol or a cholesterol derivative. This is known as formulation L082 (see Table IV).

In one embodiment, the invention features a serum-stable formulated molecular composition comprising a biologically active molecule (e.g., a siNA molecule), a cationic lipid, a neutral lipid, and a PEG-conjugate, in which the cationic lipid is pCLinDMA, the neutral lipid is distearoylphosphatidylcholine (DSPC), and the PEG conjugate is 2KPEG-cholesterol. In another embodiment, the composition further comprises cholesterol or a cholesterol derivative. This is known as formulation L083 (see Table IV).

In one embodiment, the invention features a serum-stable formulated molecular composition comprising a biologically active molecule (e.g., a siNA molecule), a cationic lipid, a neutral lipid, and a PEG-conjugate, in which the cationic lipid is CLinDMA, the neutral lipid is distearoylphosphatidylcholine (DSPC), and the PEG conjugate is 2KPEG-DMG. In another embodiment, the composition further comprises cholesterol or a cholesterol derivative and Linoleyl alcohol. This is known as formulation L086 (see Table IV).

In one embodiment, the invention features a serum-stable formulated molecular composition comprising a biologically active molecule (e.g., a siNA molecule), a cationic lipid, a neutral lipid, and a PEG-conjugate, in which the cationic lipid is DMLBA, the neutral lipid is cholesterol, and the PEG conjugate is 2KPEG-DMG. This is known as formulation L061 (see Table IV).

In one embodiment, the invention features a serum-stable formulated molecular composition comprising a biologically active molecule (e.g., a siNA molecule), a cationic lipid, a neutral lipid, and a PEG-conjugate, in which the cationic lipid is DMOBA, the neutral lipid is cholesterol, and the PEG conjugate is 2KPEG-DMG, and the nitrogen to phosphate (N/P) ratio of the formulated molecular composition is 5. This is known as formulation L060 (see Table IV).

In one embodiment, the invention features a serum-stable formulated molecular composition comprising a biologically active molecule (e.g., a siNA molecule), a cationic lipid, a neutral lipid, and a PEG-conjugate, in which the cationic lipid is DMLBA, the neutral lipid is cholesterol, and the PEG conjugate is 2KPEG-DMG. This is known as formulation L097 (see Table IV).

In one embodiment, the invention features a serum-stable formulated molecular composition comprising a biologically active molecule (e.g., a siNA molecule), a cationic lipid, a neutral lipid, and a PEG-conjugate, in which the cationic lipid is DMOBA, the neutral lipid is cholesterol, and the PEG conjugate is 2KPEG-DMG, and the nitrogen to phosphate (N/P) ratio of the formulated molecular composition is 3. This is known as formulation L098 (see Table IV).

In one embodiment, the invention features a serum-stable formulated molecular composition comprising a biologically active molecule (e.g., a siNA molecule), a cationic lipid, a neutral lipid, and a PEG-conjugate, in which the cationic lipid is DMOBA, the neutral lipid is cholesterol, and the PEG conjugate is 2KPEG-DMG, and the nitrogen to phosphate (N/P) ratio of the formulated molecular composition is 4. This is known as formulation L099 (see Table IV).

In one embodiment, the invention features a serum-stable formulated molecular composition comprising a biologically active molecule (e.g., a siNA molecule), a cationic lipid, a neutral lipid, and a PEG-conjugate, in which the cationic lipid is DMOBA, the neutral lipid is DOBA, and the PEG conjugate is 2KPEG-DMG (3%), and the nitrogen to phosphate (N/P) ratio of the formulated molecular composition is 3. This is known as formulation L100 (see Table IV).

In one embodiment, the invention features a serum-stable formulated molecular composition comprising a biologically active molecule (e.g., a siNA molecule), a cationic lipid, a neutral lipid, and a PEG-conjugate, in which the cationic lipid is DMOBA, the neutral lipid is cholesterol, and the PEG conjugate is 2K-PEG-Cholesterol. This is known as formulation L101 (see Table IV).

In one embodiment, the invention features a serum-stable formulated molecular composition comprising a biologically active molecule (e.g., a siNA molecule), a cationic lipid, a neutral lipid, and a PEG-conjugate, in which the cationic lipid is DMOBA, the neutral lipid is cholesterol, and the PEG conjugate is 2K-PEG-Cholesterol, and the nitrogen to phosphate (N/P) ratio of the formulated molecular composition is 5. This is known as formulation L102 (see Table IV).

In one embodiment, the invention features a serum-stable formulated molecular composition comprising a biologically active molecule (e.g., a siNA molecule), a cationic lipid, a neutral lipid, and a PEG-conjugate, in which the cationic lipid is DMLBA, the neutral lipid is cholesterol, and the PEG conjugate is 2K-PEG-Cholesterol. This is known as formulation L103 (see Table IV).

In one embodiment, the invention features a serum-stable formulated molecular composition comprising a biologically active molecule (e.g., a siNA molecule), a cationic lipid, a neutral lipid, and a PEG-conjugate, in which the cationic lipid is CLinDMA, the neutral lipid is distearoylphosphatidylcholine (DSPC), and the PEG conjugate is 2KPEG-cholesterol. In another embodiment, the composition further comprises cholesterol or a cholesterol derivative and Linoleyl alcohol. This is known as formulation L104 (see Table IV).

The invention additionally provides methods for determining whether a formulated molecular composition will be effective for delivery of a biologically active molecule into a biological system. In one embodiment, the method for determining whether a formulated molecular composition will be effective for delivery of a biologically active molecule into a biological system comprises (1) measuring the serum stability of the formulated molecular composition and (2) measuring the pH dependent phase transition of the formulated molecular composition, wherein a determination that the formulated molecular composition is stable in serum and a determination that the formulated molecular composition undergoes a phase transition at about pH 4 to about 7, e.g., from 5.5 to 6.5, indicates that the formulated molecular composition will be effective for delivery of a biologically active molecule into a biological system. In another embodiment, the method further comprises measuring the transfection efficiency of the formulated molecular composition in a cell in vitro.

The serum stability of the formulated molecular composition can be measured using any assay that measures the stability of the formulated molecular composition in serum, including the assays described herein and otherwise known in the art. One exemplary assay that can be used to measure the serum stability is an assay that measures the relative turbidity of the composition in serum over time. For example, the relative turbidity of a formulated molecular composition can be determined by measuring the absorbance of the formulated molecular composition in the presence or absence of serum (i.e., 50%) at several time points over a 24 hour period using a spectrophotometer. The formulated molecular composition is stable in serum if the relative turbidity, as measured by absorbance, remains constant at around 1.0 over time.

The pH dependent phase transition of the formulated molecular composition can be measured using any assay that measures the phase transition of the formulated molecular composition at about pH 5.5-6.5, including the assays described herein and otherwise known in the art. One exemplary assay that can be used to measure the pH dependent phase transition is an assay that measures the relative turbidity of the composition at different pH over time. For example, the relative turbidity of a formulated molecular composition can be determined by measuring the absorbance over time of the formulated molecular composition in buffer having a range of different pH values. The formulated molecular composition undergoes pH dependent phase transition if the relative turbidity, as measured by absorbance, decreases when the pH drops below 7.0.

In addition, the efficiency of the serum-stable formulated molecular composition that undergoes a rapid pH-dependent phase transition as a delivery agent can be determined by measuring the transfection efficiency of the formulated molecular composition. Methods for performing transfection assays are described herein and otherwise known in the art.

In one embodiment, the particles made by the methods of this invention have a size of about 50 to about 600 nm. The particles can be formed by either a detergent dialysis method or by a modification of a reverse-phase method which utilizes organic solvents to provide a single phase during mixing of the components. Without intending to be bound by any particular mechanism of formation, a molecule (e.g., a biologically active molecule such as a polynucleotide) is contacted with a detergent solution of cationic lipids to form a coated molecular complex. These coated molecules can aggregate and precipitate. However, the presence of a detergent reduces this aggregation and allows the coated molecules to react with excess lipids (typically, noncationic lipids) to form particles in which the molecule of interest is encapsulated in a lipid bilayer. The methods described below for the formation of formulated molecular compositions using organic solvents follow a similar scheme.

In one embodiment, the particles are formed using detergent dialysis. Thus, the present invention provides a method for the preparation of serum-stable formulated molecular compositions, including those that undergo pH dependent phase transition, comprising: (a) combining a molecule (e.g., a biologically active molecule such as a polynucleotide, including siNA, antisense, aptamer, decoy, ribozyme, 2-5A, triplex forming oligonucleotide, or other nucleic acid molecules) with cationic lipids in a detergent solution to form a coated molecule-lipid complex; (b) contacting noncationic lipids with the coated molecule-lipid complex to form a detergent solution comprising a siNA-lipid complex and noncationic lipids; and (c) dialyzing the detergent solution of step (b) to provide a solution of serum-stable molecule-lipid particles, wherein the molecule is encapsulated in a lipid bilayer and the particles are serum-stable and have a size of from about 50 to about 600 nm.

In one embodiment, an initial solution of coated molecule-lipid (e.g., polynucleotide-lipid) complexes is formed, for example, by combining the molecule with the cationic lipids in a detergent solution.

In these embodiments, the detergent solution is preferably an aqueous solution of a neutral detergent having a critical micelle concentration of 15-300 mM, more preferably 20-50 mM. Examples of suitable detergents include, for example, N,N'-((octanoylimino)-bis-(trimethylene))-bis-(D-gluconamide) (BIGCHAP); BRIJ 35; Deoxy-BIGCHAP; dodecylpoly(ethylene glycol) ether; Tween 20; Tween 40; Tween 60; Tween 80; Tween 85; Mega 8; Mega 9; Zwittergent® 3-08; Zwittergent® 3-10; Triton X-405; hexyl-, heptyl-, octyl- and nonyl-beta-D-glucopyranoside; and heptylthioglucopyranoside; with octyl β-D-glucopyranoside and Tween-20 being the most preferred. The concentration of detergent in the detergent solution is typically about 100 mM to about 2 M, preferably from about 200 mM to about 1.5 M.

In one embodiment, the cationic lipids and the molecule of interest (e.g., a biologically active molecule such as a polynucleotide, including siNA, antisense, aptamer, decoy, ribozyme, 2-5A, triplex forming oligonucleotide, or other nucleic acid molecules) will typically be combined to produce a charge ratio (+/−) of about 1:1 to about 20:1, preferably in a ratio of about 1:1 to about 12:1, and more preferably in a ratio of about 2:1 to about 6:1. Additionally, the overall concentration of siNA in solution will typically be from about 25 μg/mL to about 1 mg/mL, preferably from about 25 μg/mL to about 500 μg/mL, and more preferably from about 100 μg/mL to about 250 μg/mL. The combination of the molecules of interest and cationic lipids in detergent solution is kept, typically at room temperature, for a period of time which is sufficient for the coated complexes to form. Alternatively, the molecules of interest and cationic lipids can be combined in the detergent solution and warmed to temperatures of up to about 37° C. For molecules (e.g., certain polynucleotides herein) which are particularly sensitive to temperature, the coated complexes can be formed at lower temperatures, typically down to about 4° C.

In one embodiment, the siNA to lipid ratios (mass/mass ratios) in a formed formulated molecular composition range from about 0.01 to about 0.08. The ratio of the starting materials also falls within this range because the purification step typically removes the unencapsulated siNA as well as the empty liposomes. In another embodiment, the formulated siNA composition preparation uses about 400 μg siNA per 10 mg total lipid or a siNA to lipid ratio of about 0.01 to about 0.08 and, more preferably, about 0.04, which corresponds to 1.25 mg of total lipid per 50 μg of siNA. A formulated molecular composition of the invention is developed to target specific organs, tissues, or cell types. In one embodiment, a formulated molecular composition of the invention is developed to target the liver or hepatocytes. Ratios of the various components of the formulated molecular composition are adjusted to target specific organs, tissues, or cell types.

In one embodiment, the invention features a method for delivering or administering a biologically active molecule to a cell or cells in a subject or organism, comprising administering a formulated molecular composition of the invention under conditions suitable for delivery of the biologically active molecule component of the formulated molecular composition to the cell or cells of the subject or organism. In one embodiment, the formulated molecular composition is contacted with the cell or cells of the subject or organism as is generally known in the art, such as via parental administration (e.g., intravenous, intramuscular, subcutaneous administration) of the formulated molecular composition with or without excipients to facilitate the administration.

In one embodiment, the invention features a method for delivering or administering a biologically active molecule to liver or liver cells (e.g., hepatocytes) in a subject or organism, comprising administering a formulated molecular composition of the invention under conditions suitable for delivery of the biologically active molecule component of the formulated molecular composition to the liver or liver cells (e.g., hepatocytes) of the subject or organism. In one embodiment, the formulated molecular composition is contacted with the liver or liver cells of the subject or organism as is generally known in the art, such as via parental administration (e.g., intravenous, intramuscular, subcutaneous administration) or local administration (e.g., direct injection, portal vein injection, catheterization, stenting etc.) of the formulated molecular composition with or without excipients to facilitate the administration.

In one embodiment, the invention features a method for delivering or administering a biologically active molecule to kidney or kidney cells in a subject or organism, comprising administering a formulated molecular composition of the invention under conditions suitable for delivery of the biologically active molecule component of the formulated molecular composition to the kidney or kidney cells of the subject or organism. In one embodiment, the formulated molecular composition is contacted with the kidney or kidney cells of the subject or organism as is generally known in the art, such as via parental administration (e.g., intravenous, intramuscular, subcutaneous administration) or local administration (e.g., direct injection, catheterization, stenting etc.) of the formulated molecular composition with or without excipients to facilitate the administration.

In one embodiment, the invention features a method for delivering or administering a biologically active molecule to tumor or tumor cells in a subject or organism, comprising administering a formulated molecular composition of the invention under conditions suitable for delivery of the biologically active molecule component of the formulated molecular composition to the tumor or tumor cells of the subject or organism. In one embodiment, the formulated molecular composition is contacted with the tumor or tumor cells of the subject or organism as is generally known in the art, such as via parental administration (e.g., intravenous, intramuscular, subcutaneous administration) or local administration (e.g., direct injection, catheterization, stenting etc.) of the formulated molecular composition with or without excipients to facilitate the administration.

In one embodiment, the invention features a method for delivering or administering a biologically active molecule to CNS or CNS cells (e.g., brain, spinal cord) in a subject or organism, comprising administering a formulated molecular composition of the invention under conditions suitable for delivery of the biologically active molecule component of the formulated molecular composition to the CNS or CNS cells of the subject or organism. In one embodiment, the formulated molecular composition is contacted with the CNS or CNS cells of the subject or organism as is generally known in the art, such as via parental administration (e.g., intravenous, intramuscular, subcutaneous administration) or local administration (e.g., direct injection, catheterization, stenting etc.) of the formulated molecular composition with or without excipients to facilitate the administration.

In one embodiment, the invention features a method for delivering or administering a biologically active molecule to lung or lung cells in a subject or organism, comprising administering a formulated molecular composition of the invention under conditions suitable for delivery of the biologically active molecule component of the formulated molecular composition to the lung or lung cells of the subject or organism. In one embodiment, the formulated molecular composition is contacted with the lung or lung cells of the subject or organism as is generally known in the art, such as via parental administration (e.g., intravenous, intramuscular, subcutaneous administration) or local administration (e.g., pulmonary administration directly to lung tissues and cells) of the formulated molecular composition with or without excipients to facilitate the administration.

In one embodiment, the invention features a method for delivering or administering a biologically active molecule to vascular or vascular cells in a subject or organism, comprising administering a formulated molecular composition of the invention under conditions suitable for delivery of the biologically active molecule component of the formulated molecular composition to the vascular or vascular cells of the subject or organism. In one embodiment, the formulated molecular composition is contacted with the vascular or vascular cells of the subject or organism as is generally known in the art, such as via parental administration (e.g., intravenous, intramuscular, subcutaneous administration) or local administration (e.g., clamping, catheterization, stenting etc.) of the formulated molecular composition with or without excipients to facilitate the administration.

In one embodiment, the invention features a method for delivering or administering a biologically active molecule to skin or skin cells (e.g., dermis or dermis cells, follicle or follicular cells) in a subject or organism, comprising administering a formulated molecular composition of the invention under conditions suitable for delivery of the biologically active molecule component of the formulated molecular composition to the skin or skin cells of the subject or organism. In one embodiment, the formulated molecular composition is contacted with the skin or skin cells of the subject or organism as is generally known in the art, such as via parental administration (e.g., intravenous, intramuscular, subcutaneous administration) or local administration (e.g., direct dermal application, iontophoresis etc.) of the formulated molecular composition with or without excipients to facilitate the administration.

In one embodiment, the invention features a method for delivering or administering a biologically active molecule to the eye or ocular cells (e.g., macula, fovea, cornea, retina etc.) in a subject or organism, comprising administering a formulated molecular composition of the invention under conditions suitable for delivery of the biologically active molecule component of the formulated molecular composition to the eye or ocular cells of the subject or organism. In one embodiment, the formulated molecular composition is contacted with the eye or ocular cells of the subject or organism as is generally known in the art, such as via parental administration (e.g., intravenous, intramuscular, subcutaneous administration) or local administration (e.g., direct injection, intraocular injection, periocular injection, iontophoresis, use of eyedrops, inplants etc.) of the formulated molecular composition with or without excipients to facilitate the administration.

In one embodiment, the invention features a method for delivering or administering a biologically active molecule to the ear or cells of the ear (e.g., inner ear, middle ear, outer ear) in a subject or organism, comprising administering a formulated molecular composition of the invention under conditions suitable for delivery of the biologically active molecule component of the formulated molecular composition to the ear or ear cells of the subject or organism. In one embodiment, the administration comprises methods and devices as described in U.S. Pat. Nos. 5,421,818, 5,476,446, 5,474,529, 6,045,528, 6,440,102, 6,685,697, 6,120,484; and 5,572,594; all incorporated by reference in their entireties herein and the teachings of Silverstein, 1999, Ear Nose Throat J., 78, 595-8, 600; and Jackson and Silverstein, 2002, Otolaryngol Clin North Am., 35, 639-53, and adapted for use the compositions of the invention.

In one embodiment, the invention features a formulated siNA composition comprising a short interfering nucleic acid (siNA) molecule that down-regulates expression of a target gene, wherein said siNA molecule comprises about 15 to about 28 base pairs.

In one embodiment, the invention features a formulated siNA composition comprising a double stranded short interfering nucleic acid (siNA) molecule that directs cleavage of a target RNA via RNA interference (RNAi), wherein the double stranded siNA molecule comprises a first and a second strand, each strand of the siNA molecule is about 18 to about 28 nucleotides in length, the first strand of the siNA comprises nucleotide sequence having sufficient complementarity to the target RNA for the siNA molecule to direct cleavage of the target RNA via RNA interference, and the second strand of said siNA molecule comprises nucleotide sequence that is complementary to the first strand.

In one embodiment, the invention features a formulated siNA composition comprising a double stranded short interfering nucleic acid (siNA) molecule that directs cleavage of a target RNA via RNA interference (RNAi), wherein the double stranded siNA molecule comprises a first and a second strand, each strand of the siNA molecule is about 18 to about 23 nucleotides in length, the first strand of the siNA molecule comprises nucleotide sequence having sufficient complementarity to the target RNA for the siNA molecule to direct cleavage of the target RNA via RNA interference, and the second strand of said siNA molecule comprises nucleotide sequence that is complementary to the first strand.

In one embodiment, the invention features a formulated siNA composition comprising a chemically synthesized double stranded short interfering nucleic acid (siNA) molecule that directs cleavage of a target RNA via RNA interference (RNAi), wherein each strand of the siNA molecule is about 18 to about 28 nucleotides in length; and one strand of the siNA molecule comprises nucleotide sequence having sufficient complementarity to the target RNA for the siNA molecule to direct cleavage of the target RNA via RNA interference.

In one embodiment, the invention features a formulated siNA composition comprising a chemically synthesized double stranded short interfering nucleic acid (siNA) molecule that directs cleavage of a target RNA via RNA interference (RNAi), wherein each strand of the siNA molecule is about 18 to about 23 nucleotides in length; and one strand of the siNA molecule comprises nucleotide sequence having sufficient complementarity to the target RNA for the siNA molecule to direct cleavage of the target RNA via RNA interference.

In one embodiment, the invention features a formulated siNA composition comprising a siNA molecule that down-regulates expression of a target gene, for example, wherein the target gene comprises target encoding sequence. In one embodiment, the invention features a siNA molecule that down-regulates expression of a target gene, for example, wherein the target gene comprises target non-coding sequence or regulatory elements involved in target gene expression.

In one embodiment, a siNA of the invention is used to inhibit the expression of target genes or a target gene family, wherein the genes or gene family sequences share sequence homology. Such homologous sequences can be identified as is known in the art, for example using sequence alignments. siNA molecules can be designed to target such homologous sequences, for example using perfectly complementary sequences or by incorporating non-canonical base pairs, for example mismatches and/or wobble base pairs that can provide additional target sequences. In instances where mismatches are identified, non-canonical base pairs (for example, mismatches and/or wobble bases) can be used to generate siNA molecules that target more than one gene sequence. In a non-limiting example, non-canonical base pairs such as UU and CC base pairs are used to generate siNA molecules that are capable of targeting sequences for differing targets that share sequence homology. As such, one advantage of using siNAs of the invention is that a single siNA can be designed to include nucleic acid sequence that is complementary to the nucleotide sequence that is conserved between the homologous genes. In this approach, a single siNA can be used to inhibit expression of more than one gene instead of using more than one siNA molecule to target the different genes.

In one embodiment, the invention features a formulated siNA composition comprising a siNA molecule having RNAi activity against a target RNA, wherein the siNA molecule comprises a sequence complementary to any RNA having target encoding sequence. Examples of siNA molecules suitable for the formulations described herein are provided in International Application Serial Number US 04/106390 (WO 05/19453), which is hereby incorporated by reference in its entirety. Chemical modifications as described in PCT/US 2004/106390 (WO 05/19453), U.S. Ser. No. 10/444,853, filed May 23, 2003 U.S. Ser. No. 10/923,536 filed Aug. 20, 2004, U.S. Ser. No. 11/234,730, filed Sep. 23, 2005 or U.S. Ser. No. 11/299,254, filed Dec. 8, 2005, all incorporated by reference in their entireties herein, or otherwise described herein can be applied to any siNA construct of the invention. In another embodiment, a siNA molecule of the invention includes a nucleotide sequence that can interact with nucleotide sequence of a target gene and thereby mediate silencing of target gene expression, for example, wherein the siNA mediates regulation of target gene expression by cellular processes that modulate the chromatin structure or methylation patterns of the target gene and prevent transcription of the target gene.

In one embodiment, siNA molecules of the invention are used to down regulate or inhibit the expression of target proteins arising from target haplotype polymorphisms that are associated with a disease or condition (e.g. alopecia, hair loss, and/or atrichia). Analysis of target genes, or target protein or RNA levels can be used to identify subjects with such polymorphisms or those subjects who are at risk of developing traits, conditions, or diseases described herein. These subjects are amenable to treatment, for example, treatment with siNA molecules of the invention and any other composition useful in treating diseases related to target gene expression. As such, analysis of target protein or RNA levels can be used to determine treatment type and the course of therapy in treating a subject. Monitoring of target protein or RNA levels can be used to predict treatment outcome and to determine the efficacy of compounds and compositions that modulate the level and/or activity of certain target proteins associated with a trait, condition, or disease.

In one embodiment, a siNA molecule of the invention comprises an antisense strand comprising a nucleotide sequence that is complementary to a nucleotide sequence or a portion thereof encoding a target protein. The siNA further comprises a sense strand, wherein said sense strand comprises a nucleotide sequence of a target gene or a portion thereof.

In another embodiment, a siNA of the invention comprises an antisense region comprising a nucleotide sequence that is complementary to a nucleotide sequence encoding a target protein or a portion thereof. The siNA molecule further comprises a sense region, wherein said sense region comprises a nucleotide sequence of a target gene or a portion thereof.

In another embodiment, a siNA of the invention comprises a nucleotide sequence in the antisense region of the siNA molecule that is complementary to a nucleotide sequence or portion of sequence of a target gene. In another embodiment, a siNA of the invention comprises a region, for example, the antisense region of the siNA construct that is complementary to a sequence comprising a target gene sequence or a portion thereof.

In one embodiment, a siNA molecule of the invention comprises an antisense strand having about 15 to about 30 (e.g., about 15, 16, 17, 18, 19, 20, 21, 22, 23, 24, 25, 26, 27, 28, 29, or 30) nucleotides, wherein the antisense strand is complementary to a RNA sequence or a portion thereof encoding a target protein, and wherein said siNA further comprises a sense strand having about 15 to about 30 (e.g., about 15, 16, 17, 18, 19, 20, 21, 22, 23, 24, 25, 26, 27, 28, 29, or 30) nucleotides, and wherein said sense strand and said antisense strand are distinct nucleotide sequences where at least about 15 nucleotides in each strand are complementary to the other strand.

In another embodiment, a siNA molecule of the invention comprises an antisense region having about 15 to about 30 (e.g., about 15, 16, 17, 18, 19, 20, 21, 22, 23, 24, 25, 26, 27, 28, 29, or 30) nucleotides, wherein the antisense region is complementary to a RNA sequence encoding a target protein, and wherein said siNA further comprises a sense region having about 15 to about 30 (e.g., about 15, 16, 17, 18, 19, 20, 21, 22, 23, 24, 25, 26, 27, 28, 29, or 30) nucleotides, wherein said sense region and said antisense region are comprised in a linear molecule where the sense region comprises at least about 15 nucleotides that are complementary to the antisense region.

In one embodiment, a siNA molecule of the invention has RNAi activity that modulates expression of RNA encoded by a target gene. Because target genes can share some degree of sequence homology with each other, siNA molecules can be designed to target a class of target genes or alternately specific target genes (e.g., polymorphic variants) by selecting sequences that are either shared amongst different targets or alternatively that are unique for a specific target. Therefore, in one embodiment, the siNA molecule can be designed to target conserved regions of target RNA sequences having homology among several target gene variants so as to target a class of target genes with one siNA molecule. Accordingly, in one embodiment, the siNA molecule of the invention modulates the expression of one or both target alleles in a subject. In another embodiment, the siNA molecule can be designed to target a sequence that is unique to a specific target RNA sequence (e.g., a single target allele or target single nucleotide polymorphism (SNP)) due to the high degree of specificity that the siNA molecule requires to mediate RNAi activity.

In one embodiment, a siNA molecule of the invention is double-stranded. In another embodiment, the siNA molecules of the invention consist of duplex nucleic acid molecules containing about 15 to about 30 base pairs between oligonucleotides comprising about 15 to about 30 (e.g., about 15, 16, 17, 18, 19, 20, 21, 22, 23, 24, 25, 26, 27, 28, 29, or 30) nucleotides. In yet another embodiment, siNA molecules of the invention comprise duplex nucleic acid molecules with overhanging ends of about 1 to about 3 (e.g., about 1, 2, or 3) nucleotides, for example, about 21-nucleotide duplexes with about 19 base pairs and 3'-terminal mononucleotide, dinucleotide, or trinucleotide overhangs. In yet another embodiment, siNA molecules of the invention comprise duplex nucleic acid molecules with blunt ends, where both ends are blunt, or alternatively, where one of the ends is blunt.

In one embodiment, siNA molecules of the invention have specificity for nucleic acid molecules expressing target proteins, such as RNA encoding a target protein. In one embodiment, a siNA molecule of the invention is RNA based (e.g., a siNA comprising 2'-OH nucleotides) and includes one or more chemical modifications, such as those described herein. Non-limiting examples of such chemical modifications include without limitation phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy abasic residue incorporation. These chemical modifications, when used in various siNA constructs, (e.g., RNA based siNA constructs), are shown to preserve RNAi activity in cells while at the same time, dramatically increasing the serum stability of these compounds. Furthermore, contrary to the data published by Parrish et al., supra, applicant demonstrates that multiple (greater than one) phosphorothioate substitutions are well-tolerated and confer substantial increases in serum stability for modified siNA constructs.

In one embodiment, a siNA molecule of the invention comprises modified nucleotides while maintaining the ability to mediate RNAi. The modified nucleotides can be used to improve in vitro or in vivo characteristics such as stability, activity, and/or bioavailability. For example, a siNA molecule of the invention can comprise modified nucleotides as a percentage of the total number of nucleotides present in the siNA molecule. As such, a siNA molecule of the invention can generally comprise about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siNA molecule will depend on the total number of nucleotides present in the siNA. If the siNA molecule is single stranded, the percent modification can be based upon the total number of nucleotides present in the single stranded siNA molecules. Likewise, if the siNA molecule is double stranded, the percent modification can be based upon the total number of nucleotides present in the sense strand, antisense strand, or both the sense and antisense strands.

One aspect of the invention features a formulated siNA composition comprising a double-stranded short interfering nucleic acid (siNA) molecule that down-regulates expression of a target gene. In one embodiment, the double stranded siNA molecule comprises one or more chemical modifications and each strand of the double-stranded siNA is about 21 nucleotides long. In one embodiment, the double-stranded siNA molecule does not contain any ribonucleotides. In another embodiment, the double-stranded siNA molecule comprises one or more ribonucleotides. In one embodiment, each strand of the double-stranded siNA molecule independently comprises about 15 to about 30 (e.g., about 15, 16, 17, 18, 19, 20, 21, 22, 23, 24, 25, 26, 27, 28, 29, or 30) nucleotides, wherein each strand comprises about 15 to about 30 (e.g., about 15, 16, 17, 18, 19, 20, 21, 22, 23, 24, 25, 26, 27, 28, 29, or 30) nucleotides that are complementary to the nucleotides of the other strand. In one embodiment, one of the strands of the double-stranded siNA molecule comprises a nucleotide sequence that is complementary to a nucleotide sequence or a portion thereof of the target gene, and the second strand of the double-stranded siNA molecule comprises a nucleotide sequence substantially similar to the nucleotide sequence of the target gene or a portion thereof.

In another embodiment, the invention features a formulated siNA composition comprising a double-stranded short interfering nucleic acid (siNA) molecule that down-regulates expression of a target gene comprising an antisense region, wherein the antisense region comprises a nucleotide sequence that is complementary to a nucleotide sequence of the target gene or a portion thereof, and a sense region, wherein the sense region comprises a nucleotide sequence substantially similar to the nucleotide sequence of the target gene or a portion thereof. In one embodiment, the antisense region and the sense region independently comprise about 15 to about 30 (e.g. about 15, 16, 17, 18, 19, 20, 21, 22, 23, 24, 25, 26, 27, 28, 29, or 30) nucleotides, wherein the antisense region comprises about 15 to about 30 (e.g. about 15, 16, 17, 18, 19, 20, 21, 22, 23, 24, 25, 26, 27, 28, 29, or 30) nucleotides that are complementary to nucleotides of the sense region.

In another embodiment, the invention features a formulated siNA composition comprising a double-stranded short interfering nucleic acid (siNA) molecule that down-regulates expression of a target gene comprising a sense region and an antisense region, wherein the antisense region comprises a nucleotide sequence that is complementary to a nucleotide sequence of RNA encoded by the target gene or a portion thereof and the sense region comprises a nucleotide sequence that is complementary to the antisense region.

In one embodiment, a siNA molecule of the invention comprises blunt ends, i.e., ends that do not include any overhanging nucleotides. For example, a siNA molecule comprising modifications described in U.S. Ser. No. 10/444,853, filed May 23, 2003, U.S. Ser. No. 10/923,536 filed Aug. 20, 2004, or U.S. Ser. No. 11/234,730, filed Sep. 23, 2005, all incorporated by reference in their entireties herein, or any combination thereof and/or any length described herein can comprise blunt ends or ends with no overhanging nucleotides.

In one embodiment, any siNA molecule of the invention can comprise one or more blunt ends, i.e. where a blunt end does not have any overhanging nucleotides. In one embodiment, the blunt ended siNA molecule has a number of base pairs equal to the number of nucleotides present in each strand of the siNA molecule. In another embodiment, the siNA molecule comprises one blunt end, for example wherein the 5'-end of the antisense strand and the 3'-end of the sense strand do not have any overhanging nucleotides. In another example, the siNA molecule comprises one blunt end, for example wherein the 3'-end of the antisense strand and the 5'-end of the sense strand do not have any overhanging nucleotides. In another example, a siNA molecule comprises two blunt ends, for example wherein the 3'-end of the antisense strand and the 5'-end of the sense strand as well as the 5'-end of the antisense strand and 3'-end of the sense strand do not have any overhanging nucleotides. A blunt ended siNA molecule can comprise, for example, from about 15 to about 30 nucleotides (e.g., about 15, 16, 17, 18, 19, 20, 21, 22, 23, 24, 25, 26, 27, 28, 29, or 30 nucleotides). Other nucleotides present in a blunt ended siNA molecule can comprise, for example, mismatches, bulges, loops, or wobble base pairs to modulate the activity of the siNA molecule to mediate RNA interference.

By "blunt ends" is meant symmetric termini, or termini of a double stranded siNA molecule having no overhanging nucleotides. The two strands of a double stranded siNA molecule align with each other without over-hanging nucleotides at the termini. For example, a blunt ended siNA construct comprises terminal nucleotides that are complementary between the sense and antisense regions of the siNA molecule.

In one embodiment, the invention features a formulated siNA composition comprising a double-stranded short interfering nucleic acid (siNA) molecule that down-regulates expression of a target gene, wherein the siNA molecule is assembled from two separate oligonucleotide fragments wherein one fragment comprises the sense region and the second fragment comprises the antisense region of the siNA molecule. The sense region can be connected to the antisense region via a linker molecule, such as a polynucleotide linker or a non-nucleotide linker.

In one embodiment, the invention features a formulated siNA composition comprising a double-stranded short interfering nucleic acid (siNA) molecule that down-regulates expression of a target gene, wherein the siNA molecule comprises about 15 to about 30 (e.g. about 15, 16, 17, 18, 19, 20, 21, 22, 23, 24, 25, 26, 27, 28, 29, or 30) base pairs, and wherein each strand of the siNA molecule comprises one or more chemical modifications. In another embodiment, one of the strands of the double-stranded siNA molecule comprises a nucleotide sequence that is complementary to a nucleotide sequence of a target gene or a portion thereof, and the second strand of the double-stranded siNA molecule comprises a nucleotide sequence substantially similar to the nucleotide sequence or a portion thereof of the target gene. In another embodiment, one of the strands of the double-stranded siNA molecule comprises a nucleotide sequence that is complementary to a nucleotide sequence of a target gene or portion thereof, and the second strand of the double-stranded siNA molecule comprises a nucleotide sequence substantially similar to the nucleotide sequence or portion thereof of the target gene. In another embodiment, each strand of the siNA molecule comprises about 15 to about 30 (e.g. about 15, 16, 17, 18, 19, 20, 21, 22, 23, 24, 25, 26, 27, 28, 29, or 30) nucleotides, and each strand comprises at least about 15 to about 30 (e.g. about 15, 16, 17, 18, 19, 20, 21, 22, 23, 24, 25, 26, 27, 28, 29, or 30) nucleotides that are complementary to the nucleotides of the other strand.

In any of the embodiments described herein, a siNA molecule of the invention can comprise no ribonucleotides. Alternatively, a siNA molecule of the invention can comprise one or more ribonucleotides.

In one embodiment, a siNA molecule of the invention comprises an antisense region comprising a nucleotide sequence that is complementary to a nucleotide sequence of a target gene or a portion thereof, and the siNA further comprises a sense region comprising a nucleotide sequence substantially similar to the nucleotide sequence of the target gene or a portion thereof. In another embodiment, the antisense region and the sense region each comprise about 15 to about 30 (e.g. about 15, 16, 17, 18, 19, 20, 21, 22, 23, 24, 25, 26, 27, 28, 29, or 30) nucleotides and the antisense region comprises at least about 15 to about 30 (e.g. about 15, 16, 17, 18, 19, 20, 21, 22, 23, 24, 25, 26, 27, 28, 29, or 30) nucleotides that are complementary to nucleotides of the sense region. The target gene can comprise, for example, sequences referred to by Genbank Accession Nos. in PCT Publication No. WO 03/74654, serial No. PCT/US03/05028. In another embodiment, the siNA is a double stranded nucleic acid molecule, where each of the two strands of the siNA molecule independently comprise about 15 to about 40 (e.g. about 15, 16, 17, 18, 19, 20, 21, 22, 23, 24, 25, 26, 27, 28, 29, 30, 31, 23, 33, 34, 35, 36, 37, 38, 39, or 40) nucleotides, and where one of the strands of the siNA molecule comprises at least about 15 (e.g. about 15, 16, 17, 18, 19, 20, 21, 22, 23, 24 or 25 or more) nucleotides that are complementary to the nucleic acid sequence of the target gene or a portion thereof.

In one embodiment, a siNA molecule of the invention comprises a sense region and an antisense region, wherein the antisense region comprises a nucleotide sequence that is complementary to a nucleotide sequence of RNA encoded by a target gene, or a portion thereof, and the sense region comprises a nucleotide sequence that is complementary to the antisense region. In one embodiment, the siNA molecule is assembled from two separate oligonucleotide fragments, wherein one fragment comprises the sense region and the second fragment comprises the antisense region of the siNA molecule. In another embodiment, the sense region is connected to the antisense region via a linker molecule. In another embodiment, the sense region is connected to the antisense region via a linker molecule, such as a nucleotide or non-nucleotide linker. The target gene can comprise, for example, sequences referred to in PCT Publication No. WO 03/74654, serial No. PCT/US03/05028 or U.S. Ser. No. 10/923,536 or otherwise known in the art.

In one embodiment, the invention features a formulated siNA composition comprising a double-stranded short interfering nucleic acid (siNA) molecule that down-regulates expression of a target gene comprising a sense region and an antisense region, wherein the antisense region comprises a nucleotide sequence that is complementary to a nucleotide sequence of RNA encoded by the target gene or a portion thereof and the sense region comprises a nucleotide sequence that is complementary to the antisense region, and wherein the siNA molecule has one or more modified pyrimidine and/or purine nucleotides. In one embodiment, the pyrimidine nucleotides in the sense region are 2'-O-methylpyrimidine nucleotides or 2'-deoxy-2'-fluoro pyrimidine nucleotides and the purine nucleotides present in the sense region are 2'-deoxy purine nucleotides. In another embodiment, the pyrimidine nucleotides in the sense region are 2'-deoxy-2'-fluoro pyrimidine nucleotides and the purine nucleotides present in the sense region are 2'-O-methyl purine nucleotides. In another embodiment, the pyrimidine nucleotides in the sense region are 2'-deoxy-2'-fluoro pyrimidine nucleotides and the purine nucleotides present in the sense region are 2'-deoxy purine nucleotides. In one embodiment, the pyrimidine nucleotides in the antisense region are 2'-deoxy-2'-fluoro pyrimidine nucleotides and the purine nucleotides present in the antisense region are 2'-O-methyl or 2'-deoxy purine nucleotides. In another embodiment of any of the above-described siNA molecules, any nucleotides present in a non-complementary region of the sense strand (e.g. overhang region) are 2'-deoxy nucleotides.

In one embodiment, the invention features a formulated siNA composition comprising a double-stranded short interfering nucleic acid (siNA) molecule that down-regulates expression of a target gene, wherein the siNA molecule is assembled from two separate oligonucleotide fragments wherein one fragment comprises the sense region and the second fragment comprises the antisense region of the siNA molecule, and wherein the fragment comprising the sense region includes a terminal cap moiety at the 5'-end, the 3'-end, or both of the 5' and 3' ends of the fragment. In one embodiment, the terminal cap moiety is an inverted deoxy abasic moiety or glyceryl moiety. In one embodiment, each of the two fragments of the siNA molecule independently comprise about 15 to about 30 (e.g. about 15, 16, 17, 18, 19, 20, 21, 22, 23, 24, 25, 26, 27, 28, 29, or 30) nucleotides. In another embodiment, each of the two fragments of the siNA molecule independently comprise about 15 to about 40 (e.g. about 15, 16, 17, 18, 19, 20, 21, 22, 23, 24, 25, 26, 27, 28, 29, 30, 31, 23, 33, 34, 35, 36, 37, 38, 39, or 40) nucleotides. In a non-limiting example, each of the two fragments of the siNA molecule comprises about 21 nucleotides.

In one embodiment, the invention features a formulated siNA composition comprising a siNA molecule comprising at least one modified nucleotide, wherein the modified nucleotide is a 2'-deoxy-2'-fluoro nucleotide. The siNA can be, for example, about 15 to about 40 nucleotides in length. In one embodiment, all pyrimidine nucleotides present in the siNA are 2'-deoxy-2'-fluoro pyrimidine nucleotides. In one embodiment, the modified nucleotides in the siNA include at least one 2'-deoxy-2'-fluoro cytidine or 2'-deoxy-2'-fluoro uridine nucleotide. In another embodiment, the modified nucleotides in the siNA include at least one 2'-fluoro cytidine and at least one 2'-deoxy-2'-fluoro uridine nucleotides. In one embodiment, all uridine nucleotides present in the siNA are 2'-deoxy-2'-fluoro uridine nucleotides. In one embodiment, all cytidine nucleotides present in the siNA are 2'-deoxy-2'-fluoro cytidine nucleotides. In one embodiment, all adenosine nucleotides present in the siNA are 2'-deoxy-2'-fluoro adenosine nucleotides. In one embodiment, all guanosine nucleotides present in the siNA are 2'-deoxy-2'-fluoro guanosine nucleotides. The siNA can further comprise at least one modified internucleotidic linkage, such as phosphorothioate linkage. In one embodiment, the 2'-deoxy-2'-fluoronucleotides are present at specifically selected locations in the siNA that are sensitive to cleavage by ribonucleases, such as locations having pyrimidine nucleotides.

In one embodiment, the invention features a method of increasing the stability of a siNA molecule of the invention against cleavage by ribonucleases comprising introducing at least one modified nucleotide into the siNA molecule, wherein the modified nucleotide is a 2'-deoxy-2'-fluoro nucleotide. In one embodiment, all pyrimidine nucleotides present in the siNA are 2'-deoxy-2'-fluoro pyrimidine nucleotides. In one embodiment, the modified nucleotides in the siNA include at least one 2'-deoxy-2'-fluoro cytidine or 2'-deoxy-2'-fluoro uridine nucleotide. In another embodiment, the modified nucleotides in the siNA include at least one 2'-fluoro cytidine and at least one 2'-deoxy-2'-fluoro uridine nucleotides. In one embodiment, all uridine nucleotides present in the siNA are 2'-deoxy-2'-fluoro uridine nucleotides. In one embodiment, all cytidine nucleotides present in the siNA are 2'-deoxy-2'-fluoro cytidine nucleotides. In one embodiment, all adenosine nucleotides present in the siNA are 2'-deoxy-2'-fluoro adenosine nucleotides. In one embodiment, all guanosine nucleotides present in the siNA are 2'-deoxy-2'-fluoro guanosine nucleotides. The siNA can further comprise at least one modified internucleotidic linkage, such as phosphorothioate linkage. In one embodiment, the 2'-deoxy-2'-fluoronucleotides are present at specifically selected locations in the siNA that are sensitive to cleavage by ribonucleases, such as locations having pyrimidine nucleotides.

In one embodiment, the invention features a formulated siNA composition comprising a double-stranded short interfering nucleic acid (siNA) molecule that down-regulates expression of a target gene comprising a sense region and an antisense region, wherein the antisense region comprises a nucleotide sequence that is complementary to a nucleotide sequence of RNA encoded by the target gene or a portion thereof and the sense region comprises a nucleotide sequence that is complementary to the antisense region, and wherein the purine nucleotides present in the antisense region comprise 2'-deoxy-purine nucleotides. In an alternative embodiment, the purine nucleotides present in the antisense region comprise 2'-O-methyl purine nucleotides. In either of the above embodiments, the antisense region can comprise a phosphorothioate internucleotide linkage at the 3' end of the antisense region. Alternatively, in either of the above embodiments, the antisense region can comprise a glyceryl modification at the 3' end of the antisense region. In another embodiment of any of the above-described siNA molecules, any nucleotides present in a non-complementary region of the antisense strand (e.g. overhang region) are 2'-deoxy nucleotides.

In one embodiment, the antisense region of a siNA molecule of the invention comprises sequence complementary to a portion of a target transcript having sequence unique to a particular target disease related allele, such as sequence comprising a single nucleotide polymorphism (SNP) associated with the disease specific allele. As such, the antisense region of a siNA molecule of the invention can comprise sequence complementary to sequences that are unique to a particular allele to provide specificity in mediating selective RNAi against the disease, condition, or trait related allele.

In one embodiment, the invention features a formulated siNA composition comprising a double-stranded short interfering nucleic acid (siNA) molecule that down-regulates expression of a target gene, wherein the siNA molecule is assembled from two separate oligonucleotide fragments wherein one fragment comprises the sense region and the second fragment comprises the antisense region of the siNA molecule. In another embodiment, the siNA molecule is a double stranded nucleic acid molecule, where each strand is about 21 nucleotides long and where about 19 nucleotides of each fragment of the siNA molecule are base-paired to the complementary nucleotides of the other fragment of the siNA molecule, wherein at least two 3' terminal nucleotides of each fragment of the siNA molecule are not base-paired to the nucleotides of the other fragment of the siNA molecule. In another embodiment, the siNA molecule is a double stranded nucleic acid molecule, where each strand is about 19 nucleotide long and where the nucleotides of each fragment of the siNA molecule are base-paired to the complementary nucleotides of the other fragment of the siNA molecule to form at least about 15 (e.g., 15, 16, 17, 18, or 19) base pairs, wherein one or both ends of the siNA molecule are blunt ends. In one embodiment, each of the two 3' terminal nucleotides of each fragment of the siNA molecule is a 2'-deoxy-pyrimidine nucleotide, such as a 2'-deoxy-thymidine. In another embodiment, all nucleotides of each fragment of the siNA molecule are base-paired to the complementary nucleotides of the other fragment of the siNA molecule. In another embodiment, the siNA molecule is a double stranded nucleic acid molecule of about 19 to about 25 base pairs having a sense region and an antisense region, where about 19 nucleotides of the antisense region are base-paired to the nucleotide sequence or a portion thereof of the RNA encoded by the target gene. In another embodiment, about 21 nucleotides of the antisense region are base-paired to the nucleotide sequence or a portion thereof of the RNA encoded by the target gene. In any of the above embodiments, the 5'-end of the fragment comprising said antisense region can optionally include a phosphate group.

In any of the embodiments described herein, a siNA molecule of the invention can comprise one or more of the stabilization chemistries shown in Table I or described in PCT/US 2004/106390 (WO 05/19453), U.S. Ser. No. 10/444,853, filed May 23, 2003 U.S. Ser. No. 10/923,536 filed Aug. 20, 2004, U.S. Ser. No. 11/234,730, filed Sep. 23, 2005 or U.S. Ser. No. 11/299,254, filed Dec. 8, 2005, all incorporated by reference in their entireties herein.

In one embodiment, the invention features a formulated siNA composition comprising a double-stranded short interfering nucleic acid (siNA) molecule that inhibits the expression of a target RNA sequence (e.g., wherein said target RNA sequence is encoded by a target gene involved in the target pathway), wherein the siNA molecule does not contain any ribonucleotides and wherein each strand of the double-stranded siNA molecule is about 15 to about 30 nucleotides. In one embodiment, the siNA molecule is 21 nucleotides in length. Examples of non-ribonucleotide containing siNA constructs are combinations of stabilization chemistries described in PCT/US 2004/106390 (WO 05/19453), U.S. Ser. No. 10/444,853, filed May 23, 2003 U.S. Ser. No. 10/923,536 filed Aug. 20, 2004, U.S. Ser. No. 11/234,730, filed Sep. 23, 2005 or U.S. Ser. No. 11/299,254, filed Dec. 8, 2005, all incorporated by reference in their entireties herein.

In one embodiment, the invention features a formulated siNA composition comprising a chemically synthesized double stranded RNA molecule that directs cleavage of a target RNA via RNA interference, wherein each strand of said RNA molecule is about 15 to about 30 nucleotides in length; one strand of the RNA molecule comprises nucleotide sequence having sufficient complementarity to the target RNA for the RNA molecule to direct cleavage of the target RNA via RNA interference; and wherein at least one strand of the RNA molecule optionally comprises one or more chemically modified nucleotides described herein, such as without limitation deoxynucleotides, 2'-O-methyl nucleotides, 2'-deoxy-2'-fluoro nucleotides, 2'-O-methoxyethyl nucleotides etc.

In one embodiment, the invention features a composition comprising a formulated siNA composition of the invention in a pharmaceutically acceptable carrier or diluent.

In one embodiment, the invention features a double-stranded short interfering nucleic acid (siNA) molecule that inhibits the expression of a target RNA sequence, wherein the siNA molecule does not contain any ribonucleotides and wherein each strand of the double-stranded siNA molecule is about 15 to about 30 nucleotides. In one embodiment, the siNA molecule is 21 nucleotides in length. Examples of non-ribonucleotide containing siNA constructs are combinations of stabilization chemistries shown in Table I in any combination of Sense/Antisense chemistries, such as Stab 7/8, Stab 7/11, Stab 8/8, Stab 18/8, Stab 18/11, Stab 12/13, Stab 7/13, Stab 18/13, Stab 7/19, Stab 8/19, Stab 18/19, Stab 7/20, Stab 8/20, Stab 18/20, Stab 7/32, Stab 8/32, or Stab 18/32 (e.g., any siNA having Stab 7, 8, 11, 12, 13, 14, 15, 17, 18, 19, 20, or 32 sense or antisense strands or any combination thereof). Herein, numeric Stab chemistries can include both 2'-fluoro and 2'-OCF3 versions of the chemistries shown in Table I. For example, "Stab 7/8" refers to both Stab 7/8 and Stab 7F/8F etc. In one embodiment, the invention features a chemically synthesized double stranded RNA molecule that directs cleavage of a target RNA via RNA interference, wherein each strand of said RNA molecule is about 15 to about 30 nucleotides in length; one strand of the RNA molecule comprises nucleotide sequence having sufficient complementarity to the target RNA for the RNA molecule to direct cleavage of the target RNA via RNA interference; and wherein at least one strand of the RNA molecule optionally comprises one or more chemically modified nucleotides described herein, such as without limitation deoxynucleotides, 2'-O-methyl nucleotides, 2'-deoxy-2'-fluoro nucleotides, 2'-O-methoxyethyl nucleotides, 4'-thio nucleotides, 2'-O-trifluoromethyl nucleotides, 2'-O-ethyl-trifluoromethoxy nucleotides, 2'-O-difluoromethoxy-ethoxy nucleotides, etc.

In one embodiment, the invention features a chemically-modified short interfering nucleic acid (siNA) molecule capable of mediating RNA interference (RNAi) inside a cell or reconstituted in vitro system, wherein the chemical modification comprises one or more (e.g., about 1, 2, 3, 4, 5, 6, 7, 8, 9, 10, or more) nucleotides comprising a backbone modified internucleotide linkage having Formula I:

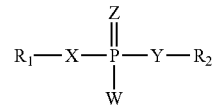

wherein each R1 and R2 is independently any nucleotide, non-nucleotide, or polynucleotide which can be naturally-occurring or chemically-modified, each X and Y is independently O, S, N, alkyl, or substituted alkyl, each Z and W is independently O, S, N, alkyl, substituted alkyl, O-alkyl, S-alkyl, alkaryl, aralkyl, or acetyl and wherein W, X, Y, and Z are optionally not all O. In another embodiment, a backbone modification of the invention comprises a phosphonoacetate and/or thiophosphonoacetate internucleotide linkage (see for example Sheehan et al., 2003, Nucleic Acids Research, 31, 4109-4118).

The chemically-modified internucleotide linkages having Formula I, for example, wherein any Z, W, X, and/or Y independently comprises a sulphur atom, can be present in one or both oligonucleotide strands of the siNA duplex, for example, in the sense strand, the antisense strand, or both strands. The siNA molecules of the invention can comprise one or more (e.g., about 1, 2, 3, 4, 5, 6, 7, 8, 9, 10, or more) chemically-modified internucleotide linkages having Formula I at the 3'-end, the 5'-end, or both of the 3' and 5'-ends of the sense strand, the antisense strand, or both strands. For example, an exemplary siNA molecule of the invention can comprise about 1 to about 5 or more (e.g., about 1, 2, 3, 4, 5, or more) chemically-modified internucleotide linkages having Formula I at the 5'-end of the sense strand, the antisense strand, or both strands. In another non-limiting example, an exemplary siNA molecule of the invention can comprise one or more (e.g., about 1, 2, 3, 4, 5, 6, 7, 8, 9, 10, or more) pyrimidine nucleotides with chemically-modified internucleotide linkages having Formula I in the sense strand, the antisense strand, or both strands. In yet another non-limiting example, an exemplary siNA molecule of the invention can comprise one or more (e.g., about 1, 2, 3, 4, 5, 6, 7, 8, 9, 10, or more) purine nucleotides with chemically-modified internucleotide linkages having Formula I in the sense strand, the antisense strand, or both strands. In another embodiment, a siNA molecule of the invention having internucleotide linkage(s) of Formula I also comprises a chemically-modified nucleotide or non-nucleotide having any of Formulae I-VII.

In one embodiment, the invention features a chemically-modified short interfering nucleic acid (siNA) molecule capable of mediating RNA interference (RNAi) inside a cell or reconstituted in vitro system, wherein the chemical modification comprises one or more (e.g., about 1, 2, 3, 4, 5, 6, 7, 8, 9, 10, or more) nucleotides or non-nucleotides having Formula II:

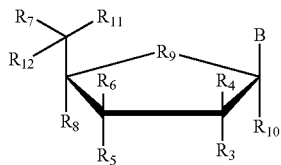

wherein each R3, R4, R5, R6, R7, R8, R10, R11 and R12 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-5-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula I or II; R9 is O, S, CH2, S=O, CHF, or CF2, and B is a nucleosidic base such as adenine, guanine, uracil, cytosine, thymine, 2-aminoadenosine, 5-methylcytosine, 2,6-diaminopurine, or any other non-naturally occurring base that can be complementary or non-complementary to target RNA or a non-nucleosidic base such as phenyl, naphthyl, 3-nitropyrrole, 5-nitroindole, nebularine, pyridone, pyridinone, or any other non-naturally occurring universal base that can be complementary or non-complementary to target RNA. In one embodiment, R3 and/or R7 comprises a conjugate moiety and a linker (e.g., a nucleotide or non-nucleotide linker as described herein or otherwise known in the art). Non-limiting examples of conjugate moieties include ligands for cellular receptors, such as peptides derived from naturally occurring protein ligands; protein localization sequences, including cellular ZIP code sequences; antibodies; nucleic acid aptamers; vitamins and other co-factors, such as folate and N-acetylgalactosamine; polymers, such as polyethyleneglycol (PEG); phospholipids; cholesterol; steroids, and polyamines, such as PEI, spermine or spermidine.

The chemically-modified nucleotide or non-nucleotide of Formula II can be present in one or both oligonucleotide strands of the siNA duplex, for example in the sense strand, the antisense strand, or both strands. The siNA molecules of the invention can comprise one or more chemically-modified nucleotides or non-nucleotides of Formula II at the 3'-end, the 5'-end, or both of the 3' and 5'-ends of the sense strand, the antisense strand, or both strands. For example, an exemplary siNA molecule of the invention can comprise about 1 to about 5 or more (e.g., about 1, 2, 3, 4, 5, or more) chemically-modified nucleotides or non-nucleotides of Formula II at the 5'-end of the sense strand, the antisense strand, or both strands. In another non-limiting example, an exemplary siNA molecule of the invention can comprise about 1 to about 5 or more (e.g., about 1, 2, 3, 4, 5, or more) chemically-modified nucleotides or non-nucleotides of Formula II at the 3'-end of the sense strand, the antisense strand, or both strands.

In one embodiment, the invention features a chemically-modified short interfering nucleic acid (siNA) molecule capable of mediating RNA interference (RNAi) inside a cell or reconstituted in vitro system, wherein the chemical modification comprises one or more (e.g., about 1, 2, 3, 4, 5, 6, 7, 8, 9, 10, or more) nucleotides or non-nucleotides having Formula III:

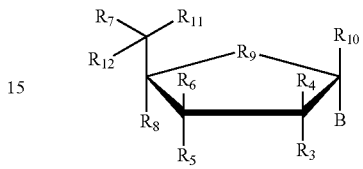

wherein each R3, R4, R5, R6, R7, R8, R10, R11 and R12 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-5-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula I or II; R9 is O, S, CH2, S=O, CHF, or CF2, and B is a nucleosidic base such as adenine, guanine, uracil, cytosine, thymine, 2-aminoadenosine, 5-methylcytosine, 2,6-diaminopurine, or any other non-naturally occurring base that can be employed to be complementary or non-complementary to target RNA or a non-nucleosidic base such as phenyl, naphthyl, 3-nitropyrrole, 5-nitroindole, nebularine, pyridone, pyridinone, or any other non-naturally occurring universal base that can be complementary or non-complementary to target RNA. In one embodiment, R3 and/or R7 comprises a conjugate moiety and a linker (e.g., a nucleotide or non-nucleotide linker as described herein or otherwise known in the art). Non-limiting examples of conjugate moieties include ligands for cellular receptors, such as peptides derived from naturally occurring protein ligands; protein localization sequences, including cellular ZIP code sequences; antibodies; nucleic acid aptamers; vitamins and other co-factors, such as folate and N-acetylgalactosamine; polymers, such as polyethyleneglycol (PEG); phospholipids; cholesterol; steroids, and polyamines, such as PEI, spermine or spermidine.

The chemically-modified nucleotide or non-nucleotide of Formula III can be present in one or both oligonucleotide strands of the siNA duplex, for example, in the sense strand, the antisense strand, or both strands. The siNA molecules of the invention can comprise one or more chemically-modified nucleotides or non-nucleotides of Formula III at the 3'-end, the 5'-end, or both of the 3' and 5'-ends of the sense strand, the antisense strand, or both strands. For example, an exemplary siNA molecule of the invention can comprise about 1 to about 5 or more (e.g., about 1, 2, 3, 4, 5, or more) chemically-modified nucleotide(s) or non-nucleotide(s) of Formula III at the 5'-end of the sense strand, the antisense strand, or both strands. In another non-limiting example, an exemplary siNA molecule of the invention can comprise about 1 to about 5 or more (e.g., about 1, 2, 3, 4, 5, or more) chemically-modified nucleotide or non-nucleotide of Formula III at the 3'-end of the sense strand, the antisense strand, or both strands.

In another embodiment, a siNA molecule of the invention comprises a nucleotide having Formula II or III, wherein the nucleotide having Formula II or III is in an inverted configuration. For example, the nucleotide having Formula II or III is connected to the siNA construct in a 3'-3', 3'-2',2'-3', or 5'-5' configuration, such as at the 3'-end, the 5'-end, or both of the 3' and 5'-ends of one or both siNA strands.

In one embodiment, the invention features a chemically-modified short interfering nucleic acid (siNA) molecule capable of mediating RNA interference (RNAi) inside a cell or reconstituted in vitro system, wherein the chemical modification comprises a 5'-terminal phosphate group having Formula IV:

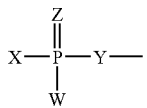

wherein each X and Y is independently O, S, N, alkyl, substituted alkyl, or alkylhalo; wherein each Z and W is independently O, S, N, alkyl, substituted alkyl, O-alkyl, S-alkyl, alkaryl, aralkyl, alkylhalo, or acetyl; and wherein W, X, Y and Z are not all O.

In one embodiment, the invention features a siNA molecule having a 5'-terminal phosphate group having Formula IV on the target-complementary strand, for example, a strand complementary to a target RNA, wherein the siNA molecule comprises an all RNA siNA molecule. In another embodiment, the invention features a siNA molecule having a 5'-terminal phosphate group having Formula IV on the target-complementary strand wherein the siNA molecule also comprises about 1 to about 3 (e.g., about 1, 2, or 3) nucleotide 3'-terminal nucleotide overhangs having about 1 to about 4 (e.g., about 1, 2, 3, or 4) deoxyribonucleotides on the 3'-end of one or both strands. In another embodiment, a 5'-terminal phosphate group having Formula IV is present on the target-complementary strand of a siNA molecule of the invention, for example a siNA molecule having chemical modifications having any of Formulae I-VII.

In one embodiment, the invention features a chemically-modified short interfering nucleic acid (siNA) molecule capable of mediating RNA interference (RNAi) inside a cell or reconstituted in vitro system, wherein the chemical modification comprises one or more phosphorothioate internucleotide linkages. For example, in a non-limiting example, the invention features a chemically-modified short interfering nucleic acid (siNA) having about 1, 2, 3, 4, 5, 6, 7, 8 or more phosphorothioate internucleotide linkages in one siNA strand. In yet another embodiment, the invention features a chemically-modified short interfering nucleic acid (siNA) individually having about 1, 2, 3, 4, 5, 6, 7, 8 or more phosphorothioate internucleotide linkages in both siNA strands. The phosphorothioate internucleotide linkages can be present in one or both oligonucleotide strands of the siNA duplex, for example in the sense strand, the antisense strand, or both strands. The siNA molecules of the invention can comprise one or more phosphorothioate internucleotide linkages at the 3'-end, the 5'-end, or both of the 3'- and 5'-ends of the sense strand, the antisense strand, or both strands. For example, an exemplary siNA molecule of the invention can comprise about 1 to about 5 or more (e.g., about 1, 2, 3, 4, 5, or more) consecutive phosphorothioate internucleotide linkages at the 5'-end of the sense strand, the antisense strand, or both strands. In another non-limiting example, an exemplary siNA molecule of the invention can comprise one or more (e.g., about 1, 2, 3, 4, 5, 6, 7, 8, 9, 10, or more) pyrimidine phosphorothioate internucleotide linkages in the sense strand, the antisense strand, or both strands. In yet another non-limiting example, an exemplary siNA molecule of the invention can comprise one or more (e.g., about 1, 2, 3, 4, 5, 6, 7, 8, 9, 10, or more) purine phosphorothioate internucleotide linkages in the sense strand, the antisense strand, or both strands.

In one embodiment, the invention features a siNA molecule, wherein the sense strand comprises one or more, for example, about 1, 2, 3, 4, 5, 6, 7, 8, 9, 10, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, 2'-O-trifluoromethyl, 2'-O-ethyl-trifluoromethoxy, 2'-O-difluoromethoxy-ethoxy and/or about one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 10 or more, specifically about 1, 2, 3, 4, 5, 6, 7, 8, 9, 10, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, 2'-O-trifluoromethyl, 2'-O-ethyl-trifluoromethoxy, 2'-O-difluoromethoxy-ethoxy, 4'-thio and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10, or more, pyrimidine nucleotides of the sense and/or antisense siNA strand are chemically-modified with 2'-deoxy, 2'-O-methyl, 2'-O-trifluoromethyl, 2'-O-ethyl-trifluoromethoxy, 2'-O-difluoromethoxy-ethoxy, 4'-thio and/or 2'-deoxy-2'-fluoro nucleotides, with or without one or more, for example about 1, 2, 3, 4, 5, 6, 7, 8, 9, 10, or more, phosphorothioate internucleotide linkages and/or a terminal cap molecule at the 3'-end, the 5'-end, or both of the 3'- and 5'-ends, being present in the same or different strand.

In another embodiment, the invention features a siNA molecule, wherein the sense strand comprises about 1 to about 5, specifically about 1, 2, 3, 4, or 5 phosphorothioate internucleotide linkages, and/or one or more (e.g. about 1, 2, 3, 4, 5, or more) 2'-deoxy, 2'-O-methyl, 2'-deoxy-2'-fluoro, 2'-O-trifluoromethyl, 2'-O-ethyl-trifluoromethoxy, 2'-O-difluoromethoxy-ethoxy, 4'-thio and/or one or more (e.g. about 1, 2, 3, 4, 5, or more) universal base modified nucleotides, and optionally a terminal cap molecule at the 3-end, the 5'-end, or both of the 3'- and 5'-ends of the sense strand; and wherein the antisense strand comprises about 1 to about 5 or more, specifically about 1, 2, 3, 4, 5, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, 2'-O-trifluoromethyl, 2'-O-ethyl-trifluoromethoxy, 2'-O-difluoromethoxy-ethoxy, 4'-thio and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10, or more, pyrimidine nucleotides of the sense and/or antisense siNA strand are chemically-modified with 2'-deoxy, 2'-O-methyl, 2'-O-trifluoromethyl, 2'-O-ethyl-trifluoromethoxy, 2'-O-difluoromethoxy-ethoxy, 4'-thio and/or 2'-deoxy-2'-fluoro nucleotides, with or without about 1 to about 5 or more, for example about 1, 2, 3, 4, 5, or more phosphorothioate internucleotide linkages and/or a terminal cap molecule at the 3'-end, the 5'-end, or both of the 3'- and 5'-ends, being present in the same or different strand.

In one embodiment, the invention features a siNA molecule, wherein the antisense strand comprises one or more, for example, about 1, 2, 3, 4, 5, 6, 7, 8, 9, 10, or more phosphorothioate internucleotide linkages, and/or about one or more (e.g., about 1, 2, 3, 4, 5, 6, 7, 8, 9, 10 or more) 2'-deoxy, 2'-O-methyl, 2'-deoxy-2'-fluoro, 2'-O-trifluoromethyl, 2'-O-ethyl-trifluoromethoxy, 2'-O-difluoromethoxy-ethoxy, 4'-thio and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 10 or more, specifically about 1, 2, 3, 4, 5, 6, 7, 8, 9, 10 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, 2'-O-trifluoromethyl, 2'-O-ethyl-trifluoromethoxy, 2'-O-difluoromethoxy-ethoxy, 4'-thio and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10 or more pyrimidine nucleotides of the sense and/or antisense siNA strand are chemically-modified with 2'-deoxy, 2'-O-methyl, 2'-O-trifluoromethyl, 2'-O-ethyl-trifluoromethoxy, 2'-O-difluoromethoxy-ethoxy, 4'-thio and/or 2'-deoxy-2'-fluoro nucleotides, with or without one or more, for example, about 1, 2, 3, 4, 5, 6, 7, 8, 9, 10 or more phosphorothioate internucleotide linkages and/or a terminal cap molecule at the 3'-end, the 5'-end, or both of the 3' and 5'-ends, being present in the same or different strand.

In another embodiment, the invention features a siNA molecule, wherein the antisense strand comprises about 1 to about 5 or more, specifically about 1, 2, 3, 4, 5 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, 2'-O-trifluoromethyl, 2'-O-ethyl-trifluoromethoxy, 2'-O-difluoromethoxy-ethoxy, 4'-thio and/or one or more (e.g. about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 5 or more, specifically about 1, 2, 3, 4, 5 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, 2'-O-trifluoromethyl, 2'-O-ethyl-trifluoromethoxy, 2'-O-difluoromethoxy-ethoxy, 4'-thio and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10 or more pyrimidine nucleotides of the sense and/or antisense siNA strand are chemically-modified with 2'-deoxy, 2'-O-methyl, 2'-O-trifluoromethyl, 2'-O-ethyl-trifluoromethoxy, 2'-O-difluoromethoxy-ethoxy, 4'-thio and/or 2'-deoxy-2'-fluoro nucleotides, with or without about 1 to about 5, for example about 1, 2, 3, 4, 5 or more phosphorothioate internucleotide linkages and/or a terminal cap molecule at the 3'-end, the 5'-end, or both of the 3'- and 5'-ends, being present in the same or different strand.

In one embodiment, the invention features a chemically-modified short interfering nucleic acid (siNA) molecule having about 1 to about 5 or more (specifically about 1, 2, 3, 4, 5 or more) phosphorothioate internucleotide linkages in each strand of the siNA molecule.

In another embodiment, the invention features a siNA molecule comprising 2'-5' internucleotide linkages. The 2'-5' internucleotide linkage(s) can be at the 3'-end, the 5'-end, or both of the 3'- and 5'-ends of one or both siNA sequence strands. In addition, the 2'-5' internucleotide linkage(s) can be present at various other positions within one or both siNA sequence strands, for example, about 1, 2, 3, 4, 5, 6, 7, 8, 9, 10, or more including every internucleotide linkage of a pyrimidine nucleotide in one or both strands of the siNA molecule can comprise a 2'-5' internucleotide linkage, or about 1, 2, 3, 4, 5, 6, 7, 8, 9, 10, or more including every internucleotide linkage of a purine nucleotide in one or both strands of the siNA molecule can comprise a 2'-5' internucleotide linkage.

In another embodiment, a chemically-modified siNA molecule of the invention comprises a duplex having two strands, one or both of which can be chemically-modified, wherein each strand is independently about 15 to about 30 (e.g., about 15, 16, 17, 18, 19, 20, 21, 22, 23, 24, 25, 26, 27, 28, 29, or 30) nucleotides in length, wherein the duplex has about 15 to about 30 (e.g., about 15, 16, 17, 18, 19, 20, 21, 22, 23, 24, 25, 26, 27, 28, 29, or 30) base pairs, and wherein the chemical modification comprises a structure having any of Formulae I-VII. For example, an exemplary chemically-modified siNA molecule of the invention comprises a duplex having two strands, one or both of which can be chemically-modified with a chemical modification having any of Formulae I-VII or any combination thereof, wherein each strand consists of about 21 nucleotides, each having a 2-nucleotide 3'-terminal nucleotide overhang, and wherein the duplex has about 19 base pairs. In another embodiment, a siNA molecule of the invention comprises a single stranded hairpin structure, wherein the siNA is about 36 to about 70 (e.g., about 36, 40, 45, 50, 55, 60, 65, or 70) nucleotides in length having about 15 to about 30 (e.g., about 15, 16, 17, 18, 19, 20, 21, 22, 23, 24, 25, 26, 27, 28, 29, or 30) base pairs, and wherein the siNA can include a chemical modification comprising a structure having any of Formulae I-VII or any combination thereof. For example, an exemplary chemically-modified siNA molecule of the invention comprises a linear oligonucleotide having about 42 to about 50 (e.g. about 42, 43, 44, 45, 46, 47, 48, 49, or 50) nucleotides that is chemically-modified with a chemical modification having any of Formulae I-VII or any combination thereof, wherein the linear oligonucleotide forms a hairpin structure having about 19 to about 21 (e.g., 19, 20, or 21) base pairs and a 2-nucleotide 3'-terminal nucleotide overhang. In another embodiment, a linear hairpin siNA molecule of the invention contains a stem loop motif, wherein the loop portion of the siNA molecule is biodegradable. For example, a linear hairpin siNA molecule of the invention is designed such that degradation of the loop portion of the siNA molecule in vivo can generate a double-stranded siNA molecule with 3'-terminal overhangs, such as 3'-terminal nucleotide overhangs comprising about 2 nucleotides.

In another embodiment, a siNA molecule of the invention comprises a hairpin structure, wherein the siNA is about 25 to about 50 (e.g., about 25, 26, 27, 28, 29, 30, 31, 32, 33, 34, 35, 36, 37, 38, 39, 40, 41, 42, 43, 44, 45, 46, 47, 48, 49, or 50) nucleotides in length having about 3 to about 25 (e.g. about 3, 4, 5, 6, 7, 8, 9, 10, 11, 12, 13, 14, 15, 16, 17, 18, 19, 20, 21, 22, 23, 24, or 25) base pairs, and wherein the siNA can include one or more chemical modifications comprising a structure having any of Formulae I-VII or any combination thereof. For example, an exemplary chemically-modified siNA molecule of the invention comprises a linear oligonucleotide having about 25 to about 35 (e.g., about 25, 26, 27, 28, 29, 30, 31, 32, 33, 34, or 35) nucleotides that is chemically-modified with one or more chemical modifications having any of Formulae I-VII or any combination thereof, wherein the linear oligonucleotide forms a hairpin structure having about 3 to about 25 (e.g., about 3, 4, 5, 6, 7, 8, 9, 10, 11, 12, 13, 14, 15, 16, 17, 18, 19, 20, 21, 22, 23, 24, or 25) base pairs and a 5'-terminal phosphate group that can be chemically modified as described herein (for example a 5'-terminal phosphate group having Formula IV). In another embodiment, a linear hairpin siNA molecule of the invention contains a stem loop motif, wherein the loop portion of the siNA molecule is biodegradable. In one embodiment, a linear hairpin siNA molecule of the invention comprises a loop portion comprising a non-nucleotide linker.

In another embodiment, a siNA molecule of the invention comprises an asymmetric hairpin structure, wherein the siNA is about 25 to about 50 (e.g., about 25, 26, 27, 28, 29, 30, 31, 32, 33, 34, 35, 36, 37, 38, 39, 40, 41, 42, 43, 44, 45, 46, 47, 48, 49, or 50) nucleotides in length having about 3 to about 25 (e.g., about 3, 4, 5, 6, 7, 8, 9, 10, 11, 12, 13, 14, 15, 16, 17, 18, 19, 20, 21, 22, 23, 24, or 25) base pairs, and wherein the siNA can include one or more chemical modifications comprising a structure having any of Formulae I-VII or any combination thereof. For example, an exemplary chemically-modified siNA molecule of the invention comprises a linear oligonucleotide having about 25 to about 35 (e.g., about 25, 26, 27, 28, 29, 30, 31, 32, 33, 34, or 35) nucleotides that is chemically-modified with one or more chemical modifications having any of Formulae I-VII or any combination thereof, wherein the linear oligonucleotide forms an asymmetric hairpin structure having about 3 to about 25 (e.g., about 3, 4, 5, 6, 7, 8, 9, 10, 11, 12, 13, 14, 15, 16, 17, 18, 19, 20, 21, 22, 23, 24, or 25) base pairs and a 5'-terminal phosphate group that can be chemically modified as described herein (for example a 5'-terminal phosphate group having Formula IV). In one embodiment, an asymmetric hairpin siNA molecule of the invention contains a stem loop motif, wherein the loop portion of the siNA molecule is biodegradable. In another embodiment, an asymmetric hairpin siNA molecule of the invention comprises a loop portion comprising a non-nucleotide linker.

In another embodiment, a siNA molecule of the invention comprises an asymmetric double stranded structure having separate polynucleotide strands comprising sense and antisense regions, wherein the antisense region is about 15 to about 30 (e.g., about 15, 16, 17, 18, 19, 20, 21, 22, 23, 24, 25, 26, 27, 28, 29, or 30) nucleotides in length, wherein the sense region is about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides in length, wherein the sense region and the antisense region have at least 3 complementary nucleotides, and wherein the siNA can include one or more chemical modifications comprising a structure having any of Formulae I-VII or any combination thereof. For example, an exemplary chemically-modified siNA molecule of the invention comprises an asymmetric double stranded structure having separate polynucleotide strands comprising sense and antisense regions, wherein the antisense region is about 18 to about 23 (e.g., about 18, 19, 20, 21, 22, or 23) nucleotides in length and wherein the sense region is about 3 to about 15 (e.g., about 3, 4, 5, 6, 7, 8, 9, 10, 11, 12, 13, 14, or 15) nucleotides in length, wherein the sense region the antisense region have at least 3 complementary nucleotides, and wherein the siNA can include one or more chemical modifications comprising a structure having any of Formulae I-VII or any combination thereof. In another embodiment, the asymmetric double stranded siNA molecule can also have a 5'-terminal phosphate group that can be chemically modified as described herein (for example a 5'-terminal phosphate group having Formula IV).

In another embodiment, a siNA molecule of the invention comprises a circular nucleic acid molecule, wherein the siNA is about 38 to about 70 (e.g., about 38, 40, 45, 50, 55, 60, 65, or 70) nucleotides in length having about 15 to about 30 (e.g., about 15, 16, 17, 18, 19, 20, 21, 22, 23, 24, 25, 26, 27, 28, 29, or 30) base pairs, and wherein the siNA can include a chemical modification, which comprises a structure having any of Formulae I-VII or any combination thereof. For example, an exemplary chemically-modified siNA molecule of the invention comprises a circular oligonucleotide having about 42 to about 50 (e.g., about 42, 43, 44, 45, 46, 47, 48, 49, or 50) nucleotides that is chemically-modified with a chemical modification having any of Formulae I-VII or any combination thereof, wherein the circular oligonucleotide forms a dumbbell shaped structure having about 19 base pairs and 2 loops.

In another embodiment, a circular siNA molecule of the invention contains two loop motifs, wherein one or both loop portions of the siNA molecule is biodegradable. For example, a circular siNA molecule of the invention is designed such that degradation of the loop portions of the siNA molecule in vivo can generate a double-stranded siNA molecule with 3'-terminal overhangs, such as 3'-terminal nucleotide overhangs comprising about 2 nucleotides.

In one embodiment, a siNA molecule of the invention comprises at least one (e.g., about 1, 2, 3, 4, 5, 6, 7, 8, 9, 10, or more) abasic moiety, for example a compound having Formula V:

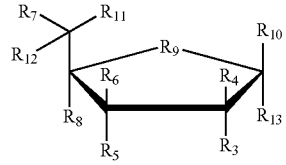

wherein each R3, R4, R5, R6, R7, R8, R10, R11, R12, and R13 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-5-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula I or II; R9 is O, S, CH2, S=O, CHF, or CF2. In one embodiment, R3 and/or R7 comprises a conjugate moiety and a linker (e.g., a nucleotide or non-nucleotide linker as described herein or otherwise known in the art). Non-limiting examples of conjugate moieties include ligands for cellular receptors, such as peptides derived from naturally occurring protein ligands; protein localization sequences, including cellular ZIP code sequences; antibodies; nucleic acid aptamers; vitamins and other co-factors, such as folate and N-acetylgalactosamine; polymers, such as polyethyleneglycol (PEG); phospholipids; cholesterol; steroids, and polyamines, such as PEI, spermine or spermidine.

In one embodiment, a siNA molecule of the invention comprises at least one (e.g., about 1, 2, 3, 4, 5, 6, 7, 8, 9, 10, or more) inverted abasic moiety, for example a compound having Formula VI:

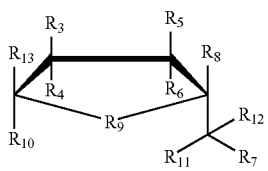

wherein each R3, R4, R5, R6, R7, R8, R10, R11, R12, and R13 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-5-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula I or II; R9 is O, S, CH2, S=O, CHF, or CF2, and either R2, R3, R8 or R13 serve as points of attachment to the siNA molecule of the invention. In one embodiment, R3 and/or R7 comprises a conjugate moiety and a linker (e.g., a nucleotide or non-nucleotide linker as described herein or otherwise known in the art). Non-limiting examples of conjugate moieties include ligands for cellular receptors, such as peptides derived from naturally occurring protein ligands; protein localization sequences, including cellular ZIP code sequences; antibodies; nucleic acid aptamers; vitamins and other co-factors, such as folate and N-acetylgalactosamine; polymers, such as polyethyleneglycol (PEG); phospholipids; cholesterol; steroids, and polyamines, such as PEI, spermine or spermidine.

In another embodiment, a siNA molecule of the invention comprises at least one (e.g., about 1, 2, 3, 4, 5, 6, 7, 8, 9, 10, or more) substituted polyalkyl moieties, for example a compound having Formula VII:

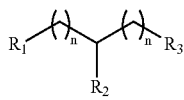

wherein each n is independently an integer from 1 to 12, each R1, R2 and R3 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-5-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or a group having Formula I, and R1, R2 or R3 serves as points of attachment to the siNA molecule of the invention. In one embodiment, R3 and/or R1 comprises a conjugate moiety and a linker (e.g., a nucleotide or non-nucleotide linker as described herein or otherwise known in the art). Non-limiting examples of conjugate moieties include ligands for cellular receptors, such as peptides derived from naturally occurring protein ligands; protein localization sequences, including cellular ZIP code sequences; antibodies; nucleic acid aptamers; vitamins and other co-factors, such as folate and N-acetylgalactosamine; polymers, such as polyethyleneglycol (PEG); phospholipids; cholesterol; steroids, and polyamines, such as PEI, spermine or spermidine.

By "ZIP code" sequences is meant, any peptide or protein sequence that is involved in cellular topogenic signaling mediated transport (see for example Ray et al., 2004, Science, 306(1501): 1505)

In another embodiment, the invention features a compound having Formula VII, wherein R1 and R2 are hydroxyl (OH) groups, n=1, and R3 comprises O and is the point of attachment to the 3'-end, the 5'-end, or both of the 3' and 5'-ends of one or both strands of a double-stranded siNA molecule of the invention or to a single-stranded siNA molecule of the invention. This modification is referred to herein as "glyceryl".

In another embodiment, a chemically modified nucleoside or non-nucleoside (e.g. a moiety having any of Formula V, VI or VII) of the invention is at the 3'-end, the 5'-end, or both of the 3' and 5'-ends of a siNA molecule of the invention. For example, chemically modified nucleoside or non-nucleoside (e.g., a moiety having Formula V, VI or VII) can be present at the 3'-end, the 5'-end, or both of the 3' and 5'-ends of the antisense strand, the sense strand, or both antisense and sense strands of the siNA molecule. In one embodiment, the chemically modified nucleoside or non-nucleoside (e.g., a moiety having Formula V, VI or VII) is present at the 5'-end and 3'-end of the sense strand and the 3'-end of the antisense strand of a double stranded siNA molecule of the invention. In one embodiment, the chemically modified nucleoside or non-nucleoside (e.g., a moiety having Formula V, VI or VII) is present at the terminal position of the 5'-end and 3'-end of the sense strand and the 3'-end of the antisense strand of a double stranded siNA molecule of the invention. In one embodiment, the chemically modified nucleoside or non-nucleoside (e.g., a moiety having Formula V, VI or VII) is present at the two terminal positions of the 5'-end and 3'-end of the sense strand and the 3'-end of the antisense strand of a double stranded siNA molecule of the invention. In one embodiment, the chemically modified nucleoside or non-nucleoside (e.g., a moiety having Formula V, VI or VII) is present at the penultimate position of the 5'-end and 3'-end of the sense strand and the 3'-end of the antisense strand of a double stranded siNA molecule of the invention. In addition, a moiety having Formula VII can be present at the 3'-end or the 5'-end of a hairpin siNA molecule as described herein.

In another embodiment, a siNA molecule of the invention comprises an abasic residue having Formula V or VI, wherein the abasic residue having Formula VI or VI is connected to the siNA construct in a 3'-3', 3'-2',2'-3', or 5'-5' configuration, such as at the 3'-end, the 5'-end, or both of the 3' and 5'-ends of one or both siNA strands.

In one embodiment, a siNA molecule of the invention comprises one or more (e.g., about 1, 2, 3, 4, 5, 6, 7, 8, 9, 10, or more) locked nucleic acid (LNA) nucleotides, for example, at the 5'-end, the 3'-end, both of the 5' and 3'-ends, or any combination thereof, of the siNA molecule.

In one embodiment, a siNA molecule of the invention comprises one or more (e.g., about 1, 2, 3, 4, 5, 6, 7, 8, 9, 10, or more) 4'-thio nucleotides, for example, at the 5'-end, the 3'-end, both of the 5' and 3'-ends, or any combination thereof, of the siNA molecule.

In another embodiment, a siNA molecule of the invention comprises one or more (e.g., about 1, 2, 3, 4, 5, 6, 7, 8, 9, 10, or more) acyclic nucleotides, for example, at the 5'-end, the 3'-end, both of the 5' and 3'-ends, or any combination thereof, of the siNA molecule.

In one embodiment, the invention features a chemically-modified short interfering nucleic acid (siNA) molecule of the invention comprising a sense region, wherein any (e.g., one or more or all) pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the sense region are 2'-deoxy purine nucleotides (e.g., wherein all purine nucleotides are 2'-deoxy purine nucleotides or alternately a plurality of purine nucleotides are 2'-deoxy purine nucleotides).

In one embodiment, the invention features a chemically-modified short interfering nucleic acid (siNA) molecule of the invention comprising a sense region, wherein any (e.g., one or more or all) pyrimidine nucleotides present in the sense region are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides (e.g., wherein all pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides or alternately a plurality of pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides), and wherein any (e.g., one or more or all) purine nucleotides present in the sense region are 2'-deoxy purine nucleotides (e.g., wherein all purine nucleotides are 2'-deoxy purine nucleotides or alternately a plurality of purine nucleotides are 2'-deoxy purine nucleotides), wherein any nucleotides comprising a 3'-terminal nucleotide overhang that are present in said sense region are 2'-deoxy nucleotides.

In one embodiment, the invention features a chemically-modified short interfering nucleic acid (siNA) molecule of the invention comprising a sense region, wherein any (e.g., one or more or all) pyrimidine nucleotides present in the sense region are 2'-deoxy-2'-fluoro, 4'-thio, 2'-O-trifluoromethyl, 2'-O-ethyl -trifluoromethoxy, or 2'-O-difluoromethoxy-ethoxy pyrimidine nucleotides (e.g., wherein all pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides or alternately a plurality of pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides), and wherein any (e.g., one or more or all) purine nucleotides present in the sense region are 2'-O-methyl purine nucleotides (e.g., wherein all purine nucleotides are 2'-O-methyl, 4'-thio, 2'-O-trifluoromethyl, 2'-O-ethyl-trifluoromethoxy, or 2'-O-difluoromethoxy-ethoxy purine nucleotides or alternately a plurality of purine nucleotides are 2'-O-methyl, 4'-thio, 2'-O-trifluoromethyl, 2'-O-ethyl-trifluoromethoxy, or 2'-O-difluoromethoxy-ethoxy purine nucleotides).

In one embodiment, the invention features a chemically-modified short interfering nucleic acid (siNA) molecule of the invention comprising a sense region, wherein any (e.g., one or more or all) pyrimidine nucleotides present in the sense region are 2'-deoxy-2'-fluoro, 4'-thio, 2'-O-trifluoromethyl, 2'-O-ethyl -trifluoromethoxy, or 2'-O-difluoromethoxy-ethoxy pyrimidine nucleotides (e.g., wherein all pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides or alternately a plurality of pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides), wherein any (e.g., one or more or all) purine nucleotides present in the sense region are 2'-O-methyl, 4'-thio, 2'-O-trifluoromethyl, 2'-O-ethyl-trifluoromethoxy, or 2'-O-difluoromethoxy-ethoxy purine nucleotides (e.g., wherein all purine nucleotides are 2'-O-methyl, 4'-thio, 2'-O-trifluoromethyl, 2'-O-ethyl-trifluoromethoxy, or 2'-O-difluoromethoxy-ethoxy purine nucleotides or alternately a plurality of purine nucleotides are 2'-O-methyl, 4'-thio, 2'-O-trifluoromethyl, 2'-O-ethyl-trifluoromethoxy, or 2'-O-difluoromethoxy-ethoxy purine nucleotides), and wherein any nucleotides comprising a 3'-terminal nucleotide overhang that are present in said sense region are 2'-deoxy nucleotides.

In one embodiment, the invention features a chemically-modified short interfering nucleic acid (siNA) molecule of the invention comprising an antisense region, wherein any (e.g., one or more or all) pyrimidine nucleotides present in the antisense region are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides (e.g., wherein all pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides or alternately a plurality of pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides), and wherein any (e.g., one or more or all) purine nucleotides present in the antisense region are 2'-O-methyl, 4'-thio, 2'-O-trifluoromethyl, 2'-O-ethyl-trifluoromethoxy, or 2'-O-difluoromethoxy-ethoxy purine nucleotides (e.g., wherein all purine nucleotides are 2'-O-methyl, 4'-thio, 2'-O-trifluoromethyl, 2'-O-ethyl-trifluoromethoxy, or 2'-O-difluoromethoxy-ethoxy purine nucleotides or alternately a plurality of purine nucleotides are 2'-O-methyl, 4'-thio, 2'-O-trifluoromethyl, 2'-O-ethyl-trifluoromethoxy, or 2'-O-difluoromethoxy-ethoxy purine nucleotides).

In one embodiment, the invention features a chemically-modified short interfering nucleic acid (siNA) molecule of the invention comprising an antisense region, wherein any (e.g., one or more or all) pyrimidine nucleotides present in the antisense region are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides (e.g., wherein all pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides or alternately a plurality of pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides), wherein any (e.g., one or more or all) purine nucleotides present in the antisense region are 2'-O-methyl, 4'-thio, 2'-O-trifluoromethyl, 2'-O-ethyl-trifluoromethoxy, or 2'-O-difluoromethoxy-ethoxy purine nucleotides (e.g., wherein all purine nucleotides are 2'-O-methyl, 4'-thio, 2'-O-trifluoromethyl, 2'-O-ethyl-trifluoromethoxy, or 2'-O-difluoromethoxy-ethoxy purine nucleotides or alternately a plurality of purine nucleotides are 2'-O-methyl, 4'-thio, 2'-O-trifluoromethyl, 2'-O-ethyl-trifluoromethoxy, or 2'-O-difluoromethoxy-ethoxy purine nucleotides), and wherein any nucleotides comprising a 3'-terminal nucleotide overhang that are present in said antisense region are 2'-deoxy nucleotides.

In one embodiment, the invention features a chemically-modified short interfering nucleic acid (siNA) molecule of the invention comprising an antisense region, wherein any (e.g., one or more or all) pyrimidine nucleotides present in the antisense region are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides (e.g., wherein all pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides or alternately a plurality of pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides), and wherein any (e.g., one or more or all) purine nucleotides present in the antisense region are 2'-deoxy purine nucleotides (e.g., wherein all purine nucleotides are 2'-deoxy purine nucleotides or alternately a plurality of purine nucleotides are 2'-deoxy purine nucleotides).

In one embodiment, the invention features a chemically-modified short interfering nucleic acid (siNA) molecule of the invention comprising an antisense region, wherein any (e.g., one or more or all) pyrimidine nucleotides present in the antisense region are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides (e.g., wherein all pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides or alternately a plurality of pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides), and wherein any (e.g., one or more or all) purine nucleotides present in the antisense region are 2'-O-methyl, 4'-thio, 2'-O-trifluoromethyl, 2'-O-ethyl-trifluoromethoxy, or 2'-O-difluoromethoxy-ethoxy purine nucleotides (e.g., wherein all purine nucleotides are 2'-O-methyl, 4'-thio, 2'-O-trifluoromethyl, 2'-O-ethyl-trifluoromethoxy, or 2'-O-difluoromethoxy-ethoxy purine nucleotides or alternately a plurality of purine nucleotides are 2'-O-methyl, 4'-thio, 2'-O-trifluoromethyl, 2'-O-ethyl-trifluoromethoxy, or 2'-O-difluoromethoxy-ethoxy purine nucleotides).

In one embodiment, the invention features a chemically-modified short interfering nucleic acid (siNA) molecule of the invention capable of mediating RNA interference (RNAi) inside a cell or reconstituted in vitro system comprising a sense region, wherein one or more pyrimidine nucleotides present in the sense region are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides (e.g., wherein all pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides or alternately a plurality of pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides), and one or more purine nucleotides present in the sense region are 2'-deoxy purine nucleotides (e.g., wherein all purine nucleotides are 2'-deoxy purine nucleotides or alternately a plurality of purine nucleotides are 2'-deoxy purine nucleotides), and an antisense region, wherein one or more pyrimidine nucleotides present in the antisense region are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides (e.g., wherein all pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides or alternately a plurality of pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides), and one or more purine nucleotides present in the antisense region are 2'-O-methyl, 4'-thio, 2'-O-trifluoromethyl, 2'-O-ethyl-trifluoromethoxy, or 2'-O-difluoromethoxy-ethoxy purine nucleotides (e.g., wherein all purine nucleotides are 2'-O-methyl, 4'-thio, 2'-O-trifluoromethyl, 2'-O-ethyl-trifluoromethoxy, or 2'-O-difluoromethoxy-ethoxy purine nucleotides or alternately a plurality of purine nucleotides are 2'-O-methyl, 4'-thio, 2'-O-trifluoromethyl, 2'-O-ethyl-trifluoromethoxy, or 2'-O-difluoromethoxy-ethoxy purine nucleotides). The sense region and/or the antisense region can have a terminal cap modification that is optionally present at the 3'-end, the 5'-end, or both of the 3' and 5'-ends of the sense and/or antisense sequence. The sense and/or antisense region can optionally further comprise a 3'-terminal nucleotide overhang having about 1 to about 4 (e.g., about 1, 2, 3, or 4) 2'-deoxynucleotides. The overhang nucleotides can further comprise one or more (e.g., about 1, 2, 3, 4 or more) phosphorothioate, phosphonoacetate, and/or thiophosphonoacetate internucleotide linkages. In any of these described embodiments, the purine nucleotides present in the sense region are alternatively 2'-O-methyl, 4'-thio, 2'-O-trifluoromethyl, 2'-O-ethyl-trifluoromethoxy, or 2'-O-difluoromethoxy-ethoxy purine nucleotides (e.g., wherein all purine nucleotides are 2'-O-methyl, 4'-thio, 2'-O-trifluoromethyl, 2'-O-ethyl-trifluoromethoxy, or 2'-O-difluoromethoxy-ethoxy purine nucleotides or alternately a plurality of purine nucleotides are 2'-O-methyl, 4'-thio, 2'-O-trifluoromethyl, 2'-O-ethyl-trifluoromethoxy, or 2'-O-difluoromethoxy-ethoxy purine nucleotides) and one or more purine nucleotides present in the antisense region are 2'-O-methyl, 4'-thio, 2'-O-trifluoromethyl, 2'-O-ethyl-trifluoromethoxy, or 2'-O-difluoromethoxy-ethoxy purine nucleotides (e.g., wherein all purine nucleotides are 2'-O-methyl, 4'-thio, 2'-O-trifluoromethyl, 2'-O-ethyl-trifluoromethoxy, or 2'-O-difluoromethoxy-ethoxy purine nucleotides or alternately a plurality of purine nucleotides are 2'-O-methyl, 4'-thio, 2'-O-trifluoromethyl, 2'-O-ethyl-trifluoromethoxy, or 2'-O-difluoromethoxy-ethoxy purine nucleotides). Also, in any of these embodiments, one or more purine nucleotides present in the sense region are alternatively purine ribonucleotides (e.g., wherein all purine nucleotides are purine ribonucleotides or alternately a plurality of purine nucleotides are purine ribonucleotides) and any purine nucleotides present in the antisense region are 2'-O-methyl, 4'-thio, 2'-O-trifluoromethyl, 2'-O-ethyl-trifluoromethoxy, or 2'-O-difluoromethoxy-ethoxy purine nucleotides (e.g., wherein all purine nucleotides are 2'-O-methyl, 4'-thio, 2'-O-trifluoromethyl, 2'-O-ethyl-trifluoromethoxy, or 2'-O-difluoromethoxy-ethoxy purine nucleotides or alternately a plurality of purine nucleotides are 2'-O-methyl, 4'-thio, 2'-O-trifluoromethyl, 2'-O-ethyl-trifluoromethoxy, or 2'-O-difluoromethoxy-ethoxy purine nucleotides). Additionally, in any of these embodiments, one or more purine nucleotides present in the sense region and/or present in the antisense region are alternatively selected from the group consisting of 2'-deoxy nucleotides, locked nucleic acid (LNA) nucleotides, 2'-methoxyethyl nucleotides, 4'-thionucleotides, 2'-O-trifluoromethyl nucleotides, 2'-O-ethyl-trifluoromethoxy nucleotides, 2'-O-difluoromethoxy-ethoxy nucleotides and 2'-O-methyl nucleotides (e.g., wherein all purine nucleotides are selected from the group consisting of 2'-deoxy nucleotides, locked nucleic acid (LNA) nucleotides, 2'-methoxyethyl nucleotides, 4'-thionucleotides, 2'-O-trifluoromethyl nucleotides, 2'-O-ethyl-trifluoromethoxy nucleotides, 2'-O-difluoromethoxy-ethoxy nucleotides and 2'-O-methyl nucleotides or alternately a plurality of purine nucleotides are selected from the group consisting of 2'-deoxy nucleotides, locked nucleic acid (LNA) nucleotides, 2'-methoxyethyl nucleotides, 4'-thionucleotides, 2'-O-trifluoromethyl nucleotides, 2'-O-ethyl -trifluoromethoxy nucleotides, 2'-O-difluoromethoxy-ethoxy nucleotides and 2'-O-methyl nucleotides).

In another embodiment, any modified nucleotides present in the siNA molecules of the invention, preferably in the antisense strand of the siNA molecules of the invention, but also optionally in the sense and/or both antisense and sense strands, comprise modified nucleotides having properties or characteristics similar to naturally occurring ribonucleotides. For example, the invention features siNA molecules including modified nucleotides having a Northern conformation (e.g., Northern pseudorotation cycle, see for example Saenger, *Principles of Nucleic Acid Structure*, Springer-Verlag ed., 1984). As such, chemically modified nucleotides present in the siNA molecules of the invention, preferably in the antisense strand of the siNA molecules of the invention, but also optionally in the sense and/or both antisense and sense strands, are resistant to nuclease degradation while at the same time maintaining the capacity to mediate RNAi. Non-limiting examples of nucleotides having a northern configuration include locked nucleic acid (LNA) nucleotides (e.g., 2'-O, 4'-C-methylene-(D-ribofuranosyl) nucleotides); 2'-methoxyethoxy (MOE) nucleotides; 2'-methyl-thio-ethyl, 2'-deoxy-2'-fluoro nucleotides, 2'-deoxy-2'-chloro nucleotides, 2'-azido nucleotides, 2'-O-trifluoromethyl nucleotides, 2'-O-ethyl-trifluoromethoxy nucleotides, 2'-O-difluoromethoxy-ethoxy nucleotides, 4'-thio nucleotides and 2'-O-methyl nucleotides.

In one embodiment, the sense strand of a double stranded siNA molecule of the invention comprises a terminal cap moiety, such as an inverted deoxyabaisc moiety, at the 3'-end, 5'-end, or both 3' and 5'-ends of the sense strand.

In one embodiment, the invention features a chemically-modified short interfering nucleic acid molecule (siNA) capable of mediating RNA interference (RNAi) inside a cell or reconstituted in vitro system, wherein the chemical modification comprises a conjugate covalently attached to the chemically-modified siNA molecule. Non-limiting examples of conjugates contemplated by the invention include conjugates and ligands described in Vargeese et al., U.S. Ser. No. 10/427,160, filed Apr. 30, 2003, incorporated by reference herein in its entirety, including the drawings. In another embodiment, the conjugate is covalently attached to the chemically-modified siNA molecule via a biodegradable linker. In one embodiment, the conjugate molecule is attached at the 3'-end of either the sense strand, the antisense strand, or both strands of the chemically-modified siNA molecule. In another embodiment, the conjugate molecule is attached at the 5'-end of either the sense strand, the antisense strand, or both strands of the chemically-modified siNA molecule. In yet another embodiment, the conjugate molecule is attached both the 3'-end and 5'-end of either the sense strand, the antisense strand, or both strands of the chemically-modified siNA molecule, or any combination thereof. In one embodiment, a conjugate molecule of the invention comprises a molecule that facilitates delivery of a chemically-modified siNA molecule into a biological system, such as a cell. In another embodiment, the conjugate molecule attached to the chemically-modified siNA molecule is a ligand for a cellular receptor, such as peptides derived from naturally occurring protein ligands; protein localization sequences, including cellular ZIP code sequences; antibodies; nucleic acid aptamers; vitamins and other co-factors, such as folate and N-acetylgalactosamine; polymers, such as polyethyleneglycol (PEG); phospholipids; cholesterol; steroids, and polyamines, such as PEI, spermine or spermidine. Examples of specific conjugate molecules contemplated by the instant invention that can be attached to chemically-modified siNA molecules are described in Vargeese et al., U.S. Ser. No. 10/201,394, filed Jul. 22, 2002 incorporated by reference in its entirety herein. The type of conjugates used and the extent of conjugation of siNA molecules of the invention can be evaluated for improved pharmacokinetic profiles, bioavailability, and/or stability of siNA constructs while at the same time maintaining the ability of the siNA to mediate RNAi activity. As such, one skilled in the art can screen siNA constructs that are modified with various conjugates to determine whether the siNA conjugate complex possesses improved properties while maintaining the ability to mediate RNAi, for example in animal models as are generally known in the art.

In one embodiment, the invention features a short interfering nucleic acid (siNA) molecule of the invention, wherein the siNA further comprises a nucleotide, non-nucleotide, or mixed nucleotide/non-nucleotide linker that joins the sense region of the siNA to the antisense region of the siNA. In one embodiment, a nucleotide, non-nucleotide, or mixed nucleotide/non-nucleotide linker is used, for example, to attach a conjugate moiety to the siNA. In one embodiment, a nucleotide linker of the invention can be a linker of >2 nucleotides in length, for example about 3, 4, 5, 6, 7, 8, 9, or 10 nucleotides in length. In another embodiment, the nucleotide linker can be a nucleic acid aptamer.

In yet another embodiment, a non-nucleotide linker of the invention comprises abasic nucleotide, polyether, polyamine, polyamide, peptide, carbohydrate, lipid, polyhydrocarbon, or other polymeric compounds (e.g. polyethylene glycols such as those having between 2 and 100 ethylene glycol units). Specific examples include those described by Seela and Kaiser, *Nucleic Acids Res.* 1990, 18:6353 and *Nucleic Acids Res.* 1987, 15:3113; Cload and Schepartz, *J. Am. Chem. Soc.* 1991, 113:6324; Richardson and Schepartz, *J. Am. Chem. Soc.* 1991, 113:5109; Ma et al., *Nucleic Acids Res.* 1993, 21:2585 and *Biochemistry* 1993, 32:1751; Durand et al., *Nucleic Acids Res.* 1990, 18:6353; McCurdy et al., *Nucleosides & Nucleotides* 1991, 10:287; Jschke et al., *Tetrahedron Lett.* 1993, 34:301; Ono et al., *Biochemistry* 1991, 30:9914; Arnold et al., International Publication No. WO 89/02439; Usman et al., International Publication No. WO 95/06731; Dudycz et al., International Publication No. WO 95/11910 and Ferentz and Verdine, *J. Am. Chem. Soc.* 1991, 113:4000, all hereby incorporated by reference herein. A "non-nucleotide" further means any group or compound that can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine, for example at the C1 position of the sugar.

In one embodiment, the invention features a short interfering nucleic acid (siNA) molecule capable of mediating RNA interference (RNAi) inside a cell or reconstituted in vitro system, wherein one or both strands of the siNA molecule that are assembled from two separate oligonucleotides do not comprise any ribonucleotides. For example, a siNA molecule can be assembled from a single oligonculeotide where the sense and antisense regions of the siNA comprise separate oligonucleotides that do not have any ribonucleotides (e.g., nucleotides having a 2'-OH group) present in the oligonucleotides. In another example, a siNA molecule can be assembled from a single oligonculeotide where the sense and antisense regions of the siNA are linked or circularized by a nucleotide or non-nucleotide linker as described herein, wherein the oligonucleotide does not have any ribonucleotides (e.g., nucleotides having a 2'-OH group) present in the oligonucleotide. Applicant has surprisingly found that the presense of ribonucleotides (e.g., nucleotides having a 2'-hydroxyl group) within the siNA molecule is not required or essential to support RNAi activity. As such, in one embodiment, all positions within the siNA can include chemically modified nucleotides and/or non-nucleotides such as nucleotides and or non-nucleotides having Formula I, II, III, IV, V, VI, or VII or any combination thereof to the extent that the ability of the siNA molecule to support RNAi activity in a cell is maintained.

In one embodiment, a siNA molecule of the invention is a single stranded siNA molecule that mediates RNAi activity in a cell or reconstituted in vitro system comprising a single stranded polynucleotide having complementarity to a target nucleic acid sequence. In another embodiment, the single stranded siNA molecule of the invention comprises a 5'-terminal phosphate group. In another embodiment, the single stranded siNA molecule of the invention comprises a 5'-terminal phosphate group and a 3'-terminal phosphate group (e.g., a 2',3'-cyclic phosphate). In another embodiment, the single stranded siNA molecule of the invention comprises about 15 to about 30 (e.g., about 15, 16, 17, 18, 19, 20, 21, 22, 23, 24, 25, 26, 27, 28, 29, or 30) nucleotides. In yet another embodiment, the single stranded siNA molecule of the invention comprises one or more chemically modified nucleotides or non-nucleotides described herein. For example, all the positions within the siNA molecule can include chemically-modified nucleotides such as nucleotides having any of Formulae I-VII, or any combination thereof to the extent that the ability of the siNA molecule to support RNAi activity in a cell is maintained.

In one embodiment, a siNA molecule of the invention is a single stranded siNA molecule that mediates RNAi activity in a cell or reconstituted in vitro system comprising a single stranded polynucleotide having complementarity to a target nucleic acid sequence, wherein one or more pyrimidine nucleotides present in the siNA are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides (e.g., wherein all pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides or alternately a plurality of pyrimidine nucleotides are 2'-deoxy-2'-fluoro, 4'-thio, 2'-O-trifluoromethyl, 2'-O-ethyl-trifluoromethoxy, or 2'-O-difluoromethoxy-ethoxy pyrimidine nucleotides), and wherein any purine nucleotides present in the antisense region are 2'-O-methyl, 4'-thio, 2'-O-trifluoromethyl, 2'-O-ethyl-trifluoromethoxy, or 2'-O-difluoromethoxy-ethoxy purine nucleotides (e.g., wherein all purine nucleotides are 2'-O-methyl, 4'-thio, 2'-O-trifluoromethyl, 2'-O-ethyl-trifluoromethoxy, or 2'-O-difluoromethoxy-ethoxy purine nucleotides or alternately a plurality of purine nucleotides are 2'-O-methyl, 4'-thio, 2'-O-trifluoromethyl, 2'-O-ethyl-trifluoromethoxy, or 2'-O-difluoromethoxy-ethoxy purine nucleotides), and a terminal cap modification that is optionally present at the 3'-end, the 5'-end, or both of the 3' and 5'-ends of the antisense sequence. The siNA optionally further comprises about 1 to about 4 or more (e.g., about 1, 2, 3, 4 or more) terminal 2'-deoxynucleotides at the 3'-end of the siNA molecule, wherein the terminal nucleotides can further comprise one or more (e.g., 1, 2, 3, 4 or more) phosphorothioate, phosphonoacetate, and/or thiophosphonoacetate internucleotide linkages, and wherein the siNA optionally further comprises a terminal phosphate group, such as a 5'-terminal phosphate group. In any of these embodiments, any purine nucleotides present in the antisense region are alternatively 2'-deoxy purine nucleotides (e.g., wherein all purine nucleotides are 2'-deoxy purine nucleotides or alternately a plurality of purine nucleotides are 2'-deoxy purine nucleotides). Also, in any of these embodiments, any purine nucleotides present in the siNA (i.e., purine nucleotides present in the sense and/or antisense region) can alternatively be locked nucleic acid (LNA) nucleotides (e.g., wherein all purine nucleotides are LNA nucleotides or alternately a plurality of purine nucleotides are LNA nucleotides). Also, in any of these embodiments, any purine nucleotides present in the siNA are alternatively 2'-methoxyethyl purine nucleotides (e.g., wherein all purine nucleotides are 2'-methoxyethyl purine nucleotides or alternately a plurality of purine nucleotides are 2'-methoxyethyl purine nucleotides).

In another embodiment, any modified nucleotides present in the single stranded siNA molecules of the invention comprise modified nucleotides having properties or characteristics similar to naturally occurring ribonucleotides. For example, the invention features siNA molecules including modified nucleotides having a Northern conformation (e.g., Northern pseudorotation cycle, see for example Saenger, *Principles of Nucleic Acid Structure*, Springer-Verlag ed., 1984). As such, chemically modified nucleotides present in the single stranded siNA molecules of the invention are preferably resistant to nuclease degradation while at the same time maintaining the capacity to mediate RNAi.

In one embodiment, a siNA molecule of the invention comprises chemically modified nucleotides or non-nucleotides (e.g., having any of Formulae I-VII, such as 2'-deoxy, 2'-deoxy-2'-fluoro, 4'-thio, 2'-O-trifluoromethyl, 2'-O-ethyl-trifluoromethoxy, 2'-O-difluoromethoxy-ethoxy or 2'-O-methyl nucleotides) at alternating positions within one or more strands or regions of the siNA molecule. For example, such chemical modifications can be introduced at every other position of a RNA based siNA molecule, starting at either the first or second nucleotide from the 3'-end or 5'-end of the siNA. In a non-limiting example, a double stranded siNA molecule of the invention in which each strand of the siNA is 21 nucleotides in length is featured wherein positions 1, 3, 5, 7, 9, 11, 13, 15, 17, 19 and 21 of each strand are chemically modified (e.g., with compounds having any of Formulae I-VII, such as such as 2'-deoxy, 2'-deoxy-2'-fluoro, 4'-thio, 2'-O-trifluoromethyl, 2'-O-ethyl-trifluoromethoxy, 2'-O-difluoromethoxy-ethoxy or 2'-O-methyl nucleotides). In another non-limiting example, a double stranded siNA molecule of the invention in which each strand of the siNA is 21 nucleotides in length is featured wherein positions 2, 4, 6, 8, 10, 12, 14, 16, 18, and 20 of each strand are chemically modified (e.g., with compounds having any of Formulae I-VII, such as such as 2'-deoxy, 2'-deoxy-2'-fluoro, 4'-thio, 2'-O-trifluoromethyl, 2'-O-ethyl-trifluoromethoxy, 2'-O-difluoromethoxy-ethoxy or 2'-O-methyl nucleotides). Such siNA molecules can further comprise terminal cap moieties and/or backbone modifications as described herein.

In one embodiment, the invention features a method for delivering or administering a biologically active molecule, such as a polynucleotide molecule (e.g., siNA, antisense, aptamer, decoy, ribozyme, 2-5A, triplex forming oligonucleotide, or other nucleic acid molecule) of the invention to a cell or cells in a subject or organism, comprising administering a formulated molecular composition of the invention under conditions suitable for delivery of the polynucleotide component of the formulated molecular composition to the cell or cells of the subject or organism. In separate embodiments, the cell is, for example, a lung cell, liver cell, CNS cell, PNS cell, tumor cell, kidney cell, vascular cell, skin cell, ocular cell, or cells of the ear.

In one embodiment, the invention features a method for delivering or administering a biologically active molecule, such as a polynucleotide molecule (e.g., siNA, antisense, aptamer, decoy, ribozyme, 2-5A, triplex forming oligonucleotide, or other nucleic acid molecule) of the invention to liver or liver cells (e.g., hepatocytes) in a subject or organism, comprising administering a formulated molecular composition of the invention under conditions suitable for delivery of the polynucleotide component of the formulated molecular composition to the liver or liver cells (e.g., hepatocytes) of the subject or organism.

In one embodiment, the invention features a method for modulating the expression of a target gene within a cell comprising, introducing a formulated molecular composition of the invention into a cell under conditions suitable to modulate the expression of the target gene in the cell. In one embodiment, the cell is a liver cell (e.g., hepatocyte). In other embodiments, the cell is, for example, a lung cell, CNS cell, PNS cell, tumor cell, kidney cell, vascular cell, skin cell, ocular cell, or cells of the ear. In one embodiment, the formulated molecular composition comprises a polynucleotide, such as a siNA, antisense, aptamer, decoy, ribozyme, 2-5A, triplex forming oligonucleotide, or other nucleic acid molecule.

In another embodiment, the invention features a method for modulating the expression of more than one target gene within a cell comprising, introducing a formulated molecular composition of the invention into the cell under conditions suitable to modulate the expression of the target genes in the cell. In one embodiment, the cell is a liver cell (e.g., hepatocyte). In other embodiments, the cell is, for example, a lung cell, CNS cell, PNS cell, tumor cell, kidney cell, vascular cell, skin cell, ocular cell, or cells of the ear. In one embodiment, the formulated molecular composition comprises a polynucleotide, such as a siNA, antisense, aptamer, decoy, ribozyme, 2-5A, triplex forming oligonucleotide, or other nucleic acid molecule.

In one embodiment, the invention features a method for treating or preventing a disease, disorder, trait or condition related to gene expression in a subject or organism comprising contacting the subject or organism with a formulated molecular composition of the invention under conditions suitable to modulate the expression of the target gene in the subject or organism. In one embodiment, the formulated molecular composition comprises a polynucleotide, such as a siNA, antisense, aptamer, decoy, ribozyme, 2-5A, triplex forming oligonucleotide, or other nucleic acid molecule. In one embodiment, the reduction of gene expression and thus reduction in the level of the respective protein/RNA relieves, to some extent, the symptoms of the disease, disorder, trait or condition.

In one embodiment, the invention features a method for treating or preventing cancer in a subject or organism comprising contacting the subject or organism with a formulated molecular composition of the invention under conditions suitable to modulate the expression of the target gene in the subject or organism whereby the treatment or prevention of cancer can be achieved. In one embodiment, the formulated molecular composition comprises a polynucleotide, such as a siNA, antisense, aptamer, decoy, ribozyme, 2-5A, triplex forming oligonucleotide, or other nucleic acid molecule. In one embodiment, the invention features contacting the subject or organism with a formulated molecular composition of the invention via local administration to relevant tissues or cells, such as cancerous cells and tissues. In one embodiment, the invention features contacting the subject or organism with a formulated molecular composition of the invention via systemic administration (such as via intravenous or subcutaneous administration of the formulated molecular composition) to relevant tissues or cells, such as tissues or cells involved in the maintenance or development of cancer in a subject or organism. The formulated molecular composition of the invention can be formulated or conjugated as described herein or otherwise known in the art to target appropriate tissues or cells in the subject or organism.

In one embodiment, the invention features a method for treating or preventing a proliferative disease or condition in a subject or organism comprising contacting the subject or organism with a formulated molecular composition of the invention under conditions suitable to modulate the expression of the target gene in the subject or organism whereby the treatment or prevention of the proliferative disease or condition can be achieved. In one embodiment, the formulated molecular composition comprises a polynucleotide, such as a siNA, antisense, aptamer, decoy, ribozyme, 2-5A, triplex forming oligonucleotide, or other nucleic acid molecule. In one embodiment, the invention features contacting the subject or organism with a formulated molecular composition of the invention via local administration to relevant tissues or cells, such as cells and tissues involved in proliferative disease. In one embodiment, the invention features contacting the subject or organism with a formulated molecular composition of the invention via systemic administration (such as via intravenous or subcutaneous administration of the formulated molecular composition) to relevant tissues or cells, such as tissues or cells involved in the maintenance or development of the proliferative disease or condition in a subject or organism. The formulated molecular composition of the invention can be formulated or conjugated as described herein or otherwise known in the art to target appropriate tissues or cells in the subject or organism.

In one embodiment, the invention features a method for treating or preventing transplant and/or tissue rejection (allograft rejection) in a subject or organism comprising contacting the subject or organism with a formulated molecular composition of the invention under conditions suitable to modulate the expression of the target gene in the subject or organism whereby the treatment or prevention of transplant and/or tissue rejection (allograft rejection) can be achieved. In one embodiment, the formulated molecular composition comprises a polynucleotide, such as a siNA, antisense, aptamer, decoy, ribozyme, 2-5A, triplex forming oligonucleotide, or other nucleic acid molecule. In one embodiment, the invention features contacting the subject or organism with a formulated molecular composition of the invention via local administration to relevant tissues or cells, such as cells and tissues involved in transplant and/or tissue rejection (allograft rejection). In one embodiment, the invention features contacting the subject or organism with a formulated molecular composition of the invention via systemic administration (such as via intravenous or subcutaneous administration of the formulated molecular composition) to relevant tissues or cells, such as tissues or cells involved in the maintenance or development of transplant and/or tissue rejection (allograft rejection) in a subject or organism. The formulated molecular composition of the invention can be formulated or conjugated as described herein or otherwise known in the art to target appropriate tissues or cells in the subject or organism.

In one embodiment, the invention features a method for treating or preventing an autoimmune disease, disorder, trait or condition in a subject or organism comprising contacting the subject or organism with a formulated molecular composition of the invention under conditions suitable to modulate the expression of the target gene in the subject or organism whereby the treatment or prevention of the autoimmune disease, disorder, trait or condition can be achieved. In one embodiment, the formulated molecular composition comprises a polynucleotide, such as a siNA, antisense, aptamer, decoy, ribozyme, 2-5A, triplex forming oligonucleotide, or other nucleic acid molecule. In one embodiment, the invention features contacting the subject or organism with a formulated molecular composition of the invention via local administration to relevant tissues or cells, such as cells and tissues involved in the autoimmune disease, disorder, trait or condition. In one embodiment, the invention features contacting the subject or organism with a formulated molecular composition of the invention via systemic administration (such as via intravenous or subcutaneous administration of the formulated molecular composition) to relevant tissues or cells, such as tissues or cells involved in the maintenance or development of the autoimmune disease, disorder, trait or condition in a subject or organism. The formulated molecular composition of the invention can be formulated or conjugated as described herein or otherwise known in the art to target appropriate tissues or cells in the subject or organism.

In one embodiment, the invention features a method for treating or preventing an infectious disease, disorder, trait or condition in a subject or organism comprising contacting the subject or organism with a formulated molecular composition of the invention under conditions suitable to modulate the expression of the target gene in the subject or organism whereby the treatment or prevention of the infectious disease, disorder, trait or condition can be achieved. In one embodiment, the formulated molecular composition comprises a polynucleotide, such as a siNA, antisense, aptamer, decoy, ribozyme, 2-5A, triplex forming oligonucleotide, or other nucleic acid molecule. In one embodiment, the invention features contacting the subject or organism with a formulated molecular composition of the invention via local administration to relevant tissues or cells, such as cells and tissues involved in the infectious disease, disorder, trait or condition. In one embodiment, the invention features contacting the subject or organism with a formulated molecular composition of the invention via systemic administration (such as via intravenous or subcutaneous administration of the formulated molecular composition) to relevant tissues or cells, such as tissues or cells involved in the maintenance or development of the infectious disease, disorder, trait or condition in a subject or organism. The formulated molecular composition of the invention can be formulated or conjugated as described herein or otherwise known in the art to target appropriate tissues or cells in the subject or organism.

In one embodiment, the invention features a method for treating or preventing an age-related disease, disorder, trait or condition in a subject or organism comprising contacting the subject or organism with a formulated molecular composition of the invention under conditions suitable to modulate the expression of the target gene in the subject or organism whereby the treatment or prevention of the age-related disease, disorder, trait or condition can be achieved. In one embodiment, the formulated molecular composition comprises a polynucleotide, such as a siNA, antisense, aptamer, decoy, ribozyme, 2-5A, triplex forming oligonucleotide, or other nucleic acid molecule. In one embodiment, the invention features contacting the subject or organism with a formulated molecular composition of the invention via local administration to relevant tissues or cells, such as cells and tissues involved in the age-related disease, disorder, trait or condition. In one embodiment, the invention features contacting the subject or organism with a formulated molecular composition of the invention via systemic administration (such as via intravenous or subcutaneous administration of the formulated molecular composition) to relevant tissues or cells, such as tissues or cells involved in the maintenance or development of the age-related disease, disorder, trait or condition in a subject or organism. The formulated molecular composition of the invention can be formulated or conjugated as described herein or otherwise known in the art to target appropriate tissues or cells in the subject or organism.

In one embodiment, the invention features a method for treating or preventing a neurologic or neurodegenerative disease, disorder, trait or condition in a subject or organism comprising contacting the subject or organism with a formulated molecular composition of the invention under conditions suitable to modulate the expression of the target gene in the subject or organism whereby the treatment or prevention of the neurologic or neurodegenerative disease, disorder, trait or condition can be achieved. In one embodiment, the formulated molecular composition comprises a polynucleotide, such as a siNA, antisense, aptamer, decoy, ribozyme, 2-5A, triplex forming oligonucleotide, or other nucleic acid molecule. In one embodiment, the invention features contacting the subject or organism with a formulated molecular composition of the invention via local administration to relevant tissues or cells, such as cells and tissues involved in the neurologic or neurodegenerative disease, disorder, trait or condition. In one embodiment, the invention features contacting the subject or organism with a formulated molecular composition of the invention via systemic administration (such as via catheterization, osmotic pump administration (e.g., intrathecal or ventricular) intravenous or subcutaneous administration of the formulated molecular composition) to relevant tissues or cells, such as tissues or cells involved in the maintenance or development of the neurologic or neurodegenerative disease, disorder, trait or condition in a subject or organism. The formulated molecular composition of the invention can be formulated or conjugated as described herein or otherwise known in the art to target appropriate tissues or cells in the subject or organism. In one embodiment, the neurologic disease is Huntington disease.

In one embodiment, the invention features a method for treating or preventing a metabolic disease, disorder, trait or condition in a subject or organism comprising contacting the subject or organism with a formulated molecular composition of the invention under conditions suitable to modulate the expression of the target gene in the subject or organism whereby the treatment or prevention of the metabolic disease, disorder, trait or condition can be achieved. In one embodiment, the formulated molecular composition comprises a polynucleotide, such as a siNA, antisense, aptamer, decoy, ribozyme, 2-5A, triplex forming oligonucleotide, or other nucleic acid molecule. In one embodiment, the invention features contacting the subject or organism with a formulated molecular composition of the invention via local administration to relevant tissues or cells, such as cells and tissues involved in the metabolic disease, disorder, trait or condition. In one embodiment, the invention features contacting the subject or organism with a formulated molecular composition of the invention via systemic administration (such as via intravenous or subcutaneous administration of the formulated molecular composition) to relevant tissues or cells, such as tissues or cells involved in the maintenance or development of the metabolic disease, disorder, trait or condition in a subject or organism. The formulated molecular composition of the invention can be formulated or conjugated as described herein or otherwise known in the art to target appropriate tissues or cells in the subject or organism.

In one embodiment, the invention features a method for treating or preventing a cardiovascular disease, disorder, trait or condition in a subject or organism comprising contacting the subject or organism with a formulated molecular composition of the invention under conditions suitable to modulate the expression of the target gene in the subject or organism whereby the treatment or prevention of the cardiovascular disease, disorder, trait or condition can be achieved. In one embodiment, the formulated molecular composition comprises a polynucleotide, such as a siNA, antisense, aptamer, decoy, ribozyme, 2-5A, triplex forming oligonucleotide, or other nucleic acid molecule. In one embodiment, the invention features contacting the subject or organism with a formulated molecular composition of the invention via local administration to relevant tissues or cells, such as cells and tissues involved in the cardiovascular disease, disorder, trait or condition. In one embodiment, the invention features contacting the subject or organism with a formulated molecular composition of the invention via systemic administration (such as via intravenous or subcutaneous administration of the formulated molecular composition) to relevant tissues or cells, such as tissues or cells involved in the maintenance or development of the cardiovascular disease, disorder, trait or condition in a subject or organism. The formulated molecular composition of the invention can be formulated or conjugated as described herein or otherwise known in the art to target appropriate tissues or cells in the subject or organism.

In one embodiment, the invention features a method for treating or preventing a respiratory disease, disorder, trait or condition in a subject or organism comprising contacting the subject or organism with a formulated molecular composition of the invention under conditions suitable to modulate the expression of the target gene in the subject or organism whereby the treatment or prevention of the respiratory disease, disorder, trait or condition can be achieved. In one embodiment, the formulated molecular composition comprises a polynucleotide, such as a siNA, antisense, aptamer, decoy, ribozyme, 2-5A, triplex forming oligonucleotide, or other nucleic acid molecule. In one embodiment, the invention features contacting the subject or organism with a formulated molecular composition of the invention via local administration to relevant tissues or cells, such as cells and tissues involved in the respiratory disease, disorder, trait or condition. In one embodiment, the invention features contacting the subject or organism with a formulated molecular composition of the invention via systemic administration (such as via intravenous or subcutaneous administration of the formulated molecular composition) to relevant tissues or cells, such as tissues or cells involved in the maintenance or development of the respiratory disease, disorder, trait or condition in a subject or organism. The formulated molecular composition of the invention can be formulated or conjugated as described herein or otherwise known in the art to target appropriate tissues or cells in the subject or organism.

In one embodiment, the invention features a method for treating or preventing an ocular disease, disorder, trait or condition in a subject or organism comprising contacting the subject or organism with a formulated molecular composition of the invention under conditions suitable to modulate the expression of the target gene in the subject or organism whereby the treatment or prevention of the ocular disease, disorder, trait or condition can be achieved. In one embodiment, the formulated molecular composition comprises a polynucleotide, such as a siNA, antisense, aptamer, decoy, ribozyme, 2-5A, triplex forming oligonucleotide, or other nucleic acid molecule. In one embodiment, the invention features contacting the subject or organism with a formulated molecular composition of the invention via local administration to relevant tissues or cells, such as cells and tissues involved in the ocular disease, disorder, trait or condition. In one embodiment, the invention features contacting the subject or organism with a formulated molecular composition of the invention via systemic administration (such as via intravenous or subcutaneous administration of the formulated molecular composition) to relevant tissues or cells, such as tissues or cells involved in the maintenance or development of the ocular disease, disorder, trait or condition in a subject or organism. The formulated molecular composition of the invention can be formulated or conjugated as described herein or otherwise known in the art to target appropriate tissues or cells in the subject or organism.

In one embodiment, the invention features a method for treating or preventing a dermatological disease, disorder, trait or condition in a subject or organism comprising contacting the subject or organism with a formulated molecular composition of the invention under conditions suitable to modulate the expression of the target gene in the subject or organism whereby the treatment or prevention of the dermatological disease, disorder, trait or condition can be achieved. In one embodiment, the formulated molecular composition comprises a polynucleotide, such as a siNA, antisense, aptamer, decoy, ribozyme, 2-5A, triplex forming oligonucleotide, or other nucleic acid molecule. In one embodiment, the invention features contacting the subject or organism with a formulated molecular composition of the invention via local administration to relevant tissues or cells, such as cells and tissues involved in the dermatological disease, disorder, trait or condition. In one embodiment, the invention features contacting the subject or organism with a formulated molecular composition of the invention via systemic administration (such as via intravenous or subcutaneous administration of the formulated molecular composition) to relevant tissues or cells, such as tissues or cells involved in the maintenance or development of the dermatological disease, disorder, trait or condition in a subject or organism. The formulated molecular composition of the invention can be formulated or conjugated as described herein or otherwise known in the art to target appropriate tissues or cells in the subject or organism.

In one embodiment, the invention features a method for treating or preventing a liver disease, disorder, trait or condition (e.g., hepatitis, HCV, HBV, diabetis, cirrhosis, hepatocellular carcinoma etc.) in a subject or organism comprising contacting the subject or organism with a formulated molecular composition of the invention under conditions suitable to modulate the expression of the target gene in the subject or organism whereby the treatment or prevention of the liver disease, disorder, trait or condition can be achieved. In one embodiment, the formulated molecular composition comprises a polynucleotide, such as a siNA, antisense, aptamer, decoy, ribozyme, 2-5A, triplex forming oligonucleotide, or other nucleic acid molecule. In one embodiment, the invention features contacting the subject or organism with a formulated molecular composition of the invention via local administration to relevant tissues or cells, such as liver cells and tissues involved in the liver disease, disorder, trait or condition. In one embodiment, the invention features contacting the subject or organism with a formulated molecular composition of the invention via systemic administration (such as via intravenous or subcutaneous administration of the formulated molecular composition) to relevant tissues or cells, such as tissues or cells involved in the maintenance or development of the liver disease, disorder, trait or condition in a subject or organism. The formulated molecular composition of the invention can be formulated or conjugated as described herein or otherwise known in the art to target appropriate tissues or cells in the subject or organism.

In one embodiment, the invention features a method for treating or preventing a kidney/renal disease, disorder, trait or condition (e.g., polycystic kidney disease etc.) in a subject or organism comprising contacting the subject or organism with a formulated molecular composition of the invention under conditions suitable to modulate the expression of the target gene in the subject or organism whereby the treatment or prevention of the kidney/renal disease, disorder, trait or condition can be achieved. In one embodiment, the formulated molecular composition comprises a polynucleotide, such as a siNA, antisense, aptamer, decoy, ribozyme, 2-5A, triplex forming oligonucleotide, or other nucleic acid molecule. In one embodiment, the invention features contacting the subject or organism with a formulated molecular composition of the invention via local administration to relevant tissues or cells, such as kidney/renal cells and tissues involved in the kidney/renal disease, disorder, trait or condition. In one embodiment, the invention features contacting the subject or organism with a formulated molecular composition of the invention via systemic administration (such as via intravenous or subcutaneous administration of the formulated molecular composition) to relevant tissues or cells, such as tissues or cells involved in the maintenance or development of the kidney/renal disease, disorder, trait or condition in a subject or organism. The formulated molecular composition of the invention can be formulated or conjugated as described herein or otherwise known in the art to target appropriate tissues or cells in the subject or organism.

In one embodiment, the invention features a method for treating or preventing an auditory disease, disorder, trait or condition (e.g., hearing loss, deafness, etc.) in a subject or organism comprising contacting the subject or organism with a formulated molecular composition of the invention under conditions suitable to modulate the expression of the target gene in the subject or organism whereby the treatment or prevention of the auditory disease, disorder, trait or condition can be achieved. In one embodiment, the formulated molecular composition comprises a polynucleotide, such as a siNA, antisense, aptamer, decoy, ribozyme, 2-5A, triplex forming oligonucleotide, or other nucleic acid molecule. In one embodiment, the invention features contacting the subject or organism with a formulated molecular composition of the invention via local administration to relevant tissues or cells, such as cells and tissues of the ear, inner hear, or middle ear involved in the auditory disease, disorder, trait or condition. In one embodiment, the invention features contacting the subject or organism with a formulated molecular composition of the invention via systemic administration (such as via intravenous or subcutaneous administration of the formulated molecular composition) to relevant tissues or cells, such as tissues or cells involved in the maintenance or development of the auditory disease, disorder, trait or condition in a subject or organism. The formulated molecular composition of the invention can be formulated or conjugated as described herein or otherwise known in the art to target appropriate tissues or cells in the subject or organism.

In one embodiment, the invention features a method for treating or preventing a disease or condition as described herein in a subject or organism, comprising administering to the subject or organism a formulated molecular composition of the invention; wherein the formulated molecular composition is administered under conditions suitable for reducing or inhibiting the level of target gene expression in the subject compared to a subject not treated with the formulated molecular composition. In one embodiment, the formulated molecular composition comprises a lipid nanoparticle and a siNA molecule of the invention.

In one embodiment, the invention features a method for treating or preventing a disease or condition as described herein in a subject or organism, comprising administering to the subject a formulated molecular composition of the invention; wherein (a) the formulated molecular composition comprises a double stranded nucleic acid molecule having a sense strand and an antisense strand; (b) each strand of the double stranded nucleic acid molecule is 15 to 28 nucleotides in length; (c) at least 15 nucleotides of the sense strand are complementary to the antisense strand (d) the antisense strand of the double stranded nucleic acid molecule has complementarity to a target RNA; and wherein the formulated molecular composition is administered under conditions suitable for reducing or inhibiting the target RNA in the subject compared to a subject not treated with the formulated molecular composition. In one embodiment, the formulated molecular composition comprises a lipid nanoparticle and a siNA molecule of the invention.

In one embodiment, the invention features a method for treating or preventing a disease or condition as described herein in a subject or organism, comprising administering to the subject a formulated molecular composition of the invention; wherein (a) the formulated molecular composition comprises a double stranded nucleic acid molecule having a sense strand and an antisense strand; (b) each strand of the double stranded nucleic acid molecule is 15 to 28 nucleotides in length; (c) at least 15 nucleotides of the sense strand are complementary to the antisense strand (d) the antisense strand of the double stranded nucleic acid molecule has complementarity to a target RNA; (e) at least 20% of the internal nucleotides of each strand of the double stranded nucleic acid molecule are modified nucleosides having a chemical modification; and (f) at least two of the chemical modifications are different from each other, and wherein the formulated molecular composition is administered under conditions suitable for reducing or inhibiting the level of target RNA in the subject compared to a subject not treated with the formulated molecular composition. In one embodiment, the formulated molecular composition comprises a lipid nanoparticle and a siNA molecule of the invention.

In any of the methods of treatment of the invention, the formulated molecular composition can be administered to the subject as a course of treatment, for example administration at various time intervals, such as once per day over the course of treatment, once every two days over the course of treatment, once every three days over the course of treatment, once every four days over the course of treatment, once every five days over the course of treatment, once every six days over the course of treatment, once per week over the course of treatment, once every other week over the course of treatment, once per month over the course of treatment, etc. In one embodiment, the course of treatment is once every 1, 2, 3, 4, 5, 6, 7, 8, 9, or 10 weeks. In one embodiment, the course of treatment is from about one to about 52 weeks or longer (e.g. indefinitely). In one embodiment, the course of treatment is from about one to about 48 months or longer (e.g., indefinitely).

In one embodiment, a course of treatment involves an initial course of treatment, such as once every 1, 2, 3, 4, 5, 6, 7, 8, 9, 10 or more weeks for a fixed interval (e.g., 1×, 2×, 3×, 4×, 5×, 6×, 7×, 8×, 9×, 10× or more) followed by a maintenance course of treatment, such as once every 4, 6, 8, 10, 15, 20, 25, 30, 35, 40, or more weeks for an additional fixed interval (e.g. 1×, 2×, 3×, 4×, 5×, 6×, 7×, 8×, 9×, 10× or more).

In any of the methods of treatment of the invention, the formulated molecular composition can be administered to the subject systemically as described herein or otherwise known in the art. Systemic administration can include, for example, intravenous, subcutaneous, intramuscular, catheterization, nasopharyngeal, transdermal, or gastrointestinal administration as is generally known in the art.

In one embodiment, in any of the methods of treatment or prevention of the invention, the formulated molecular composition can be administered to the subject locally or to local tissues as described herein or otherwise known in the art. Local administration can include, for example, catheterization, implantation, osmotic pumping, direct injection, dermal/transdermal application, stenting, ear/eye drops, or portal vein administration to relevant tissues, or any other local administration technique, method or procedure, as is generally known in the art.

In one embodiment, the invention features a composition comprising a formulated molecular composition of the invention, in a pharmaceutically acceptable carrier or diluent. In another embodiment, the invention features a pharmaceutical composition comprising formulated molecular compositions of the invention, targeting one or more genes in a pharmaceutically acceptable carrier or diluent. In another embodiment, the invention features a method for diagnosing a disease or condition in a subject comprising administering to the subject a formulated molecular composition of the invention under conditions suitable for the diagnosis of the disease or condition in the subject. In another embodiment, the invention features a method for treating or preventing a disease, trait, or condition in a subject, comprising administering to the subject a formulated molecular composition of the invention under conditions suitable for the treatment or prevention of the disease, trait or condition in the subject, alone or in conjunction with one or more other therapeutic compounds.

In one embodiment, the method of synthesis of polynucleotide molecules of the invention, including but not limited to siNA, antisense, aptamer, decoy, ribozyme, 2-5A, triplex forming oligonucleotide, or other nucleic acid molecules, comprises the teachings of Scaringe et al., U.S. Pat. Nos. 5,889,136; 6,008,400; and 6,111,086, incorporated by reference herein in their entirety.

In another embodiment, the invention features a method for generating formulated polynucleotide (e.g., to siNA, antisense, aptamer, decoy, ribozyme, 2-5A, triplex forming oligonucleotide, or other nucleic acid molecule) compositions with increased nuclease resistance comprising (a) introducing modified nucleotides into a polynucleotide component of a formulated molecular composition of the invention, and (b) assaying the formulated molecular composition of step (a) under conditions suitable for isolating formulated polynucleotide compositions having increased nuclease resistance.

In another embodiment, the invention features a method for generating polynucleotide (e.g., to siNA, antisense, aptamer, decoy, ribozyme, 2-5A, triplex forming oligonucleotide, or other nucleic acid molecule) molecules with improved toxicologic profiles (e.g., having attenuated or no immunstimulatory properties) comprising (a) introducing nucleotides having any of Formula I-VII (e.g., siNA motifs referred to in Table I) or any combination thereof into a polynucleotide molecule, and (b) assaying the polynucleotide molecule of step (a) under conditions suitable for isolating siNA molecules having improved toxicologic profiles.

In another embodiment, the invention features a method for generating formulated siNA compositions with improved toxicologic profiles (e.g., having attenuated or no immunstimulatory properties) comprising (a) generating a formulated siNA composition comprising a siNA molecule of the invention and a delivery vehicle or delivery particle as described herein or as otherwise known in the art, and (b) assaying the siNA formulation of step (a) under conditions suitable for isolating formulated siNA compositions having improved toxicologic profiles.

In another embodiment, the invention features a method for generating siNA molecules that do not stimulate an interferon response (e.g., no interferon response or attenuated interferon response) in a cell, subject, or organism, comprising (a) introducing nucleotides having any of Formula I-VII (e.g., siNA motifs referred to in Table I) or any combination thereof into a siNA molecule, and (b) assaying the siNA molecule of step (a) under conditions suitable for isolating siNA molecules that do not stimulate an interferon response.

In another embodiment, the invention features a method for generating formulated siNA compositions that do not stimulate an interferon response (e.g., no interferon response or attenuated interferon response) in a cell, subject, or organism, comprising (a) generating a formulated siNA composition comprising a siNA molecule of the invention and a delivery vehicle or delivery particle as described herein or as otherwise known in the art, and (b) assaying the siNA formulation of step (a) under conditions suitable for isolating formulated siNA compositions that do not stimulate an interferon response. In one embodiment, the interferon comprises interferon alpha.

In another embodiment, the invention features a method for generating siNA molecules that do not stimulate an inflammatory or proinflammatory cytokine response (e.g., no cytokine response or attenuated cytokine response) in a cell, subject, or organism, comprising (a) introducing nucleotides having any of Formula I-VII (e.g., siNA motifs referred to in Table I) or any combination thereof into a siNA molecule, and (b) assaying the siNA molecule of step (a) under conditions suitable for isolating siNA molecules that do not stimulate a cytokine response. In one embodiment, the cytokine comprises an interleukin such as interleukin-6 (IL-6) and/or tumor necrosis factor alpha (TNF-α).

In another embodiment, the invention features a method for generating formulated siNA compositions that do not stimulate an inflammatory or proinflammatory cytokine response (e.g., no cytokine response or attenuated cytokine response) in a cell, subject, or organism, comprising (a) generating a formulated siNA composition comprising a siNA molecule of the invention and a delivery vehicle or delivery particle as described herein or as otherwise known in the art, and (b) assaying the siNA formulation of step (a) under conditions suitable for isolating formulated siNA compositions that do not stimulate a cytokine response. In one embodiment, the cytokine comprises an interleukin such as interleukin-6 (IL-6) and/or tumor necrosis alpha (TNF-α).

In another embodiment, the invention features a method for generating siNA molecules that do not stimulate Toll-like Receptor (TLR) response (e.g., no TLR response or attenuated TLR response) in a cell, subject, or organism, comprising (a) introducing nucleotides having any of Formula I-VII (e.g., siNA motifs referred to in Table I) or any combination thereof into a siNA molecule, and (b) assaying the siNA molecule of step (a) under conditions suitable for isolating siNA molecules that do not stimulate a TLR response. In one embodiment, the TLR comprises TLR3, TLR7, TLR8 and/or TLR9.

In another embodiment, the invention features a method for generating formulated siNA compositions that do not stimulate a Toll-like Receptor (TLR) response (e.g., no TLR response or attenuated TLR response) in a cell, subject, or organism, comprising (a) generating a formulated siNA composition comprising a siNA molecule of the invention and a delivery vehicle or delivery particle as described herein or as otherwise known in the art, and (b) assaying the siNA formulation of step (a) under conditions suitable for isolating formulated siNA compositions that do not stimulate a TLR response. In one embodiment, the TLR comprises TLR3, TLR7, TLR8 and/or TLR9.

By "improved toxicologic profile", is meant that the polynucleotide, formulated molecular composition, siNA or formulated siNA composition exhibits decreased toxicity in a cell, subject, or organism compared to an unmodified polynucleotide, formulated molecular composition, siNA or formulated siNA composition, or siNA molecule having fewer modifications or modifications that are less effective in imparting improved toxicology. In a non-limiting example, polynucleotides, formulated molecular compositions, siNAs or formulated siNA compositions with improved toxicologic profiles are associated with reduced immunostimulatory properties, such as a reduced, decreased or attenuated immunostimulatory response in a cell, subject, or organism compared to an unmodified polynucleotide, formulated molecular composition, siNA or formulated siNA composition, or polynucleotide (e.g., siNA) molecule having fewer modifications or modifications that are less effective in imparting improved toxicology. Such an improved toxicologic profile is characterized by abrogated or reduced immunostimulation, such as reduction or abrogation of induction of interferons (e.g., interferon alpha), inflammatory cytokines (e.g., interleukins such as IL-6, and/or TNF-alpha), and/or toll like receptors (e.g., TLR-3, TLR-7, TLR-8, and/or TLR-9). In one embodiment, a polynucleotide, formulated molecular composition, siNA or formulated siNA composition with an improved toxicological profile comprises no ribonucleotides. In one embodiment, a polynucleotide, formulated molecular composition, siNA or formulated siNA composition with an improved toxicological profile comprises less than 5 ribonucleotides (e.g., 1, 2, 3, or 4 ribonucleotides). In one embodiment, a siNA or formulated siNA composition with an improved toxicological profile comprises Stab 7, Stab 8, Stab 11, Stab 12, Stab 13, Stab 16, Stab 17, Stab 18, Stab 19, Stab 20, Stab 23, Stab 24, Stab 25, Stab 26, Stab 27, Stab 28, Stab 29, Stab 30, Stab 31, Stab 32, Stab 33, Stab 34 or any combination thereof (see Table I). Herein, numeric Stab chemistries include both 2'-fluoro and 2'-OCF3 versions of the chemistries shown in Table IV. For example, "Stab 7/8" refers to both Stab 7/8 and Stab 7F/8F etc. In one embodiment, a siNA or formulated siNA composition with an improved toxicological profile comprises a siNA molecule as described in United States Patent Application Publication No. 20030077829, incorporated by reference herein in its entirety including the drawings.

In one embodiment, the level of immunostimulatory response associated with a given polynucleotide, formulated molecular composition, siNA molecule or formulated siNA composition can be measured as is described herein or as is otherwise known in the art, for example by determining the level of PKR/interferon response, proliferation, B-cell activation, and/or cytokine production in assays to quantitate the immunostimulatory response of particular polynucleotide molecules (see, for example, Leifer et al., 2003, *J Immunother.* 26, 313-9; and U.S. Pat. No. 5,968,909, incorporated in its entirety by reference). In one embodiment, the reduced immunostimulatory response is between about 10% and about 100% compared to an unmodified or minimally modified siRNA molecule, e.g., about 10%, 20%, 30%, 40%, 50%, 60%, 70%, 80%, 90% or 100% reduced immunostimulatory response. In one embodiment, the immunostimulatory response associated with a siNA molecule can be modulated by the degree of chemical modification. For example, a siNA molecule having between about 10% and about 100%, e.g., about 10%, 20%, 30%, 40%, 50%, 60%, 70%, 80%, 90% or 100% of the nucleotide positions in the siNA molecule modified can be selected to have a corresponding degree of immunostimulatory properties as described herein.

In one embodiment, the degree of reduced immunostimulatory response is selected for optimized RNAi activity. For example, retaining a certain degree of immunostimulation can be preferred to treat viral infection, where less than 100% reduction in immunostimulation may be preferred for maximal antiviral activity (e.g., about 10%, 20%, 30%, 40%, 50%, 60%, 70%, 80%, or 90% reduction in immunostimulation) whereas the inhibition of expression of an endogenous gene target may be preferred with siNA molecules that posses minimal immunostimulatory properties to prevent non-specific toxicity or off target effects (e.g., about 90% to about 100% reduction in immunostimulation).

In one embodiment, a formulated siNA composition of the invention is designed such that the composition is not toxic to cells or has a minimized toxicological profile such that the composition does not interfere with the efficacy of RNAi mediated by the siNA component of the formulated siNA composition or result in toxicity to the cells.

The term "formulated molecular composition" or "lipid nanoparticle", or "lipid nanoparticle composition" or "LNP as used herein refers to a composition comprising one or more biologically active molecules independently or in combination with a cationic lipid, a neutral lipid, and/or a polyethyleneglycol-diacylglycerol (i.e., polyethyleneglycol diacylglycerol (PEG-DAG), PEG-cholesterol, or PEG-DMB) conjugate. A formulated molecular composition can further comprise cholesterol or a cholesterol derivative (see FIG. 5). The cationic lipid of the invention can comprise a compound having any of Formulae CLI, CLII, CLIII, CLIV, CLV, CLVI, CLVII, CLVIII, CLIX, CLX, CLXI, CLXII, CLXIII, CLXIV, CLXV, CLXVI, CLXVII, CLXVIII, CLXIX, CLXX, CLXXI, CLXXII, CLXXIII, CLXXIV, CLXXV, CLXXVI, CLXXVII, CLXXVIII, CLXXIX, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-Dioleoyl-3-Dimethylammonium-propane (DODAP), 1,2-Dioleoylcarbamyl-3-Dimethylammonium-propane (DOCDAP), 1,2-Dilineoyl-3-Dimethylammonium-propane (DLINDAP), 3-Dimethylamino-2-(Cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethyl-1-(cis,cis-9', 12'-octadecadienoxy)propane (CpLin DMA), N,N-Dimethyl-3,4-dioleyloxybenzylamine (DMOBA) and/or a mixture thereof. The neutral lipid can comprise dioleoylphosphatidylethanolamine (DOPE), palmitoyloleoylphosphatidylcholine (POPC), egg phosphatidylcholine (EPC), distearoylphosphatidylcholine (DSPC), cholesterol, and/or a mixture thereof. The PEG conjugate can comprise a PEG-dilaurylglycerol (C12), a PEG-dimyristylglycerol (C14), a PEG-dipalmitoylglycerol (C16), a PEG-disterylglycerol (C18), PEG-dilaurylglycamide (C12), PEG-dimyristylglycamide (C14), PEG-dipalmitoylglycamide (C16), PEG-disterylglycamide (C18), PEG-cholesterol, or PEG-DMB. The cationic lipid component can comprise from about 2% to about 60%, from about 5% to about 45%, from about 5% to about 15%, or from about 40% to about 50% of the total lipid present in the formulation. The neutral lipid component can comprise from about 5% to about 90%, or from about 20% to about 85% of the total lipid present in the formulation.

The PEG-DAG conjugate (e.g., polyethyleneglycol diacylglycerol (PEG-DAG), PEG-cholesterol, or PEG-DMB) can comprise from about 1% to about 20%, or from about 4% to about 15% of the total lipid present in the formulation. The cholesterol component can comprise from about 10% to about 60%, or from about 20% to about 45% of the total lipid present in the formulation. In one embodiment, a formulated molecular composition of the invention comprises a cationic lipid component comprising about 7.5% of the total lipid present in the formulation, a neutral lipid comprising about 82.5% of the total lipid present in the formulation, and a PEG conjugate comprising about 10% of the total lipid present in the formulation. In one embodiment, a formulated molecular composition of the invention comprises a biologically active molecule, DODMA, DSPC, and a PEG-DAG conjugate. In one embodiment, the PEG-DAG conjugate is PEG-dilaurylglycerol (C12), PEG-dimyristylglycerol (C14), PEG-dipalmitoylglycerol (C16), or PEG-disterylglycerol (C18). In another embodiment, the formulated molecular composition also comprises cholesterol or a cholesterol derivative. In one embodiment, the formulated molecular composition comprises a lipid nanoparticle formulation as shown in Table IV.

The term "formulated siNA composition" as used herein refers to a composition comprising one or more siNA molecules or a vector encoding one or more siNA molecules independently or in combination with a cationic lipid, a neutral lipid, and/or a polyethyleneglycol-diacylglycerol (PEG-DAG) or PEG-cholesterol (PEG-Chol) conjugate. A formulated siNA composition can further comprise cholesterol or a cholesterol derivative. The cationic lipid of the invention can comprise a compound having any of Formulae CLI, CLII, CLIII, CLIV, CLV, CLVI, CLVII, CLVIII, CLIX, CLX, CLXI, CLXII, CLXIII, CLXIV, CLXV, CLXVI, CLXVII, CLXVIII, CLXIX, CLXX, CLXXI, CLXXII, CLXXIII, CLXXIV, CLXXV, CLXXVI, CLXXVII, CLXXVIII, CLXXIX, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-Dioleoyl-3-Dimethylammonium-propane (DODAP), 1,2-Dioleoylcarbamyl-3-Dimethylammonium-propane (DOCDAP), 1,2-Dilineoyl-3-Dimethylammonium-propane (DLINDAP), 3-Dimethylamino-2-(Cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethyl-1-(cis,cis-9', 12'-octadecadienoxy)propane (CpLin DMA), N,N-Dimethyl-3,4-dioleyloxybenzylamine (DMOBA) and/or a mixture thereof. The neutral lipid can comprise a compound having any of Formulae NLI-NLVII, dioleoylphosphatidylethanolamine (DOPE), palmitoyloleoylphosphatidylcholine (POPC), egg phosphatidylcholine (EPC), distearoylphosphatidylcholine (DSPC), cholesterol, and/or a mixture thereof. The PEG conjugate can comprise a PEG-dilaurylglycerol (C12), a PEG-dimyristylglycerol (C14), a PEG-dipalmitoylglycerol (C16), a PEG-disterylglycerol (C18), PEG-dilaurylglycamide (C12), PEG-dimyristylglycamide (C14), PEG-dipalmitoylglycamide (C16), PEG-disterylglycamide (C18), PEG-cholesterol, or PEG-DMB. The cationic lipid component can comprise from about 2% to about 60%, from about 5% to about 45%, from about 5% to about 15%, or from about 40% to about 50% of the total lipid present in the formulation. The neutral lipid component can comprise from about 5% to about 90%, or from about 20% to about 85% of the total lipid present in the formulation. The PEG-DAG conjugate can comprise from about 1% to about 20%, or from about 4% to about 15% of the total lipid present in the formulation. The cholesterol component can comprise from about 10% to about 60%, or from about 20% to about 45% of the total lipid present in the formulation. In one embodiment, a formulated siNA composition of the invention comprises a cationic lipid component comprising about 7.5% of the total lipid present in the formulation, a neutral lipid comprising about 82.5% of the total lipid present in the formulation, and a PEG-DAG conjugate comprising about 10% of the total lipid present in the formulation. In one embodiment, a formulated siNA composition of the invention comprises a siNA molecule, DODMA, DSPC, and a PEG-DAG conjugate. In one embodiment, the PEG-DAG conjugate is PEG-dilaurylglycerol (C12), PEG-dimyristylglycerol (C14), PEG-dipalmitoylglycerol (C16), or PEG-disterylglycerol (C18). In another embodiment, the formulated siNA composition also comprises cholesterol or a cholesterol derivative.

By "cationic lipid" as used herein is meant any lipophilic compound having cationic change, such as a compound having any of Formulae CLI-CLXXIX.

By "neutral lipid" as used herein is meant any lipophilic compound having non-cationic change (e.g., anionic or neutral charge).

By "PEG" is meant, any polyethylene glycol or other polyalkylene ether or equivalent polymer.

By "nanoparticle" is meant a microscopic particle whose size is measured in nanometers. Nanoparticles of the invention typically range from about 1 to about 999 nm in diameter, and can include an encapsulated or enclosed biologically active molecule.

By "microparticle" is meant a is a microscopic particle whose size is measured in micrometers. Microparticles of the invention typically range from about 1 to about 100 micrometers in diameter, and can include an encapsulated or enclosed biologically active molecule.

The terms "short interfering nucleic acid", "siNA", "short interfering RNA", "siRNA", "short interfering nucleic acid molecule", "short interfering oligonucleotide molecule", and "chemically-modified short interfering nucleic acid molecule" as used herein refer to any nucleic acid molecule capable of inhibiting or down regulating gene expression or viral replication by mediating RNA interference "RNAi" or gene silencing in a sequence-specific manner (see PCT/US 2004/106390 (WO 05/19453), U.S. Ser. No. 10/444,853, filed May 23, 2003 U.S. Ser. No. 10/923,536 filed Aug. 20, 2004, U.S. Ser. No. 11/234,730, filed Sep. 23, 2005 or U.S. Ser. No. 11/299,254, filed Dec. 8, 2005, all incorporated by reference in their entireties herein). For example the siNA can be a double-stranded nucleic acid molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure, for example wherein the double stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the siNA molecule are complementary to the target nucleic acid or a portion thereof). Alternatively, the siNA is assembled from a single oligonucleotide, where the self-complementary sense and antisense regions of the siNA are linked by means of a nucleic acid based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (for example, where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, *Cell.,* 110, 563-574 and Schwarz et al., 2002, *Molecular Cell,* 10, 537-568), or 5',3'-diphosphate. In certain embodiments, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the siNA molecules of the invention comprise nucleotide sequence that is complementary to nucleotide sequence of a target gene. In another embodiment, the siNA molecule of the invention interacts with nucleotide sequence of a target gene in a manner that causes inhibition of expression of the target gene. As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. Applicant describes in certain embodiments short interfering nucleic acids that do not require the presence of nucleotides having a 2'-hydroxy group for mediating RNAi and as such, short interfering nucleic acid molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON." As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. Non limiting examples of siNA molecules of the invention are shown in U.S. Ser. No. 11/234,730, filed Sep. 23, 2005, incorporated by reference in its entirety herein. Such siNA molecules are distinct from other nucleic acid technologies known in the art that mediate inhibition of gene expression, such as ribozymes, antisense, triplex forming, aptamer, 2,5-A chimera, or decoy oligonucleotides.

By "RNA interference" or "RNAi" is meant a biological process of inhibiting or down regulating gene expression in a cell as is generally known in the art and which is mediated by short interfering nucleic acid molecules, see for example Zamore and Haley, 2005, *Science,* 309, 1519-1524; Vaughn and Martienssen, 2005, *Science,* 309, 1525-1526; Zamore et al., 2000, *Cell,* 101, 25-33; Bass, 2001, *Nature,* 411, 428-429; Elbashir et al., 2001, *Nature,* 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, *Science,* 297, 1818-1819; Volpe et al., 2002, *Science,* 297, 1833-1837; Jenuwein, 2002, *Science,* 297, 2215-2218; and Hall et al., 2002, *Science,* 297, 2232-2237; Hutvagner and Zamore, 2002, *Science,* 297, 2056-60; McManus et al., 2002, *RNA,* 8, 842-850; Reinhart et al., 2002, *Gene & Dev.,* 16, 1616-1626; and Reinhart & Bartel, 2002, *Science,* 297, 1831). In addition, as used herein, the term RNAi is meant to be equivalent to other terms used to describe sequence specific RNA interference, such as post transcriptional gene silencing, translational inhibition, transcriptional inhibition, or epigenetics. For example, siNA molecules of the invention can be used to epigenetically silence genes at both the post-transcriptional level or the pre-transcriptional level. In a non-limiting example, epigenetic modulation of gene expression by siNA molecules of the invention can result from siNA mediated modification of chromatin structure or methylation patterns to alter gene expression (see, for example, Verdel et al., 2004, *Science,* 303, 672-676; Pal-Bhadra et al., 2004, *Science,* 303, 669-672; Allshire, 2002, *Science,* 297, 1818-1819; Volpe et al., 2002, *Science,* 297, 1833-1837; Jenuwein, 2002, *Science,* 297, 2215-2218; and Hall et al., 2002, *Science,* 297, 2232-2237). In another non-limiting example, modulation of gene expression by siNA molecules of the invention can result from siNA mediated cleavage of RNA (either coding or non-coding RNA) via RISC, or alternately, translational inhibition as is known in the art. In another embodiment, modulation of gene expression by siNA molecules of the invention can result from transcriptional inhibition (see for example Janowski et al., 2005, *Nature Chemical Biology,* 1, 216-222).

By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule of the invention can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siNA molecule of the invention can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region.

The term "polynucleotide" or "nucleic acid molecule" as used herein, refers to a molecule having nucleotides. The nucleic acid can be single, double, or multiple stranded and can comprise modified or unmodified nucleotides or non-nucleotides or various mixtures and combinations thereof.

The term "enzymatic nucleic acid molecule" as used herein refers to a nucleic acid molecule which has complementarity in a substrate binding region to a specified gene target, and also has an enzymatic activity which is active to specifically cleave target RNA. That is, the enzymatic nucleic acid molecule is able to intermolecularly cleave RNA and thereby inactivate a target RNA molecule. These complementary regions allow sufficient hybridization of the enzymatic nucleic acid molecule to the target RNA and thus permit cleavage. One hundred percent complementarity is preferred, but complementarity as low as 50-75% can also be useful in this invention (see for example Werner and Uhlenbeck, 1995, Nucleic Acids Research, 23, 2092-2096; Hammann et al., 1999, Antisense and Nucleic Acid Drug Dev., 9, 25-31). The nucleic acids can be modified at the base, sugar, and/or phosphate groups. The term enzymatic nucleic acid is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. The specific enzymatic nucleic acid molecules described in the instant application are not limiting in the invention and those skilled in the art will recognize that all that is important in an enzymatic nucleic acid molecule of this invention is that it has a specific substrate binding site which is complementary to one or more of the target nucleic acid regions, and that it have nucleotide sequences within or surrounding that substrate binding site which impart a nucleic acid cleaving and/or ligation activity to the molecule (Cech et al., U.S. Pat. No. 4,987,071; Cech et al., 1988, 260 JAMA 3030). Ribozymes and enzymatic nucleic molecules of the invention can be chemically modified as is generally known in the art or as described herein.

The term "antisense nucleic acid", as used herein, refers to a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. For a review of current antisense strategies, see Schmajuk et al., 1999, J. Biol. Chem., 274, 21783-21789, Delihas et al., 1997, Nature, 15, 751-753, Stein et al., 1997, Antisense N. A. Drug Dev., 7, 151, Crooke, 2000, Methods Enzymol., 313, 3-45; Crooke, 1998, Biotech. Genet. Eng. Rev., 15, 121-157, Crooke, 1997, Ad. Pharmacol., 40, 1-49. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof. Antisense molecules of the invention can be chemically modified as is generally known in the art or as described herein.

The term "RNase H activating region" as used herein, refers to a region (generally greater than or equal to 4-25 nucleotides in length, preferably from 5-11 nucleotides in length) of a nucleic acid molecule capable of binding to a target RNA to form a non-covalent complex that is recognized by cellular RNase H enzyme (see for example Arrow et al., U.S. Pat. No. 5,849,902; Arrow et al., U.S. Pat. No. 5,989,912). The RNase H enzyme binds to the nucleic acid molecule-target RNA complex and cleaves the target RNA sequence. The RNase H activating region comprises, for example, phosphodiester, phosphorothioate (preferably at least four of the nucleotides are phosphorothiote substitutions; more specifically, 4-11 of the nucleotides are phosphorothiote substitutions); phosphorodithioate, 5'-thiophosphate, or methylphosphonate backbone chemistry or a combination thereof. In addition to one or more backbone chemistries described above, the RNase H activating region can also comprise a variety of sugar chemistries. For example, the RNase H activating region can comprise deoxyribose, arabino, fluoroarabino or a combination thereof, nucleotide sugar chemistry. Those skilled in the art will recognize that the foregoing are non-limiting examples and that any combination of phosphate, sugar and base chemistry of a nucleic acid that supports the activity of RNase H enzyme is within the scope of the definition of the RNase H activating region and the instant invention.

The term "2-5A antisense chimera" as used herein, refers to an antisense oligonucleotide containing a 5'-phosphorylated 2'-5'-linked adenylate residue. These chimeras bind to target RNA in a sequence-specific manner and activate a cellular 2-5A-dependent ribonuclease which, in turn, cleaves the target RNA (Torrence et al., 1993 Proc. Natl. Acad. Sci. USA 90, 1300; Silverman et al., 2000, Methods Enzymol., 313, 522-533; Player and Torrence, 1998, Pharmacol. Ther., 78, 55-113). 2-5A antisense chimera molecules of the invention can be chemically modified as is generally known in the art or as described herein.

The term "triplex forming oligonucleotides" as used herein, refers to an oligonucleotide that can bind to a double-stranded DNA in a sequence-specific manner to form a triple-strand helix. Formation of such triple helix structure has been shown to inhibit transcription of the targeted gene (Duval-Valentin et al., 1992 Proc. Natl. Acad. Sci. USA 89, 504; Fox, 2000, Curr. Med. Chem., 7, 17-37; Praseuth et. al., 2000, Biochim. Biophys. Acta, 1489, 181-206). Triplex forming oligonucleotide molecules of the invention can be chemically modified as is generally known in the art or as described herein.

The term "decoy RNA" as used herein, refers to a RNA molecule or aptamer that is designed to preferentially bind to a predetermined ligand. Such binding can result in the inhibition or activation of a target molecule. The decoy RNA or aptamer can compete with a naturally occurring binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger et al., 1990, Cell, 63, 601-608). This is but a specific example and those in the art will recognize that other embodiments can be readily generated using techniques generally known in the art, see for example Gold et al., 1995, Annu. Rev. Biochem., 64, 763; Brody and Gold, 2000, J. Biotechnol., 74, 5; Sun, 2000, Curr. Opin. Mol. Ther., 2, 100; Kusser, 2000, J. Biotechnol., 74, 27; Hermann and Patel, 2000, Science, 287, 820; and Jayasena, 1999, Clinical Chemistry, 45, 1628. Similarly, a decoy RNA can be designed to bind to a receptor and block the binding of an effector molecule or a decoy RNA can be designed to bind to receptor of interest and prevent interaction with the receptor. Decoy molecules of the invention can be chemically modified as is generally known in the art or as described herein.

The term "single stranded RNA" (ssRNA) as used herein refers to a naturally occurring or synthetic ribonucleic acid molecule comprising a linear single strand, for example a ssRNA can be a messenger RNA (mRNA), transfer RNA (tRNA), ribosomal RNA (rRNA) etc. of a gene.

The term "single stranded DNA" (ssDNA) as used herein refers to a naturally occurring or synthetic deoxyribonucleic acid molecule comprising a linear single strand, for example, a ssDNA can be a sense or antisense gene sequence or EST (Expressed Sequence Tag).

The term "double stranded RNA" or "dsRNA" as used herein refers to a double stranded RNA molecule capable of RNA interference, including short interfering RNA (siNA).

The term "allozyme" as used herein refers to an allosteric enzymatic nucleic acid molecule, see for example George et al., U.S. Pat. Nos. 5,834,186 and 5,741,679, Shih et al., U.S. Pat. No. 5,589,332, Nathan et al., U.S. Pat. No. 5,871,914, Nathan and Ellington, International PCT publication No. WO 00/24931, Breaker et al., International PCT Publication Nos. WO 00/26226 and 98/27104, and Sullenger et al., International PCT publication No. WO 99/29842.

By "aptamer" or "nucleic acid aptamer" as used herein is meant a polynucleotide that binds specifically to a target molecule wherein the nucleic acid molecule has sequence that is distinct from sequence recognized by the target molecule in its natural setting. Alternately, an aptamer can be a nucleic acid molecule that binds to a target molecule where the target molecule does not naturally bind to a nucleic acid. The target molecule can be any molecule of interest. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art, see for example Gold et al., 1995, Annu. Rev. Biochem., 64, 763; Brody and Gold, 2000, J. Biotechnol., 74, 5; Sun, 2000, Curr. Opin. Mol. Ther., 2, 100; Kusser, 2000, J. Biotechnol., 74, 27; Hermann and Patel, 2000, Science, 287, 820; and Jayasena, 1999, Clinical Chemistry, 45, 1628. Aptamer molecules of the invention can be chemically modified as is generally known in the art or as described herein.

By "modulate" is meant that the expression of the gene, or level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

By "inhibit", "down-regulate", or "reduce", it is meant that the expression of the gene, or level of RNA molecules or equivalent RNA molecules encoding one or more proteins or protein subunits, or activity of one or more proteins or protein subunits, is reduced below that observed in the absence of the nucleic acid molecules (e.g., siNA) of the invention. In one embodiment, inhibition, down-regulation or reduction with a siNA molecule is below that level observed in the presence of an inactive or attenuated molecule. In another embodiment, inhibition, down-regulation, or reduction with siNA molecules is below that level observed in the presence of, for example, a siNA molecule with scrambled sequence or with mismatches. In another embodiment, inhibition, down-regulation, or reduction of gene expression with a nucleic acid molecule of the instant invention is greater in the presence of the nucleic acid molecule than in its absence. In one embodiment, inhibition, down regulation, or reduction of gene expression is associated with post transcriptional silencing, such as RNAi mediated cleavage of a target nucleic acid molecule (e.g. RNA) or inhibition of translation. In one embodiment, inhibition, down regulation, or reduction of gene expression is associated with pretranscriptional silencing.

By "up-regulate", or "promote", it is meant that the expression of the gene, or level of RNA molecules or equivalent RNA molecules encoding one or more proteins or protein subunits, or activity of one or more proteins or protein subunits, is increased above that observed in the absence of the nucleic acid molecules (e.g., siNA) of the invention. In one embodiment, up-regulation or promotion of gene expression with an siNA molecule is above that level observed in the presence of an inactive or attenuated molecule. In another embodiment, up-regulation or promotion of gene expression with siNA molecules is above that level observed in the presence of, for example, an siNA molecule with scrambled sequence or with mismatches. In another embodiment, up-regulation or promotion of gene expression with a nucleic acid molecule of the instant invention is greater in the presence of the nucleic acid molecule than in its absence. In one embodiment, up-regulation or promotion of gene expression is associated with inhibition of RNA mediated gene silencing, such as RNAi mediated cleavage or silencing of a coding or non-coding RNA target that down regulates, inhibits, or silences the expression of the gene of interest to be up-regulated. The down regulation of gene expression can, for example, be induced by a coding RNA or its encoded protein, such as through negative feedback or antagonistic effects. The down regulation of gene expression can, for example, be induced by a non-coding RNA having regulatory control over a gene of interest, for example by silencing expression of the gene via translational inhibition, chromatin structure, methylation, RISC mediated RNA cleavage, or translational inhibition. As such, inhibition or down regulation of targets that down regulate, suppress, or silence a gene of interest can be used to up-regulate or promote expression of the gene of interest toward therapeutic use.

By "gene", or "target gene", is meant a nucleic acid that encodes RNA, for example, nucleic acid sequences including, but not limited to, structural genes encoding a polypeptide. A gene or target gene can also encode a functional RNA (FRNA) or non-coding RNA (ncRNA), such as small temporal RNA (stRNA), micro RNA (miRNA), small nuclear RNA (snRNA), short interfering RNA (siRNA), small nucleolar RNA (snRNA), ribosomal RNA (rRNA), transfer RNA (tRNA) and precursor RNAs thereof. Such non-coding RNAs can serve as target nucleic acid molecules for siNA mediated RNA interference in modulating the activity of FRNA or ncRNA involved in functional or regulatory cellular processes. Abberant FRNA or ncRNA activity leading to disease can therefore be modulated by siNA molecules of the invention. siNA molecules targeting FRNA and ncRNA can also be used to manipulate or alter the genotype or phenotype of a subject, organism or cell, by intervening in cellular processes such as genetic imprinting, transcription, translation, or nucleic acid processing (e.g., transamination, methylation etc.). The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus. Non-limiting examples of plants include monocots, dicots, or gymnosperms. Non-limiting examples of animals include vertebrates or invertebrates. Non-limiting examples of fungi include molds or yeasts. For a review, see for example Snyder and Gerstein, 2003, *Science*, 300, 258-260.

By "target" as used herein is meant, any target protein, peptide, or polypeptide encoded by a target gene. The term "target" also refers to nucleic acid sequences encoding any target protein, peptide, or polypeptide having target activity, such as encoded by target RNA. The term "target" is also meant to include other target encoding sequence, such as other target isoforms, mutant target genes, splice variants of target genes, and target gene polymorphisms. By "target nucleic acid" is meant any nucleic acid sequence whose expression or activity is to be modulated. The target nucleic acid can be DNA or RNA.

By "non-canonical base pair" is meant any non-Watson Crick base pair, such as mismatches and/or wobble base pairs, including flipped mismatches, single hydrogen bond mismatches, trans-type mismatches, triple base interactions, and quadruple base interactions. Non-limiting examples of such non-canonical base pairs include, but are not limited to, AC reverse Hoogsteen, AC wobble, AU reverse Hoogsteen, GU wobble, AA N7 amino, CC 2-carbonyl-amino(H1)-N-3-amino(H2), GA sheared, UC 4-carbonyl-amino, UU imino-carbonyl, AC reverse wobble, AU Hoogsteen, AU reverse Watson Crick, CG reverse Watson Crick, GC N3-amino-amino N3, AA N1-amino symmetric, AA N7-amino symmetric, GA N7-N1 amino-carbonyl, GA+ carbonyl-amino N7-N1, GG N1-carbonyl symmetric, GG N3-amino symmetric, CC carbonyl-amino symmetric, CC N3-amino symmetric, UU 2-carbonyl-imino symmetric, UU 4-carbonyl-imino symmetric, AA amino-N3, AA N1-amino, AC amino 2-carbonyl, AC N3-amino, AC N7-amino, AU amino-4-carbonyl, AU N1-imino, AU N3-imino, AU N7-imino, CC carbonyl-amino, GA amino-N1, GA amino-N7, GA carbonyl-amino, GA N3-amino, GC amino-N3, GC carbonyl-amino, GC N3-amino, GC N7-amino, GG amino-N7, GG carbonyl-imino, GG N7-amino, GU amino-2-carbonyl, GU carbonyl-imino, GU imino-2-carbonyl, GU N7-imino, psiU imino-2-carbonyl, UC 4-carbonyl-amino, UC imino-carbonyl, UU imino-4-carbonyl, AC C2-H-N3, GA carbonyl-C2-H, UU imino-4-carbonyl 2 carbonyl-C5-H, AC amino(A) N3(C)-carbonyl, GC imino amino-carbonyl, Gpsi imino-2-carbonyl amino-2-carbonyl, and GU imino amino-2-carbonyl base pairs.

By "target" as used herein is meant, any target protein, peptide, or polypeptide, such as encoded by Genbank Accession Nos. shown in U.S. Ser. No. 10/923,536 and U.S. Ser. No. 10/923,536, both incorporated by reference herein. The term "target" also refers to nucleic acid sequences or target polynucleotide sequence encoding any target protein, peptide, or polypeptide, such as proteins, peptides, or polypeptides encoded by sequences having Genbank Accession Nos. shown in U.S. Ser. No. 10/923,536 and U.S. Ser. No. 10/923,536. The target of interest can include target polynucleotide sequences, such as target DNA or target RNA. The term "target" is also meant to include other sequences, such as differing isoforms, mutant target genes, splice variants of target polynucleotides, target polymorphisms, and non-coding (e.g., ncRNA, miRNA, sRNA) or other regulatory polynucleotide sequences as described herein. Therefore, in various embodiments of the invention, a double stranded nucleic acid molecule of the invention (e.g., siNA) having complementarity to a target RNA can be used to inhibit or down regulate miRNA or other ncRNA activity. In one embodiment, inhibition of miRNA or ncRNA activity can be used to down regulate or inhibit gene expression (e.g., gene targets described herein or otherwise known in the art) or viral replication (e.g., viral targets described herein or otherwise known in the art) that is dependent on miRNA or ncRNA activity. In another embodiment, inhibition of miRNA or ncRNA activity by double stranded nucleic acid molecules of the invention (e.g. siNA) having complementarity to the miRNA or ncRNA can be used to up regulate or promote target gene expression (e.g., gene targets described herein or otherwise known in the art) where the expression of such genes is down regulated, suppressed, or silenced by the miRNA or ncRNA. Such up-regulation of gene expression can be used to treat diseases and conditions associated with a loss of function or haploinsufficiency as are generally known in the art (e.g., muscular dystrophies, cystic fibrosis, or neurologic diseases and conditions described herein such as epilepsy, including severe myoclonic epilepsy of infancy or Dravet syndrome).

By "homologous sequence" is meant, a nucleotide sequence that is shared by one or more polynucleotide sequences, such as genes, gene transcripts and/or non-coding polynucleotides. For example, a homologous sequence can be a nucleotide sequence that is shared by two or more genes encoding related but different proteins, such as different members of a gene family, different protein epitopes, different protein isoforms or completely divergent genes, such as a cytokine and its corresponding receptors. A homologous sequence can be a nucleotide sequence that is shared by two or more non-coding polynucleotides, such as noncoding DNA or RNA, regulatory sequences, introns, and sites of transcriptional control or regulation. Homologous sequences can also include conserved sequence regions shared by more than one polynucleotide sequence. Homology does not need to be perfect homology (e.g., 100%), as partially homologous sequences are also contemplated by the instant invention (e.g., 99%, 98%, 97%, 96%, 95%, 94%, 93%, 92%, 91%, 90%, 89%, 88%, 87%, 86%, 85%, 84%, 83%, 82%, 81%, 80% etc.).

By "conserved sequence region" is meant, a nucleotide sequence of one or more regions in a polynucleotide does not vary significantly between generations or from one biological system, subject, or organism to another biological system, subject, or organism. The polynucleotide can include both coding and non-coding DNA and RNA.

By "sense region" is meant a nucleotide sequence of a siNA molecule having complementarity to an antisense region of the siNA molecule. In addition, the sense region of a siNA molecule can comprise a nucleic acid sequence having homology with a target nucleic acid sequence. In one embodiment, the sense region of the siNA molecule is referred to as the sense strand or passenger strand.

By "antisense region" is meant a nucleotide sequence of a siNA molecule having complementarity to a target nucleic acid sequence. In addition, the antisense region of a siNA molecule can optionally comprise a nucleic acid sequence having complementarity to a sense region of the siNA molecule. In one embodiment, the antisense region of the siNA molecule is referred to as the antisense strand or guide strand.

By "target nucleic acid" or "target polynucleotide" is meant any nucleic acid sequence whose expression or activity is to be modulated. The target nucleic acid can be DNA or RNA. In one embodiment, a target nucleic acid of the invention is target RNA or DNA.

By "complementarity" is meant that a nucleic acid can form hydrogen bond(s) with another nucleic acid sequence by either traditional Watson-Crick or other non-traditional types as described herein. In one embodiment, a double stranded nucleic acid molecule of the invention, such as an siNA molecule, wherein each strand is between 15 and 30 nucleotides in length, comprises between about 10% and about 100% (e.g., about 10%, 20%, 30%, 40%, 50%, 60%, 70%, 80%, 90%, or 100%) complementarity between the two strands of the double stranded nucleic acid molecule. In another embodiment, a double stranded nucleic acid molecule of the invention, such as an siNA molecule, where one strand is the sense strand and the other stand is the antisense strand, wherein each strand is between 15 and 30 nucleotides in length, comprises between at least about 10% and about 100% (e.g., at least about 10%, 20%, 30%, 40%, 50%, 60%, 70%, 80%, 90%, or 100%) complementarity between the nucleotide sequence in the antisense strand of the double stranded nucleic acid molecule and the nucleotide sequence of its corresponding target nucleic acid molecule, such as a target RNA or target mRNA or viral RNA. In one embodiment, a double stranded nucleic acid molecule of the invention, such as an siNA molecule, where one strand comprises nucleotide sequence that is referred to as the sense region and the other strand comprises a nucleotide sequence that is referred to as the antisense region, wherein each strand is between 15 and 30 nucleotides in length, comprises between about 10% and about 100% (e.g., about 10%, 20%, 30%, 40%, 50%, 60%, 70%, 80%, 90%, or 100%) complementarity between the sense region and the antisense region of the double stranded nucleic acid molecule. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, CSH Symp. Quant. Biol. LII pp. 123-133; Frier et al., 1986, Proc. Nat. Acad. Sci. USA 83:9373-9377; Turner et al., 1987, J. Am. Chem. Soc. 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). In one embodiment, a siNA molecule of the invention has perfect complementarity between the sense strand or sense region and the antisense strand or antisense region of the siNA molecule. In one embodiment, a siNA molecule of the invention is perfectly complementary to a corresponding target nucleic acid molecule. "Perfectly complementary" means that all the contiguous residues of a nucleic acid sequence will hydrogen bond with the same number of contiguous residues in a second nucleic acid sequence. In one embodiment, a siNA molecule of the invention comprises about 15 to about 30 or more (e.g., about 15, 16, 17, 18, 19, 20, 21, 22, 23, 24, 25, 26, 27, 28, 29, or 30 or more) nucleotides that are complementary to one or more target nucleic acid molecules or a portion thereof. In one embodiment, a siNA molecule of the invention has partial complementarity (i.e., less than 100% complementarity) between the sense strand or sense region and the antisense strand or antisense region of the siNA molecule or between the antisense strand or antisense region of the siNA molecule and a corresponding target nucleic acid molecule. For example, partial complementarity can include various mismatches or non-based paired nucleotides (e.g., 1, 2, 3, 4, 5 or more mismatches or non-based paired nucleotides) within the siNA structure which can result in bulges, loops, or overhangs that result between the between the sense strand or sense region and the antisense strand or antisense region of the siNA molecule or between the antisense strand or antisense region of the siNA molecule and a corresponding target nucleic acid molecule.

In one embodiment, a double stranded nucleic acid molecule of the invention, such as siNA molecule, has perfect complementarity between the sense strand or sense region and the antisense strand or antisense region of the nucleic acid molecule. In one embodiment, double stranded nucleic acid molecule of the invention, such as siNA molecule, is perfectly complementary to a corresponding target nucleic acid molecule.

In one embodiment, double stranded nucleic acid molecule of the invention, such as siNA molecule, has partial complementarity (i.e., less than 100% complementarity) between the sense strand or sense region and the antisense strand or antisense region of the double stranded nucleic acid molecule or between the antisense strand or antisense region of the nucleic acid molecule and a corresponding target nucleic acid molecule. For example, partial complementarity can include various mismatches or non-base paired nucleotides (e.g., 1, 2, 3, 4, 5 or more mismatches or non-based paired nucleotides, such as nucleotide bulges) within the double stranded nucleic acid molecule, structure which can result in bulges, loops, or overhangs that result between the sense strand or sense region and the antisense strand or antisense region of the double stranded nucleic acid molecule or between the antisense strand or antisense region of the double stranded nucleic acid molecule and a corresponding target nucleic acid molecule.

In one embodiment, double stranded nucleic acid molecule of the invention is a microRNA (miRNA). By "mircoRNA" or "miRNA" is meant, a small double stranded RNA that regulates the expression of target messenger RNAs either by mRNA cleavage, translational repression/inhibition or heterochromatic silencing (see for example Ambros, 2004, Nature, 431, 350-355; Bartel, 2004, Cell, 116, 281-297; Cullen, 2004, Virus Research., 102, 3-9; He et al., 2004, Nat. Rev. Genet., 5, 522-531; and Ying et al., 2004, Gene, 342, 25-28). In one embodiment, the microRNA of the invention, has partial complementarity (i.e., less than 100% complementarity) between the sense strand or sense region and the antisense strand or antisense region of the miRNA molecule or between the antisense strand or antisense region of the miRNA and a corresponding target nucleic acid molecule. For example, partial complementarity can include various mismatches or non-base paired nucleotides (e.g., 1, 2, 3, 4, 5 or more mismatches or non-based paired nucleotides, such as nucleotide bulges) within the double stranded nucleic acid molecule, structure which can result in bulges, loops, or overhangs that result between the sense strand or sense region and the antisense strand or antisense region of the miRNA or between the antisense strand or antisense region of the miRNA and a corresponding target nucleic acid molecule.

In one embodiment, compositions of the invention such as formulated molecular compositions and formulated siNA compositions of the invention that down regulate or reduce target gene expression are used for preventing or treating diseases, disorders, conditions, or traits in a subject or organism as described herein or otherwise known in the art.

By "proliferative disease" or "cancer" as used herein is meant, any disease, condition, trait, genotype or phenotype characterized by unregulated cell growth or replication as is known in the art; including leukemias, for example, acute myelogenous leukemia (AML), chronic myelogenous leukemia (CML), acute lymphocytic leukemia (ALL), and chronic lymphocytic leukemia, AIDS related cancers such as Kaposi's sarcoma; breast cancers; bone cancers such as Osteosarcoma, Chondrosarcomas, Ewing's sarcoma, Fibrosarcomas, Giant cell tumors, Adamantinomas, and Chordomas; Brain cancers such as Meningiomas, Glioblastomas, Lower-Grade Astrocytomas, Oligodendrocytomas, Pituitary Tumors, Schwannomas, and Metastatic brain cancers; cancers of the head and neck including various lymphomas such as mantle cell lymphoma, non-Hodgkins lymphoma, adenoma, squamous cell carcinoma, laryngeal carcinoma, gallbladder and bile duct cancers, cancers of the retina such as retinoblastoma, cancers of the esophagus, gastric cancers, multiple myeloma, ovarian cancer, uterine cancer, thyroid cancer, testicular cancer, endometrial cancer, melanoma, colorectal cancer, lung cancer, bladder cancer, prostate cancer, lung cancer (including non-small cell lung carcinoma), pancreatic cancer, sarcomas, Wilms' tumor, cervical cancer, head and neck cancer, skin cancers, nasopharyngeal carcinoma, liposarcoma, epithelial carcinoma, renal cell carcinoma, gallbladder adeno carcinoma, parotid adenocarcinoma, endometrial sarcoma, multidrug resistant cancers; and proliferative diseases and conditions, such as neovascularization associated with tumor angiogenesis, macular degeneration (e.g., wet/dry AMD), corneal neovascularization, diabetic retinopathy, neovascular glaucoma, myopic degeneration and other proliferative diseases and conditions such as restenosis and polycystic kidney disease, and any other cancer or proliferative disease, condition, trait, genotype or phenotype that can respond to the modulation of disease related gene expression in a cell or tissue, alone or in combination with other therapies.

By "inflammatory disease" or "inflammatory condition" as used herein is meant any disease, condition, trait, genotype or phenotype characterized by an inflammatory or allergic process as is known in the art, such as inflammation, acute inflammation, chronic inflammation, respiratory disease, atherosclerosis, psoriasis, dermatitis, restenosis, asthma, allergic rhinitis, atopic dermatitis, septic shock, rheumatoid arthritis, inflammatory bowel disease, inflammotory pelvic disease, pain, ocular inflammatory disease, celiac disease, Leigh Syndrome, Glycerol Kinase Deficiency, Familial eosinophilia (FE), autosomal recessive spastic ataxia, laryngeal inflammatory disease; Tuberculosis, Chronic cholecystitis, Bronchiectasis, Silicosis and other pneumoconioses, and any other inflammatory disease, condition, trait, genotype or phenotype that can respond to the modulation of disease related gene expression in a cell or tissue, alone or in combination with other therapies.

By "autoimmune disease" or "autoimmune condition" as used herein is meant, any disease, condition, trait, genotype or phenotype characterized by autoimmunity as is known in the art, such as multiple sclerosis, diabetes mellitus, lupus, celiac disease, Crohn's disease, ulcerative colitis, Guillain-Barre syndrome, scleroderms, Goodpasture's syndrome, Wegener's granulomatosis, autoimmune epilepsy, Rasmussen's encephalitis, Primary biliary sclerosis, Sclerosing cholangitis, Autoimmune hepatitis, Addison's disease, Hashimoto's thyroiditis, Fibromyalgia, Menier's syndrome; transplantation rejection (e.g., prevention of allograft rejection) pernicious anemia, rheumatoid arthritis, systemic lupus erythematosus, dermatomyositis, Sjogren's syndrome, lupus erythematosus, multiple sclerosis, myasthenia gravis, Reiter's syndrome, Grave's disease, and any other autoimmune disease, condition, trait, genotype or phenotype that can respond to the modulation of disease related gene expression in a cell or tissue, alone or in combination with other therapies.

By "infectious disease" is meant any disease, condition, trait, genotype or phenotype associated with an infectious agent, such as a virus, bacteria, fungus, prion, or parasite. Non-limiting examples of various viral genes that can be targeted using siNA molecules of the invention include Hepatitis C Virus (HCV, for example Genbank Accession Nos: D11168, D50483.1, L38318 and S82227), Hepatitis B Virus (HBV, for example GenBank Accession No. AF100308.1), Human Immunodeficiency Virus type 1 (HIV-1, for example GenBank Accession No. U51188), Human Immunodeficiency Virus type 2 (HIV-2, for example GenBank Accession No. X60667), West Nile Virus (WNV for example GenBank accession No. NC_001563), cytomegalovirus (CMV for example GenBank Accession No. NC_001347), respiratory syncytial virus (RSV for example GenBank Accession No. NC_001781), influenza virus (for example GenBank Accession No. AF037412, rhinovirus (for example, GenBank accession numbers: D00239, X02316, X01087, L24917, M16248, K02121, X01087), papillomavirus (for example GenBank Accession No. NC_001353), Herpes Simplex Virus (HSV for example GenBank Accession No. NC_001345), and other viruses such as HTLV (for example GenBank Accession No. AJ430458). Due to the high sequence variability of many viral genomes, selection of siNA molecules for broad therapeutic applications would likely involve the conserved regions of the viral genome. Nonlimiting examples of conserved regions of the viral genomes include but are not limited to 5'-Non Coding Regions (NCR), 3'-Non Coding Regions (NCR) and/or internal ribosome entry sites (IRES). siNA molecules designed against conserved regions of various viral genomes will enable efficient inhibition of viral replication in diverse patient populations and may ensure the effectiveness of the siNA molecules against viral quasi species which evolve due to mutations in the non-conserved regions of the viral genome. Non-limiting examples of bacterial infections include Actinomycosis, Anthrax, Aspergillosis, Bacteremia, Bacterial Infections and Mycoses, *Bartonella* Infections, Botulism, Brucellosis, Burkholderia Infections, *Campylobacter* Infections, Candidiasis, Cat-Scratch Disease, *Chlamydia* Infections, Cholera, *Clostridium* Infections, Coccidioidomycosis, Cross Infection, Cryptococcosis, Dermatomycoses, Dermatomycoses, Diphtheria, Ehrlichiosis, *Escherichia coli* Infections, Fasciitis, Necrotizing, *Fusobacterium* Infections, Gas Gangrene, Gram-Negative Bacterial Infections, Gram-Positive Bacterial Infections, Histoplasmosis, Impetigo, *Klebsiella* Infections, Legionellosis, Leprosy, Leptospirosis, *Listeria* Infections, Lyme Disease, Maduromycosis, Melioidosis, *Mycobacterium* Infections, *Mycoplasma* Infections, Mycoses, *Nocardia* Infections, Onychomycosis, Ornithosis, Plague, Pneumococcal Infections, *Pseudomonas* Infections, Q Fever, Rat-Bite Fever, Relapsing Fever, Rheumatic Fever, *Rickettsia* Infections, Rocky Mountain Spotted Fever, *Salmonella* Infections, Scarlet Fever, Scrub Typhus, Sepsis, Sexually Transmitted Diseases—Bacterial, Bacterial Skin Diseases, Staphylococcal Infections, Streptococcal Infections, Tetanus, Tick-Borne Diseases, Tuberculosis, Tularemia, Typhoid Fever, Typhus, Epidemic Louse-Borne, *Vibrio* Infections, Yaws, *Yersinia* Infections, Zoonoses, and Zygomycosis. Non-limiting examples of fungal infections include Aspergillosis, Blastomycosis, Coccidioidomycosis, Cryptococcosis, Fungal Infections of Fingernails and Toenails, Fungal Sinusitis, Histoplasmosis, Histoplasmosis, Mucormycosis, Nail Fungal Infection, Paracoccidioidomycosis, Sporotrichosis, Valley Fever (Coccidioidomycosis), and Mold Allergy.

By "neurologic disease" or "neurological disease" is meant any disease, disorder, or condition affecting the central or peripheral nervous system, inlcuding ADHD, AIDS—Neurological Complications, Absence of the Septum Pellucidum, Acquired Epileptiform Aphasia, Acute Disseminated Encephalomyelitis, Adrenoleukodystrophy, Agenesis of the Corpus Callosum, Agnosia, Aicardi Syndrome, Alexander Disease, Alpers' Disease, Alternating Hemiplegia, Alzheimer's Disease, Amyotrophic Lateral Sclerosis, Anencephaly, Aneurysm, Angelman Syndrome, Angiomatosis, Anoxia, Aphasia, Apraxia, Arachnoid Cysts, Arachnoiditis, Arnold-Chiari Malformation, Arteriovenous Malformation, Aspartame, Asperger Syndrome, Ataxia Telangiectasia, Ataxia, Attention Deficit-Hyperactivity Disorder, Autism, Autonomic Dysfunction, Back Pain, Barth Syndrome, Batten Disease, Behcet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain Aneurysm, Brain Injury, Brain and Spinal Tumors, Brown-Sequard Syndrome, Bulbospinal Muscular Atrophy, Canavan Disease, Carpal Tunnel Syndrome, Causalgia, Cavernomas, Cavernous Angioma, Cavernous Malformation, Central Cervical Cord Syndrome, Central Cord Syndrome, Central Pain Syndrome, Cephalic Disorders, Cerebellar Degeneration, Cerebellar Hypoplasia, Cerebral Aneurysm, Cerebral Arteriosclerosis, Cerebral Atrophy, Cerebral Beriberi, Cerebral Gigantism, Cerebral Hypoxia, Cerebral Palsy, Cerebro-Oculo-Facio-Skeletal Syndrome, Charcot-Marie-Tooth Disorder, Chiari Malformation, Chorea, Choreoacanthocytosis, Chronic Inflammatory Demyelinating Polyneuropathy (CIDP), Chronic Orthostatic Intolerance, Chronic Pain, Cockayne Syndrome Type II, Coffin Lowry Syndrome, Coma, including Persistent Vegetative State, Complex Regional Pain Syndrome, Congenital Facial Diplegia, Congenital Myasthenia, Congenital Myopathy, Congenital Vascular Cavernous Malformations, Corticobasal Degeneration, Cranial Arteritis, Craniosynostosis, Creutzfeldt-Jakob Disease, Cumulative Trauma Disorders, Cushing's Syndrome, Cytomegalic Inclusion Body Disease (CIBD), Cytomegalovirus Infection, Dancing Eyes-Dancing Feet Syndrome, Dandy-Walker Syndrome, Dawson Disease, De Morsier's Syndrome, Dejerine-Klumpke Palsy, Dementia—Multi-Infarct, Dementia—Subcortical, Dementia With Lewy Bodies, Dermatomyositis, Developmental Dyspraxia, Devic's Syndrome, Diabetic Neuropathy, Diffuse Sclerosis, Dravet's Syndrome, Dysautonomia, Dysgraphia, Dyslexia, Dysphagia, Dyspraxia, Dystonias, Early Infantile Epileptic Encephalopathy, Empty Sella Syndrome, Encephalitis Lethargica, Encephalitis and Meningitis, Encephaloceles, Encephalopathy, Encephalotrigeminal Angiomatosis, Epilepsy, Erb's Palsy, Erb-Duchenne and Dejerine-Klumpke Palsies, Fabry's Disease, Fahr's Syndrome, Fainting, Familial Dysautonomia, Familial Hemangioma, Familial Idiopathic Basal Ganglia Calcification, Familial Spastic Paralysis, Febrile Seizures (e.g., GEFS and GEFS plus), Fisher Syndrome, Floppy Infant Syndrome, Friedreich's Ataxia, Gaucher's Disease, Gerstmann's Syndrome, Gerstmann-Straussler-Scheinker Disease, Giant Cell Arteritis, Giant Cell Inclusion Disease, Globoid Cell Leukodystrophy, Glossopharyngeal Neuralgia, Guillain-Barre Syndrome, HTLV-1 Associated Myelopathy, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster Oticus, Herpes Zoster, Hirayama Syndrome, Holoprosencephaly, Huntington's Disease, Hydranencephaly, Hydrocephalus—Normal Pressure, Hydrocephalus, Hydromyelia, Hypercortisolism, Hypersomnia, Hypertonia, Hypotonia, Hypoxia, Immune-Mediated Encephalomyelitis, Inclusion Body Myositis, Incontinentia Pigmenti, Infantile Hypotonia, Infantile Phytanic Acid Storage Disease, Infantile Refsum Disease, Infantile Spasms, Inflammatory Myopathy, Intestinal Lipodystrophy, Intracranial Cysts, Intracranial Hypertension, Isaac's Syndrome, Joubert Syndrome, Kearns-Sayre Syndrome, Kennedy's Disease, Kinsbourne syndrome, Kleine-Levin syndrome, Klippel Feil Syndrome, Klippel-Trenaunay Syndrome (KTS), Klilver-Bucy Syndrome, Korsakoffs Amnesic Syndrome, Krabbe Disease, Kugelberg-Welander Disease, Kuru, Lambert-Eaton Myasthenic Syndrome, Landau-Kleffner Syndrome, Lateral Femoral Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lissencephaly, Locked-In Syndrome, Lou Gehrig's Disease, Lupus—Neurological Sequelae, Lyme Disease—Neurological Complications, Machado-Joseph Disease, Macrencephaly, Megalencephaly, Melkersson-Rosenthal Syndrome, Meningitis, Menkes Disease, Meralgia Paresthetica, Metachromatic Leukodystrophy, Microcephaly, Migraine, Miller Fisher Syndrome, Mini- Strokes, Mitochondrial Myopathies, Mobius Syndrome, Monomelic Amyotrophy, Motor Neuron Diseases, Moyamoya Disease, Mucolipidoses, Mucopolysaccharidoses, Multi-Infarct Dementia, Multifocal Motor Neuropathy, Multiple Sclerosis, Multiple System Atrophy with Orthostatic Hypotension, Multiple System Atrophy, Muscular Dystrophy, Myasthenia—Congenital, Myasthenia Gravis, Myelinoclastic Diffuse Sclerosis, Myoclonic Encephalopathy of Infants, Myoclonus, Myopathy—Congenital, Myopathy—Thyrotoxic, Myopathy, Myotonia Congenita, Myotonia, Narcolepsy, Neuroacanthocytosis, Neurodegeneration with Brain Iron Accumulation, Neurofibromatosis, Neuroleptic Malignant Syndrome, Neurological Complications of AIDS, Neurological Manifestations of Pompe Disease, Neuromyelitis Optica, Neuromyotonia, Neuronal Ceroid Lipofuscinosis, Neuronal Migration Disorders, Neuropathy—Hereditary, Neurosarcoidosis, Neurotoxicity, Nevus Cavernosus, Niemann-Pick Disease, O'Sullivan-McLeod Syndrome, Occipital Neuralgia, Occult Spinal Dysraphism Sequence, Ohtahara Syndrome, Olivopontocerebellar Atrophy, Opsoclonus Myoclonus, Orthostatic Hypotension, Overuse Syndrome, Pain—Chronic, Paraneoplastic Syndromes, Paresthesia, Parkinson's Disease, Parmyotonia Congenita, Paroxysmal Choreoathetosis, Paroxysmal Hemicrania, Parry-Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Pick's Disease, Piriformis Syndrome, Pituitary Tumors, Polymyositis, Pompe Disease, Porencephaly, Post-Polio Syndrome, Postherpetic Neuralgia, Postinfectious Encephalomyelitis, Postural Hypotension, Postural Orthostatic Tachycardia Syndrome, Postural Tachycardia Syndrome, Primary Lateral Sclerosis, Prion Diseases, Progressive Hemifacial Atrophy, Progressive Locomotor Ataxia, Progressive Multifocal Leukoencephalopathy, Progressive Sclerosing Poliodystrophy, Progressive Supranuclear Palsy, Pseudotumor Cerebri, Pyridoxine Dependent and Pyridoxine Responsive Siezure Disorders, Ramsay Hunt Syndrome Type I, Ramsay Hunt Syndrome Type II, Rasmussen's Encephalitis and other autoimmune epilepsies, Reflex Sympathetic Dystrophy Syndrome, Refsum Disease—Infantile, Refsum Disease, Repetitive Motion Disorders, Repetitive Stress Injuries, Restless Legs Syndrome, Retrovirus-Associated Myelopathy, Rett Syndrome, Reye's Syndrome, Riley-Day Syndrome, SUNCT Headache, Sacral Nerve Root Cysts, Saint Vitus Dance, Salivary Gland Disease, Sandhoff Disease, Schilder's Disease, Schizencephaly, Seizure Disorders, Septo-Optic Dysplasia, Severe Myoclonic Epilepsy of Infancy (SMEI), Shaken Baby Syndrome, Shingles, Shy-Drager Syndrome, Sjogren's Syndrome, Sleep Apnea, Sleeping Sickness, Soto's Syndrome, Spasticity, Spina Bifida, Spinal Cord Infarction, Spinal Cord Injury, Spinal Cord Tumors, Spinal Muscular Atrophy, Spinocerebellar Atrophy, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, Swallowing Disorders, Sydenham Chorea, Syncope, Syphilitic Spinal Sclerosis, Syringohydromyelia, Syringomyelia, Systemic Lupus Erythematosus, Tabes Dorsalis, Tardive Dyskinesia, Tarlov Cysts, Tay-Sachs Disease, Temporal Arteritis, Tethered Spinal Cord Syndrome, Thomsen Disease, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Tuberous Sclerosis, Vascular Erectile Tumor, Vasculitis including Temporal Arteritis, Von Economo's Disease, Von Hippel-Lindau disease (VHL), Von Recklinghausen's Disease, Wallenberg's Syndrome, Werdnig-Hoffman Disease, Wernicke-Korsakoff Syndrome, West Syndrome, Whipple's Disease, Williams Syndrome, Wilson's Disease, X-Linked Spinal and Bulbar Muscular Atrophy, and Zellweger Syndrome.

By "respiratory disease" is meant, any disease or condition affecting the respiratory tract, such as asthma, chronic obstructive pulmonary disease or "COPD", allergic rhinitis, sinusitis, pulmonary vasoconstriction, inflammation, allergies, impeded respiration, respiratory distress syndrome, cystic fibrosis, pulmonary hypertension, pulmonary vasoconstriction, emphysema, and any other respiratory disease, condition, trait, genotype or phenotype that can respond to the modulation of disease related gene expression in a cell or tissue, alone or in combination with other therapies.

By "cardiovascular disease" is meant and disease or condition affecting the heart and vasculature, inlcuding but not limited to, coronary heart disease (CHD), cerebrovascular disease (CVD), aortic stenosis, peripheral vascular disease, atherosclerosis, arteriosclerosis, myocardial infarction (heart attack), cerebrovascular diseases (stroke), transient ischaemic attacks (TIA), angina (stable and unstable), atrial fibrillation, arrhythmia, vavular disease, congestive heart failure, hypercholoesterolemia, type I hyperlipoproteinemia, type II hyperlipoproteinemia, type III hyperlipoproteinemia, type IV hyperlipoproteinemia, type V hyperlipoproteinemia, secondary hypertrigliceridemia, and familial lecithin cholesterol acyltransferase deficiency.

By "ocular disease" as used herein is meant, any disease, condition, trait, genotype or phenotype of the eye and related structures as is known in the art, such as Cystoid Macular Edema, Asteroid Hyalosis, Pathological Myopia and Posterior Staphyloma, Toxocariasis (Ocular Larva Migrans), Retinal Vein Occlusion, Posterior Vitreous Detachment, Tractional Retinal Tears, Epiretinal Membrane, Diabetic Retinopathy, Lattice Degeneration, Retinal Vein Occlusion, Retinal Artery Occlusion, Macular Degeneration (e.g., age related macular degeneration such as wet AMD or dry AMD), Toxoplasmosis, Choroidal Melanoma, Acquired Retinoschisis, Hollenhorst Plaque, Idiopathic Central Serous Chorioretinopathy, Macular Hole, Presumed Ocular Histoplasmosis Syndrome, Retinal Macroaneursym, Retinitis Pigmentosa, Retinal Detachment, Hypertensive Retinopathy, Retinal Pigment Epithelium (RPE) Detachment, Papillophlebitis, Ocular Ischemic Syndrome, Coats' Disease, Leber's Miliary Aneurysm, Conjunctival Neoplasms, Allergic Conjunctivitis, Vernal Conjunctivitis, Acute Bacterial Conjunctivitis, Allergic Conjunctivitis & Vernal Keratoconjunctivitis, Viral Conjunctivitis, Bacterial Conjunctivitis, Chlamydial & Gonococcal Conjunctivitis, Conjunctival Laceration, Episcleritis, Scleritis, Pingueculitis, Pterygium, Superior Limbic Keratoconjunctivitis (SLK of Theodore), Toxic Conjunctivitis, Conjunctivitis with Pseudomembrane, Giant Papillary Conjunctivitis, Terrien's Marginal Degeneration, Acanthamoeba Keratitis, Fungal Keratitis, Filamentary Keratitis, Bacterial Keratitis, Keratitis Sicca/Dry Eye Syndrome, Bacterial Keratitis, Herpes Simplex Keratitis, Sterile Corneal Infiltrates, Phlyctenulosis, Corneal Abrasion & Recurrent Corneal Erosion, Corneal Foreign Body, Chemical Burs, Epithelial Basement Membrane Dystrophy (EBMD), Thygeson's Superficial Punctate Keratopathy, Corneal Laceration, Salzmann's Nodular Degeneration, Fuchs' Endothelial Dystrophy, Crystalline Lens Subluxation, Ciliary-Block Glaucoma, Primary Open-Angle Glaucoma, Pigment Dispersion Syndrome and Pigmentary Glaucoma, Pseudoexfoliation Syndrom and Pseudoexfoliative Glaucoma, Anterior Uveitis, Primary Open Angle Glaucoma, Uveitic Glaucoma & Glaucomatocyclitic Crisis, Pigment Dispersion Syndrome & Pigmentary Glaucoma, Acute Angle Closure Glaucoma, Anterior Uveitis, Hyphema, Angle Recession Glaucoma, Lens Induced Glaucoma, Pseudoexfoliation Syndrome and Pseudoexfoliative Glaucoma, Axenfeld-Rieger Syndrome, Neovascular Glaucoma, Pars Planitis, Choroidal Rupture, Duane's Retraction Syndrome, Toxic/Nutritional Optic Neuropathy, Aberrant Regeneration of Cranial Nerve III, Intracranial Mass Lesions, Carotid-Cavernous Sinus Fistula, Anterior Ischemic Optic Neuropathy, Optic Disc Edema & Papilledema, Cranial Nerve III Palsy, Cranial Nerve IV Palsy, Cranial Nerve VI Palsy, Cranial Nerve VII (Facial Nerve) Palsy, Horner's Syndrome, Internuclear Opthalmoplegia, Optic Nerve Head Hypoplasia, Optic Pit, Tonic Pupil, Optic Nerve Head Drusen, Demyelinating Optic Neuropathy (Optic Neuritis, Retrobulbar Optic Neuritis), Amaurosis Fugax and Transient Ischemic Attack, Pseudotumor Cerebri, Pituitary Adenoma, Molluscum Contagiosum, Canaliculitis, Verruca and Papilloma, Pediculosis and Pthiriasis, Blepharitis, Hordeolum, Preseptal Cellulitis, Chalazion, Basal Cell Carcinoma, Herpes Zoster Ophthalmicus, Pediculosis & Phthiriasis, Blow-out Fracture, Chronic Epiphora, Dacryocystitis, Herpes Simplex Blepharitis, Orbital Cellulitis, Senile Entropion, and Squamous Cell Carcinoma.

By "metabolic disease" is meant any disease or condition affecting metabolic pathways as in known in the art. Metabolic disease can result in an abnormal metabolic process, either congenital due to inherited enzyme abnormality (inborn errors of metabolism) or acquired due to disease of an endocrine organ or failure of a metabolically important organ such as the liver. In one embodiment, metabolic disease includes obesity, insulin resistance, and diabetes (e.g., type I and/or type II diabetes).

By "dermatological disease" is meany any disease or condition of the skin, dermis, or any substructure therein such as hair, follicle, etc. Dermatological diseases, disorders, conditions, and traits can include psoriasis, ectopic dermatitis, skin cancers such as melanoma and basal cell carcinoma, hair loss, hair removal, alterations in pigmentation, and any other disease, condition, or trait associated with the skin, dermis, or structures therein.

By "auditory disease" is meany any disease or condition of the auditory system, including the ear, such as the inner ear, middle ear, outer ear, auditory nerve, and any substructures therein. Auditory diseases, disorders, conditions, and traits can include hearing loss, deafness, tinnitus, Meniere's Disease, vertigo, balance and motion disorders, and any other disease, condition, or trait associated with the ear, or structures therein.

In one embodiment of the present invention, each sequence of a siNA molecule of the invention is independently about 15 to about 30 nucleotides in length, in specific embodiments about 15, 16, 17, 18, 19, 20, 21, 22, 23, 24, 25, 26, 27, 28, 29, or 30 nucleotides in length. In another embodiment, the siNA duplexes of the invention independently comprise about 15 to about 30 base pairs (e.g., about 15, 16, 17, 18, 19, 20, 21, 22, 23, 24, 25, 26, 27, 28, 29, or 30). In another embodiment, one or more strands of the siNA molecule of the invention independently comprises about 15 to about 30 nucleotides (e.g., about 15, 16, 17, 18, 19, 20, 21, 22, 23, 24, 25, 26, 27, 28, 29, or 30) that are complementary to a target nucleic acid molecule. In yet another embodiment, siNA molecules of the invention comprising hairpin or circular structures are about 35 to about 55 (e.g., about 35, 40, 45, 50 or 55) nucleotides in length, or about 38 to about 44 (e.g., about 38, 39, 40, 41, 42, 43, or 44) nucleotides in length and comprising about 15 to about 25 (e.g., about 15, 16, 17, 18, 19, 20, 21, 22, 23, 24, or 25) base pairs.

As used herein "cell" is used in its usual biological sense, and does not refer to an entire multicellular organism, e.g., specifically does not refer to a human. The cell can be present in an organism, e.g., birds, plants and mammals such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell.

In one embodiment, a formulated molecular composition or formulated siNA composition of the invention is locally administered to relevant tissues ex vivo, or in vivo through direct injection, catheterization, or stenting (e.g., portal vein catherization/stenting).

In one embodiment, a formulated molecular composition or formulated siNA composition of the invention is systemically delivered to a subject or organism through parental administration as is known in the art, such as via intravenous, intramuscular, or subcutaneous injection.

In another aspect, the invention provides mammalian cells containing one or more formulated molecular composition or formulated siNA compositions of this invention. The one or more formulated molecular composition or formulated siNA compositions can independently be targeted to the same or different sites.

By "RNA" is meant a molecule comprising at least one ribonucleotide residue. By "ribonucleotide" is meant a nucleotide with a hydroxyl group at the 2' position of a β-D-ribofuranose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

By "subject" is meant an organism, which is a donor or recipient of explanted cells or the cells themselves. "Subject" also refers to an organism to which the nucleic acid molecules of the invention can be administered. A subject can be a mammal or mammalian cells, including a human or human cells.

The term "phosphorothioate" as used herein refers to an internucleotide linkage having Formula I, wherein Z and/or W comprise a sulfur atom. Hence, the term phosphorothioate refers to both phosphorothioate and phosphorodithioate internucleotide linkages.

The term "phosphonoacetate" as used herein refers to an internucleotide linkage having Formula I, wherein Z and/or W comprise an acetyl or protected acetyl group.

The term "thiophosphonoacetate" as used herein refers to an internucleotide linkage having Formula I, wherein Z comprises an acetyl or protected acetyl group and W comprises a sulfur atom or alternately W comprises an acetyl or protected acetyl group and Z comprises a sulfur atom.

The term "universal base" as used herein refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see for example Loakes, 2001, *Nucleic Acids Research*, 29, 2437-2447).

The term "acyclic nucleotide" as used herein refers to any nucleotide having an acyclic ribose sugar, for example where any of the ribose carbons (C1, C2, C3, C4, or C5), are independently or in combination absent from the nucleotide.

In a further embodiment, the formulated molecular compositions and formulated siNA compositions can be used in combination with other known treatments to inhibit, reduce, or prevent diseases, traits, and conditions described herein or otherwise known in the art in a subject or organism. For example, the described molecules could be used in combination with one or more known compounds, treatments, or procedures to inhibit, reduce, or prevent diseases, traits, and conditions described herein or otherwise known in the art in a subject or organism. In a non-limiting example, formulated molecular composition and formulated siNA compositions that are used to treat HCV infection and comorbid conditions that are associated with HBV infection are used in combination with other HCV treatments, such as HCV vaccines; anti-HCV antibodies such as HepeX-C and Civacir; protease inhibitors such as VX-950; pegylated interferons such as PEG-Intron, and/or other antivirals such as Ribavirin and/or Valopicitabine.

In one embodiment, a formulated siNA composition of the invention comprises an expression vector comprising a nucleic acid sequence encoding at least one polynucleotide molecule of the invention (e.g., siNA, antisense, aptamer, decoy, ribozyme, 2-5A, triplex forming oligonucleotide, or other nucleic acid molecule) in a manner which allows expression of the siNA molecule. For example, the vector can contain sequence(s) encoding both strands of a siNA molecule comprising a duplex. The vector can also contain sequence(s) encoding a single nucleic acid molecule that is self-complementary and thus forms a siNA molecule. Non-limiting examples of such expression vectors are described in Paul et al., 2002, *Nature Biotechnology*, 19, 505; Miyagishi and Taira, 2002, *Nature Biotechnology*, 19, 497; Lee et al., 2002, *Nature Biotechnology*, 19, 500; and Novina et al., 2002, *Nature Medicine*, advance online publication doi:10.1038/nm725. In one embodiment, an expression vector of the invention comprises a nucleic acid sequence encoding two or more siNA molecules, which can be the same or different.

In another aspect of the invention, polynucleotides of the invention such as siNA molecules that interact with target RNA molecules and down-regulate gene encoding target RNA molecules (for example target RNA molecules referred to by Genbank Accession numbers herein) are expressed from transcription units inserted into DNA or RNA vectors. The recombinant vectors can be DNA plasmids or viral vectors. Polynucleotide expressing viral vectors can be constructed based on, but not limited to, adeno-associated virus, retrovirus, adenovirus, or alphavirus. The recombinant vectors capable of expressing the polynucleotide molecules can be delivered as described herein, and persist in target cells. Alternatively, viral vectors can be used that provide for transient expression of polynucleotide molecules. Such vectors can be repeatedly administered as necessary. For example, once expressed, the siNA molecules bind and down-regulate gene function or expression via RNA interference (RNAi). Delivery of formulated molecular compositions expressing vectors can be systemic, such as by intravenous or intramuscular administration, by administration to target cells explanted from a subject followed by reintroduction into the subject, or by any other means that would allow for introduction into the desired target cell.

By "vectors" is meant any nucleic acid- and/or viral-based technique used to deliver a desired nucleic acid.

Other features and advantages of the invention will be apparent from the following description of the preferred embodiments thereof, and from the claims.

BRIEF DESCRIPTION OF THE DRAWINGS

FIG. 7 shows a schematic diagram of the lamellar structure and inverted hexagonal structure that can be adopted by a formulated molecular composition.

FIG. 14 shows a non-limiting example of chemical modifications of siNA molecules of the invention.

FIG. 44 shows a non-limiting example of LNP formulated siNA mediated inhibition of huntingtin (htt) gene expression in vivo. Using Alzet osmotic pumps, siNAs encapsulated in LNPs were infused into mouse lateral ventrical or striatum for 7 or 14 days, respectively, at concentrations ranging from 0.1 to 1 mg/ml (total dose ranging from 8.4 to 84 µg). Animals treated with active siNA formulated with LNP-098 or LNP-061 were compared to mismatch control siNA formulated with LNP-061 and untreated animal controls. Huntingtin (htt) gene expression levels were determined by QPCR.

DETAILED DESCRIPTION OF THE INVENTION

Figure 1:
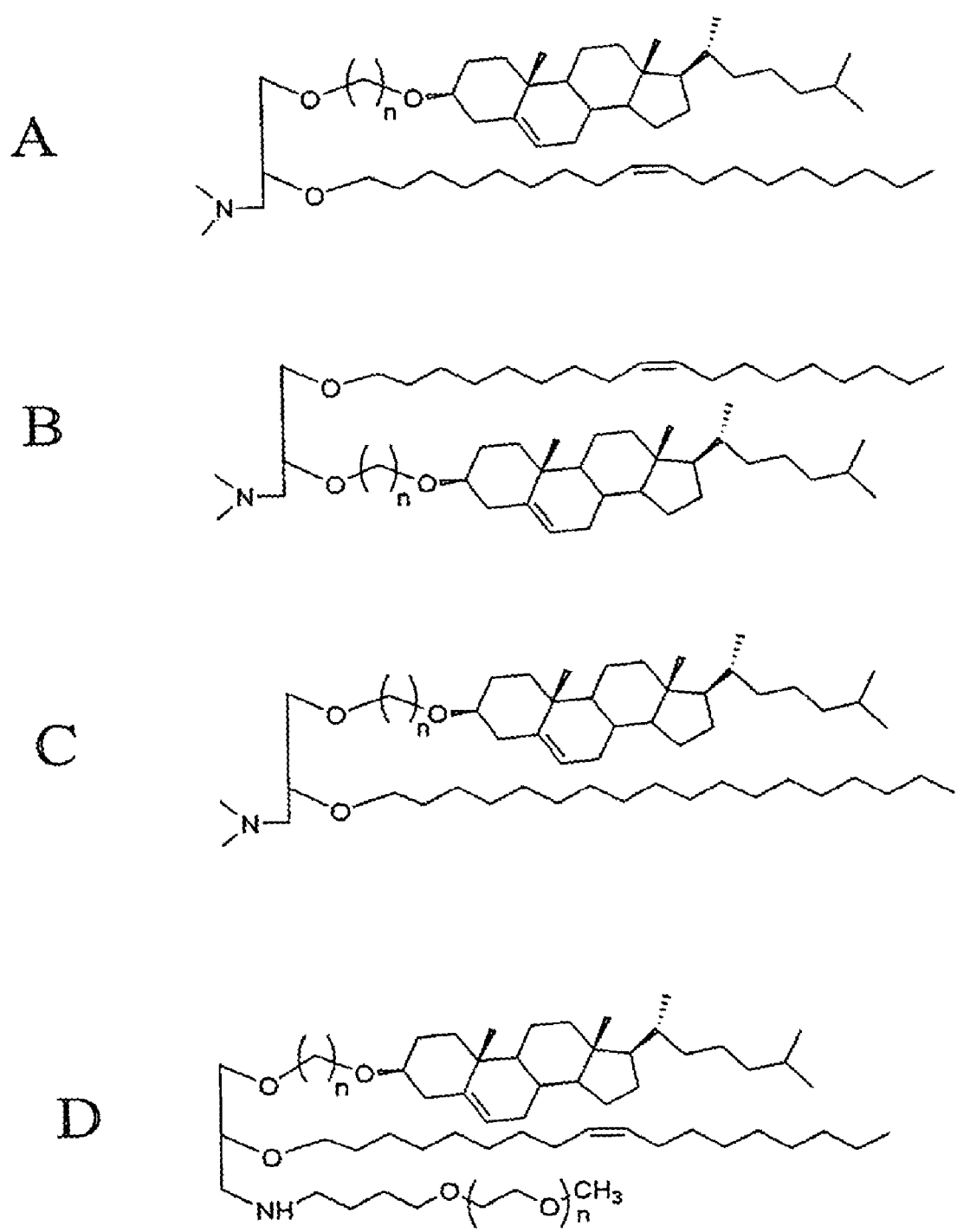
FIG. 1 shows non-limiting examples of cationic lipid compounds of the invention.
Figure 2:
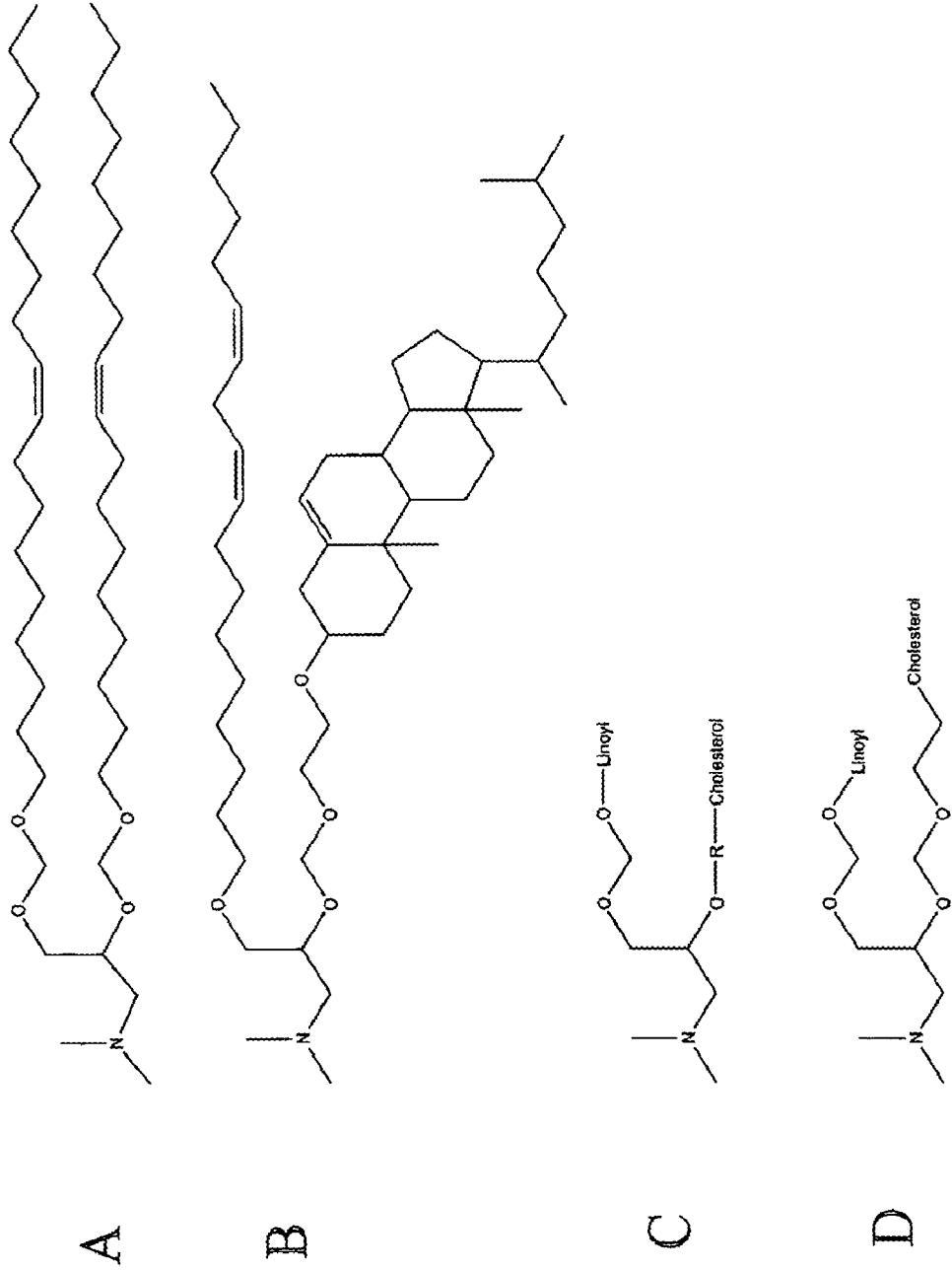
FIG. 2 shows non-limiting examples of acetal linked cationic lipid compounds of the invention.
Figure 3:
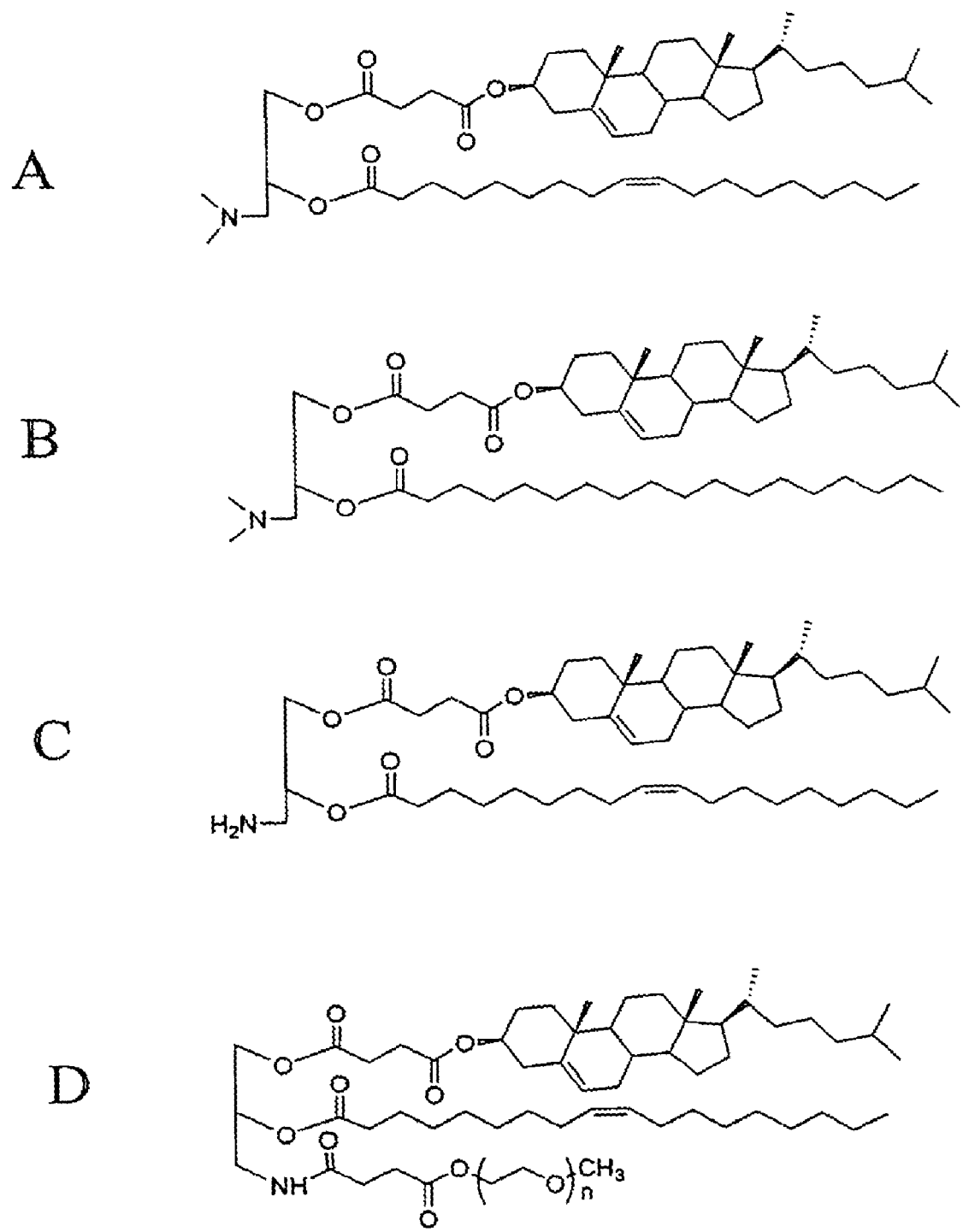
FIG. 3 shows non-limiting examples of succinyl/acyl linked cationic lipid compounds of the invention.
Figure 4:
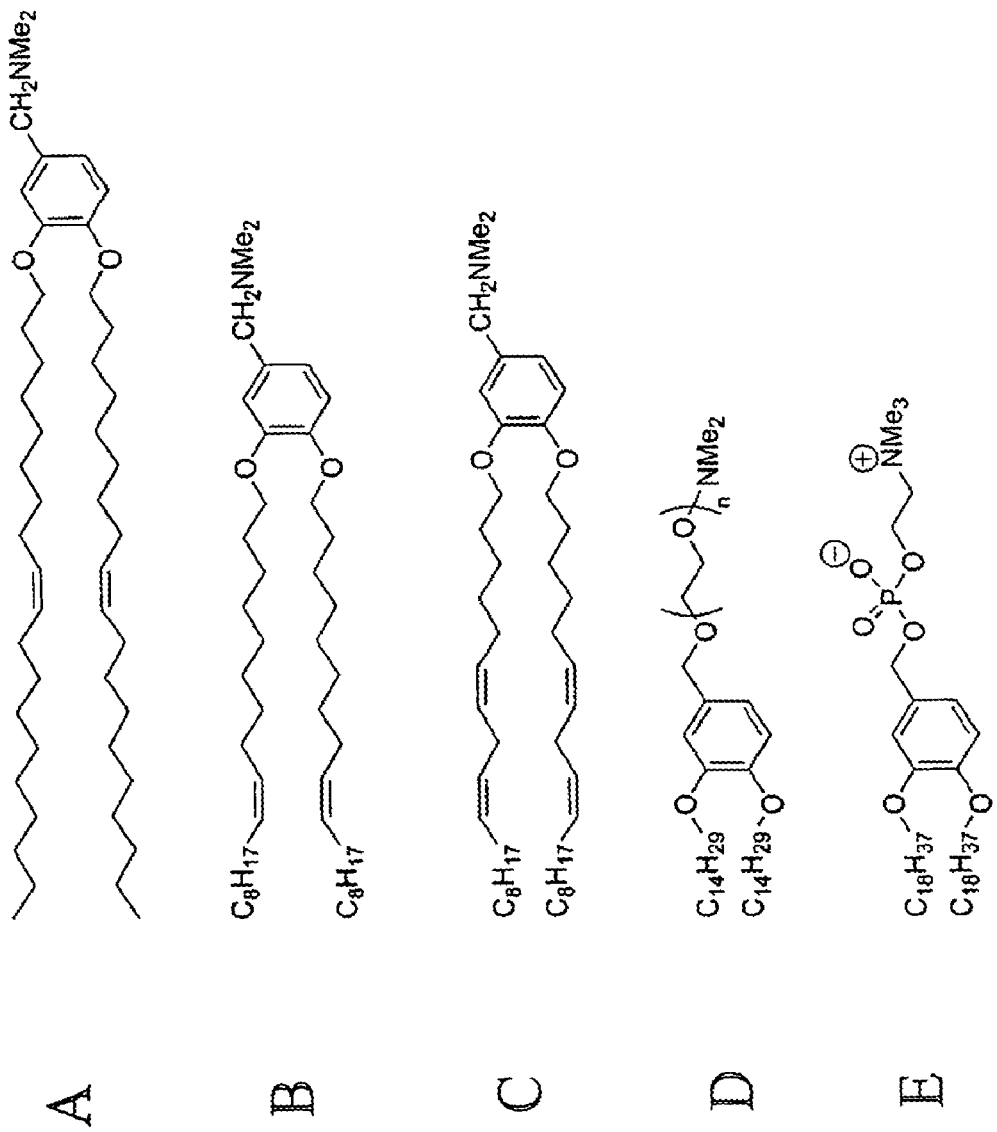
FIG. 4 shows non-limiting examples of aromatic cationic lipid compounds of the invention.
Figure 5:
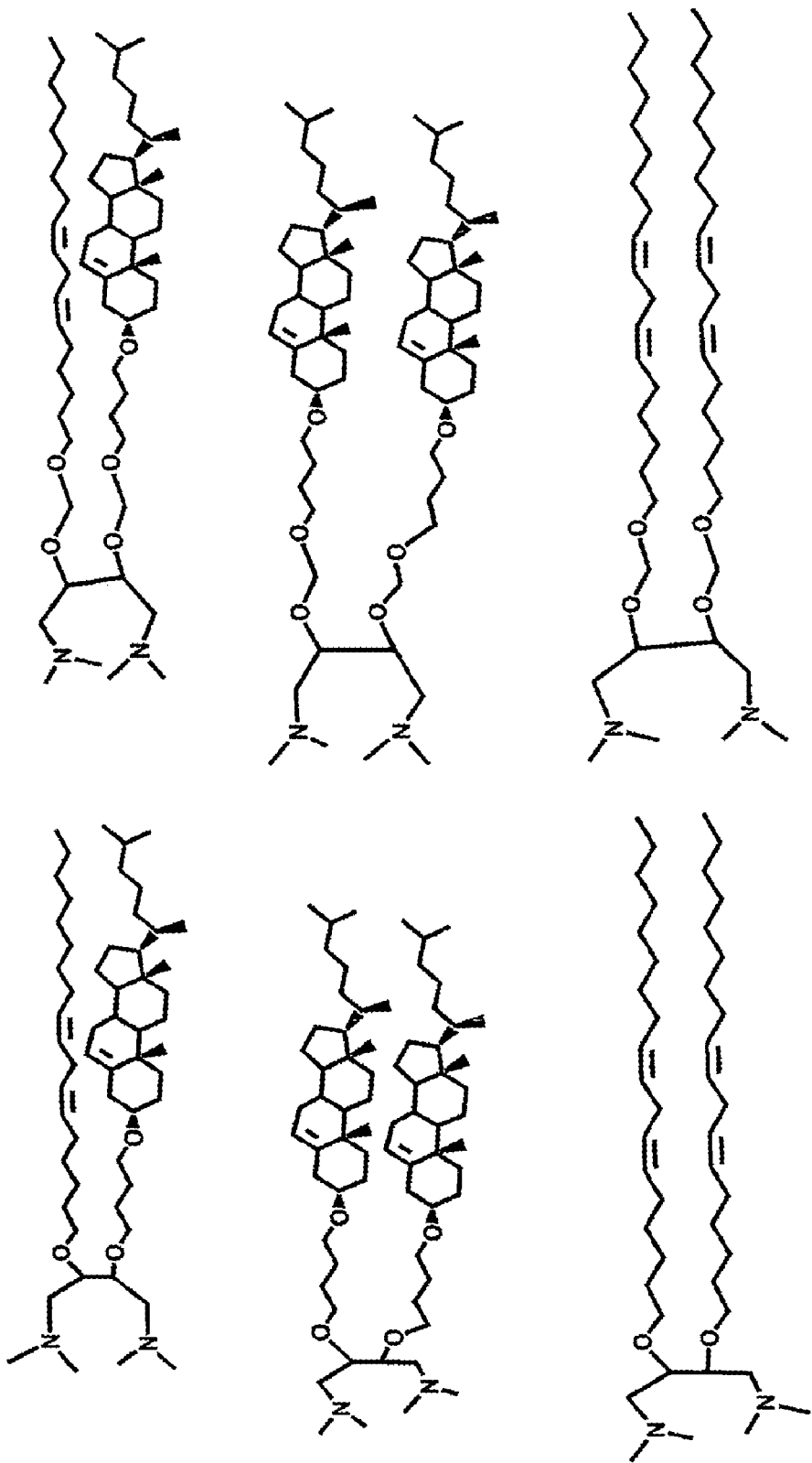
FIG. 5 shows non-limiting examples of additional cationic lipid compounds of the invention.
Figure 6:
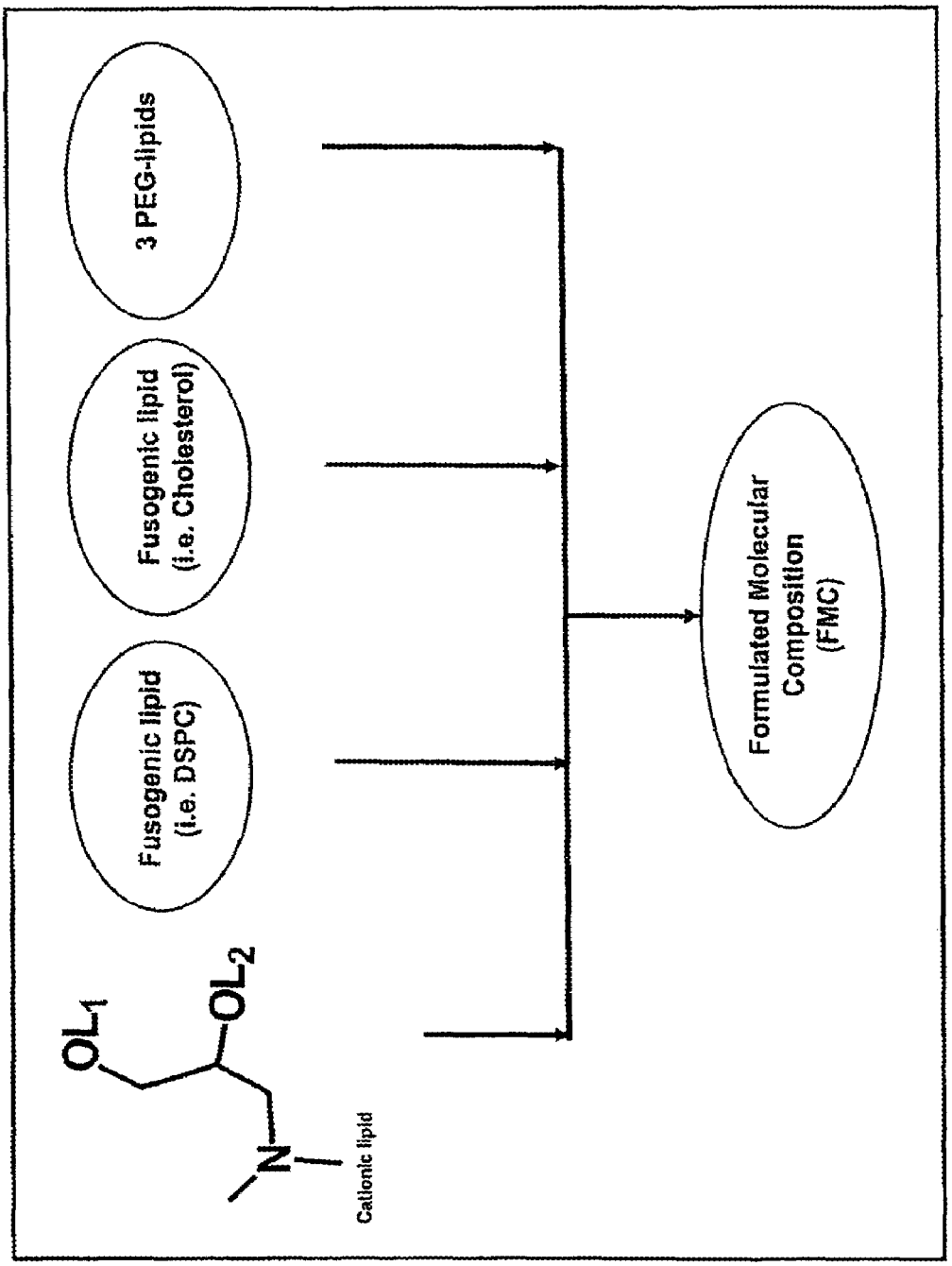
FIG. 6 shows a schematic of the components of a formulated molecular composition.

Mechanism of Action of Nucleic Acid Molecules of the Invention

Aptamer: Nucleic acid aptamers can be selected to specifically bind to a particular ligand of interest (see for example Gold et al., U.S. Pat. No. 5,567,588 and U.S. Pat. No. 5,475,096, Gold et al., 1995, *Annu. Rev. Biochem.*, 64, 763; Brody and Gold, 2000, *J. Biotechnol.*, 74, 5; Sun, 2000, *Curr. Opin. Mol. Ther.*, 2, 100; Kusser, 2000, *J. Biotechnol.*, 74, 27; Hermann and Patel, 2000, *Science*, 287, 820; and Jayasena, 1999, *Clinical Chemistry*, 45, 1628). For example, the use of in vitro selection can be applied to evolve nucleic acid aptamers with binding specificity for CylA. Nucleic acid aptamers can include chemical modifications and linkers as described herein. Nucleic apatmers of the invention can be double stranded or single stranded and can comprise one distinct nucleic acid sequence or more than one nucleic acid sequences complexed with one another. Aptamer molecules of the invention that bind to CylA, can modulate the protease activity of CylA and subsequent activation of cytolysin, and therefore modulate the acute toxicity associated with enterococcal infection.

Antisense: Antisense molecules can be modified or unmodified RNA, DNA, or mixed polymer oligonucleotides and primarily function by specifically binding to matching sequences resulting in modulation of peptide synthesis (Wu-Pong, November 1994, *BioPharm*, 20-33). The antisense oligonucleotide binds to target RNA by Watson Crick base-pairing and blocks gene expression by preventing ribosomal translation of the bound sequences either by steric blocking or by activating RNase H enzyme. Antisense molecules may also alter protein synthesis by interfering with RNA processing or transport from the nucleus into the cytoplasm (Mukhopadhyay & Roth, 1996, *Crit. Rev. in Oncogenesis* 7, 151-190).

In addition, binding of single stranded DNA to RNA may result in nuclease degradation of the heteroduplex (Wu-Pong, supra; Crooke, supra). To date, the only backbone modified DNA chemistry which will act as substrates for RNase H are phosphorothioates, phosphorodithioates, and borontrifluoridates. Recently, it has been reported that 2'-arabino and 2'-fluoro arabino- containing oligos can also activate RNase H activity.

A number of antisense molecules have been described that utilize novel configurations of chemically modified nucleotides, secondary structure, and/or RNase H substrate domains (Woolf et al., U.S. Pat. No. 5,989,912; Thompson et al., U.S. Ser. No. 60/082,404 which was filed on Apr. 20, 1998; Hartmann et al., U.S. Ser. No. 60/101,174 which was filed on Sep. 21, 1998) all of these are incorporated by reference herein in their entirety.

Antisense DNA can be used to target RNA by means of DNA-RNA interactions, thereby activating RNase H, which digests the target RNA in the duplex. Antisense DNA can be chemically synthesized or can be expressed via the use of a single stranded DNA intracellular expression vector or the equivalent thereof.

Triplex Forming Oligonucleotides (TFO): Single stranded oligonucleotide can be designed to bind to genomic DNA in a sequence specific manner. TFOs can be comprised of pyrimidine-rich oligonucleotides which bind DNA helices through Hoogsteen Base-pairing (Wu-Pong, supra). In addition, TFOs can be chemically modified to increase binding affinity to target DNA sequences. The resulting triple helix composed of the DNA sense, DNA antisense, and TFO disrupts RNA synthesis by RNA polymerase. The TFO mechanism can result in gene expression or cell death since binding may be irreversible (Mukhopadhyay & Roth, supra)

2'-5' Oligoadenylates: The 2-5A system is an interferon-mediated mechanism for RNA degradation found in higher vertebrates (Mitra et al., 1996, *Proc Nat Acad Sci USA* 93, 6780-6785). Two types of enzymes, 2-5A synthetase and RNase L, are required for RNA cleavage. The 2-5A synthetases require double stranded RNA to form 2'-5' oligoadenylates (2-5A). 2-5A then acts as an allosteric effector for utilizing RNase L, which has the ability to cleave single stranded RNA. The ability to form 2-5A structures with double stranded RNA makes this system particularly useful for modulation of viral replication.

(2'-5') oligoadenylate structures can be covalently linked to antisense molecules to form chimeric oligonucleotides capable of RNA cleavage (Torrence, supra). These molecules putatively bind and activate a 2-5A-dependent RNase, the oligonucleotide/enzyme complex then binds to a target RNA molecule which can then be cleaved by the RNase enzyme. The covalent attachment of 2'-5' oligoadenylate structures is not limited to antisense applications, and can be further elaborated to include attachment to nucleic acid molecules of the instant invention.

Enzymatic Nucleic Acid: Several varieties of naturally occurring enzymatic RNAs are presently known (Doherty and Doudna, 2001, *Annu. Rev. Biophys. Biomol. Struct.*, 30, 457-475; Symons, 1994, *Curr. Opin. Struct. Biol.*, 4, 322-30). In addition, several in vitro selection (evolution) strategies (Orgel, 1979, *Proc. R. Soc. London, B* 205, 435) have been used to evolve new nucleic acid catalysts capable of catalyzing cleavage and ligation of phosphodiester linkages (Joyce, 1989, *Gene*, 82, 83-87; Beaudry et al., 1992, *Science* 257, 635-641; Joyce, 1992, *Scientific American* 267, 90-97; Breaker et al., 1994, *TIBTECH* 12, 268; Bartel et al., 1993, *Science* 261:1411-1418; Szostak, 1993, *TIBS* 17, 89-93; Kumar et al., 1995, *FASEB J.*, 9, 1183; Breaker, 1996, *Curr. Op. Biotech.*, 7, 442; Santoro et al., 1997, *Proc. Natl. Acad. Sci.*, 94, 4262; Tang et al., 1997, *RNA* 3, 914; Nakamaye & Eckstein, 1994, supra; Long & Uhlenbeck, 1994, supra; Ishizaka et al., 1995, supra; Vaish et al., 1997, *Biochemistry* 36, 6495). Each can catalyze a series of reactions including the hydrolysis of phosphodiester bonds in trans (and thus can cleave other RNA molecules) under physiological conditions.

The enzymatic nature of an enzymatic nucleic acid has significant advantages, such as the concentration of nucleic acid necessary to affect a therapeutic treatment is low. This advantage reflects the ability of the enzymatic nucleic acid molecule to act enzymatically. Thus, a single enzymatic nucleic acid molecule is able to cleave many molecules of target RNA. In addition, the enzymatic nucleic acid molecule is a highly specific modulator, with the specificity of modulation depending not only on the base-pairing mechanism of binding to the target RNA, but also on the mechanism of target RNA cleavage. Single mismatches, or base-substitutions, near the site of cleavage can be chosen to completely eliminate catalytic activity of an enzymatic nucleic acid molecule.

Nucleic acid molecules having an endonuclease enzymatic activity are able to repeatedly cleave other separate RNA molecules in a nucleotide base sequence-specific manner. With proper design and construction, such enzymatic nucleic acid molecules can be targeted to any RNA transcript, and efficient cleavage achieved in vitro (Zaug et al., 324, *Nature* 429 1986; Uhlenbeck, 1987 *Nature* 328, 596; Kim et al., 84 *Proc. Natl. Acad. Sci. USA* 8788, 1987; Dreyfus, 1988, *Einstein Quart. J. Bio. Med.*, 6, 92; Haseloff and Gerlach, 334 *Nature* 585, 1988; Cech, 260 *JAMA* 3030, 1988; and Jefferies et al., 17 *Nucleic Acids Research* 1371, 1989; Chartrand et al., 1995, *Nucleic Acids Research* 23, 4092; Santoro et al., 1997, *PNAS* 94, 4262).

Because of their sequence specificity, trans-cleaving enzymatic nucleic acid molecules show promise as therapeutic agents for human disease (Usman & McSwiggen, 1995 *Ann. Rep. Med. Chem.* 30, 285-294; Christoffersen and Marr, 1995 *J. Med. Chem.* 38, 2023-2037). Enzymatic nucleic acid molecule can be designed to cleave specific RNA targets within the background of cellular RNA. Such a cleavage event renders the RNA non-functional and abrogates protein expression from that RNA. In this manner, synthesis of a protein associated with a disease state can be selectively modulated (Warashina et al., 1999, *Chemistry and Biology*, 6, 237-250).

The present invention also features nucleic acid sensor molecules or allozymes having sensor domains comprising nucleic acid decoys and/or aptamers of the invention. Interaction of the nucleic acid sensor molecule's sensor domain with a molecular target can activate or inactivate the enzymatic nucleic acid domain of the nucleic acid sensor molecule, such that the activity of the nucleic acid sensor molecule is modulated in the presence of the target-signaling molecule. The nucleic acid sensor molecule can be designed to be active in the presence of the target molecule or alternately, can be designed to be inactive in the presence of the molecular target. For example, a nucleic acid sensor molecule is designed with a sensor domain comprising an aptamer with binding specificity for a ligand. In a non-limiting example, interaction of the ligand with the sensor domain of the nucleic acid sensor molecule can activate the enzymatic nucleic acid domain of the nucleic acid sensor molecule such that the sensor molecule catalyzes a reaction, for example cleavage of RNA that encodes the ligand. In this example, the nucleic acid sensor molecule is activated in the presence of ligand, and can be used as a therapeutic to treat a disease or condition associated with the ligand. Alternately, the reaction can comprise cleavage or ligation of a labeled nucleic acid reporter molecule, providing a useful diagnostic reagent to detect the presence of ligand in a system.

RNA interference: The discussion that follows discusses the proposed mechanism of RNA interference mediated by short interfering RNA as is presently known, and is not meant to be limiting and is not an admission of prior art. Applicant demonstrates herein that chemically-modified short interfering nucleic acids possess similar or improved capacity to mediate RNAi as do siRNA molecules and are expected to possess improved stability and activity in vivo; therefore, this discussion is not meant to be limiting only to siRNA and can be applied to siNA as a whole. By "improved capacity to mediate RNAi" or "improved RNAi activity" is meant to include RNAi activity measured in vitro and/or in vivo where the RNAi activity is a reflection of both the ability of the siNA to mediate RNAi and the stability of the siNAs of the invention. In this invention, the product of these activities can be increased in vitro and/or in vivo compared to an all RNA siRNA or a siNA containing a plurality of ribonucleotides. In some cases, the activity or stability of the siNA molecule can be decreased (i.e., less than ten-fold), but the overall activity of the siNA molecule is enhanced in vitro and/or in vivo.

RNA interference refers to the process of sequence specific post-transcriptional gene silencing in animals mediated by short interfering RNAs (siRNAs) (Fire et al., 1998, *Nature*, 391, 806). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes which is commonly shared by diverse flora and phyla (Fire et al., 1999, *Trends Genet.*, 15, 358). Such protection from foreign gene expression may have evolved in response to the production of double-stranded RNAs (dsRNAs) derived from viral infection or the random integration of transposon elements into a host genome via a cellular response that specifically destroys homologous single-stranded RNA or viral genomic RNA. The presence of dsRNA in cells triggers the RNAi response though a mechanism that has yet to be fully characterized. This mechanism appears to be different from the interferon response that results from dsRNA-mediated activation of protein kinase PKR and 2',5'-oligoadenylate synthetase resulting in non-specific cleavage of mRNA by ribonuclease L.

The presence of long dsRNAs in cells stimulates the activity of a ribonuclease III enzyme referred to as Dicer. Dicer is involved in the processing of the dsRNA into short pieces of dsRNA known as short interfering RNAs (siRNAs) (Berstein et al., 2001, *Nature,* 409, 363). Short interfering RNAs derived from Dicer activity are typically about 21 to about 23 nucleotides in length and comprise about 19 base pair duplexes. Dicer has also been implicated in the excision of 21- and 22-nucleotide small temporal RNAs (stRNAs) from precursor RNA of conserved structure that are implicated in translational control (Hutvagner et al., 2001, *Science,* 293, 834). The RNAi response also features an endonuclease complex containing a siRNA, commonly referred to as an RNA-induced silencing complex (RISC), which mediates cleavage of single-stranded RNA having sequence homologous to the siRNA. Cleavage of the target RNA takes place in the middle of the region complementary to the guide sequence of the siRNA duplex (Elbashir et al., 2001, *Genes Dev.,* 15, 188). In addition, RNA interference can also involve small RNA (e.g., micro-RNA or miRNA) mediated gene silencing, presumably though cellular mechanisms that regulate chromatin structure and thereby prevent transcription of target gene sequences (see for example Allshire, 2002, *Science,* 297, 1818-1819; Volpe et al., 2002, *Science,* 297, 1833-1837; Jenuwein, 2002, *Science,* 297, 2215-2218; and Hall et al., 2002, *Science,* 297, 2232-2237). As such, siNA molecules of the invention can be used to mediate gene silencing via interaction with RNA transcripts or alternately by interaction with particular gene sequences, wherein such interaction results in gene silencing either at the transcriptional level or post-transcriptional level.

RNAi has been studied in a variety of systems. Fire et al., 1998, *Nature,* 391, 806, were the first to observe RNAi in *C. elegans*. Wianny and Goetz, 1999, *Nature Cell Biol.,* 2, 70, describe RNAi mediated by dsRNA in mouse embryos. Hammond et al., 2000, *Nature,* 404, 293, describe RNAi in *Drosophila* cells transfected with dsRNA. Elbashir et al., 2001, *Nature,* 411, 494, describe RNAi induced by introduction of duplexes of synthetic 21-nucleotide RNAs in cultured mammalian cells including human embryonic kidney and HeLa cells. Recent work in *Drosophila* embryonic lysates has revealed certain requirements for siRNA length, structure, chemical composition, and sequence that are essential to mediate efficient RNAi activity. These studies have shown that 21 nucleotide siRNA duplexes are most active when containing two 2-nucleotide 3'-terminal nucleotide overhangs. Furthermore, substitution of one or both siRNA strands with 2'-deoxy or 2'-O-methyl nucleotides abolishes RNAi activity, whereas substitution of 3'-terminal siRNA nucleotides with deoxy nucleotides was shown to be tolerated. Mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end (Elbashir et al., 2001, *EMBO J.,* 20, 6877). Other studies have indicated that a 5'-phosphate on the target-complementary strand of a siRNA duplex is required for siRNA activity and that ATP is utilized to maintain the 5'-phosphate moiety on the siRNA (Nykanen et al., 2001, *Cell,* 107, 309); however, siRNA molecules lacking a 5'-phosphate are active when introduced exogenously, suggesting that 5'-phosphorylation of siRNA constructs may occur in vivo.

Synthesis of Nucleic Acid Molecules

Synthesis of nucleic acids greater than 100 nucleotides in length is difficult using automated methods and the therapeutic cost of such molecules is prohibitive. In this invention, small nucleic acid motifs ("small" refers to nucleic acid motifs no more than 100 nucleotides in length, preferably no more than 80 nucleotides in length, and most preferably no more than 50 nucleotides in length; e.g., individual siNA oligonucleotide sequences or siNA sequences synthesized in tandem) are preferably used for exogenous delivery. The simple structure of these molecules increases the ability of the nucleic acid to invade targeted regions of protein and/or RNA structure. Exemplary molecules of the instant invention are chemically synthesized, and others can similarly be synthesized.

Oligonucleotides (e.g., certain modified oligonucleotides or portions of oligonucleotides lacking ribonucleotides) are synthesized using protocols known in the art, for example as described in Caruthers et al., 1992, *Methods in Enzymology* 211, 3-19, Thompson et al., International PCT Publication No. WO 99/54459, Wincott et al., 1995, *Nucleic Acids Res.* 23, 2677-2684, Wincott et al., 1997, *Methods Mol. Bio.,* 74, 59, Brennan et al., 1998, *Biotechnol Bioeng.,* 61, 33-45, and Brennan, U.S. Pat. No. 6,001,311. All of these references are incorporated herein by reference. The synthesis of oligonucleotides makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 μmol scale protocol with a 2.5 min coupling step for 2'-O-methylated nucleotides and a 45 second coupling step for 2'-deoxy nucleotides or 2'-deoxy-2'-fluoro nucleotides. Table II outlines the amounts and the contact times of the reagents used in the synthesis cycle. Alternatively, syntheses at the 0.2 μmol scale can be performed on a 96-well plate synthesizer, such as the instrument produced by Protogene (Palo Alto, Calif.) with minimal modification to the cycle. A 33-fold excess (60 μL of 0.11 M=6.6 μmol) of 2'-O-methyl phosphoramidite and a 105-fold excess of S-ethyl tetrazole (60 μL of 0.25 M=15 μmol) can be used in each coupling cycle of 2'-O-methyl residues relative to polymer-bound 5'-hydroxyl. A 22-fold excess (40 μL of 0.11 M=4.4 μmol) of deoxy phosphoramidite and a 70-fold excess of S-ethyl tetrazole (40 μL of 0.25 M=10 μmol) can be used in each coupling cycle of deoxy residues relative to polymer-bound 5'-hydroxyl. Average coupling yields on the 394 Applied Biosystems, Inc. synthesizer, determined by calorimetric quantitation of the trityl fractions, are typically 97.5-99%. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF (ABI); and oxidation solution is 16.9 mM $I_2$, 49 mM pyridine, 9% water in THF (PerSeptive Biosystems, Inc.). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide, 0.05 M in acetonitrile) is used.

Deprotection of the DNA-based oligonucleotides is performed as follows: the polymer-bound trityl-on oligoribonucleotide is transferred to a 4 mL glass screw top vial and suspended in a solution of 40% aqueous methylamine (1 mL) at 65° C. for 10 minutes. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder.

The method of synthesis used for RNA including certain siNA molecules of the invention follows the procedure as described in Usman et al., 1987, *J. Am. Chem. Soc.*, 109, 7845; Scaringe et al., 1990, *Nucleic Acids Res.*, 18, 5433; and Wincott et al., 1995, *Nucleic Acids Res.* 23, 2677-2684 Wincott et al., 1997, *Methods Mol. Bio.*, 74, 59, and makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 μmol scale protocol with a 7.5 min coupling step for alkylsilyl protected nucleotides and a 2.5 min coupling step for 2'-O-methylated nucleotides. Table II outlines the amounts and the contact times of the reagents used in the synthesis cycle. Alternatively, syntheses at the 0.2 μmol scale can be done on a 96-well plate synthesizer, such as the instrument produced by Protogene (Palo Alto, Calif.) with minimal modification to the cycle. A 33-fold excess (60 μL of 0.11 M=6.6 μmol) of 2'-O-methyl phosphoramidite and a 75-fold excess of S-ethyl tetrazole (60 μL of 0.25 M=15 μmol) can be used in each coupling cycle of 2'-O-methyl residues relative to polymer-bound 5'-hydroxyl. A 66-fold excess (120 μL of 0.11 M=13.2 μmol) of alkylsilyl (ribo) protected phosphoramidite and a 150-fold excess of S-ethyl tetrazole (120 μL of 0.25 M=30 μmol) can be used in each coupling cycle of ribo residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/ 10% 2,6-lutidine in THF (ABI); oxidation solution is 16.9 mM $I_2$, 49 mM pyridine, 9% water in THF (PerSeptive Biosystems, Inc.). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide 0.05 M in acetonitrile) is used.

Deprotection of the RNA is performed using either a two-pot or one-pot protocol. For the two-pot protocol, the polymer-bound trityl-on oligoribonucleotide is transferred to a 4 mL glass screw top vial and suspended in a solution of 40% aq. methylamine (1 mL) at 65° C. for 10 min. After cooling to −20° C., the supernatant is removed from the polymer support. The support is washed three times with 1.0 mL of EtOH: MeCN:H2O/3:1:1, vortexed and the supernatant is then added to the first supernatant. The combined supernatants, containing the oligoribonucleotide, are dried to a white powder. The base deprotected oligoribonucleotide is resuspended in anhydrous TEA/HF/NMP solution (300 μL of a solution of 1.5 mL N-methylpyrrolidinone, 750 μL TEA and 1 mL TEA.3HF to provide a 1.4 M HF concentration) and heated to 65° C. After 1.5 h, the oligomer is quenched with 1.5 M $NH_4HCO_3$.

Alternatively, for the one-pot protocol, the polymer-bound trityl-on oligoribonucleotide is transferred to a 4 mL glass screw top vial and suspended in a solution of 33% ethanolic methylamine/DMSO: 1/1 (0.8 mL) at 65° C. for 15 minutes. The vial is brought to room temperature TEA.3HF (0.1 mL) is added and the vial is heated at 65° C. for 15 minutes. The sample is cooled at −20° C. and then quenched with 1.5 M $NH_4HCO_3$.

For purification of the trityl-on oligomers, the quenched $NH_4HCO_3$ solution is loaded onto a C-18 containing cartridge that had been prewashed with acetonitrile followed by 50 mM TEAA. After washing the loaded cartridge with water, the RNA is detritylated with 0.5% TFA for 13 minutes. The cartridge is then washed again with water, salt exchanged with 1 M NaCl and washed with water again. The oligonucleotide is then eluted with 30% acetonitrile.

The average stepwise coupling yields are typically >98% (Wincott et al., 1995 *Nucleic Acids Res.* 23, 2677-2684). Those of ordinary skill in the art will recognize that the scale of synthesis can be adapted to be larger or smaller than the example described above including but not limited to 96-well format.

Alternatively, the nucleic acid molecules of the present invention can be synthesized separately and joined together post-synthetically, for example, by ligation (Moore et al., 1992, *Science* 256, 9923; Draper et al., International PCT publication No. WO 93/23569; Shabarova et al., 1991, *Nucleic Acids Research* 19, 4247; Bellon et al., 1997, *Nucleosides & Nucleotides,* 16, 951; Bellon et al., 1997, *Bioconjugate Chem.* 8, 204), or by hybridization following synthesis and/or deprotection.

The siNA molecules of the invention can also be synthesized via a tandem synthesis methodology as described in Example 1 herein, wherein both siNA strands are synthesized as a single contiguous oligonucleotide fragment or strand separated by a cleavable linker which is subsequently cleaved to provide separate siNA fragments or strands that hybridize and permit purification of the siNA duplex. The linker can be a polynucleotide linker or a non-nucleotide linker. The tandem synthesis of siNA as described herein can be readily adapted to both multiwell/multiplate synthesis platforms such as 96 well or similarly larger multi-well platforms. The tandem synthesis of siNA as described herein can also be readily adapted to large scale synthesis platforms employing batch reactors, synthesis columns and the like.

A siNA molecule can also be assembled from two distinct nucleic acid strands or fragments wherein one fragment includes the sense region and the second fragment includes the antisense region of the RNA molecule.

The nucleic acid molecules of the present invention can be modified extensively to enhance stability by modification with nuclease resistant groups, for example, 2'-amino, 2'-C-allyl, 2'-fluoro, 2'-O-methyl, 2'-H (for a review see Usman and Cedergren, 1992, *TIBS* 17, 34; Usman et al., 1994, *Nucleic Acids Symp. Ser.* 31, 163). siNA constructs can be purified by gel electrophoresis using general methods or can be purified by high pressure liquid chromatography (HPLC; see Wincott et al., supra, the totality of which is hereby incorporated herein by reference) and re-suspended in water.

In another aspect of the invention, siNA molecules of the invention are expressed from transcription units inserted into DNA or RNA vectors. The recombinant vectors can be DNA plasmids or viral vectors. siNA expressing viral vectors can be constructed based on, but not limited to, adeno-associated virus, retrovirus, adenovirus, or alphavirus. The recombinant vectors capable of expressing the siNA molecules can be delivered as described herein, and persist in target cells. Alternatively, viral vectors can be used that provide for transient expression of siNA molecules.

Preparation of Formulated Molecular Compositions

The method of preparation of nucleic acid formulations are disclosed in U.S. Pat. No. 5,976,567, U.S. Pat. No. 5,981,501 and PCT Patent Publication No. WO 96/40964, the teachings of all of which are incorporated in their entireties herein by reference. Cationic lipids that are useful in the present invention can be any of a number of lipid species which carry a net positive charge at a selected pH, such as physiological pH. Suitable cationic lipids include, but are not limited to, a compound having any of Formulae CLI-CLXXIX, DODAC, DOTMA, DDAB, DOTAP, DODAP, DOCDAP, DLINDAP, DOSPA, DOGS, DC-Chol and DMRIE, as well as other cationic lipids described herein, or combinations thereof. A number of these cationic lipids and related analogs, which are also useful in the present invention, have been described in U.S. Ser. No. 08/316,399; U.S. Pat. Nos. 5,208,036, 5,264,618, 5,279,833 and 5,283,185, the disclosures of which are incorporated herein by reference. Additionally, a number of commercial preparations of cationic lipids are available and can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic liposomes comprising DOGS from Promega Corp., Madison, Wis., USA).

The noncationic lipids used in the present invention can be any of a variety of neutral uncharged, zwitterionic or anionic lipids capable of producing a stable complex. They are preferably neutral, although they can alternatively be positively or negatively charged. Examples of noncationic lipids useful in the present invention include phospholipid-related materials, such as lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal). Noncationic lipids or sterols such as cholesterol may be present. Additional nonphosphorous containing lipids are, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkylaryl sulfate polyethyloxylated fatty acid amides, dioctadecyldimethyl ammonium bromide and the like, diacylphosphatidylcholine, diacylphosphatidylethanolamine, ceramide, sphingomyelin, cephalin, and cerebrosides. Other lipids such as lysophosphatidylcholine and lysophosphatidylethanolamine may be present. Noncationic lipids also include polyethylene glycol-based polymers such as PEG 2000, PEG 5000 and polyethylene glycol conjugated to phospholipids or to ceramides (referred to as PEG-Cer), as described in co-pending U.S. Ser. No. 08/316,429, incorporated herein by reference.

In one embodiment, the noncationic lipids are diacylphosphatidylcholine (e.g., distearoylphosphatidylcholine, dioleoylphosphatidylcholine, dipalmitoylphosphatidylcholine or dilinoleoylphosphatidylcholine), diacylphosphatidylethanolamine (e.g., dioleoylphosphatidylethanolamine and palmitoyloleoylphosphatidylethanolamine), ceramide or sphingomyelin. The acyl groups in these lipids are preferably acyl groups derived from fatty acids having about C10 to about C24 carbon chains. In one embodiment, the acyl groups are lauroyl, myristoyl, palmitoyl, stearoyl or oleoyl. In additional embodiments, the noncationic lipid comprises cholesterol, 1,2-sn-dioleoylphosphatidylethanol-amine, or egg sphingomyelin (ESM).

In addition to cationic and neutral lipids, the formulated molecular compositions of the present invention comprise a polyethyleneglycol (PEG) conjugate. The PEG conjugate can comprise a diacylglycerol-polyethyleneglycol conjugate, i.e., a DAG-PEG conjugate. The term "diacylglycerol" refers to a compound having 2-fatty acyl chains, R1 and R2, both of which have independently between 2 and 30 carbons bonded to the 1- and 2-position of glycerol by ester linkages. The acyl groups can be saturated or have varying degrees of unsaturation. Diacylglycerols have the following general formula VIII:

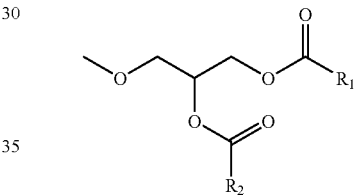

wherein R1 and R2 are each an alkyl, substituted alkyl, aryl, substituted aryl, lipid, or a ligand. In one embodiment, R1 and R2 are each independently a C2 to C30 alkyl group.

In one embodiment, the DAG-PEG conjugate is a dilaurylglycerol (C 12)-PEG conjugate, a dimyristylglycerol (C14)-PEG conjugate, a dipalmitoylglycerol (C16)-PEG conjugate, a disterylglycerol (C18)-PEG conjugate, a PEG-dilaurylglycamide conjugate (C12), a PEG-dimyristylglycamide conjugate (C14), a PEG-dipalmitoylglycamide conjugate (C16), or a PEG-disterylglycamide (C18). Those of skill in the art will readily appreciate that other diacylglycerols can be used in the DAG-PEG conjugates of the present invention.

The PEG conjugate can alternatively comprise a conjugate other than a DAG-PEG conjugate, such as a PEG-cholesterol conjugate or a PEG-DMB conjugate.

In addition to the foregoing components, the formulated molecular compositions of the present invention can further comprise cationic poly(ethylene glycol) (PEG) lipids, or CPLs, that have been designed for insertion into lipid bilayers to impart a positive charge (see for example Chen, et al., 2000, *Bioconj. Chem.* 11, 433-437). Suitable formulations for use in the present invention, and methods of making and using such formulations are disclosed, for example in U.S. application Ser. No. 09/553,639, which was filed Apr. 20, 2000, and PCT Patent Application No. CA 00/00451, which was filed Apr. 20, 2000 and which published as WO 00/62813 on Oct. 26, 2000, the teachings of each of which is incorporated herein in its entirety by reference.

The formulated molecular compositions of the present invention, i.e., those formulated molecular compositions containing DAG-PEG conjugates, can be made using any of a number of different methods. For example, the lipid-nucleic acid particles can be produced via hydrophobic siNA-lipid intermediate complexes. The complexes are preferably charge-neutralized. Manipulation of these complexes in either detergent-based or organic solvent-based systems can lead to particle formation in which the nucleic acid is protected.

The present invention provides a method of preparing serum-stable formulated molecular compositions, including formulations that undergo pH-dependent phase transition, in which the biologically active molecule is encapsulated in a lipid bilayer and is protected from degradation. Additionally, the formulated particles formed in the present invention are preferably neutral or negatively-charged at physiological pH. For in vivo applications, neutral particles are advantageous, while for in vitro applications the particles are more preferably negatively charged. This provides the further advantage of reduced aggregation over the positively-charged liposome formulations in which a biologically active molecule can be encapsulated in cationic lipids.

The formulated particles made by the methods of this invention have a size of about 50 to about 600 nm or more, with certain of the particles being about 65 to 85 nm. The particles can be formed by either a detergent dialysis method or by a modification of a reverse-phase method which utilizes organic solvents to provide a single phase during mixing of the components. Without intending to be bound by any particular mechanism of formation, a biologically active molecule is contacted with a detergent solution of cationic lipids to form a coated molecular complex. These coated molecules can aggregate and precipitate. However, the presence of a detergent reduces this aggregation and allows the coated molecules to react with excess lipids (typically, noncationic lipids) to form particles in which the biologically active molecule is encapsulated in a lipid bilayer. The methods described below for the formation of formulated molecular compositions using organic solvents follow a similar scheme.

In some embodiments, the particles are formed using detergent dialysis. Thus, the present invention provides a method for the preparation of serum-stable formulated molecular compositions (including formulations that undergo pH-dependent phase transition) comprising: (a) combining a molecule of interest with cationic lipids in a detergent solution to form a coated molecule-lipid complex; (b) contacting noncationic lipids with the coated molecule-lipid complex to form a detergent solution comprising a molecule-lipid complex and noncationic lipids; and (c) dialyzing the detergent solution of step (b) to provide a solution of serum-stable molecule-lipid particles, wherein the molecule of interest is encapsulated in a lipid bilayer and the particles have a size of from about 50 to about 600 nm. In one embodiment, the particles have a size of from about 50 to about 150 nm.

An initial solution of coated molecule-lipid complexes is formed, for example, by combining the molecule of interest with the cationic lipids in a detergent solution.

In these embodiments, the detergent solution is preferably an aqueous solution of a neutral detergent having a critical micelle concentration of 15-300 mM, more preferably 20-50 mM. Examples of suitable detergents include, for example, N,N'-((octanoylimino)-bis-(trimethylene))-bis-(D-gluconamide) (BIGCHAP); BRIJ 35; Deoxy-BIGCHAP; dodecylpoly(ethylene glycol) ether; Tween 20; Tween 40; Tween 60; Tween 80; Tween 85; Mega 8; Mega 9; Zwittergent® 3-08; Zwittergent® 3-10; Triton X-405; hexyl-, heptyl-, octyl- and nonyl-beta-D-glucopyranoside; and heptylthioglucopyranoside. In one embodiment, the detergent is octyl β-D-glucopyranoside or Tween-20. The concentration of detergent in the detergent solution is typically about 100 mM to about 2 M, preferably from about 200 mM to about 1.5 M.

The cationic lipids and molecules to be encapsulated will typically be combined to produce a charge ratio (+/−) of about 1:1 to about 20:1, preferably in a ratio of about 1:1 to about 12:1, and more preferably in a ratio of about 2:1 to about 6:1. Additionally, the overall concentration of the molecules of interest in solution will typically be from about 25 μg/mL to about 1 mg/mL, preferably from about 25 μg/mL to about 500 μg/mL, and more preferably from about 100 μg/mL to about 250 μg/mL. The combination of molecules and cationic lipids in detergent solution is kept, typically at room temperature, for a period of time which is sufficient for the coated complexes to form. Alternatively, the molecules and cationic lipids can be combined in the detergent solution and warmed to temperatures of up to about 37° C. For molecules which are particularly sensitive to temperature, the coated complexes can be formed at lower temperatures, typically down to about 4° C.

In one embodiment, the molecule to lipid ratios (mass/mass ratios) in a formed formulated molecular composition will range from about 0.01 to about 0.08. The ratio of the starting materials also falls within this range because the purification step typically removes the unencapsulated molecule as well as the empty liposomes. In another embodiment, the formulated molecular composition preparation uses about 400 μg siNA per 10 mg total lipid or a molecule to lipid ratio of about 0.01 to about 0.08 and, more preferably, about 0.04, which corresponds to 1.25 mg of total lipid per 50 μg of siNA.

The detergent solution of the coated molecule-lipid complexes is then contacted with neutral lipids to provide a detergent solution of molecule-lipid complexes and neutral lipids. The neutral lipids which are useful in this step include, among others, diacylphosphatidylcholine, diacylphosphatidylethanolamine, ceramide, sphingomyelin, cephalin, cardiolipin, and cerebrosides. In preferred embodiments, the neutral lipids are diacylphosphatidylcholine, diacylphosphatidylethanolamine, ceramide or sphingomyelin. The acyl groups in these lipids are preferably acyl groups derived from fatty acids having C10-C24 carbon chains. More preferably the acyl groups are lauroyl, myristoyl, palmitoyl, stearoyl or oleoyl. In preferred embodiments, the neutral lipid is 1,2-sn-dioleoylphosphatidylethanolamine (DOPE), palmitoyl oleoyl phosphatidylcholine (POPC), egg phosphatidylcholine (EPC), distearoylphosphatidylcholine (DSPC), cholesterol, or a mixture thereof. In the most preferred embodiments, the siNA-lipid particles are fusogenic particles with enhanced properties in vivo and the neutral lipid is DSPC or DOPE. As explained above, the siNA-lipid particles of the present invention can further comprise PEG conjugates, such as DAG-PEG conjugates, PEG-cholesterol conjugates, and PEG-DMB conjugates. In addition, the siNA-lipid particles of the present invention can further comprise cholesterol.

The amount of neutral lipid which is used in the present methods is typically about 0.5 to about 10 mg of total lipids to 50 μg of the molecule of interest. Preferably the amount of total lipid is from about 1 to about 5 mg per 50 μg of the molecule of interest.

Following formation of the detergent solution of molecule-lipid complexes and neutral lipids, the detergent is removed, preferably by dialysis. The removal of the detergent results in the formation of a lipid-bilayer which surrounds the molecule of interest providing serum-stable molecule-lipid particles which have a size of from about 50 nm to about 150 or 50 nm to about 600 nm. The particles thus formed do not aggregate and are optionally sized to achieve a uniform particle size.

The serum-stable molecule-lipid particles can be sized by any of the methods available for sizing liposomes as are known in the art. The sizing can be conducted in order to achieve a desired size range and relatively narrow distribution of particle sizes.

Several techniques are available for sizing the particles to a desired size. One sizing method, used for liposomes and equally applicable to the present particles is described in U.S. Pat. No. 4,737,323, incorporated herein by reference. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles can be extruded through successively smaller-pore membranes, to achieve a gradual reduction in size.

In another group of embodiments, the present invention provides a method for the preparation of a formulated molecular composition, comprising: (a) preparing a mixture comprising cationic lipids and noncationic lipids in an organic solvent; (b) contacting an aqueous solution of molecule of interest with the mixture in step (a) to provide a clear single phase; and (c) removing the organic solvent to provide a suspension of molecule-lipid particles, wherein the molecule of interest is encapsulated in a lipid bilayer, and the particles are stable in serum and have a size of from about 50 to about 150 nm or alternately 50 to about 600 nm.

The molecules of interest, cationic lipids and noncationic lipids which are useful in this group of embodiments are as described for the detergent dialysis methods above.

The selection of an organic solvent will typically involve consideration of solvent polarity and the ease with which the solvent can be removed at the later stages of particle formation. The organic solvent, which is also used as a solubilizing agent, is in an amount sufficient to provide a clear single phase mixture of biologically active molecules and lipids. Suitable solvents include, but are not limited to, chloroform, dichloromethane, diethylether, cyclohexane, cyclopentane, benzene, toluene, methanol, or other aliphatic alcohols such as propanol, isopropanol, butanol, tert-butanol, iso-butanol, pentanol and hexanol. Combinations of two or more solvents can also be used in the present invention.

Contacting the molecules of interest with the organic solution of cationic and neutral lipids is accomplished by mixing together a first solution of the molecule of interest, which is typically an aqueous solution, and a second organic solution of the lipids. One of skill in the art will understand that this mixing can take place by any number of methods, for example by mechanical means such as by using vortex mixers.

After the molecule of interest has been contacted with the organic solution of lipids, the organic solvent is removed, thus forming an aqueous suspension of serum-stable molecule-lipid particles. The methods used to remove the organic solvent will typically involve evaporation at reduced pressures or blowing a stream of inert gas (e.g., nitrogen or argon) across the mixture.

The formulated molecular compositions thus formed will typically be sized from about 50 nm to 150 nm or alternately from about 50 nm to 600 nm. To achieve further size reduction or homogeneity of size in the particles, sizing can be conducted as described above.

In other embodiments, the methods will further comprise adding nonlipid polycations which are useful to effect the transformation of cells using the present compositions. Examples of suitable nonlipid polycations include, but are limited to, hexadimethrine bromide (sold under the brandname POLYBRENE, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine and polyethyleneimine.

In certain embodiments, the formation of the formulated molecular compositions can be carried out either in a monophase system (e.g., a Bligh and Dyer monophase or similar mixture of aqueous and organic solvents) or in a two-phase system with suitable mixing.

When formation of the complexes is carried out in a monophase system, the cationic lipids and molecules of interest are each dissolved in a volume of the mono-phase mixture. Combination of the two solutions provides a single mixture in which the complexes form. Alternatively, the complexes can form in two-phase mixtures in which the cationic lipids bind to the molecule (which is present in the aqueous phase), and "pull" it into the organic phase.

In another embodiment, the present invention provides a method for the preparation of formulated molecular composition, comprising: (a) contacting molecules of interest with a solution comprising noncationic lipids and a detergent to form a molecule-lipid mixture; (b) contacting cationic lipids with the molecule-lipid mixture to neutralize a portion of the negative charge of the molecule of interest and form a charge-neutralized mixture of molecules and lipids; and (c) removing the detergent from the charge-neutralized mixture to provide the formulated molecular composition.

In one group of embodiments, the solution of neutral lipids and detergent is an aqueous solution. Contacting the molecules of interest with the solution of neutral lipids and detergent is typically accomplished by mixing together a first solution of the molecule of interest and a second solution of the lipids and detergent. One of skill in the art will understand that this mixing can take place by any number of methods, for example, by mechanical means such as by using vortex mixers. Preferably, the molecule solution is also a detergent solution. The amount of neutral lipid which is used in the present method is typically determined based on the amount of cationic lipid used, and is typically of from about 0.2 to 5 times the amount of cationic lipid, preferably from about 0.5 to about 2 times the amount of cationic lipid used.

The molecule-lipid mixture thus formed is contacted with cationic lipids to neutralize a portion of the negative charge which is associated with the molecule of interest (or other polyanionic materials) present. The amount of cationic lipids used is typically the amount sufficient to neutralize at least 50% of the negative charge of the molecule of interest. Preferably, the negative charge will be at least 70% neutralized, more preferably at least 90% neutralized. Cationic lipids which are useful in the present invention include, for example, compounds having any of formulae CLI-CLXXIX, DODAC, DOTMA, DDAB, DOTAP, DC-Chol, DMOBA, CLinDMA, and DMRIE. These lipids and related analogs have been described in U.S. Ser. No. 08/316,399; U.S. Pat. Nos. 5,208,036, 5,264,618, 5,279,833 and 5,283,185, the disclosures of which are incorporated by reference in their entireties herein. Additionally, a number of commercial preparations of cationic lipids are available and can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic lipids comprising DOGS in ethanol from Promega Corp., Madison, Wis., USA).

Contacting the cationic lipids with the molecule-lipid mixture can be accomplished by any of a number of techniques, preferably by mixing together a solution of the cationic lipid and a solution containing the molecule-lipid mixture. Upon mixing the two solutions (or contacting in any other manner), a portion of the negative charge associated with the molecule of interest is neutralized.

After the cationic lipids have been contacted with the molecule-lipid mixture, the detergent (or combination of detergent and organic solvent) is removed, thus forming the formulated molecular composition. The methods used to remove the detergent typically involve dialysis. When organic solvents are present, removal is typically accomplished by evaporation at reduced pressures or by blowing a stream of inert gas (e.g., nitrogen or argon) across the mixture.

The formulated molecular composition particles thus formed is typically sized from about 50 nm to several microns. To achieve further size reduction or homogeneity of size in the particles, the formulated molecular composition particles can be sonicated, filtered or subjected to other sizing techniques which are used in liposomal formulations and are known to those of skill in the art.

In other embodiments, the methods further comprise adding nonlipid polycations which are useful to affect the lipofection of cells using the present compositions. Examples of suitable nonlipid polycations include, hexadimethrine bromide (sold under the brandname POLYBRENE, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine and polyethyleneimine. Addition of these salts is preferably after the particles have been formed.

In another aspect, the present invention provides methods for the preparation of formulated siNA compositions, comprising: (a) contacting an amount of cationic lipids with siNA in a solution; the solution comprising from about 15-35% water and about 65-85% organic solvent and the amount of cationic lipids being sufficient to produce a +/− charge ratio of from about 0.85 to about 2.0, to provide a hydrophobic lipid-siNA complex; (b) contacting the hydrophobic, lipid-siNA complex in solution with neutral lipids, to provide a siNA-lipid mixture; and (c) removing the organic solvents from the lipid-siNA mixture to provide formulated siNA composition particles.

The siNA, neutral lipids, cationic lipids and organic solvents which are useful in this aspect of the invention are the same as those described for the methods above which used detergents. In one group of embodiments, the solution of step (a) is a mono-phase. In another group of embodiments, the solution of step (a) is two-phase.

In one embodiment, the cationic lipids used in a formulation of the invention are selected from a compound having Formula CLI, CLII, CLIII, CLIV, CLV, CLVI, CLVII, CLVIII, CLIX, CLX, CLXI, CLXII, CLXIII, CLXIV, CLXV, CLXVI, CLXVII, CLXVIII, CLXIX, CLXX, CLXXI, CLXXII, CLXXIII, CLXXIV, CLXXV, CLXXVI, CLXXVII, CLXXVIII, CLXXIX, and DODAC, DODAP, DOCDAP, DLINDAP, DOSPA, DMRIE, DOGS, DMOBA, CLinDMA, and combinations thereof.

In one embodiment, the noncationic lipids are selected from ESM, DOPE, DOPC, DSPC, polyethylene glycol-based polymers (e.g., PEG 2000, PEG 5000 or PEG-modified diacylglycerols), distearoylphosphatidylcholine (DSPC), cholesterol, and combinations thereof. In one embodiment, the organic solvents are selected from methanol, chloroform, methylene chloride, ethanol, diethyl ether and combinations thereof.

In one embodiment, the cationic lipid is a compound having Formula CLI, CLII, CLIII, CLIV, CLV, CLVI, CLVII, CLVIII, CLIX, CLX, CLXI, CLXII, CLXIII, CLXIV, CLXV, CLXVI, CLXVII, CLXVIII, CLXVII, CLXVIII, CLXIX, CLXX, CLXXI, CLXXII, CLXXIII, CLXXIV, CLXXV, CLXXVI, CLXXVII, CLXXVIII, CLXXIX or DODAC, DOTAP, DODAP, DOCDAP, DLINDAP, DDAB, DOTMA, DOSPA, DMRIE, DOGS or combinations thereof, the noncationic lipid is ESM, DOPE, DAG-PEGs, distearoylphosphatidylcholine (DSPC), cholesterol, or combinations thereof (e.g. DSPC and DAG-PEGs); and the organic solvent is methanol, chloroform, methylene chloride, ethanol, diethyl ether or combinations thereof.

As above, contacting the siNA with the cationic lipids is typically accomplished by mixing together a first solution of siNA and a second solution of the lipids, preferably by mechanical means such as by using vortex mixers. The resulting mixture contains complexes as described above. These complexes are then converted to particles by the addition of neutral lipids and the removal of the organic solvent. The addition of the neutral lipids is typically accomplished by simply adding a solution of the neutral lipids to the mixture containing the complexes. A reverse addition can also be used. Subsequent removal of organic solvents can be accomplished by methods known to those of skill in the art and also described above.

The amount of neutral lipids which is used in this aspect of the invention is typically an amount of from about 0.2 to about 15 times the amount (on a mole basis) of cationic lipids which was used to provide the charge-neutralized lipid-nucleic acid complex. Preferably, the amount is from about 0.5 to about 9 times the amount of cationic lipids used.

In yet another aspect, the present invention provides formulated siNA compositions which are prepared by the methods described above. In these embodiments, the formulated siNA compositions are either net charge neutral or carry an overall charge which provides the formulated siNA compositions with greater lipofection activity. In one embodiment, the noncationic lipid is egg sphingomyelin and the cationic lipid is DODAC. In one embodiment, the noncationic lipid is a mixture of DSPC and cholesterol, and the cationic lipid is DOTMA. In another embodiment, the noncationic lipid can further comprise cholesterol.

A variety of general methods for making formulated siNA composition-CPLs (CPL-containing formulated siNA compositions) are discussed herein. Two general techniques include "post-insertion" technique, that is, insertion of a CPL into for example, a preformed formulated siNA composition, and the "standard" technique, wherein the CPL is included in the lipid mixture during for example, the formulated siNA composition formation steps. The post-insertion technique results in formulated siNA compositions having CPLs mainly in the external face of the formulated siNA composition bilayer membrane, whereas standard techniques provide formulated siNA compositions having CPLs on both internal and external faces.

In particular, "post-insertion" involves forming formulated siNA compositions (by any method), and incubating the preformed formulated siNA compositions in the presence of CPL under appropriate conditions (preferably 2-3 hours at 60° C.). Between 60-80% of the CPL can be inserted into the external leaflet of the recipient vesicle, giving final concentrations up to about 5 to 10 mol % (relative to total lipid). The method is especially useful for vesicles made from phospholipids (which can contain cholesterol) and also for vesicles containing PEG-lipids (such as PEG-DAGs).

In an example of a "standard" technique, the CPL-formulated siNA compositions of the present invention can be formed by extrusion. In this embodiment, all of the lipids including the CPL, are co-dissolved in chloroform, which is then removed under nitrogen followed by high vacuum. The lipid mixture is hydrated in an appropriate buffer, and extruded through two polycarbonate filters with a pore size of 100 nm. The resulting formulated siNA compositions contain CPL on both of the internal and external faces. In yet another standard technique, the formation of CPL-formulated siNA compositions can be accomplished using a detergent dialysis or ethanol dialysis method, for example, as discussed in U.S. Pat. Nos. 5,976,567 and 5,981,501, both of which are incorporated by reference in their entireties herein.

The formulated siNA compositions of the present invention can be administered either alone or in mixture with a physiologically-acceptable carrier (such as physiological saline or phosphate buffer) selected in accordance with the route of administration and standard pharmaceutical practice. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc.

The pharmaceutical carrier is generally added following formulated siNA composition formation. Thus, after the formulated siNA composition is formed, the formulated siNA composition can be diluted into pharmaceutically acceptable carriers such as normal saline.

The concentration of formulated siNA compositions in the pharmaceutical formulations can vary widely, i.e., from less than about 0.05%, usually at or at least about 2-5% to as much as 10 to 30% by weight and will be selected primarily by fluid volumes, viscosities, etc., in accordance with the particular mode of administration selected. For example, the concentration can be increased to lower the fluid load associated with treatment. This may be particularly desirable in patients having atherosclerosis-associated congestive heart failure or severe hypertension. Alternatively, formulated siNA compositions composed of irritating lipids can be diluted to low concentrations to lessen inflammation at the site of administration.

As described above, the formulated siNA compositions of the present invention comprise DAG-PEG conjugates. It is often desirable to include other components that act in a manner similar to the DAG-PEG conjugates and that serve to prevent particle aggregation and to provide a means for increasing circulation lifetime and increasing the delivery of the formulated siNA compositions to the target tissues. Such components include, but are not limited to, PEG-lipid conjugates, such as PEG-ceramides or PEG-phospholipids (such as PEG-PE), ganglioside GM1-modified lipids or ATTA-lipids to the particles. Typically, the concentration of the component in the particle will be about 1-20% and, more preferably from about 3-10%.

The pharmaceutical compositions of the present invention can be sterilized by conventional, well known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension can include lipid-protective agents which protect lipids against free-radical and lipid-peroxidative damages on storage. Lipophilic free-radical quenchers, such as alphatocopherol and water-soluble iron-specific chelators, such as ferrioxamine, are suitable In another example of their use, formulated molecular compositions can be incorporated into a broad range of topical dosage forms including, but not limited to, gels, oils, emulsions and the like. For instance, the suspension containing the formulated molecular compositions can be formulated and administered as topical creams, pastes, ointments, gels, lotions and the like.

Once formed, the formulated molecular compositions of the present invention are useful for the introduction of biologically active molecules into cells. Accordingly, the present invention also provides methods for introducing a biologically active molecule into a cell. The methods are carried out in vitro or in vivo by first forming the formulated molecular compositions as described above and then contacting the formulated molecular compositions with the cells for a period of time sufficient for transfection to occur.

The formulated molecular compositions of the present invention can be adsorbed to almost any cell type with which they are mixed or contacted. Once adsorbed, the formulations can either be endocytosed by a portion of the cells, exchange lipids with cell membranes, or fuse with the cells. Transfer or incorporation of the biologically active molecule portion of the formulation can take place via any one of these pathways. In particular, when fusion takes place, the particle membrane is integrated into the cell membrane and the contents of the particle, i.e., biologically active molecules, combine with the intracellular fluid, for example, the cytoplasm. The serum stable formulated molecular compositions that undergo pH-dependent phase transition demonstrate an increase in cell fusion at early endosomal pH (i.e., about pH 5.5-6.5), resulting in efficient delivery of the contents of the particle, i.e., biologically active molecules, to the cell.

Using the Endosomal Release Parameter (ERP) assay of the present invention, the transfection efficiency of the formulated molecular composition or other lipid-based carrier system can be optimized. More particularly, the purpose of the ERP assay is to distinguish the effect of various cationic lipids and helper lipid components of formulated molecular compositions based on their relative effect on binding/uptake or fusion with/destabilization of the endosomal membrane. This assay allows one to determine quantitatively how each component of the formulated molecular composition or other lipid-based carrier system effects transfection efficacy, thereby optimizing the formulated molecular compositions or other lipid-based carrier systems. As explained herein, the Endosomal Release Parameter or, alternatively, ERP is defined as: Reporter Gene Expression/Cell divided by formulated molecular composition Uptake/Cell.

It will be readily apparent to those of skill in the art that any reporter gene (e.g., luciferase, beta-galactosidase, green fluorescent protein, etc.) can be used in the assay. In addition, the lipid component (or, alternatively, any component of the formulated molecular composition) can be labeled with any detectable label provided the does inhibit or interfere with uptake into the cell. Using the ERP assay of the present invention, one of skill in the art can assess the impact of the various lipid components (e.g., cationic lipid, neutral lipid, PEG-lipid derivative, PEG-DAG conjugate, ATTA-lipid derivative, calcium, CPLs, cholesterol, etc.) on cell uptake and transfection efficiencies, thereby optimizing the formulated siNA composition. By comparing the ERPs for each of the various formulated molecular compositions, one can readily determine the optimized system, e.g., the formulated molecular composition that has the greatest uptake in the cell coupled with the greatest transfection efficiency.

Suitable labels for carrying out the ERP assay of the present invention include, but are not limited to, spectral labels, such as fluorescent dyes (e.g., fluorescein and derivatives, such as fluorescein isothiocyanate (FITC) and Oregon Green9; rhodamine and derivatives, such Texas red, tetrarhodimine isothiocynate (TRITC), etc., digoxigenin, biotin, phycoerythrin, AMCA, CyDyes, and the like; radiolabels, such as $^3$H, $^{125}$I, $^{35}$S, $^{14}$C, $^{32}$P, $^{33}$P, etc.; enzymes, such as horse radish peroxidase, alkaline phosphatase, etc.; spectral calorimetric labels, such as colloidal gold or colored glass or plastic beads, such as polystyrene, polypropylene, latex, etc. The label can be coupled directly or indirectly to a component of the formulated molecular composition using methods well known in the art. As indicated above, a wide variety of labels can be used, with the choice of label depending on sensitivity required, ease of conjugation with the formulated siNA composition, stability requirements, and available instrumentation and disposal provisions.

In addition, the transfection efficiency of the formulated molecular composition or other lipid-based carrier system can be determined by measuring the stability of the composition in serm and/or measuring the pH dependent phase transition of the formulated molecular composition, wherein a determination that the formulated molecular composition is stable in serum and a determination that the formulated molecular composition undergoes a phase transition at about pH 5.5-6.5 indicates that the formulated molecular composition will have increased transfection efficiency. The serum stability of the formulated molecular composition can be measured using, for example, an assay that measures the relative turbidity of the composition in serum and determining that the turbity of the composition in serum remains constant over time. The pH dependent phase transition of the formulated molecular composition can be measured using an assay that measures the relative turbidity of the composition at different pH over time and determining that the turbidity changes when the pH differs from physiologic pH.

Optimizing Activity of the Nucleic Acid Molecule of the Invention.

Chemically synthesizing nucleic acid molecules (e.g., siNA, antisense, aptamer, decoy, ribozyme, 2-5A, triplex forming oligonucleotide, or other nucleic acid molecule) with modifications (base, sugar and/or phosphate) can prevent their degradation by serum ribonucleases, which can increase their potency (see e.g. Eckstein et al., International Publication No. WO 92/07065; Perrault et al., 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; Gold et al., U.S. Pat. No. 6,300,074; and Burgin et al., supra; all of which are incorporated by reference herein). All of the above references describe various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, Tetrahedron Lett., 39, 1131; Earnshaw and Gait, 1998, Biopolymers (Nucleic Acid Sciences), 48, 39-55; Verma and Eckstein, 1998, Annu. Rev. Biochem., 67, 99-134; and Burlina et al., 1997, Bioorg. Med. Chem., 5, 1999-2010; all of the references are hereby incorporated in their totality by reference herein). Such publications describe general methods and strategies to determine the location of incorporation of sugar, base and/or phosphate modifications and the like into nucleic acid molecules without modulating catalysis, and are incorporated by reference herein. In view of such teachings, similar modifications can be used as described herein to modify the siNA nucleic acid molecules of the instant invention so long as the ability of siNA to promote RNAi cells is not significantly inhibited.

While chemical modification of oligonucleotide internucleotide linkages with phosphorothioate, phosphorodithioate, and/or 5'-methylphosphonate linkages improves stability, excessive modifications can cause some toxicity or decreased activity. Therefore, when designing nucleic acid molecules, the amount of these internucleotide linkages should be minimized. The reduction in the concentration of these linkages should lower toxicity, resulting in increased efficacy and higher specificity of these molecules.

Polynucleotides (e.g., siNA, antisense, aptamer, decoy, ribozyme, 2-5A, triplex forming oligonucleotide, or other nucleic acid molecule) having chemical modifications that maintain or enhance activity are provided. Such a nucleic acid is also generally more resistant to nucleases than an unmodified nucleic acid. Accordingly, the in vitro and/or in vivo activity should not be significantly lowered. In cases in which modulation is the goal, therapeutic nucleic acid molecules delivered exogenously should optimally be stable within cells until translation of the target RNA has been modulated long enough to reduce the levels of the undesirable protein. This period of time varies between hours to days depending upon the disease state. Improvements in the chemical synthesis of RNA and DNA (Wincott et al., 1995, *Nucleic Acids Res.* 23, 2677; Caruthers et al., 1992, *Methods in Enzymology* 211, 3-19 (incorporated by reference herein)) have expanded the ability to modify nucleic acid molecules by introducing nucleotide modifications to enhance their nuclease stability, as described above.

In one embodiment, nucleic acid molecules of the invention include one or more (e.g., about 1, 2, 3, 4, 5, 6, 7, 8, 9, 10, or more) G-clamp nucleotides. A G-clamp nucleotide is a modified cytosine analog wherein the modifications confer the ability to hydrogen bond both Watson-Crick and Hoogsteen faces of a complementary guanine within a duplex, see for example Lin and Matteucci, 1998, *J. Am. Chem. Soc.*, 120, 8531-8532. A single G-clamp analog substitution within an oligonucleotide can result in substantially enhanced helical thermal stability and mismatch discrimination when hybridized to complementary oligonucleotides. The inclusion of such nucleotides in nucleic acid molecules of the invention results in both enhanced affinity and specificity to nucleic acid targets, complementary sequences, or template strands. In another embodiment, nucleic acid molecules of the invention include one or more (e.g., about 1, 2, 3, 4, 5, 6, 7, 8, 9, 10, or more) LNA "locked nucleic acid" nucleotides such as a 2',4'-C methylene bicyclo nucleotide (see for example Wengel et al., International PCT Publication No. WO 00/66604 and WO 99/14226).

In another embodiment, the invention features conjugates and/or complexes of siNA molecules of the invention. Such conjugates and/or complexes can be used to facilitate delivery of siNA molecules into a biological system, such as a cell. The conjugates and complexes provided by the instant invention can impart therapeutic activity by transferring therapeutic compounds across cellular membranes, altering the pharmacokinetics, and/or modulating the localization of nucleic acid molecules of the invention. The present invention encompasses the design and synthesis of novel conjugates and complexes for the delivery of molecules, including, but not limited to, small molecules, lipids, cholesterol, phospholipids, nucleosides, nucleotides, nucleic acids, antibodies, toxins, negatively charged polymers and other polymers, for example proteins, peptides, hormones, carbohydrates, polyethylene glycols, or polyamines, across cellular membranes. In general, the transporters described are designed to be used either individually or as part of a multi-component system, with or without degradable linkers. These compounds are expected to improve delivery and/or localization of nucleic acid molecules of the invention into a number of cell types originating from different tissues, in the presence or absence of serum (see Sullenger and Cech, U.S. Pat. No. 5,854,038). Conjugates of the molecules described herein can be attached to biologically active molecules via linkers that are biodegradable, such as biodegradable nucleic acid linker molecules.

The term "biodegradable linker" as used herein, refers to a nucleic acid or non-nucleic acid linker molecule that is designed as a biodegradable linker to connect one molecule to another molecule, for example, a biologically active molecule to a siNA molecule of the invention or the sense and antisense strands of a siNA molecule of the invention. The biodegradable linker is designed such that its stability can be modulated for a particular purpose, such as delivery to a particular tissue or cell type. The stability of a nucleic acid-based biodegradable linker molecule can be modulated by using various chemistries, for example combinations of ribonucleotides, deoxyribonucleotides, and chemically-modified nucleotides, such as 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus-based linkage, for example, a phosphoramidate or phosphodiester linkage. The biodegradable nucleic acid linker molecule can also comprise nucleic acid backbone, nucleic acid sugar, or nucleic acid base modifications.

The term "biodegradable" as used herein, refers to degradation in a biological system, for example, enzymatic degradation or chemical degradation.

The term "phospholipid" as used herein, refers to a hydrophobic molecule comprising at least one phosphorus group. For example, a phospholipid can comprise a phosphorus-containing group and saturated or unsaturated alkyl group, optionally substituted with OH, COOH, oxo, amine, or substituted or unsubstituted aryl groups.

Therapeutic nucleic acid molecules (e.g., siNA, antisense, aptamer, decoy, ribozyme, 2-5A, triplex forming oligonucleotide, or other nucleic acid molecule) delivered exogenously optimally are stable within cells until reverse transcription of the RNA has been modulated long enough to reduce the levels of the RNA transcript. The nucleic acid molecules are resistant to nucleases in order to function as effective intracellular therapeutic agents. Improvements in the chemical synthesis of nucleic acid molecules described in the instant invention and in the art have expanded the ability to modify nucleic acid molecules by introducing nucleotide modifications to enhance their nuclease stability as described above.

In yet another embodiment, siNA molecules having chemical modifications that maintain or enhance enzymatic activity of proteins involved in RNAi are provided. Such nucleic acids are also generally more resistant to nucleases than unmodified nucleic acids. Thus, in vitro and/or in vivo the activity should not be significantly lowered.

Use of the nucleic acid-based molecules of the invention will lead to better treatments by affording the possibility of combination therapies (e.g., multiple siNA molecules targeted to different genes; nucleic acid molecules coupled with known small molecule modulators; or intermittent treatment with combinations of molecules, including different motifs and/or other chemical or biological molecules).

In another aspect a polynucleotide molecule of the invention (e.g., siNA, antisense, aptamer, decoy, ribozyme, 2-5A, triplex forming oligonucleotide, or other nucleic acid molecule) comprises one or more 5' and/or a 3'-cap structure, for example, on only the sense siNA strand, the antisense siNA strand, or both siNA strands.

By "cap structure" is meant chemical modifications, which have been incorporated at either terminus of the oligonucleotide (see, for example, Adamic et al., U.S. Pat. No. 5,998,203, incorporated by reference herein). These terminal modifications protect the nucleic acid molecule from exonuclease degradation, and may help in delivery and/or localization within a cell. The cap may be present at the 5'-terminus (5'-cap) or at the 3'-terminal (3'-cap) or may be present on both termini. In non-limiting examples, the 5'-cap includes, but is not limited to, glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety Non-limiting examples of the 3'-cap include, but are not limited to, glyceryl, inverted deoxy abasic residue (moiety), 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, *Tetrahedron* 49, 1925; incorporated by reference herein).

By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine and therefore lacks a base at the 1'-position.

An "alkyl" group refers to a saturated aliphatic hydrocarbon, including straight-chain, branched-chain, and cyclic alkyl groups. Preferably, and unless expressly stated to the contrary, the alkyl group has 1 to 12 carbons. More preferably, it is a lower alkyl of from 1 to 7 carbons, more preferably 1 to 4 carbons. The alkyl group can be substituted or unsubstituted. When substituted the substituted group(s) is preferably, hydroxyl, cyano, alkoxy, =O, =S, $NO_2$ or $N(CH_3)_2$, amino, or SH. The term also includes alkenyl groups that are unsaturated hydrocarbon groups containing at least one carbon-carbon double bond, including straight-chain, branched-chain, and cyclic groups. Preferably, the alkenyl group has 1 to 12 carbons. More preferably, it is a lower alkenyl of from 1 to 7 carbons, more preferably 1 to 4 carbons. The alkenyl group may be substituted or unsubstituted. When substituted the substituted group(s) is preferably, hydroxyl, cyano, alkoxy, =O, =S, $NO_2$, halogen, $N(CH_3)_2$, amino, or SH. The term "alkyl" also includes alkynyl groups that have an unsaturated hydrocarbon group containing at least one carbon-carbon triple bond, including straight-chain, branched-chain, and cyclic groups. Preferably, the alkynyl group has 1 to 12 carbons. More preferably, it is a lower alkynyl of from 1 to 7 carbons, more preferably 1 to 4 carbons. The alkynyl group may be substituted or unsubstituted. When substituted the substituted group(s) is preferably, hydroxyl, cyano, alkoxy, =O, =S, $NO_2$ or $N(CH_3)_2$, amino or SH.

Such alkyl groups can also include aryl, alkylaryl, carbocyclic aryl, heterocyclic aryl, amide and ester groups. An "aryl" group refers to an aromatic group that has at least one ring having a conjugated pi electron system and includes carbocyclic aryl, heterocyclic aryl and biaryl groups, all of which may be optionally substituted. The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR, where R is either alkyl, aryl, alkylaryl or hydrogen.

By "nucleotide" as used herein is as recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, for example, Usman and McSwiggen, supra; Eckstein et al., International PCT Publication No. WO 92/07065; Usman et al., International PCT Publication No. WO 93/15187; Uhlman & Peyman, supra, all are hereby incorporated by reference herein). There are several examples of modified nucleic acid bases known in the art as summarized by Limbach et al., 1994, *Nucleic Acids Res.* 22, 2183. Some of the non-limiting examples of base modifications that can be introduced into nucleic acid molecules include, inosine, purine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidines (e.g. 5-methylcytidine), 5-alkyluridines (e.g. ribothymidine), 5-halouridine (e.g., 5-bromouridine) or 6-azapyrimidines or 6-alkylpyrimidines (e.g. 6-methyluridine), propyne, and others (Burgin et al., 1996, *Biochemistry,* 35, 14090; Uhlman & Peyman, supra). By "modified bases" in this aspect is meant nucleotide bases other than adenine, guanine, cytosine and uracil at 1' position or their equivalents.

In one embodiment, the invention features modified polynucleotide molecules (e.g., siNA, antisense, aptamer, decoy, ribozyme, 2-5A, triplex forming oligonucleotide, or other nucleic acid molecule), with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications, see Hunziker and Leumann, 1995, *Nucleic Acid Analogues: Synthesis and Properties,* in *Modern Synthetic Methods,* VCH, 331-417, and Mesmaeker et al., 1994, *Novel Backbone Replacements for Oligonucleotides,* in *Carbohydrate Modifications in Antisense Research,* ACS, 24-39.

By "abasic" is meant sugar moieties lacking a base or having other chemical groups in place of a base at the 1' position, see for example Adamic et al., U.S. Pat. No. 5,998, 203.

By "unmodified nucleoside" is meant one of the bases adenine, cytosine, guanine, thymine, or uracil joined to the 1' carbon of β-D-ribo-furanose.

By "modified nucleoside" is meant any nucleotide base which contains a modification in the chemical structure of an unmodified nucleotide base, sugar and/or phosphate. Non-limiting examples of modified nucleotides are shown by Formulae I-VII and/or other modifications described herein.

In connection with 2'-modified nucleotides as described for the present invention, by "amino" is meant 2'-NH$_2$ or 2'-O—NH$_2$, which can be modified or unmodified. Such modified groups are described, for example, in Eckstein et al., U.S. Pat. No. 5,672,695 and Matulic-Adamic et al., U.S. Pat. No. 6,248,878, which are both incorporated by reference in their entireties.

Various modifications to nucleic acid siNA structure can be made to enhance the utility of these molecules. Such modifications will enhance shelf-life, half-life in vitro, stability, and ease of introduction of such oligonucleotides to the target site, e.g. to enhance penetration of cellular membranes, and confer the ability to recognize and bind to targeted cells.

By "cholesterol derivative" is meant, any compound consisting essentially of a cholesterol structure, including additions, substitutions and/or deletions thereof. The term cholesterol derivative herein also includes steroid hormones and bile acids as are generally recognized in the art.

Administration of Formulated siNA Compositions

A formulated molecular composition of the invention can be adapted for use to prevent, inhibit, or reduce any trait, disease or condition that is related to or will respond to the levels of target gene expression in a cell or tissue, alone or in combination with other therapies.

In one embodiment, formulated molecular compositions can be administered to cells by a variety of methods known to those of skill in the art, including, but not restricted to, by injection, by iontophoresis or by incorporation into other vehicles, such as biodegradable polymers, hydrogels, cyclodextrins (see for example Gonzalez et al., 1999, *Bioconjugate Chem.*, 10, 1068-1074; Wang et al., International PCT publication Nos. WO 03/47518 and WO 03/46185). In one embodiment, a formulated molecular compositions of the invention are complexed with membrane disruptive agents such as those described in U.S. Patent Application Publication No. 20010007666, incorporated by reference herein in its entirety including the drawings. In another embodiment, the membrane disruptive agent or agents and the biologically active molecule are also complexed with a cationic lipid or helper lipid molecule, such as those lipids described in U.S. Pat. No. 6,235,310, incorporated by reference herein in its entirety including the drawings.

In one embodiment, delivery systems of the invention include, for example, aqueous and nonaqueous gels, creams, multiple emulsions, microemulsions, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a transdermal enhancer.

In one embodiment, delivery systems of the invention include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

In one embodiment, the invention features a pharmaceutical composition comprising one or more formulated siNA compositions of the invention in an acceptable carrier, such as a stabilizer, buffer, and the like. The formulated molecular compositions of the invention can be administered and introduced to a subject by any standard means, with or without stabilizers, buffers, and the like, to form a pharmaceutical composition. The compositions of the present invention can also be formulated and used as creams, gels, sprays, oils and other suitable compositions for topical, dermal, or transdermal administration as is known in the art.

In one embodiment, the invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g. systemic or local administration, into a cell or subject, including for example a human. Suitable forms, in part, depend upon the use or the route of entry, for example oral, transdermal, or by injection. Such forms should not prevent the composition or formulation from reaching a target cell (i.e., a cell to which the siNA is desirable for delivery). For example, pharmacological compositions injected into the blood stream should be soluble. Other factors are known in the art, and include considerations such as toxicity and forms that prevent the composition or formulation from exerting its effect.

In one embodiment, formulated molecular compositions of the invention are administered to a subject by systemic administration in a pharmaceutically acceptable composition or formulation. By "systemic administration" is meant in vivo systemic absorption or accumulation of drugs in the blood stream followed by distribution throughout the entire body. Administration routes that lead to systemic absorption include, without limitation: intravenous, subcutaneous, intraperitoneal, inhalation, oral, intrapulmonary and intramuscular. Each of these administration routes exposes the siNA molecules of the invention to an accessible diseased tissue. The rate of entry of a drug into the circulation has been shown to be a function of molecular weight or size.

By "pharmaceutically acceptable formulation" or "pharmaceutically acceptable composition" is meant, a composition or formulation that allows for the effective distribution of the formulated molecular A compositions of the instant invention in the physical location most suitable for their desired activity. Non-limiting examples of agents suitable for formulation with the formulated molecular compositions of the instant invention include: P-glycoprotein inhibitors (such as Pluronic P85); biodegradable polymers, such as poly (DL-lactide-coglycolide) microspheres for sustained release delivery (Emerich, D F et al, 1999, *Cell Transplant*, 8, 47-58); and loaded nanoparticles, such as those made of polybutylcyanoacrylate. Other non-limiting examples of delivery strategies for the nucleic acid molecules of the instant invention include material described in Boado et al., 1998, *J. Pharm. Sci.*, 87, 1308-1315; Tyler et al., 1999, FEBS Lett., 421, 280-284; Pardridge et al., 1995, *PNAS USA.*, 92, 5592-5596; Boado, 1995, *Adv. Drug Delivery Rev.*, 15, 73-107; Aldrian-Herrada et al., 1998, *Nucleic Acids Res.*, 26, 4910-4916; and Tyler et al., 1999, *PNAS USA.*, 96, 7053-7058.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985), hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the formulated siNA composition.

The formulated molecular compositions of the invention can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g. intravenous), intramuscular, or intrathecal injection or infusion techniques and the like. In addition, there is provided a pharmaceutical formulation comprising a formulated molecular composition of the invention and a pharmaceutically acceptable carrier. One or more formulated molecular compositions of the invention can be present in association with one or more non-toxic pharmaceutically acceptable carriers and/or diluents and/or adjuvants, and if desired other active ingredients. The pharmaceutical compositions containing formulated molecular compositions of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The formulated molecular compositions of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Formulated molecular compositions of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depending upon the host treated and the particular mode of administration. Dosage unit forms generally contain between from about 1 mg to about 500 mg of an active ingredient.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The formulated molecular compositions of the present invention can also be administered to a subject in combination with other therapeutic compounds to increase the overall therapeutic effect. The use of multiple compounds to treat an indication can increase the beneficial effects while reducing the presence of side effects.

EXAMPLES

The following are non-limiting examples showing the selection, isolation, synthesis and activity of nucleic acids of the instant invention.

Example 1

Identification of Potential siNA Target Sites in any RNA Sequence

The sequence of an RNA target of interest, such as a viral or human mRNA transcript, is screened for target sites, for example by using a computer folding algorithm. In a non-limiting example, the sequence of a gene or RNA gene transcript derived from a database, such as Genbank, is used to generate siNA targets having complementarity to the target. Such sequences can be obtained from a database, or can be determined experimentally as known in the art. Target sites that are known, for example, those target sites determined to be effective target sites based on studies with other nucleic acid molecules, for example ribozymes or antisense, or those targets known to be associated with a disease or condition such as those sites containing mutations or deletions, can be used to design siNA molecules targeting those sites. Various parameters can be used to determine which sites are the most suitable target sites within the target RNA sequence. These parameters include but are not limited to secondary or tertiary RNA structure, the nucleotide base composition of the target sequence, the degree of homology between various regions of the target sequence, or the relative position of the target sequence within the RNA transcript. Based on these determinations, any number of target sites within the RNA transcript can be chosen to screen siNA molecules for efficacy, for example by using in vitro RNA cleavage assays, cell culture, or animal models. In a non-limiting example, anywhere from 1 to 1000 target sites are chosen within the transcript based on the size of the siNA construct to be used. High throughput screening assays can be developed for screening siNA molecules using methods known in the art, such as with multi-well or multi-plate assays to determine efficient reduction in target gene expression. These methods can also be used to determine target sites for, example, antisense, ribozyme, 2-5-A, triplex, and decoy nucleic acid molecules of the invention.

Example 2

Selection of siNA Molecule Target Sites in a RNA

The following non-limiting steps can be used to carry out the selection of siNAs targeting a given gene sequence or transcript.

1. The target sequence is parsed in silico into a list of all fragments or subsequences of a particular length, for example 23 nucleotide fragments, contained within the target sequence. This step is typically carried out using a custom Perl script, but commercial sequence analysis programs such as Oligo, MacVector, or the GCG Wisconsin Package can be employed as well.

2. In some instances the siNAs correspond to more than one target sequence; such would be the case for example in targeting different transcripts of the same gene, targeting different transcripts of more than one gene, or for targeting both the human gene and an animal homolog. In this case, a subsequence list of a particular length is generated for each of the targets, and then the lists are compared to find matching sequences in each list. The subsequences are then ranked according to the number of target sequences that contain the given subsequence; the goal is to find subsequences that are present in most or all of the target sequences. Alternately, the ranking can identify subsequences that are unique to a target sequence, such as a mutant target sequence. Such an approach would enable the use of siNA to target specifically the mutant sequence and not effect the expression of the normal sequence.

3. In some instances the siNA subsequences are absent in one or more sequences while present in the desired target sequence; such would be the case if the siNA targets a gene with a paralogous family member that is to remain untargeted. As in case 2 above, a subsequence list of a particular length is generated for each of the targets, and then the lists are compared to find sequences that are present in the target gene but are absent in the untargeted paralog.

4. The ranked siNA subsequences can be further analyzed and ranked according to GC content. A preference can be given to sites containing 30-70% GC, with a further preference to sites containing 40-60% GC.

5. The ranked siNA subsequences can be further analyzed and ranked according to self-folding and internal hairpins. Weaker internal folds are preferred; strong hairpin structures are to be avoided.

6. The ranked siNA subsequences can be further analyzed and ranked according to whether they have runs of GGG or CCC in the sequence. GGG (or even more Gs) in either strand can make oligonucleotide synthesis problematic and can potentially interfere with RNAi activity, so it is avoided whenever better sequences are available. CCC is searched in the target strand because that will place GGG in the antisense strand.

7. The ranked siNA subsequences can be further analyzed and ranked according to whether they have the dinucleotide UU (uridine dinucleotide) on the 3'-end of the sequence, and/or AA on the 5'-end of the sequence (to yield 3' UU on the antisense sequence). These sequences allow one to design siNA molecules with terminal TT thymidine dinucleotides.

8. Four or five target sites are chosen from the ranked list of subsequences as described above. For example, in subsequences having 23 nucleotides, the right 21 nucleotides of each chosen 23-mer subsequence are then designed and synthesized for the upper (sense) strand of the siNA duplex, while the reverse complement of the left 21 nucleotides of each chosen 23-mer subsequence are then designed and synthesized for the lower (antisense) strand of the siNA duplex. If terminal TT residues are desired for the sequence (as described in paragraph 7), then the two 3' terminal nucleotides of both the sense and antisense strands are replaced by TT prior to synthesizing the oligos.

9. The siNA molecules are screened in an in vitro, cell culture or animal model system to identify the most active siNA molecule or the most preferred target site within the target RNA sequence.

10. Other design considerations can be used when selecting target nucleic acid sequences, see, for example, Reynolds et al., 2004, *Nature Biotechnology Advanced Online Publication,* 1 Feb. 2004, doi:10.1038/nbt936 and Ui-Tei et al., 2004, Nucleic Acids Research, 32, doi:10.1093/nar/gkh247.

Example 3 siNA Design siNA target sites were chosen by analyzing sequences of the target RNA target and optionally prioritizing the target sites on the basis of folding (structure of any given sequence analyzed to determine siNA accessibility to the target), by using a library of siNA molecules, or alternately by using an in vitro siNA system as described herein. siNA molecules are designed that could bind each target and are optionally individually analyzed by computer folding to assess whether the siNA molecule can interact with the target sequence. Varying the length of the siNA molecules can be chosen to optimize activity. Generally, a sufficient number of complementary nucleotide bases are chosen to bind to, or otherwise interact with, the target RNA, but the degree of complementarity can be modulated to accommodate siNA duplexes or varying length or base composition. By using such methodologies, siNA molecules can be designed to target sites within any known RNA sequence, for example those RNA sequences corresponding to the any gene transcript.

Chemically modified siNA constructs are designed to provide nuclease stability for systemic administration in vivo and/or improved pharmacokinetic, localization, and delivery properties while preserving the ability to mediate RNAi activity. Chemical modifications as described herein are introduced synthetically using synthetic methods described herein and those generally known in the art. The synthetic siNA constructs are then assayed for nuclease stability in serum and/or cellular/tissue extracts (e.g. liver extracts). The synthetic siNA constructs are also tested in parallel for RNAi activity using an appropriate assay, such as a luciferase reporter assay as described herein or another suitable assay that can quantity RNAi activity. Synthetic siNA constructs that possess both nuclease stability and RNAi activity can be further modified and re-evaluated in stability and activity assays. The chemical modifications of the stabilized active siNA constructs can then be applied to any siNA sequence targeting any chosen RNA and used, for example, in target screening assays to pick lead siNA compounds for therapeutic development.

Example 4

Chemical Synthesis and Purification of siNA siNA molecules can be designed to interact with various sites in the RNA message, for example, target sequences within the RNA sequences described herein. The sequence of one strand of the siNA molecule(s) is complementary to the target site sequences described above. The siNA molecules can be chemically synthesized using methods described herein. Inactive siNA molecules that are used as control sequences can be synthesized by scrambling the sequence of the siNA molecules such that it is not complementary to the target sequence. Generally, siNA constructs can by synthesized using solid phase oligonucleotide synthesis methods as described herein (see for example Usman et al., U.S. Pat. Nos. 5,804,683; 5,831,071; 5,998,203; 6,117,657; 6,353,098; 6,362,323; 6,437,117; 6,469,158; Scaringe et al., U.S. Pat. Nos. 6,111,086; 6,008,400; 6,111,086 all incorporated by reference in their entireties herein).

In a non-limiting example, RNA oligonucleotides are synthesized in a stepwise fashion using the phosphoramidite chemistry as is known in the art. Standard phosphoramidite chemistry involves the use of nucleosides comprising any of 5'-O-dimethoxytrityl, 2'-O-tert-butyldimethylsilyl, 3'-O-2-Cyanoethyl N,N-diisopropylphosphoroamidite groups, and exocyclic amine protecting groups (e.g. N6-benzoyl adenosine, N4 acetyl cytidine, and N2-isobutyryl guanosine). Alternately, 2'-O-Silyl Ethers can be used in conjunction with acid-labile 2'-O-orthoester protecting groups in the synthesis of RNA as described by Scaringe supra. Differing 2' chemistries can require different protecting groups, for example 2'-deoxy-2'-amino nucleosides can utilize N-phthaloyl protection as described by Usman et al., U.S. Pat. No. 5,631,360, incorporated by reference herein in its entirety).

During solid phase synthesis, each nucleotide is added sequentially (3'- to 5'-direction) to the solid support-bound oligonucleotide. The first nucleoside at the 3'-end of the chain is covalently attached to a solid support (e.g., controlled pore glass or polystyrene) using various linkers. The nucleotide precursor, a ribonucleoside phosphoramidite, and activator are combined resulting in the coupling of the second nucleoside phosphoramidite onto the 5'-end of the first nucleoside. The support is then washed and any unreacted 5'-hydroxyl groups are capped with a capping reagent such as acetic anhydride to yield inactive 5'-acetyl moieties. The trivalent phosphorus linkage is then oxidized to a more stable phosphate linkage. At the end of the nucleotide addition cycle, the 5'-O-protecting group is cleaved under suitable conditions (e.g., acidic conditions for trityl-based groups and Fluoride for silyl-based groups). The cycle is repeated for each subsequent nucleotide.

Modification of synthesis conditions can be used to optimize coupling efficiency, for example by using differing coupling times, differing reagent/phosphoramidite concentrations, differing contact times, differing solid supports and solid support linker chemistries depending on the particular chemical composition of the siNA to be synthesized. Deprotection and purification of the siNA can be performed as is generally described in Usman et al., U.S. Pat. No. 5,831,071, U.S. Pat. No. 6,353,098, U.S. Pat. No. 6,437,117, and Bellon et al, U.S. Pat. No. 6,054,576, U.S. Pat. No. 6,162,909, U.S. Pat. No. 6,303,773, or Scaringe supra, incorporated by reference herein in their entireties. Additionally, deprotection conditions can be modified to provide the best possible yield and purity of siNA constructs. For example, applicant has observed that oligonucleotides comprising 2'-deoxy-2'-fluoro nucleotides can degrade under inappropriate deprotection conditions. Such oligonucleotides are deprotected using aqueous methylamine at about 35° C. for 30 minutes. If the 2'-deoxy-2'-fluoro containing oligonucleotide also comprises ribonucleotides, after deprotection with aqueous methylamine at about 35° C. for 30 minutes, TEA-HF is added and the reaction maintained at about 65° C. for an additional 15 minutes. siNA molecules that are deprotected, purified, and/or annealed are then formulated as described herein.

Example 5

RNAi in vitro Assay to Assess siNA Activity

An in vitro assay that recapitulates RNAi in a cell-free system is used to evaluate siNA constructs targeting RNA targets. The assay comprises the system described by Tuschl et al., 1999, *Genes and Development*, 13, 3191-3197 and Zamore et al., 2000, *Cell*, 101, 25-33 adapted for use with target RNA. A *Drosophila* extract derived from syncytial blastoderm is used to reconstitute RNAi activity in vitro. Target RNA is generated via in vitro transcription from an appropriate hairless expressing plasmid using T7 RNA polymerase or via chemical synthesis as described herein. Sense and antisense siNA strands (for example 20 uM each) are annealed by incubation in buffer (such as 100 mM potassium acetate, 30 mM HEPES-KOH, pH 7.4, 2 mM magnesium acetate) for 1 minute at 90° C. followed by 1 hour at 37° C., then diluted in lysis buffer (for example 100 mM potassium acetate, 30 mM HEPES-KOH at pH 7.4, 2 mM magnesium acetate). Annealing can be monitored by gel electrophoresis on an agarose gel in TBE buffer and stained with ethidium bromide. The *Drosophila* lysate is prepared using zero to two-hour-old embryos from Oregon R flies collected on yeasted molasses agar that are dechorionated and lysed. The lysate is centrifuged and the supernatant isolated. The assay comprises a reaction mixture containing 50% lysate [vol/vol], RNA (10-50 pM final concentration), and 10% [vol/vol] lysis buffer containing siNA (10 nM final concentration). The reaction mixture also contains 10 mM creatine phosphate, 10 ug/ml creatine phosphokinase, 100 um GTP, 100 uM UTP, 100 uM CTP, 500 uM ATP, 5 mM DTT, 0.1 U/uL RNasin (Promega), and 100 uM of each amino acid. The final concentration of potassium acetate is adjusted to 100 mM. The reactions are pre-assembled on ice and preincubated at 25° C. for 10 minutes before adding RNA, then incubated at 25° C. for an additional 60 minutes. Reactions are quenched with 4 volumes of 1.25× Passive Lysis Buffer (Promega). Target RNA cleavage is assayed by RT-PCR analysis or other methods known in the art and are compared to control reactions in which siNA is omitted from the reaction.

Alternately, internally-labeled target RNA for the assay is prepared by in vitro transcription in the presence of [alpha-$^{32}$P] CTP, passed over a G 50 Sephadex column by spin chromatography and used as target RNA without further purification. Optionally, target RNA is 5'-$^{32}$P-end labeled using T4 polynucleotide kinase enzyme. Assays are performed as described above and target RNA and the specific RNA cleavage products generated by RNAi are visualized on an autoradiograph of a gel. The percentage of cleavage is determined by PHOSPHOR IMAGER® (autoradiography) quantitation of bands representing intact control RNA or RNA from control reactions without siNA and the cleavage products generated by the assay.

In one embodiment, this assay is used to determine target sites the RNA target for siNA mediated RNAi cleavage, wherein a plurality of siNA constructs are screened for RNAi mediated cleavage of the RNA target, for example, by analyzing the assay reaction by electrophoresis of labeled target RNA, or by northern blotting, as well as by other methodology well known in the art.

Example 6

Nucleic Acid Inhibition of Target RNA siNA molecules targeted to the human target RNA are designed and synthesized as described above. These nucleic acid molecules can be tested for cleavage activity in vivo, for example, using the following procedure.

Two formats are used to test the efficacy of siNAs targeting target. First, the reagents are tested in cell culture to determine the extent of RNA and protein inhibition. siNA reagents are selected against the target as described herein. RNA inhibition is measured after delivery of these reagents by a suitable transfection agent to cells. Relative amounts of target RNA are measured versus actin using real-time PCR monitoring of amplification (e.g. ABI 7700 TAQMAN®). A comparison is made to a mixture of oligonucleotide sequences made to unrelated targets or to a randomized siNA control with the same overall length and chemistry, but randomly substituted at each position. Primary and secondary lead reagents are chosen for the target and optimization performed. After an optimal transfection agent concentration is chosen, a RNA time-course of inhibition is performed with the lead siNA molecule. In addition, a cell-plating format can be used to determine RNA inhibition.

Delivery of siNA to Cells

Cells are seeded, for example, at 1×10$^5$ cells per well of a six-well dish in EGM-2 (BioWhittaker) the day before transfection. Formulated siNA compositions are complexed in EGM basal media (Bio Whittaker) at 37° C. for 30 minutes in polystyrene tubes. Following vortexing, the complexed formulated siNA composition is added to each well and incubated for the times indicated. For initial optimization experiments, cells are seeded, for example, at 1×10$^3$ in 96 well plates and siNA complex added as described. Efficiency of delivery of siNA to cells is determined using a fluorescent siNA complexed with lipid. Cells in 6-well dishes are incubated with siNA for 24 hours, rinsed with PBS and fixed in 2% paraformaldehyde for 15 minutes at room temperature. Uptake of siNA is visualized using a fluorescent microscope.

TAQMAN® (Real-time PCR Monitoring of Amplification) and Lightcycler Quantification of mRNA Total RNA is prepared from cells following siNA delivery, for example, using Qiagen RNA purification kits for 6-well or Rneasy extraction kits for 96-well assays. For TAQMAN® analysis (real-time PCR monitoring of amplification), dual-labeled probes are synthesized with the reporter dye, FAM or JOE, covalently linked at the 5'-end and the quencher dye TAMRA conjugated to the 3'-end. One-step RT-PCR amplifications are performed on, for example, an ABI PRISM 7700 Sequence Detector using 50 µl reactions consisting of 10 µl total RNA, 100 nM forward primer, 900 nM reverse primer, 100 nM probe, 1×TaqMan PCR reaction buffer (PE-Applied Biosystems), 5.5 mM $MgCl_2$, 300 µM each dATP, dCTP, dGTP, and dTTP, 10 U RNase Inhibitor (Promega), 1.25 U AMPLITAQ GOLD® (DNA polymerase) (PE-Applied Biosystems) and 10 U M-MLV Reverse Transcriptase (Promega). The thermal cycling conditions can consist of 30 minutes at 48° C., 10 minutes at 95° C., followed by 40 cycles of 15 seconds at 95° C. and 1 minute at 60° C. Quantitation of mRNA levels is determined relative to standards generated from serially diluted total cellular RNA (300, 100, 33, 11 ng/rxn) and normalizing to β-actin or GAPDH mRNA in parallel TAQMAN® reactions (real-time PCR monitoring of amplification). For each gene of interest an upper and lower primer and a fluorescently labeled probe are designed. Real time incorporation of SYBR Green I dye into a specific PCR product can be measured in glass capillary tubes using a lightcyler. A standard curve is generated for each primer pair using control cRNA. Values are represented as relative expression to GAPDH in each sample.

Western Blotting

Nuclear extracts can be prepared using a standard micro preparation technique (see for example Andrews and Faller, 1991, *Nucleic Acids Research*, 19, 2499). Protein extracts from supernatants are prepared, for example using TCA precipitation. An equal volume of 20% TCA is added to the cell supernatant, incubated on ice for 1 hour and pelleted by centrifugation for 5 minutes. Pellets are washed in acetone, dried and resuspended in water. Cellular protein extracts are run on a 10% Bis-Tris NuPage (nuclear extracts) or 4-12% Tris-Glycine (supernatant extracts) polyacrylamide gel and transferred onto nitro-cellulose membranes. Non-specific binding can be blocked by incubation, for example, with 5% non-fat milk for 1 hour followed by primary antibody for 16 hour at 4° C. Following washes, the secondary antibody is applied, for example (1:10,000 dilution) for 1 hour at room temperature and the signal detected with SuperSignal reagent (Pierce).

Example 7

Evaluation of Serum Stability of Formulated siNA Compositions

As discussed herein, one way to determine the transfection or delivery efficiency of the formulated lipid composition is to determine the stability of the formulated composition in serum in vitro. Relative turbity measurement can be used to determine the in vitro serum stability of the formulated siNA compositions.

Figure 8:
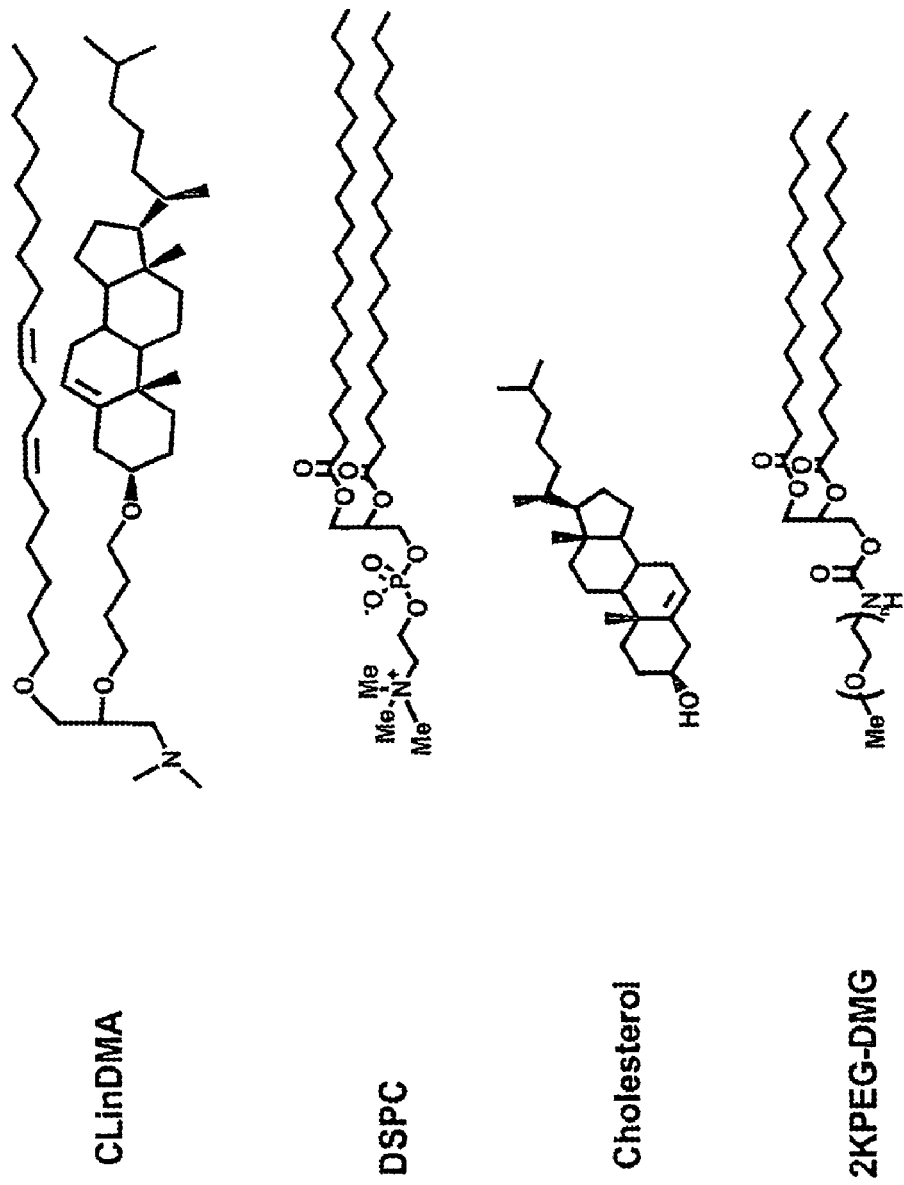
FIG. 8 shows the components of L051, a serum-stable formulated molecular composition that undergoes a rapid pH-dependent phase transition.
Figure 9:
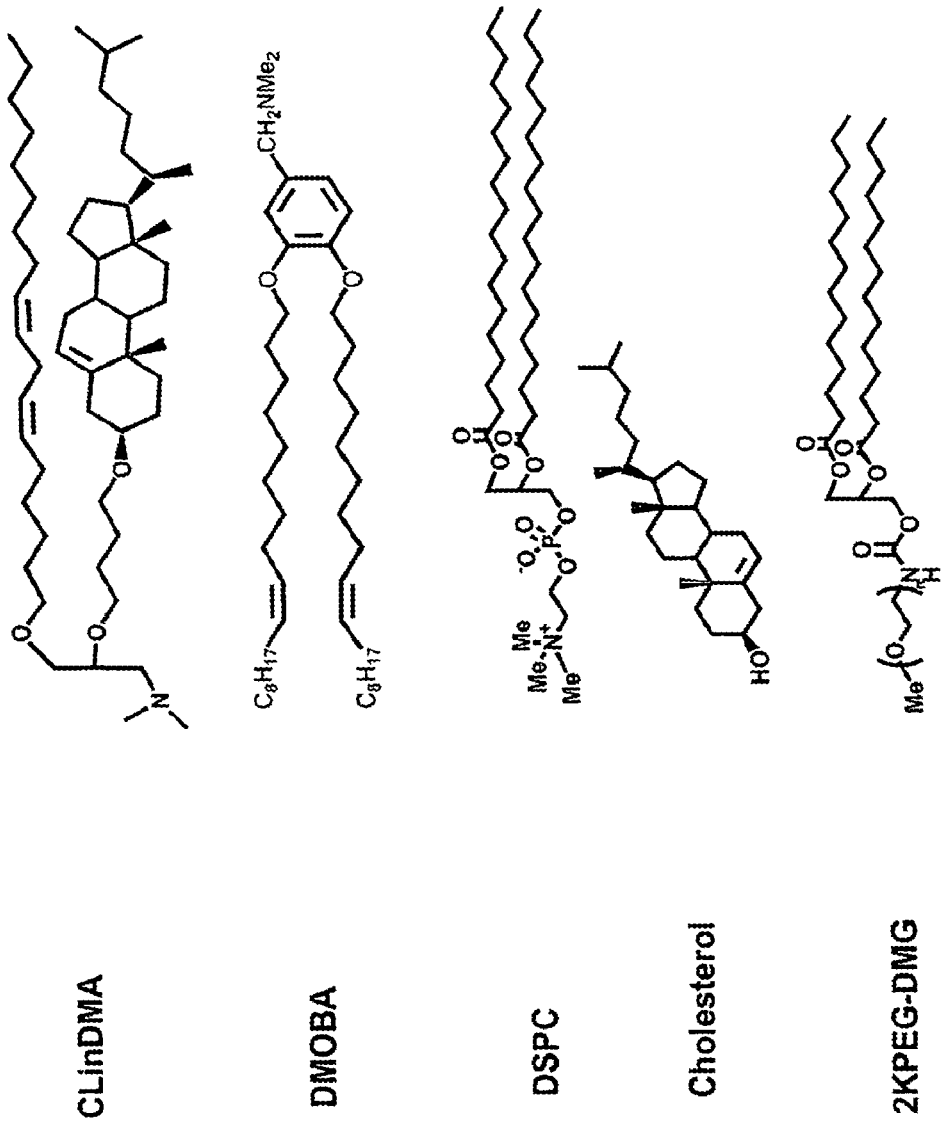
FIG. 9 shows the components of L073, a serum-stable formulated molecular composition that undergoes a rapid pH-dependent phase transition.
Figure 10:
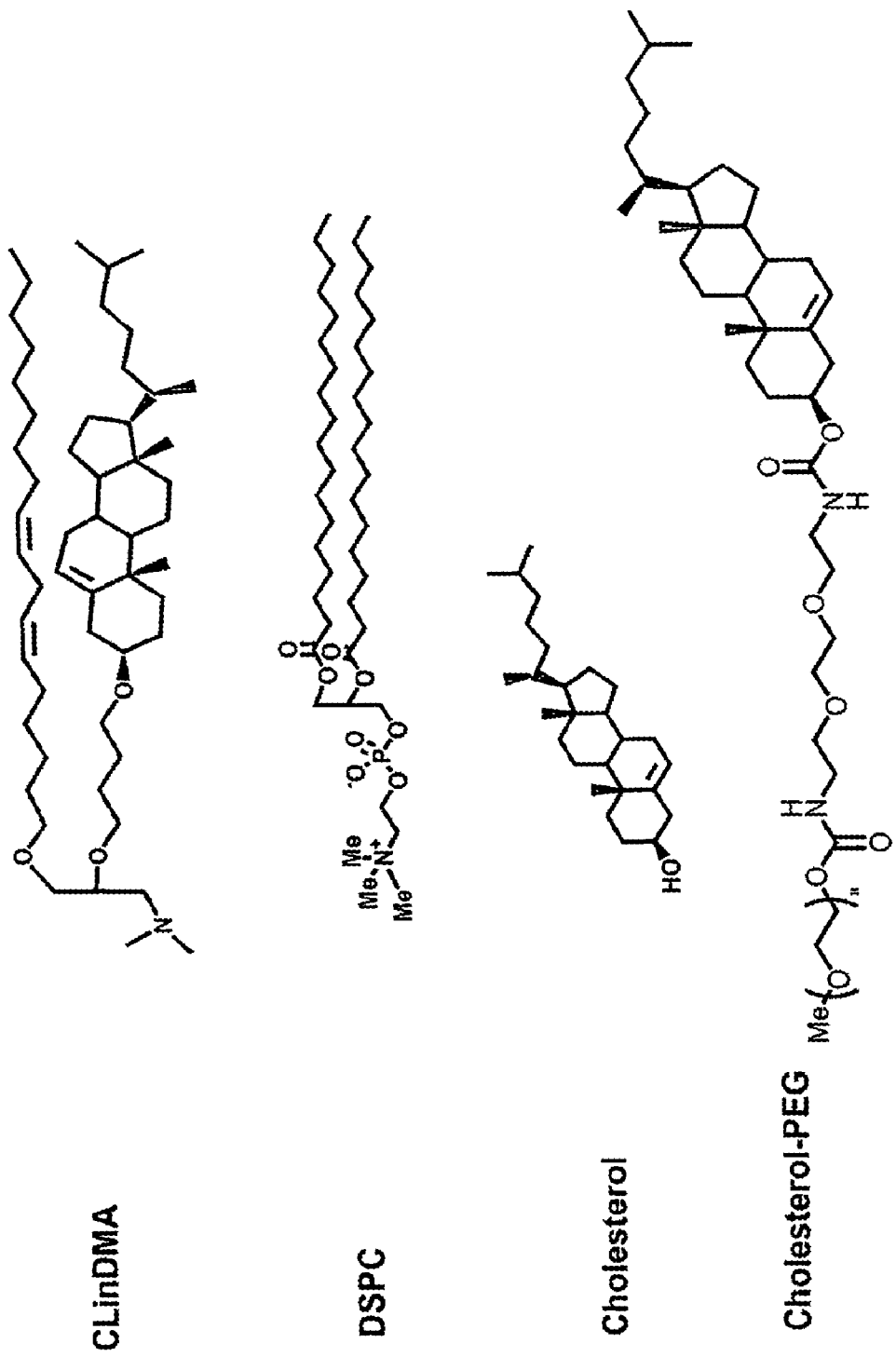
FIG. 10 shows the components of L069, a serum-stable formulated molecular composition that undergoes a rapid pH-dependent phase transition.
Figure 11:
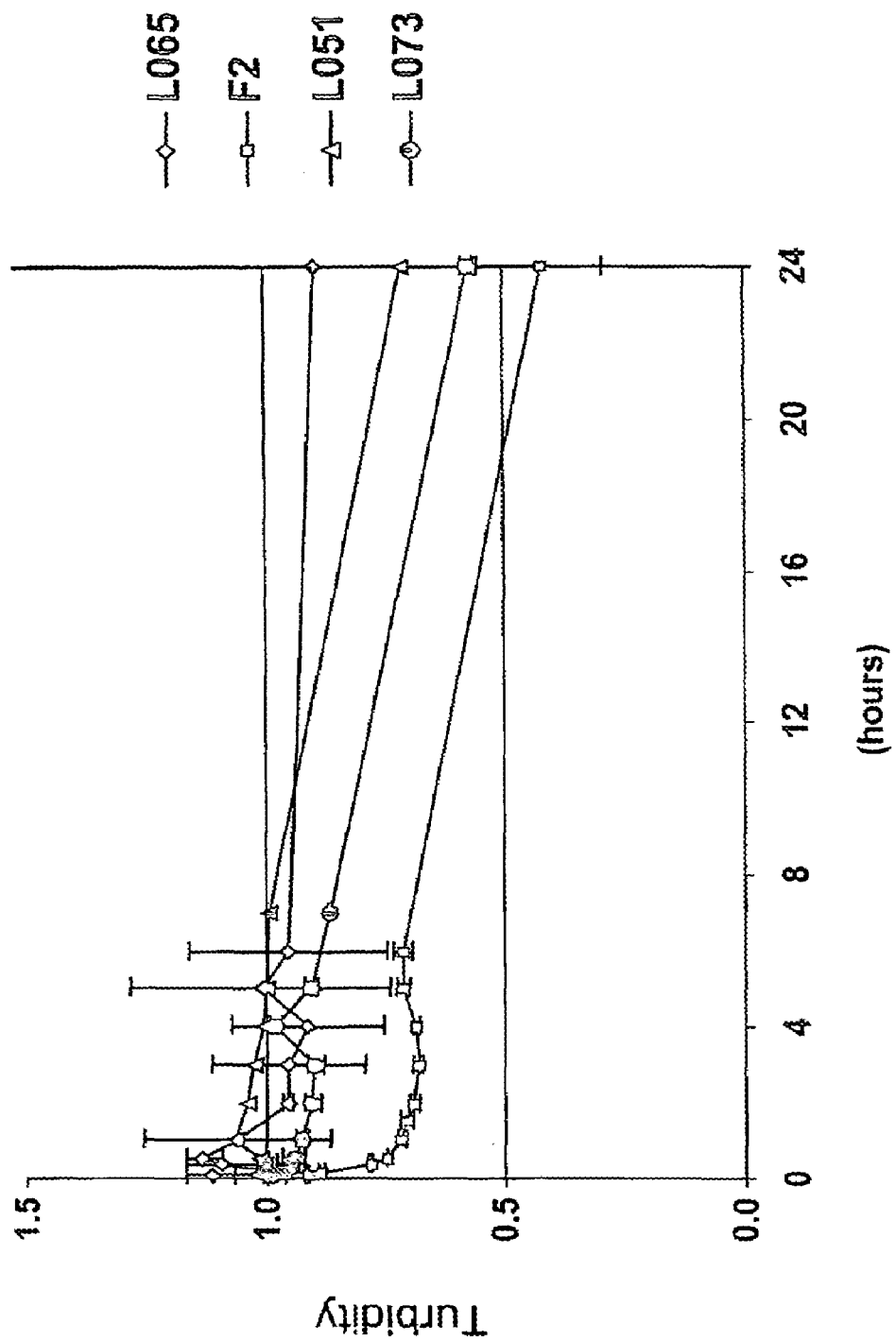
FIG. 11 shows a graph depicting the serum stability of formulated molecular compositions L065, F2, L051, and L073 as determined by the relative turbidity of the formulated molecular compositions in 50% serum measured by absorbance at 500 nm. Formulated molecular compositions L065, L051, and L073 are stable in serum.
Figure 33:
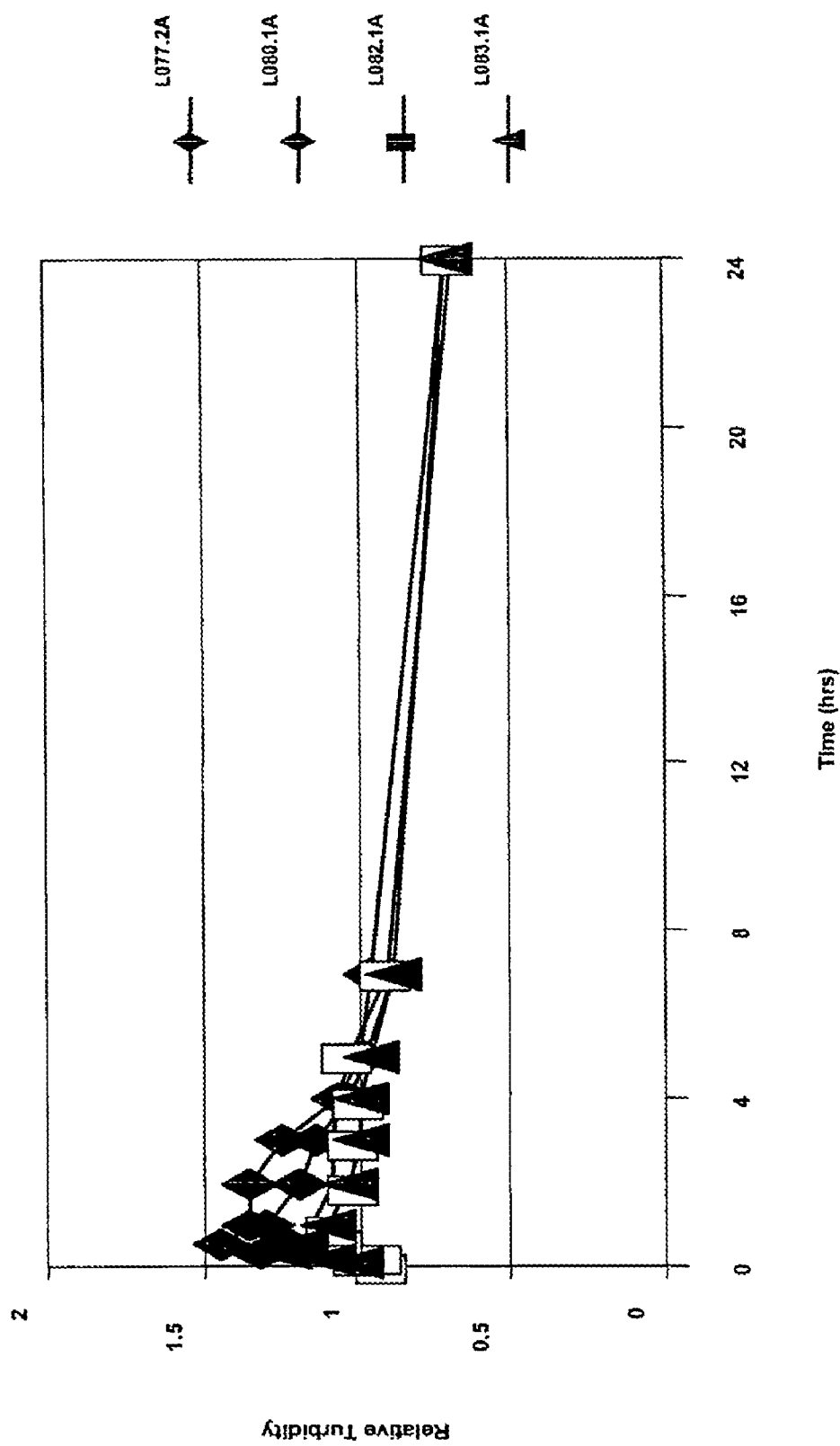
FIG. 33 shows a non-limiting example of the serum stability of siNA L077, L080, L082, and L083 (Table IV) nanoparticle formulations.

Turbidity measurements were employed to monitor the serum stability of lipid particle formulations L065, F2, L051, and L073 (see FIGS. 8 and 9 for the lipid formulations of L051 and L073). The lipid formulation of L065 comprises cationic lipid CpLinDMA, neutral lipid DSPC, cholesterol, and 2 kPEG-DMG. The lipid formulation F2 comprises DODAP. The absorbance of formulated siNA compositions (0.1 mg/ml) in the absence and presence of 50% serum was measured at 500 nm with a corresponding amount of serum alone as a reference by using SpectraMax® Plus384 microplate spectrophotometer from Molecular Devices (Sunnyvale, Calif.). The formulations were incubated at 37° C. and analyzed at 2 min, 5 min, 10 min, 20 min, 30 min, 1 h, 2 h, 3 h, 4 h, 5 h, 7 h and 24 h. Relative turbidity was determined by dividing the sample turbidity by the turbidity of 2 min formulated siNA compositions incubated in 50% serum. A formulated molecular composition is stable in serum if the relative turbidity remains constant around 1.0 over time. As shown in FIG. 11, formulated siNA compositions L065, L051, and L073 are serum-stable lipid nanoparticle compositions. As shown in FIG. 33, formulated siNA compositions L077, L080, L082 and L083, are serum-stable lipid nanoparticle compositions.

Example 8

Evaluation of pH-dependent Phase Transition of Formulated siNA Compositions

Additionally, the transfection or delivery efficiency of the formulated lipid composition can be determined by determining the pH-dependent phase transition of the formulated composition in vitro. Relative turbity measurement can be used to determine the pH-dependent phase transition of formulated siNA compositions in vitro.

Figure 12:
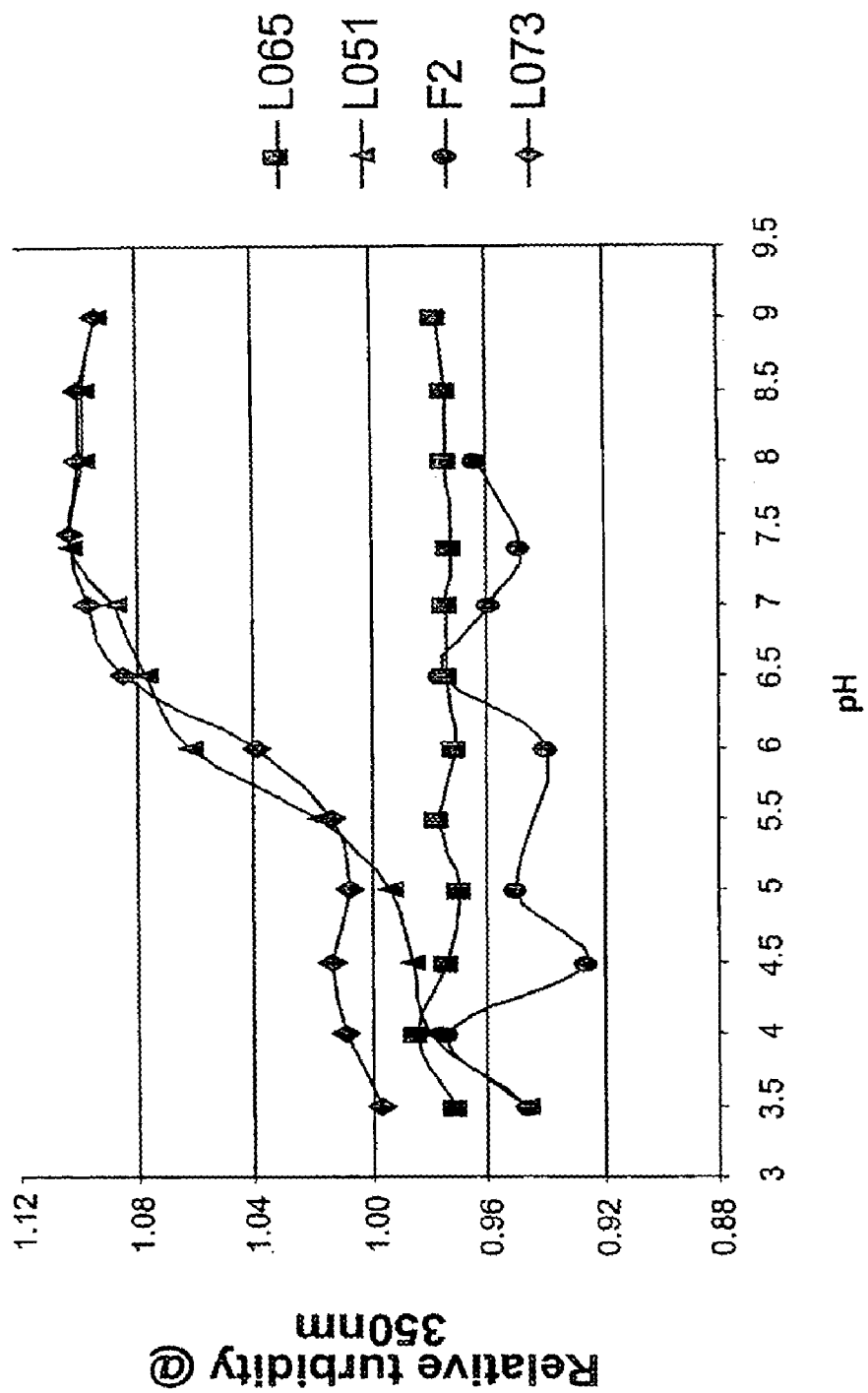
FIG. 12 shows a graph depicting the pH-dependent phase transition of formulated molecular compositions L065, F2, L051, and L073 as determined by the relative turbidity of the formulated molecular compositions in buffer solutions ranging from pH 3.5 to pH 9.0 measured by absorbance at 350 nm. Formulated molecular compositions L051 and L073 each undergo a rapid pH-dependent phase transition at pH 5.5-pH 6.5.
Figure 13:
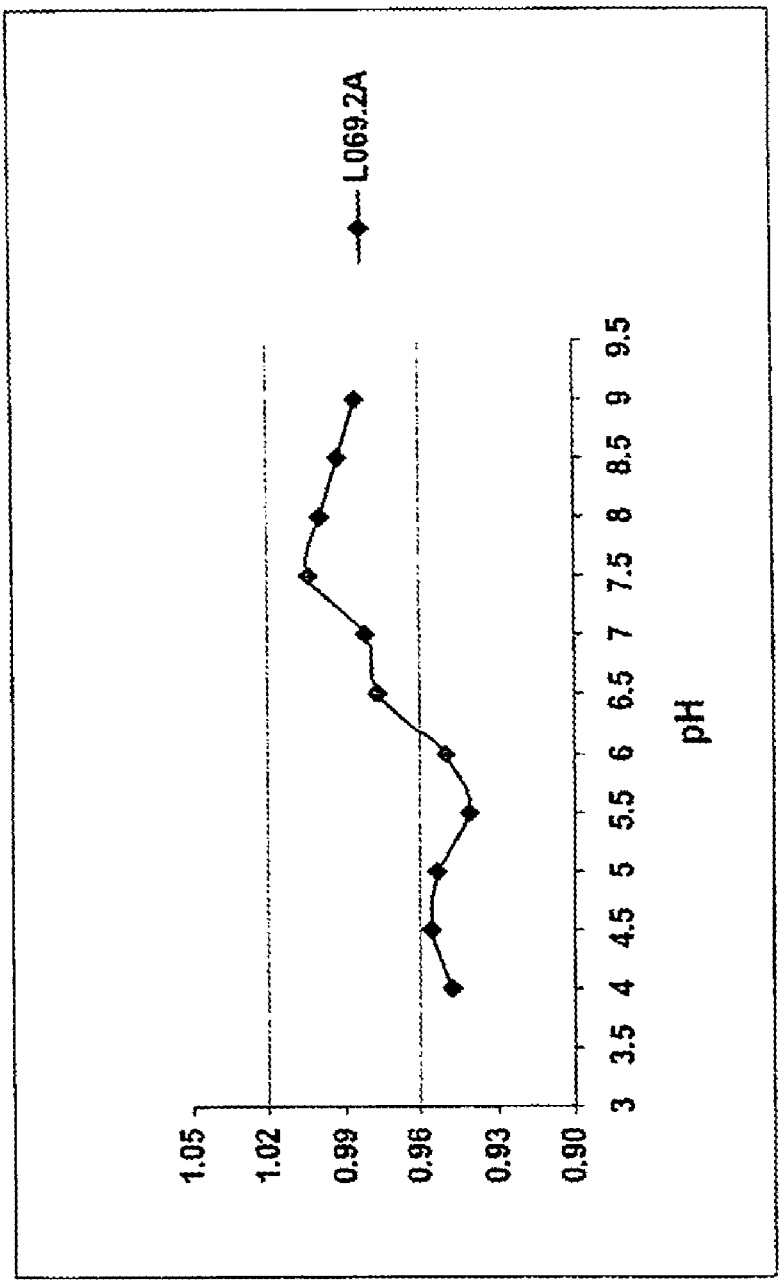
FIG. 13 shows a graph depicting the pH-dependent phase transition of formulated molecular composition L069 as determined by the relative turbidity of the formulated molecular composition in buffer solutions ranging from pH 3.5 to pH 9.0 measured by absorbance at 350 nm. Formulated molecular composition L069 undergoes a rapid pH-dependent phase transition at pH 5.5-pH 6.5.
Figure 34:
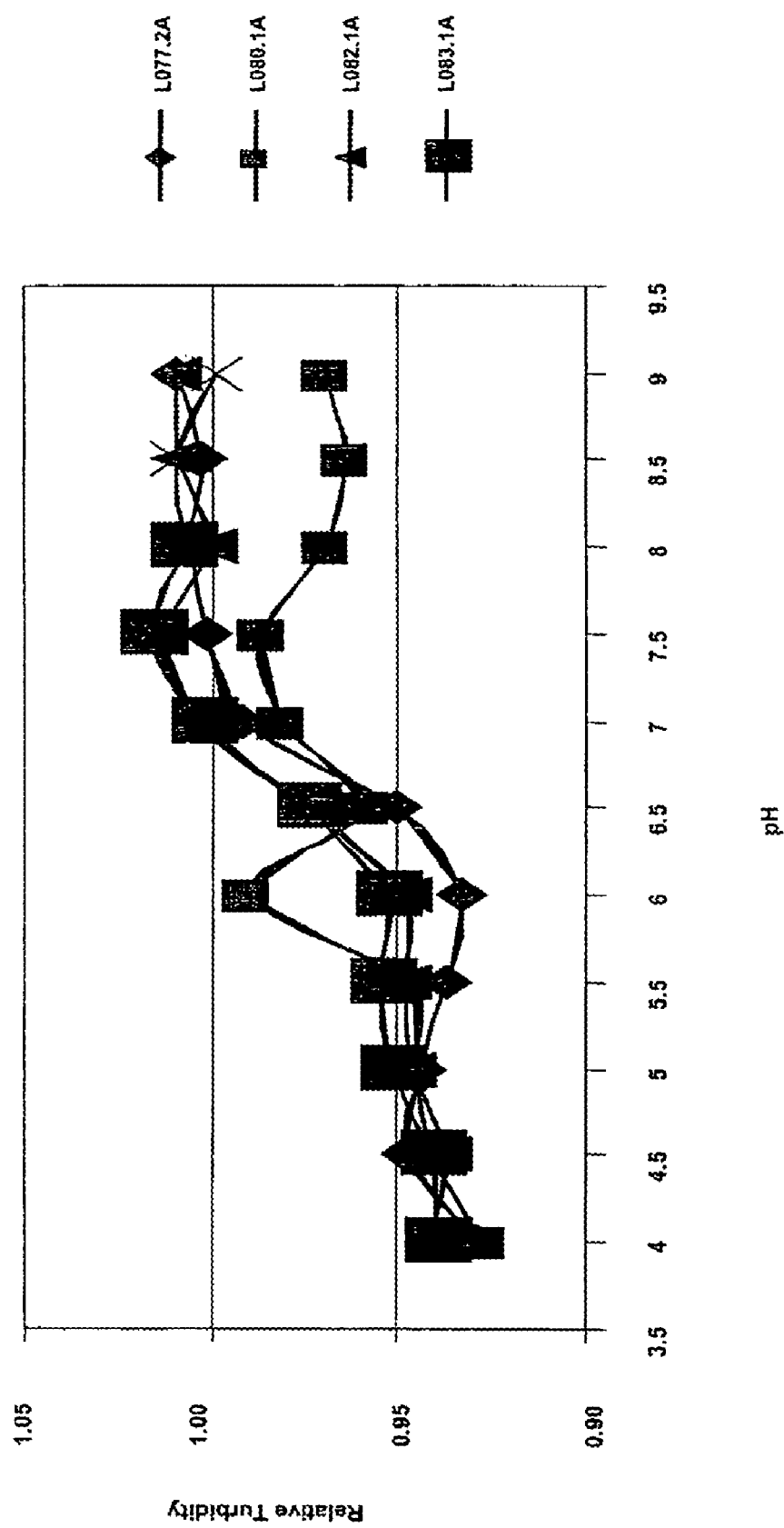
FIG. 34 shows a graph depicting the pH-dependent phase transition of siNA L077, L080, L082, and L083 (Table IV) nanoparticle formulations as determined by the relative turbidity of the formulated molecular composition in buffer solutions ranging from pH 3.5 to pH 9.0 measured by absorbance at 350 nm. Formulated molecular composition L069 undergoes a rapid pH-dependent phase transition at pH 5.5-pH 6.5.

Turbidity measurement was employed to monitor the phase transition of formulated siNA compositions L065, L051, F2, L073, and L069. The absorbance of lipid particle formulations (0.1 mg/ml) in 0.1 M phosphate buffer with pH at 3.5, 4.0, 4.5, 5.0, 5.5, 6.0, 6.5, 7.0, 7.5, 8.0, 8.5 and 9.0 was measured at 350 nm with a corresponding amount of buffer alone as a reference by using SpectraMax® Plus384 microplate spectrophotometer from Molecular Devices (Sunnyvale, Calif.). This assay measures the relative light scattering of the formulations at various pH. The lamellar structure (i.e., serum stable structure) having relatively bigger particle size is expected to scatter more light than the corresponding inverted hexagonal structure. The samples were incubated at 37° C. and analyzed at 2 min, 5 min, 10 min, 30 min, and 2 h. Relative turbidity was determined by dividing the sample turbidity by the turbidity of 2 min formulated siNA compositions incubated in phosphate buffer at pH 7.5. A formulated molecular composition undergoes pH-dependent phase transition if there is a change in the relative turbidity when measured between pH 7.5-pH 5.0. As shown in FIG. 12, formulated siNA compositions L051 and L073 undergo pH-dependent phase transition at pH 6.5-pH 5.0. As shown in FIG. 13, formulated siNA composition L069 undergoes pH-dependent phase transition at pH 6.5-pH 5.0. As shown in FIG. 34, formulated siNA compositions L077, L080, L082, and L083 undergo pH-dependent phase transition at pH 6.5-pH5.0.

Example 9

Evaluation of Formulated siNA Compositions in Models of Chronic HBV Infection

In Vitro Analysis of siNA Nanoparticle Activity

Figure 15:
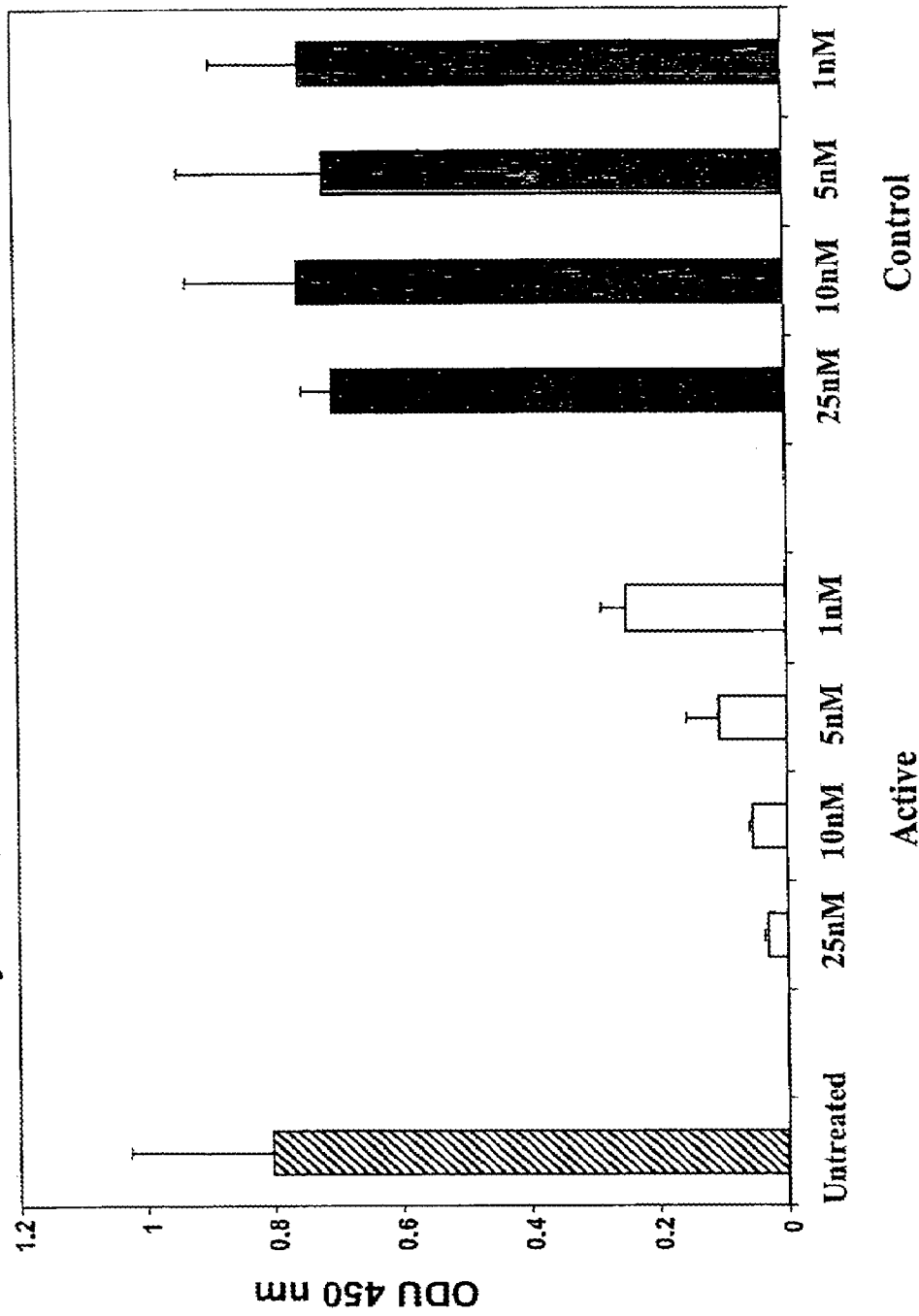
FIG. 15 shows a non-limiting example of in vitro efficacy of siNA nanoparticles in reducing HBsAg levels in HepG2 cells. Active chemically modified siNA molecules were designed to target HBV site 263 RNA (siNA sequences are shown in FIG. 14). The figure shows the level of HBsAg in cells treated with formulated active siNA L051 nanoparticles (see Table IV) compared to untreated or negative control treated cells. A dose dependent reduction in HBsAg levels was observed in the active siNA treated cells, while no reduction is observed in the negative control treated cells.
Figure 16:
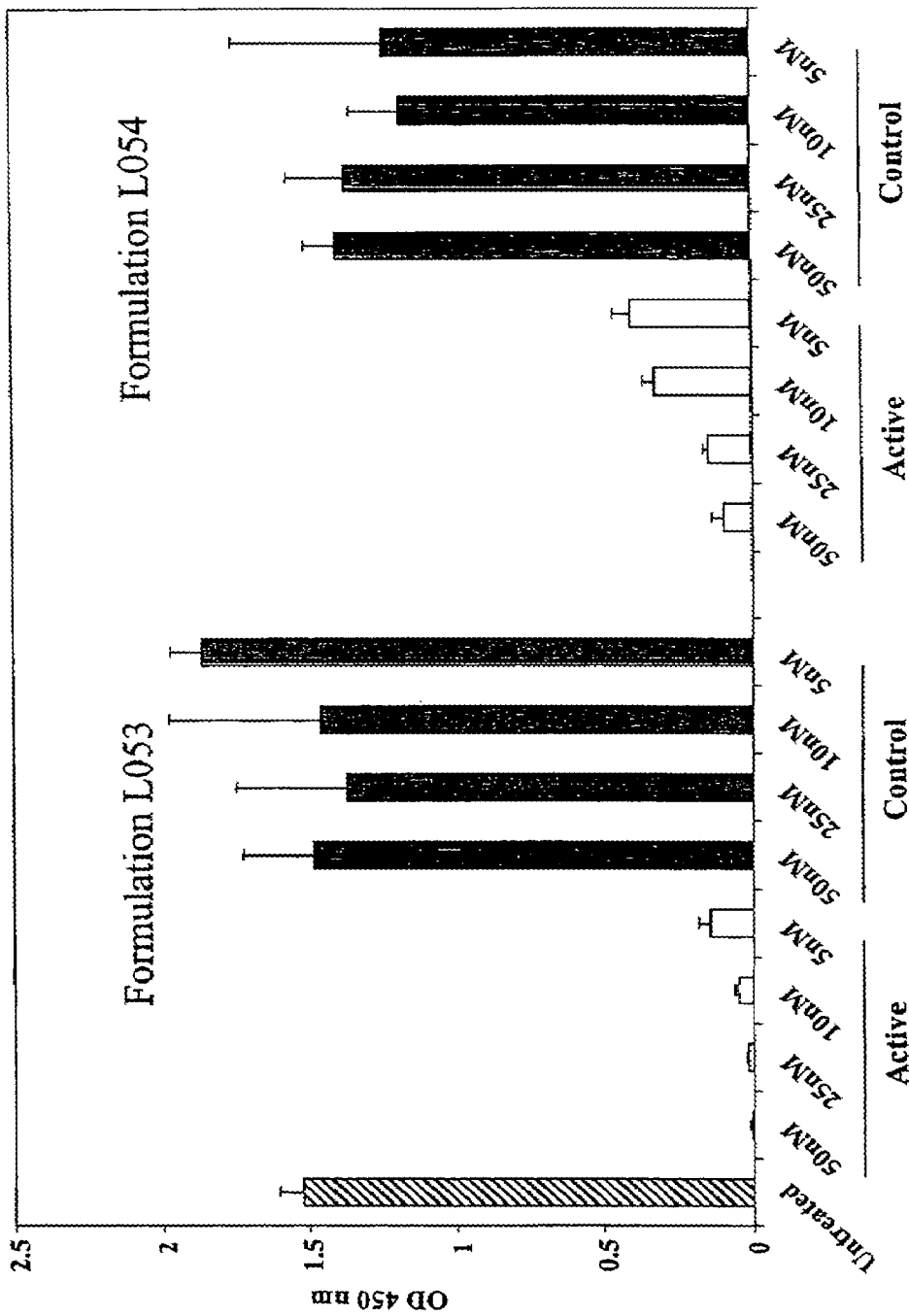
FIG. 16 shows a non-limiting example of in vitro efficacy of siNA nanoparticles in reducing HBsAg levels in HepG2 cells. Active chemically modified siNA molecules were designed to target HBV site 263 RNA (siNA sequences are shown in FIG. 14). The figure shows the level of HBsAg in cells treated with formulated active siNA L053 and L054 nanoparticles (see Table IV) compared to untreated or negative control treated cells. A dose dependent reduction in HBsAg levels was observed in the active siNA treated cells, while no reduction is observed in the negative control treated cells.
Figure 17:
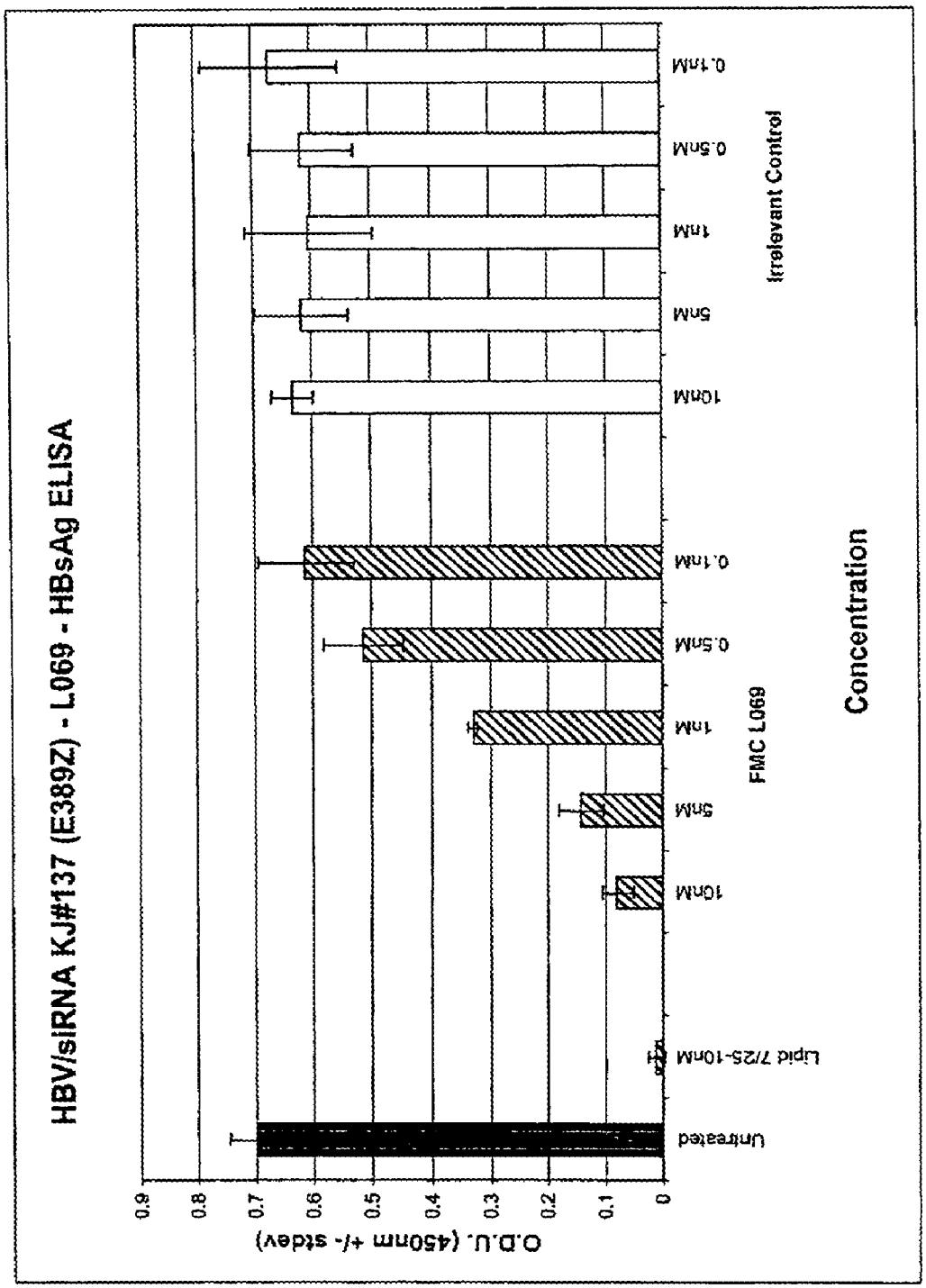
FIG. 17 shows a non-limiting example of in vitro efficacy of siNA nanoparticles in reducing HBsAg levels in HepG2 cells. Active chemically modified siNA molecules were designed to target HBV site 263 RNA (siNA sequences are shown in FIG. 14). The figure shows the level of HBsAg in cells treated with formulated molecular composition L069 comprising active siNA (see Table IV) compared to untreated or negative control treated cells. A dose dependent reduction in HBsAg levels was observed in the active siNA treated cells, while no reduction is observed in the negative control treated cells.
Figure 30:
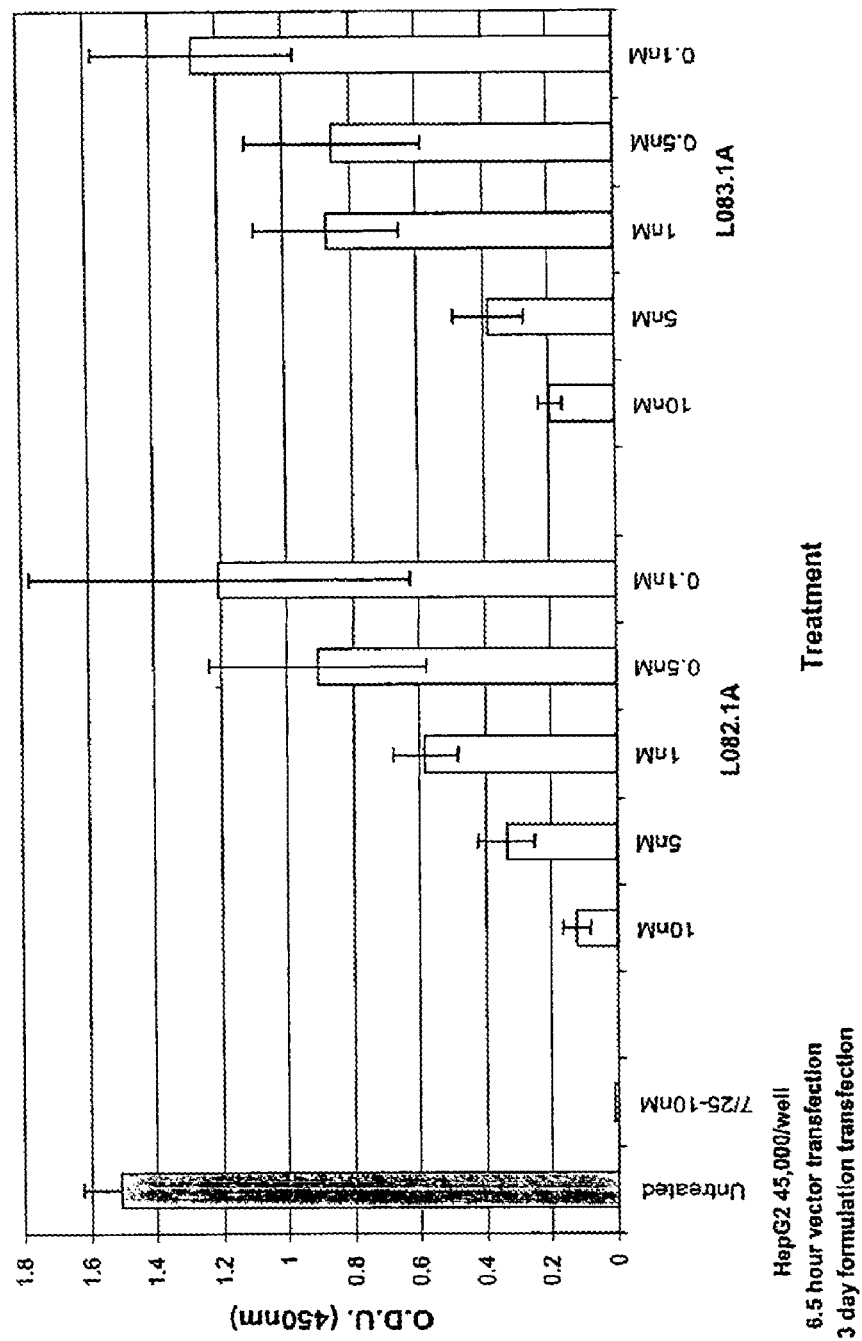
FIG. 30 shows a non-limiting example of the dose response activity of systemically administered siNA L083 and L084 (Table IV) nanoparticles in an HBV mouse model. A hydrodynamic tail vein injection was done containing 0.3 µg of the pWTD HBV vector. The nanoparticle encapsulated active siNA molecules were administered at 3 mg/kg/day for three days via standard IV injection beginning 6 days post-HDI. Groups (N=5) of animals were sacrificed at 3 and 7 days following the last dose, and the levels of serum HBsAg was measured. The serum HBsAg levels were assayed by ELISA and expressed as mean log 10 pg/ml (±SEM).
Figure 31:
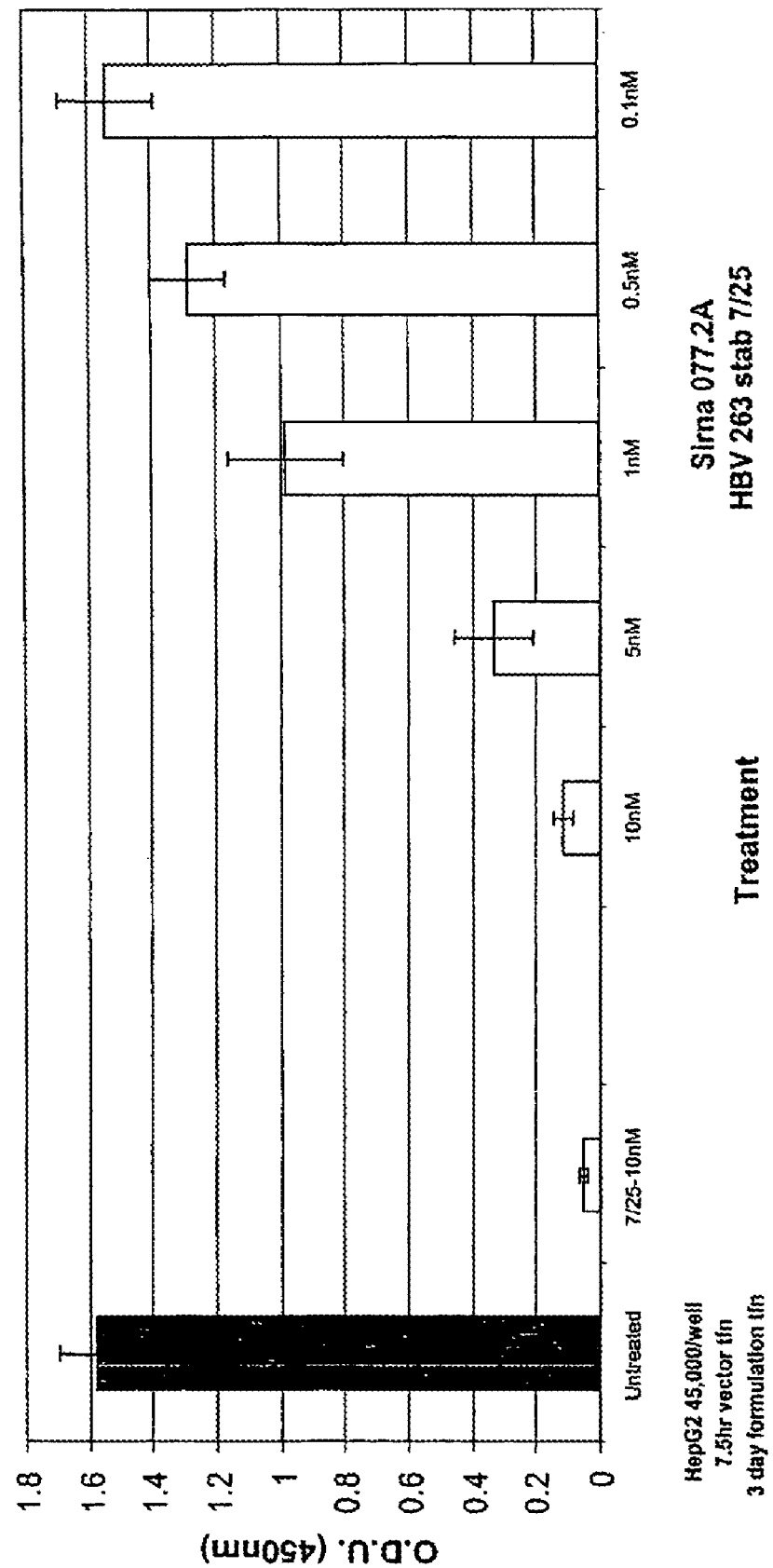
FIG. 31 shows a non-limiting example of the dose response activity of systemically administered siNA L077 (Table IV) nanoparticles in an HBV mouse model. A hydrodynamic tail vein injection was done containing 0.3 µg of the pWTD HBV vector. The nanoparticle encapsulated active siNA molecules were administered at 3 mg/kg/day for three days via standard IV injection beginning 6 days post-HDI. Groups (N=5) of animals were sacrificed at 3 and 7 days following the last dose, and the levels of serum HBsAg was measured. The serum HBsAg levels were assayed by ELISA and expressed as mean log 10 pg/ml (±SEM).
Figure 32:
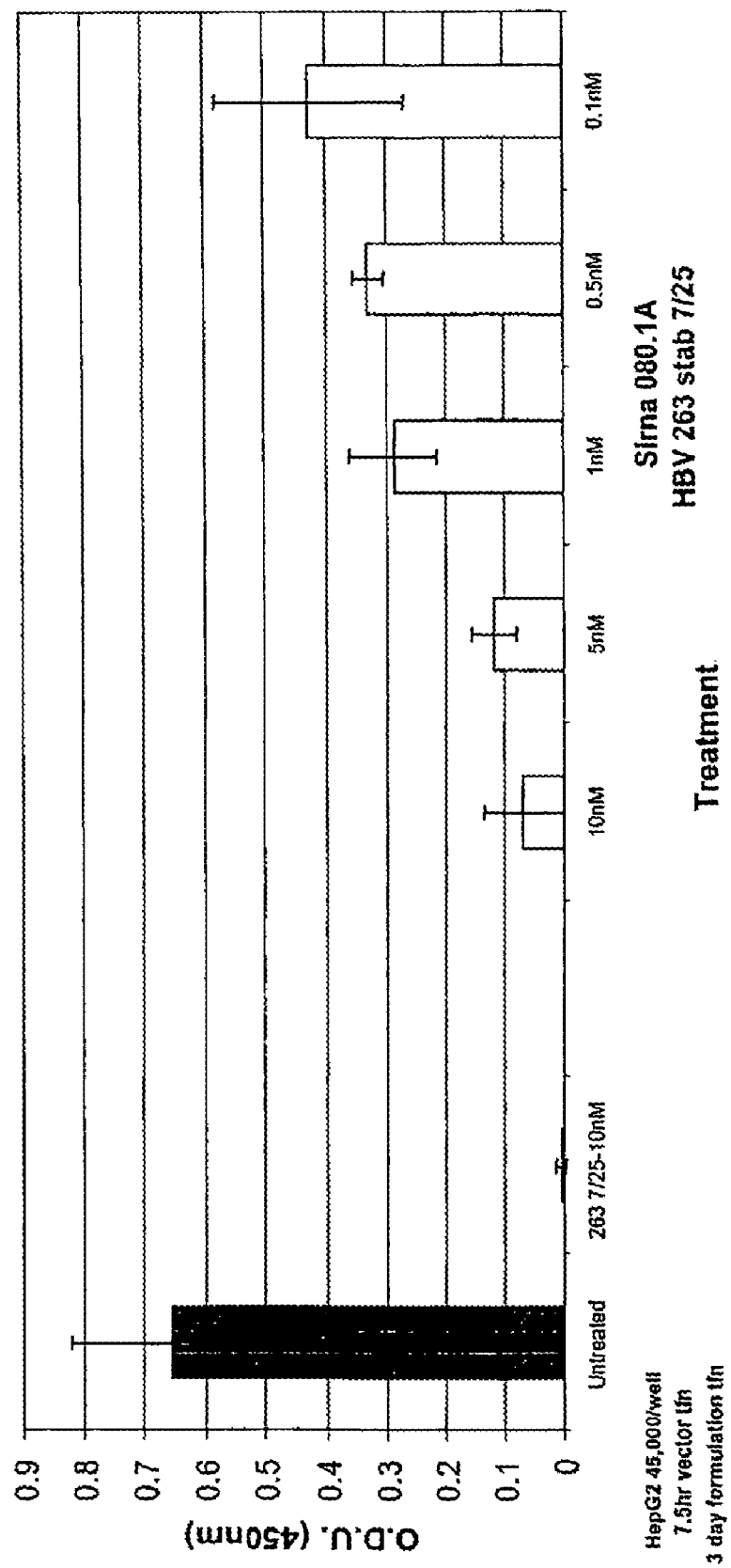
FIG. 32 shows a non-limiting example of the dose response activity of systemically administered siNA L080 (Table IV) nanoparticles in an HBV mouse model. A hydrodynamic tail vein injection was done containing 0.3 µg of the pWTD HBV vector. The nanoparticle encapsulated active siNA molecules were administered at 3 mg/kg/day for three days via standard IV injection beginning 6 days post-HDI. Groups (N=5) of animals were sacrificed at 3 and 7 days following the last dose, and the levels of serum HBsAg was measured. The serum HBsAg levels were assayed by ELISA and expressed as mean log 10 pg/ml (±SEM).

Hep G2 cells were grown in EMEM (Cellgro Cat#10-010-CV) with non-essential amino acids, sodium pyruvate (90%), and 10% fetal bovine serum (HyClone Cat#SH30070.03). Replication competent cDNA was generated by the excision and re-ligation of the HBV genomic sequences from the psHBV-1 vector. HepG2 cells were plated ($3 \times 10^4$ cells/well) in 96-well microtiter plates and incubated overnight. A cationic lipid/DNA complex was formed containing (at final concentrations) cationic lipid (11-15 µg/mL), and re-ligated psHBV-1 (4.5 µg/mL) in growth media. Following a 15 min incubation at 37° C., 20 µL of the complex was added to the plated HepG2 cells in 80 µL of growth media minus antibiotics. After 7.5 hours at 37° C., the media was then removed, the cells rinsed once with media, and 100 μL of fresh media was added to each well. 50 μL of the siNA nanoparticle formulation (see Example 9 for formulation details) (diluted into media at a 3× concentration) was added per well, with 3 replicate wells per concentration. The cells were incubated for 4 days, the media was then removed, and assayed for HBsAg levels. FIG. 15 shows level of HBsAg from formulated (Formulation L051, Table IV) active siNA treated cells compared to untreated or negative control treated cells. FIG. 16 shows level of HBsAg from formulated (Formulations L053 and L054, Table IV) active siNA treated cells compared to untreated or negative control treated cells. FIG. 17 shows level of HBsAg from formulated (Formulation L051, Table IV) active siNA treated cells compared to untreated or negative control treated cells. FIG. 30 shows level of HBsAg from formulated (Formulations L083 and L084, Table IV) active siNA treated cells compared to untreated or negative control treated cells. FIG. 31 shows level of HBsAg from formulated (Formulation L077, Table IV) active siNA treated cells compared to untreated or negative control treated cells. FIG. 32 shows level of HBsAg from formulated (Formulation L080, Table IV) active siNA treated cells compared to untreated or negative control treated cells. In these studies, a dose dependent reduction in HBsAg levels was observed in the active formulated siNA treated cells using nanoparticle formulations L051, L053, and L054, while no reduction is observed in the negative control treated cells. This result indicates that the formulated siNA compositions are able to enter the cells, and effectively engage the cellular RNAi machinery to inhibit viral gene expression.

Analysis of Formulated siRNA Activity in a Mouse Model of HBV Replication

Figure 18:
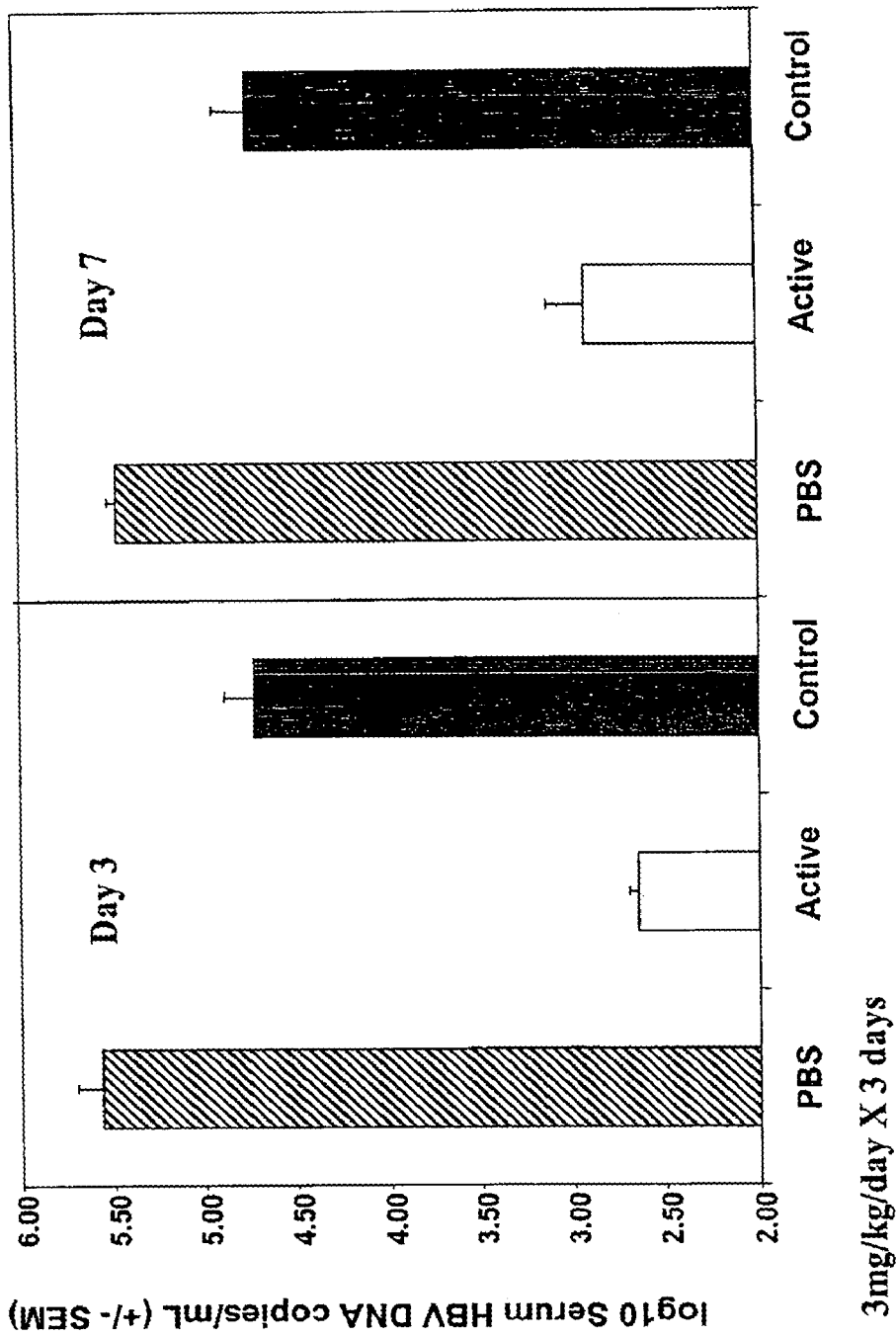
FIG. 18 shows a non-limiting example of the activity of systemically administered siNA L051 (Table IV) nanoparticles in an HBV mouse model. A hydrodynamic tail vein injection was done containing 0.3 µg of the pWTD HBV vector. The nanoparticle encapsulated active siNA molecules were administered at 3 mg/kg/day for three days via standard IV injection beginning 6 days post-HDI. Groups (N=5) of animals were sacrificed at 3 and 7 days following the last dose, and the levels of serum HBV DNA was measured. HBV DNA titers were determined by quantitative real-time PCR and expressed as mean log 10 copies/ml (±SEM).
Figure 19:
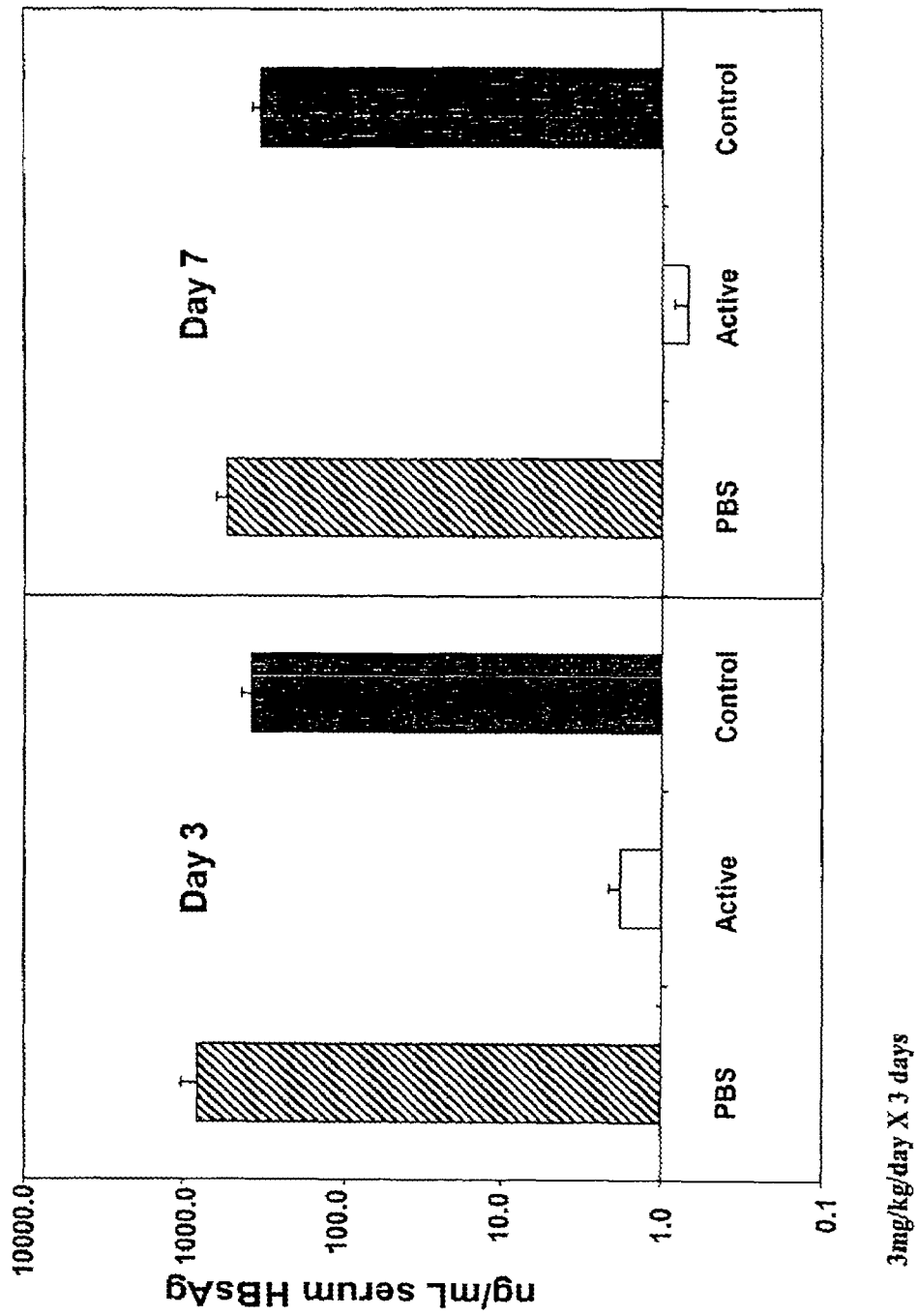
FIG. 19 shows a non-limiting example of the activity of systemically administered siNA L051 (Table IV) nanoparticles in an HBV mouse model. A hydrodynamic tail vein injection was done containing 0.3 µg of the pWTD HBV vector. The nanoparticle encapsulated active siNA molecules were administered at 3 mg/kg/day for three days via standard IV injection beginning 6 days post-HDI. Groups (N=5) of animals were sacrificed at 3 and 7 days following the last dose, and the levels of serum HBsAg was measured. The serum HBsAg levels were assayed by ELISA and expressed as mean log 10 pg/ml (±SEM).
Figure 29:
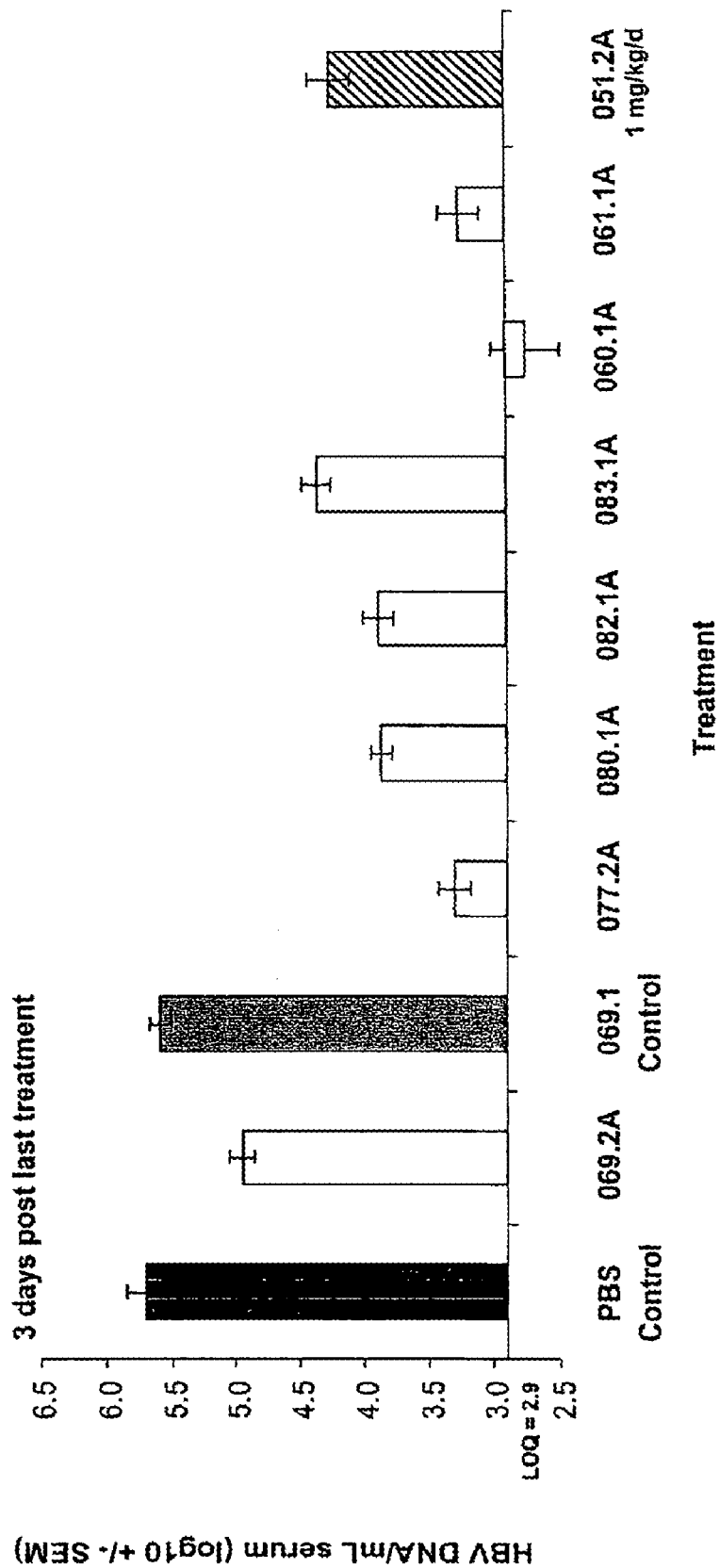
FIG. 29 shows a non-limiting example of the activity of systemically administered siNA L077, L069, L080, L082, L083, L060, L061, and L051 (Table IV) nanoparticles in an HBV mouse model. A hydrodynamic tail vein injection was done containing 0.3 µg of the pWTD HBV vector. The nanoparticle encapsulated active siNA molecules were administered at 3 mg/kg/day for three days via standard IV injection beginning 6 days post-HDI. Groups (N=5) of animals were sacrificed at 3 and 7 days following the last dose, and the levels of serum HBV DNA was measured. HBV DNA titers were determined by quantitative real-time PCR and expressed as mean log 10 copies/ml (±SEM).

To assess the activity of chemically stabilized siNA nanoparticle (see Example 9 for formulation details) compositions against HBV, systemic dosing of the formulated siNA composition (Formulation L051, Table IV) was performed following hydrodynamic injection (HDI) of the HBV vector in mouse strain NOD.CB17-Prkdc$^{scid}$/J (Jackson Laboratory, Bar Harbor, Me.). Female mice were 5-6 weeks of age and approximately 20 grams at the time of the study. The HBV vector used, pWTD, is a head-to-tail dimer of the complete HBV genome. For a 20-gram mouse, a total injection of 1.6 ml containing pWTD in saline, was injected into the tail vein within 5 seconds. A total of 0.3 μg of the HBV vector was injected per mouse. In order to allow recovery of the liver from the disruption caused by HDI, dosing of the formulated siNA compositions were started 6 days post-HDI. Encapsulated active or negative control siRNA were administered at 3 mg/kg/day for three days via standard IV injection. Groups (N=5) of animals were sacrificed at 3 and 7 days following the last dose, and the levels of serum HBV DNA and HBsAg were measured. HBV DNA titers were determined by quantitative real-time PCR and expressed as mean log 10 copies/ml (±SEM). The serum HBsAg levels were assayed by ELISA and expressed as mean log 10 pg/ml (±SEM). Significant reductions in serum HBV DNA (FIGS. 18 and 29) and HBsAg (FIGS. 19, 30, 31, and 32)) were observed at both the 3 and 7-day time points in the active formulated siNA composition treated groups as compared to both the PBS and negative control groups.

Materials and Methods

Oligonucleotide Synthesis and Characterization

All RNAs were synthesized as described herein. Complementary strands were annealed in PBS, desalted and lyophilized. The sequences of the active site 263 HBV siNAs are shown in FIG. 14. The modified siNAs used in vivo are termed HBV263M and HBV1583M, while versions containing unmodified ribonucleotides and inverted abasic terminal caps are called HBV263R and HBV1583R. Some pharmacokinetic studies were done with siNA targeting two other sites, HBV1580M and HBV1580R.

The siNA sequences for HCV irrelevant control are:

```
                                          (SEQ ID NO: 1)
sense strand:      5' B-cuGAuAGGGuGcuuGcGAGTT-B 3'

(SEQ ID NO: 2)
antisense strand:  5' CUCGcAAGcAcccuAucAGTsT 3'
```

(where lower case=2'-deoxy-2'-fluoro; Upper Case italic=2'-deoxy; Upper Case underline=2'-O-methyl; Upper Case Bold=ribonucleotide; T=thymidine; B=inverted deoxyabasic; and s=phosphorothioate)

The inverted control sequences are inverted from 5' to 3'.

HBsAg ELISA Assay

Levels of HBsAg were determined using the Genetic Systems/Bio-Rad (Richmond, Va.) HBsAg ELISA kit, as per the manufacturer's instructions. The absorbance of cells not transfected with the HBV vector was used as background for the assay, and thus subtracted from the experimental sample values.

HBV DNA Analysis

Viral DNA was extracted from 50 μL mouse serum using QIAmp 96 DNA Blood kit (Qiagen, Valencia, Calif.), according to manufacture's instructions. HBV DNA levels were analyzed using an ABI Prism 7000 sequence detector (Applied Biosystems, Foster City, Calif.). Quantitative real time PCR was carried out using the following primer and probe sequences: forward primer 5'-CCTGTATTCCCATC-CCATCGT (SEQ ID NO: 3, HBV nucleotide 2006-2026), reverse primer 5'-TGAGCCAAGAGAAACGGACTG (SEQ ID NO: 4, HBV nucleotide 2063-2083) and probe FAM 5'-TTCGCA AAATACCTATGGGAGTGGGCC (SEQ ID NO: 5, HBV nucleotide 2035-2062). The psHBV-1 vector, containing the full length HBV genome, was used as a standard curve to calculate HBV copies per mL of serum.

Example 10

Figure 20:
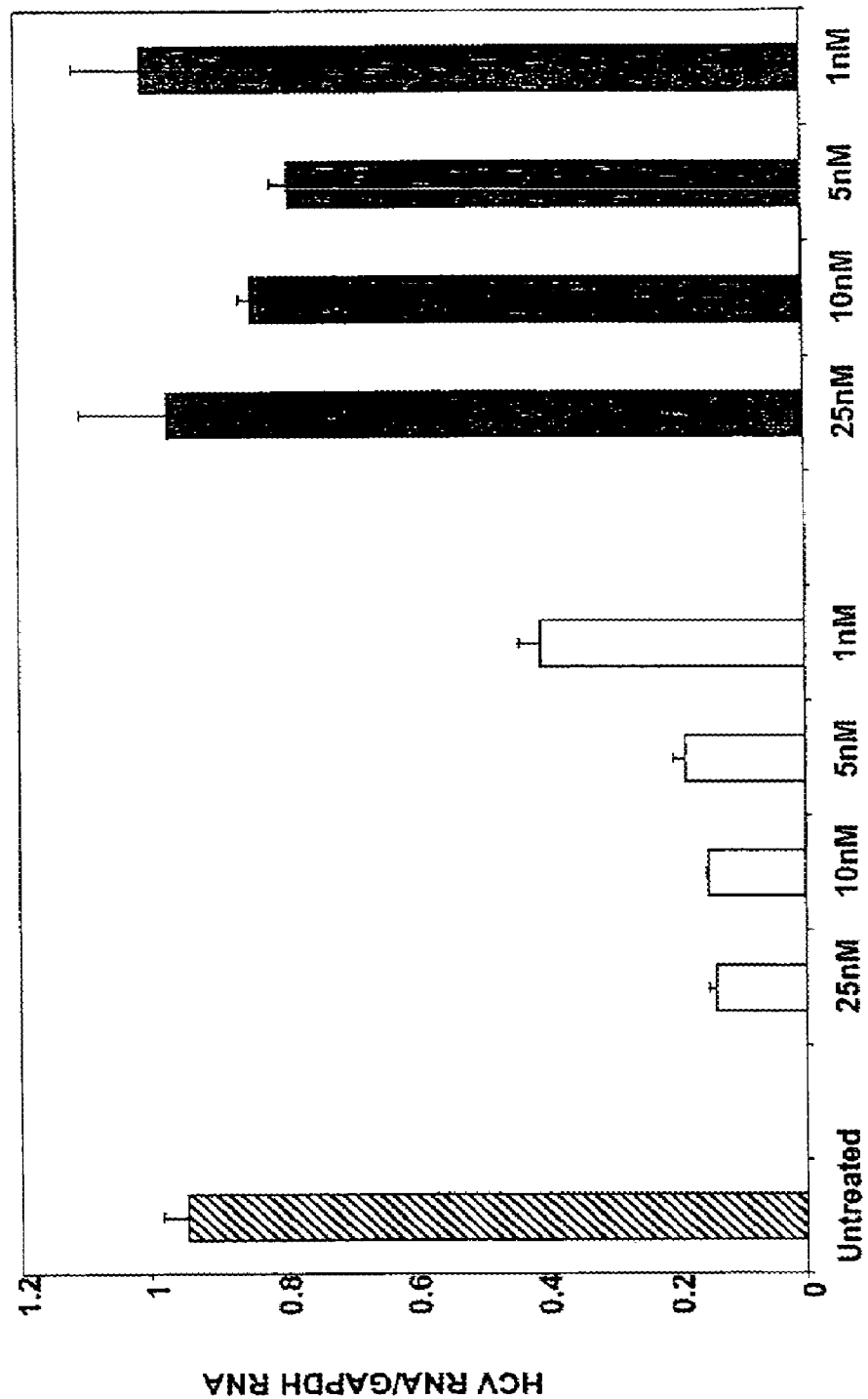
FIG. 20 shows a non-limiting example of formulated siNA L051 (Table IV) nanoparticle constructs targeting viral replication in a Huh7 HCV replicon system in a dose dependent manner. Active siNA formulations were evaluated at 1, 5, 10, and 25 nM in comparison to untreated cells ("untreated"), and formulated inactive siNA scrambled control constructs at the same concentration.
Figure 21:
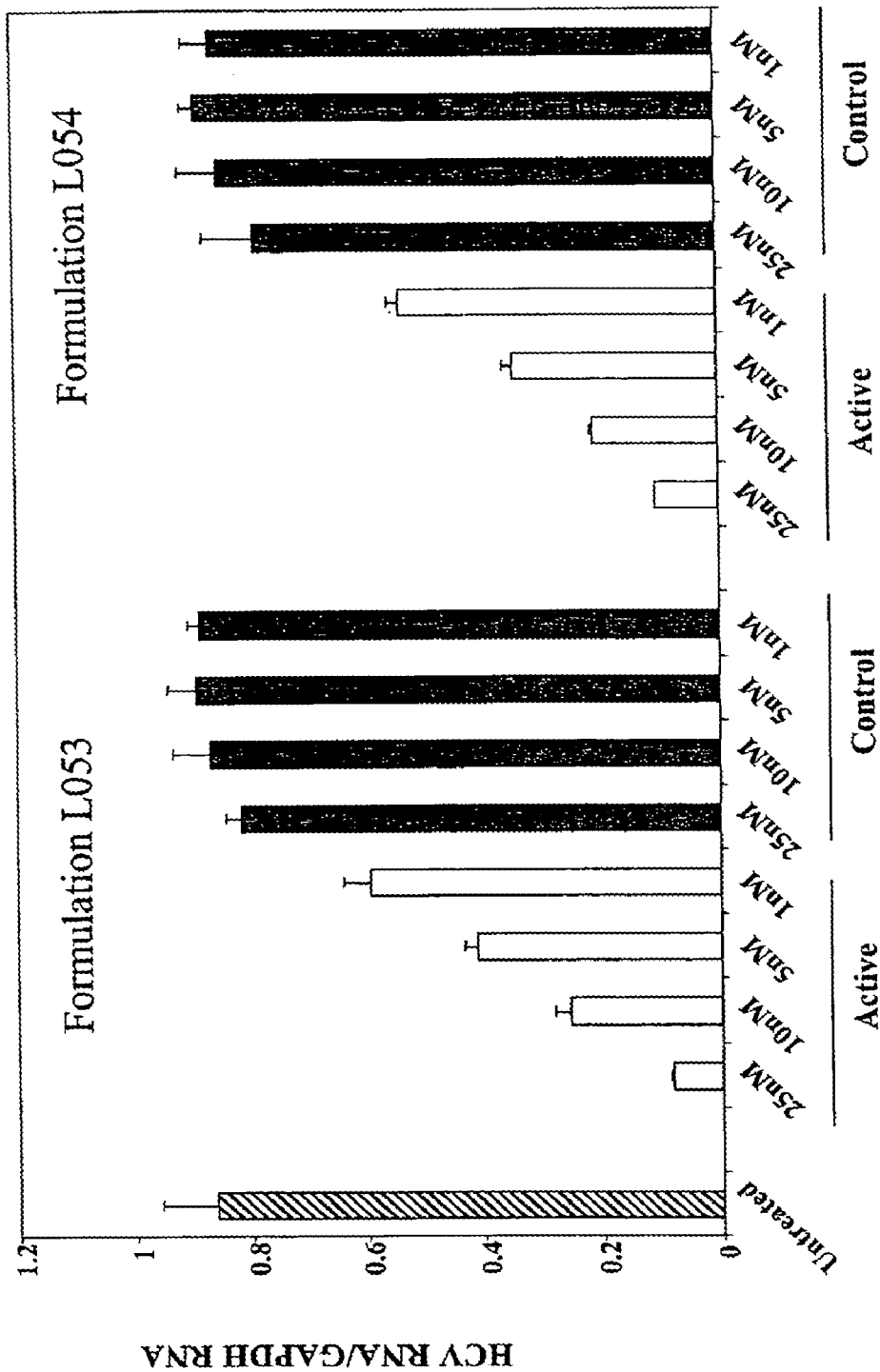
FIG. 21 shows a non-limiting example of formulated siNA L053 and L054 (Table IV) nanoparticle constructs targeting viral replication in a Huh7 HCV replicon system in a dose dependent manner. Active siNA formulations were evaluated at 1, 5, 10, and 25 nM in comparison to untreated cells ("untreated"), and formulated inactive siNA scrambled control constructs at the same concentration.

Evaluation of Formulated siNA Compositions in an in vitro HCV Replicon Model of HCV Infection An HCV replicon system was used to test the efficacy of siNAs targeting HCV RNA. The reagents were tested in cell culture using Huh7 cells (see for example Randall et al., 2003, PNAS USA, 100, 235-240) to determine the extent of RNA inhibition. siNA were selected against the HCV target as described herein. The active siNA sequences for HCV site 304 are as follows: sense strand: (SEQ ID NO: 1); antisense strand: (SEQ ID NO: 2) (these were used as inactive sequences in Example 8 above). The siNA inactive control sequences used in the study target HBV site 263 and are as follows: sense strand: (SEQ ID NO: 6); antisense strand: (SEQ ID NO: 7), (these were used as active sequences in Example 8 above). The active and inactive siNAs were formulated as Formulation L051, L053, or L054 as described in Example 9 above. Huh7 cells, containing the stably transfected Clone A HCV subgenomic replicon (Apath, LLC, St. Louis, Mo.), were grown in DMEM (Invitrogen catalog #11965-118) with 5 mls of 100× (10 mM) Non-Essential Amino Acids (Invitrogen catalog #11140-050), 5 uL of 200 mM Glutamine (Cellgro catalog#25-005-C1), 50 uL of heat inactivated Fetal Bovine Serum (Invitrogen catalog #26140-079) and 1 mg/mL G418 (Invitrogen catalog#11811-023). For transfection with siNA formulations, cells are plated at 9,800 cells per well into a 96-well CoStar tissue culture plate using DMEM with NEAA and 10% FIBS, (no antibiotics). After 20-24 hours, cells were transfected with formulated siNA for a final concentration of 1-25 nM. After incubating for 3 days, the cells were lysed and RNA extracted using the RNaqueous-96 kit (Ambion Cat#1920) as per the manufacturers instructions. FIG. 20 shows level of HCV RNA from formulated (Formulation L051, Table IV) active siNA treated cells compared to untreated or negative control treated cells. FIG. 21 shows level of HCV RNA from formulated (Formulations L053 and L054, Table IV) active siNA treated cells compared to untreated or negative control treated cells. In these studies, a dose dependent reduction in HCV RNA levels was observed in the active formulated siNA treated cells using formulations L051, L053, and L054, while no reduction is observed in the negative control treated cells. This result indicates that the formulated siNA compositions are able to enter the cells, and effectively inhibit viral gene expression.

Example 11

Figure 22:
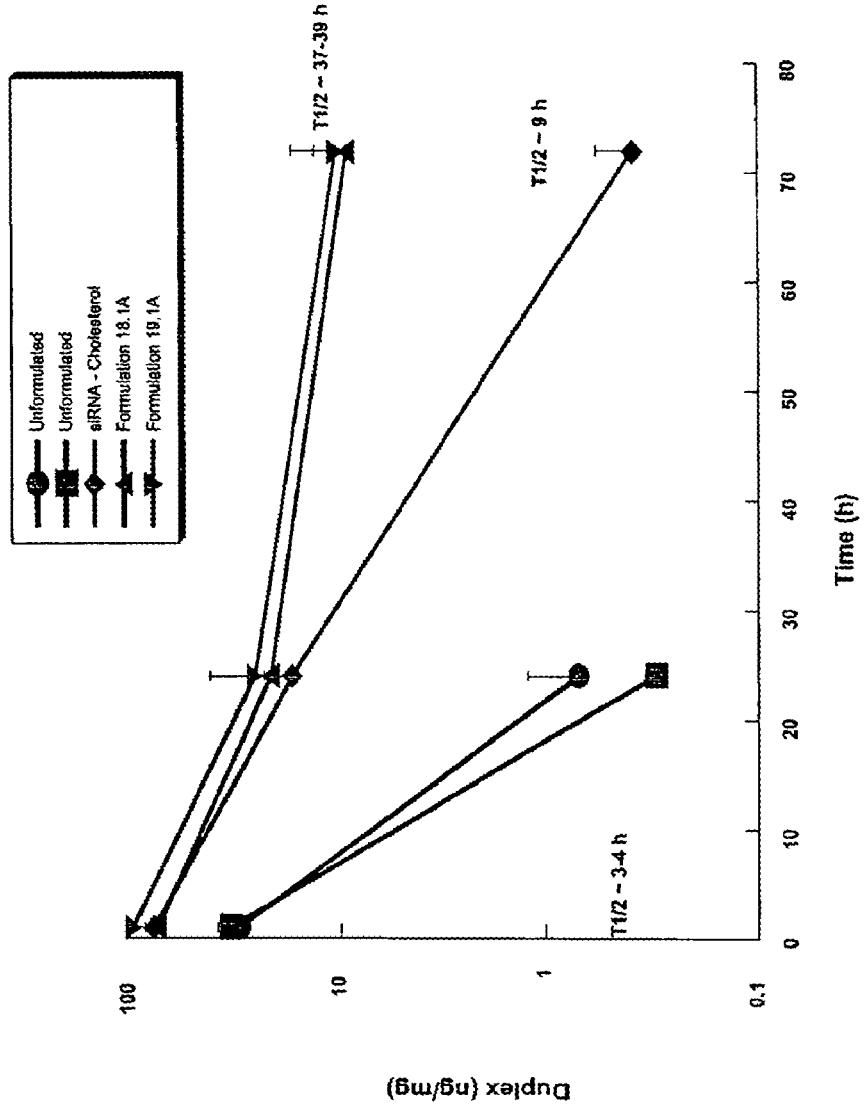
FIG. 22 shows the distribution of siNA in lung tissue of mice following intratracheal dosing of unformulated siNA, cholesterol-conjugated siNA, and formulated siNA (formulated molecular compositions 18.1 and 19.1). As shown, the longest half lives of exposure in lung tissue were observed with the siNA formulated in molecular compositions T018.1 or T019.1.

Lung Distribution of Unformulated and Formulated siNA After Intratracheal Dosing To determine the efficiency of delivery of siNA molecules to the lung, unformulated siRNA (naked), cholesterol conjugated siNA, or siRNA in formulated molecular compositions (T018.1 and T019.1) were administered via the trachea to the lungs of mice. Unformulated siNA comprises naked nucleic acid. Cholesterol conjugated siNA comprises siNA linked to cholesterol. Formulated molecular compositions T018.1 and T019.1 comprise siNA formulated with DOcarbDAP, DSPC, cholesterol and PEG-DMG, and DODMA, DSPC, cholesterol and PEG-DMG, respectively. Groups of three female C57 Bl/6 mice were placed under anesthesia with ketamine and xylazine. Filtered dosing solutions were administered via the trachea at 10 mg/kg duplexed siRNA, using a Penncentury model #1A-1C microsprayer and a Penncentury model #FMJ250 syringe to aerosolize the siRNA (TGFβ site 1264 stabilization chemistry 7/8) directly into the lungs. Animals were dosed with unformulated siNA, cholesterol-conjugated siNA or siNA in formulated molecular compositions. At 1, 24 or 72 hours after dosing, the animals were euthanized, exsanguinated and perfused with sterile veterinary grade saline via the heart. The lungs were removed, placed in a pre-weighed homogenization tube and frozen on dry ice. Lung weights were determined by subtraction after weighing the tubes plus lungs. Levels of siNA in the lung tissue were determined using a hybridization assay. FIG. 22, shows the levels of siNA in lung tissue after direct dosing of (i) unformulated siNA, (ii) cholesterol conjugated siNA or (iii) siNA in formulated molecular compositions T018.1 or T019.1. Half lives of exposure in lung tissue were 3-4 hours for the unformulated siNA, 9 hours for the cholesterol conjugated siNA and 37-39 hours for the siNA in formulated molecular compositions T018.1 or T019.1.

Example 12

Efficient Transfection of Various Cell Lines Using siNA LNP Formulations of the Invention The transfection efficacy of LNP formulations of the invention was determined in various cell lines, including 6.12 spleen, Raw 264.7 tumor, MM14Lu, NIH 3T3, D10.G4.1 Th2 helper, and lung primary macrophage cells by targeting endogenous MAP Kinase 14 (p38) gene expression. A potent lead siNA against MapK14 (p38a) was selected by in vitro screening using Lipofectamine 2000 (LF2K) as the delivery agent. The sense strand sequence of this siNA comprised 5'-B cuGGuAcAGAccAuAuuGATT B-3' (SEQ ID NO: 6) and the antisense strand sequence comprised 5'-UCA<u>A</u>u<u>A</u>u<u>GG</u>ucu Gu<u>A</u>cc<u>A</u>GTsT-3' (SEQ ID NO: 7), where lower case=2'-deoxy-2'-fluoro; Upper Case italic=2'-deoxy; Upper Case underline=2'-O-methyl; Upper Case Bold=ribonucleotide; T=thymidine; B=inverted deoxyabasic; and s=phosphorothioate).

Figure 35:
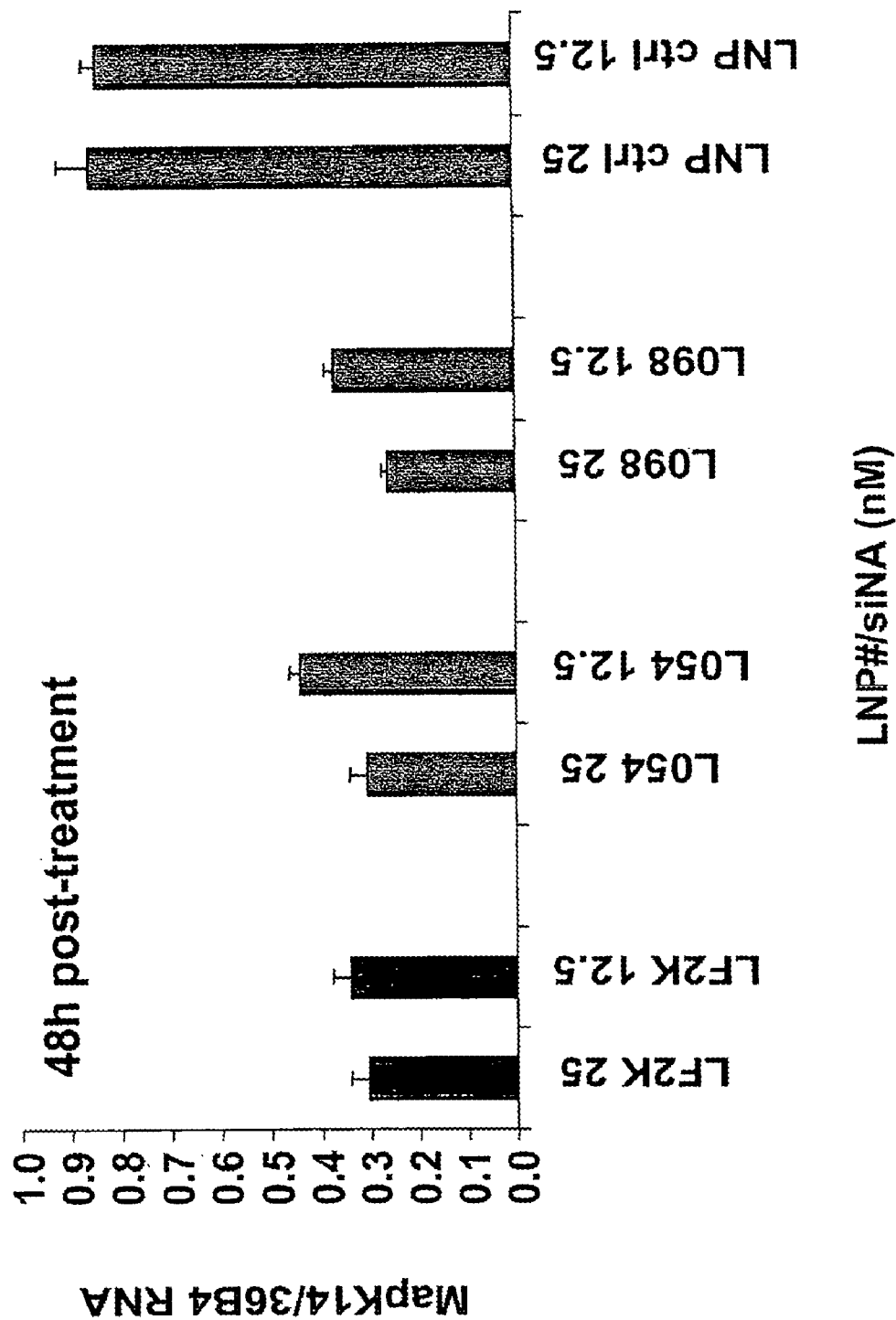
FIG. 35 shows efficacy data for LNP 58 and LNP 98 formulations targeting MapK14 site 1033 in RAW 264.7 mouse macrophage cells compared to LFK2000 and a formulated irrelevant siNA control.
Figure 36:
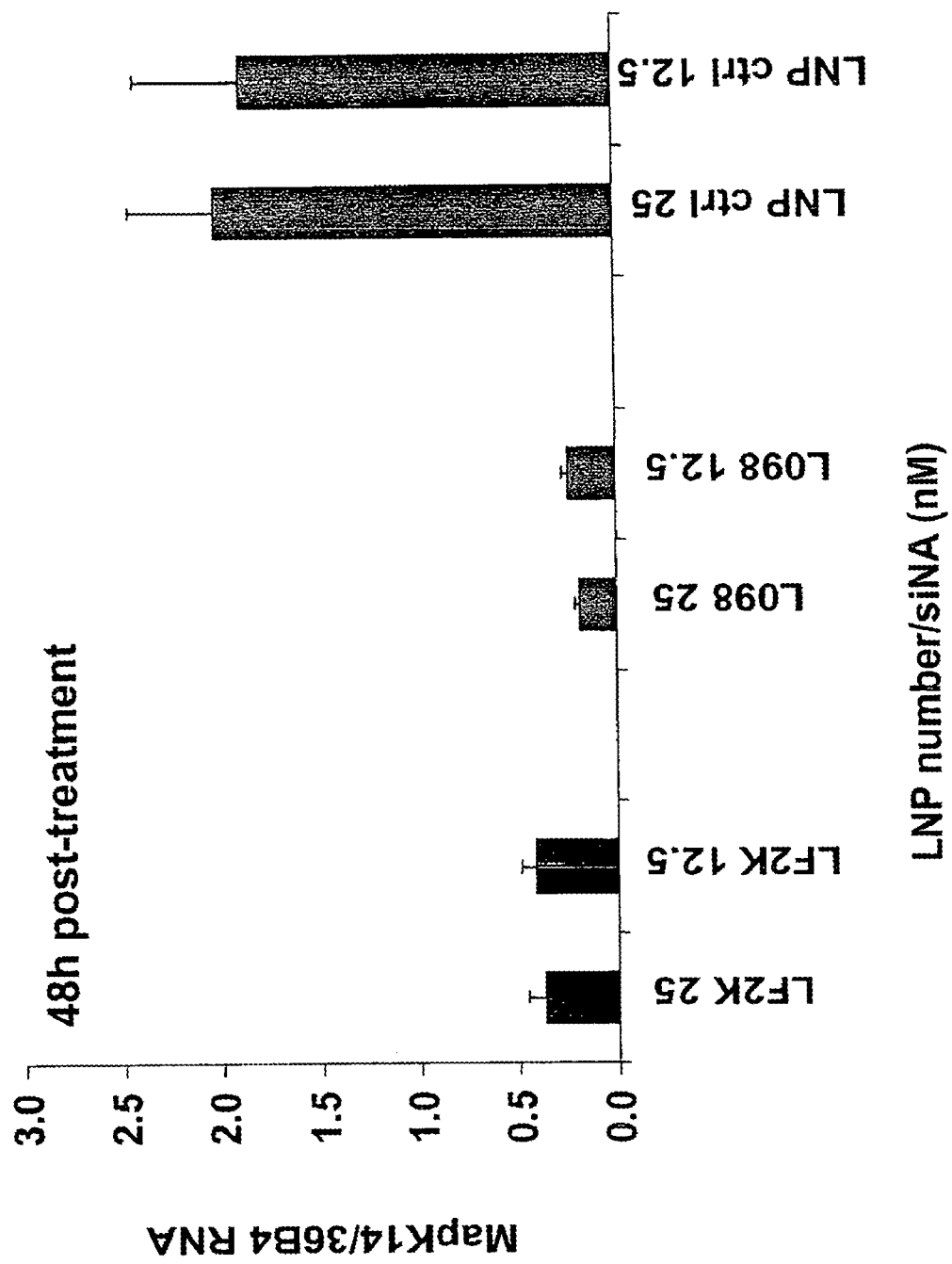
FIG. 36 shows efficacy data for LNP 98 formulations targeting MapK14 site 1033 in MM14.Lu normal mouse lung cells compared to LFK2000 and a formulated irrelevant siNA control.
Figure 37:
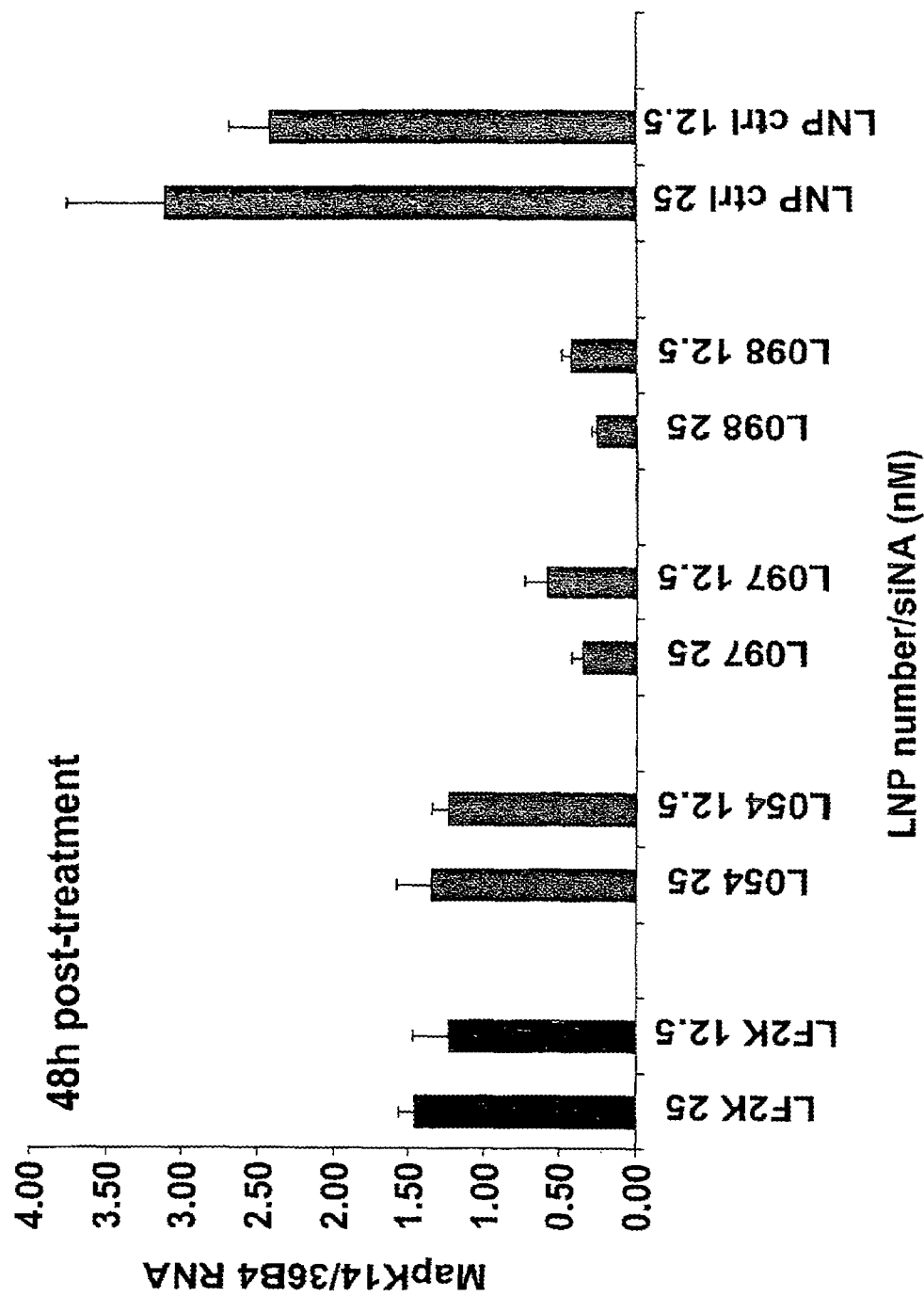
FIG. 37 shows efficacy data for LNP 54, LNP 97, and LNP 98 formulations targeting MapK14 site 1033 in 6.12 B lymphocyte cells compared to LFK2000 and a formulated irrelevant siNA control.
Figure 38:
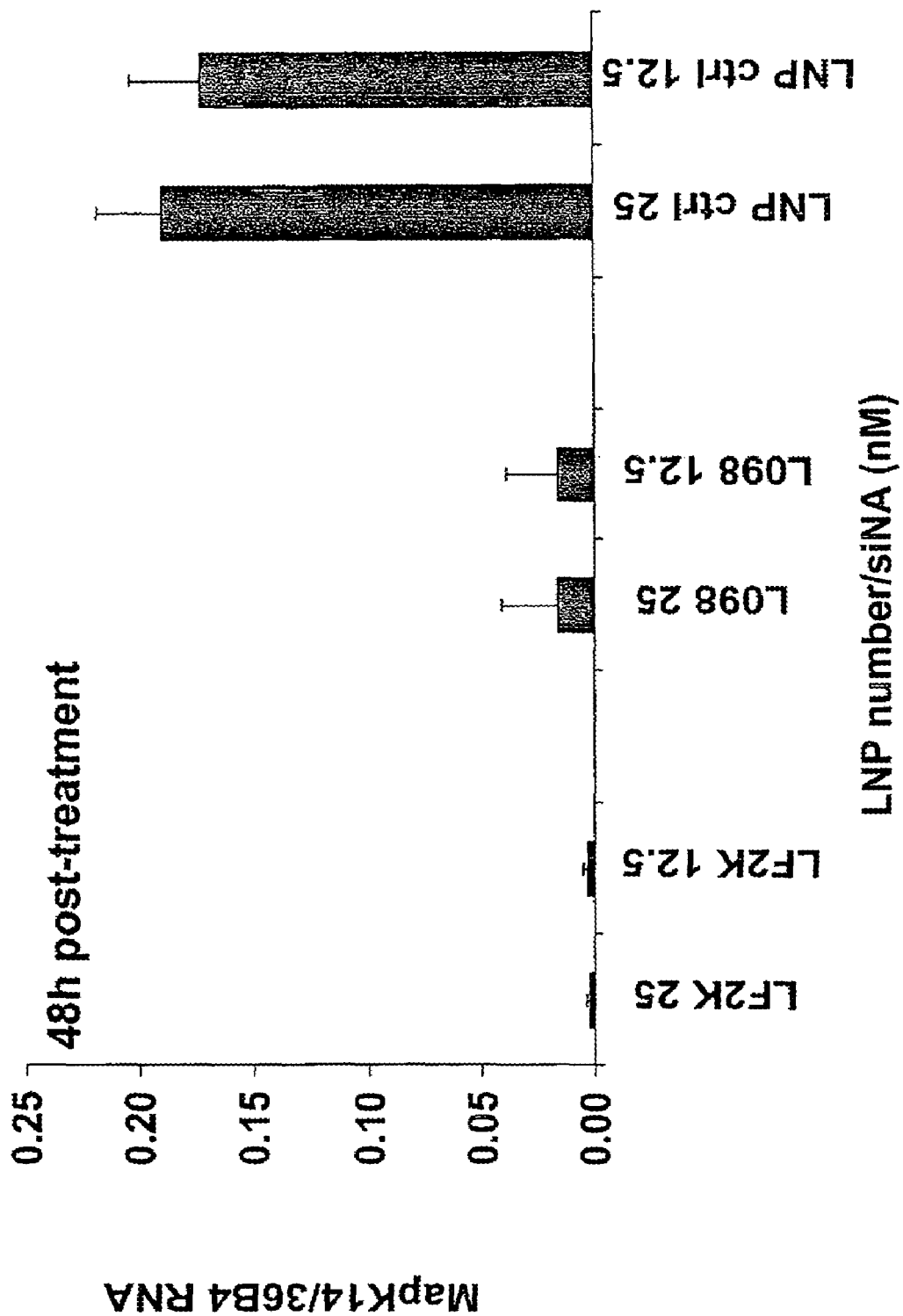
FIG. 38 shows efficacy data for LNP 98 formulations targeting MapK14 site 1033 in NIH 3T3 cells compared to LFK2000 and a formulated irrelevant siNA control.
Figure 39:
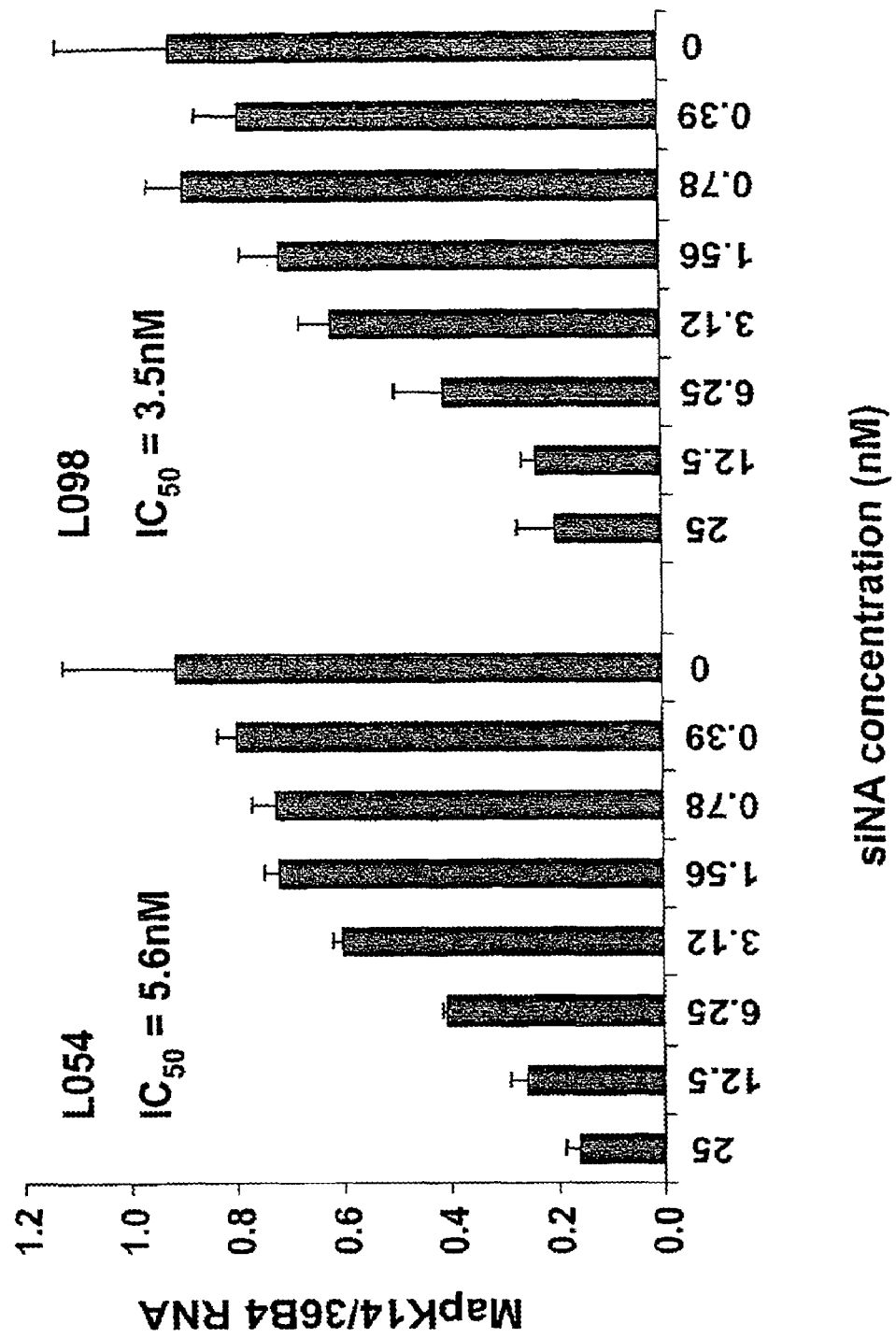
FIG. 39 shows the dose-dependent reduction of MapK14 RNA via MapK14 LNP 54 and LNP 98 formulated siNAs in RAW 264.7 cells.
Figure 40:
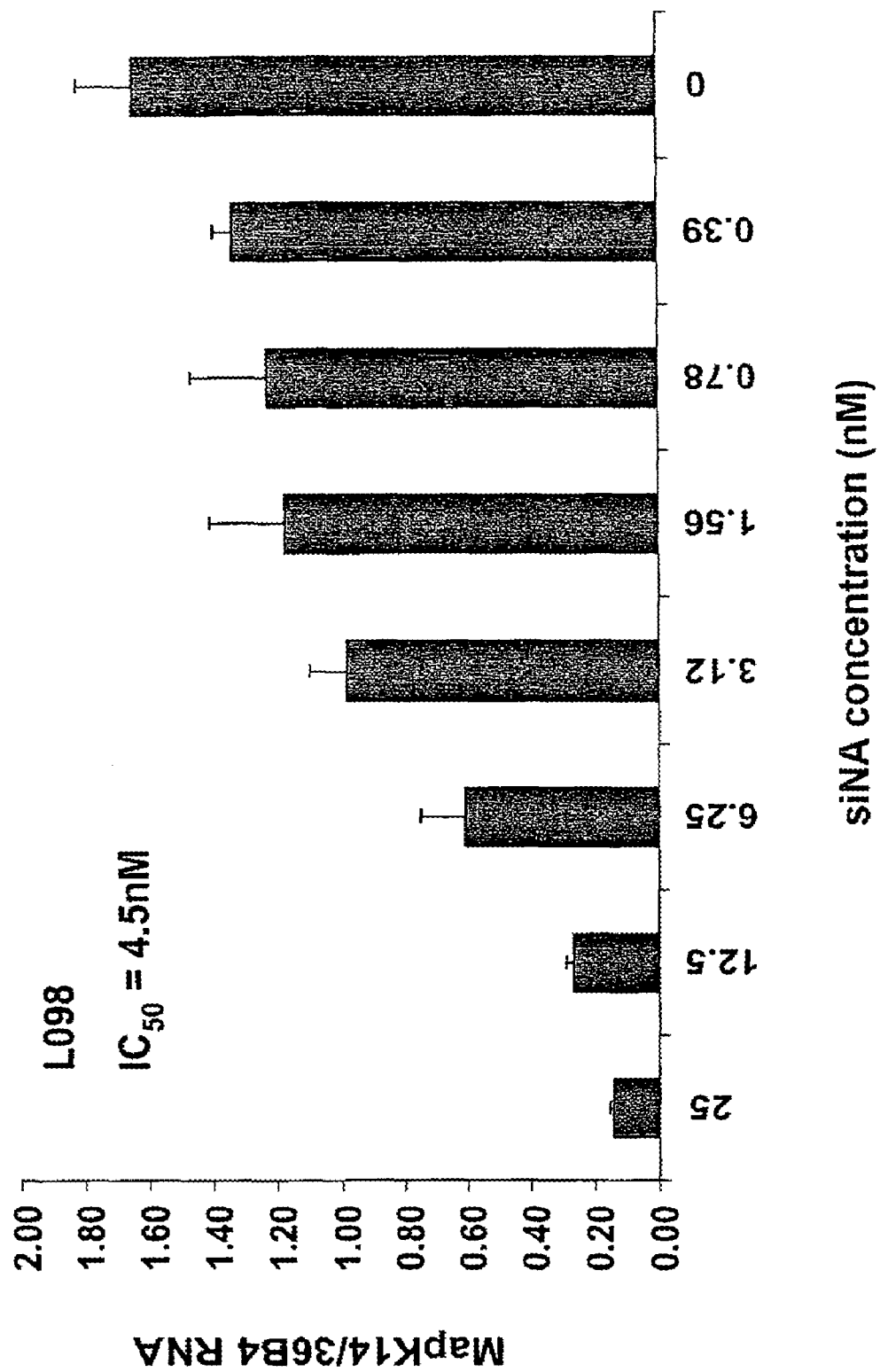
FIG. 40 shows the dose-dependent reduction of MapK14 RNA via MapK14 LNP 98 formulated siNAs in MM14.Lu cells.
Figure 41:
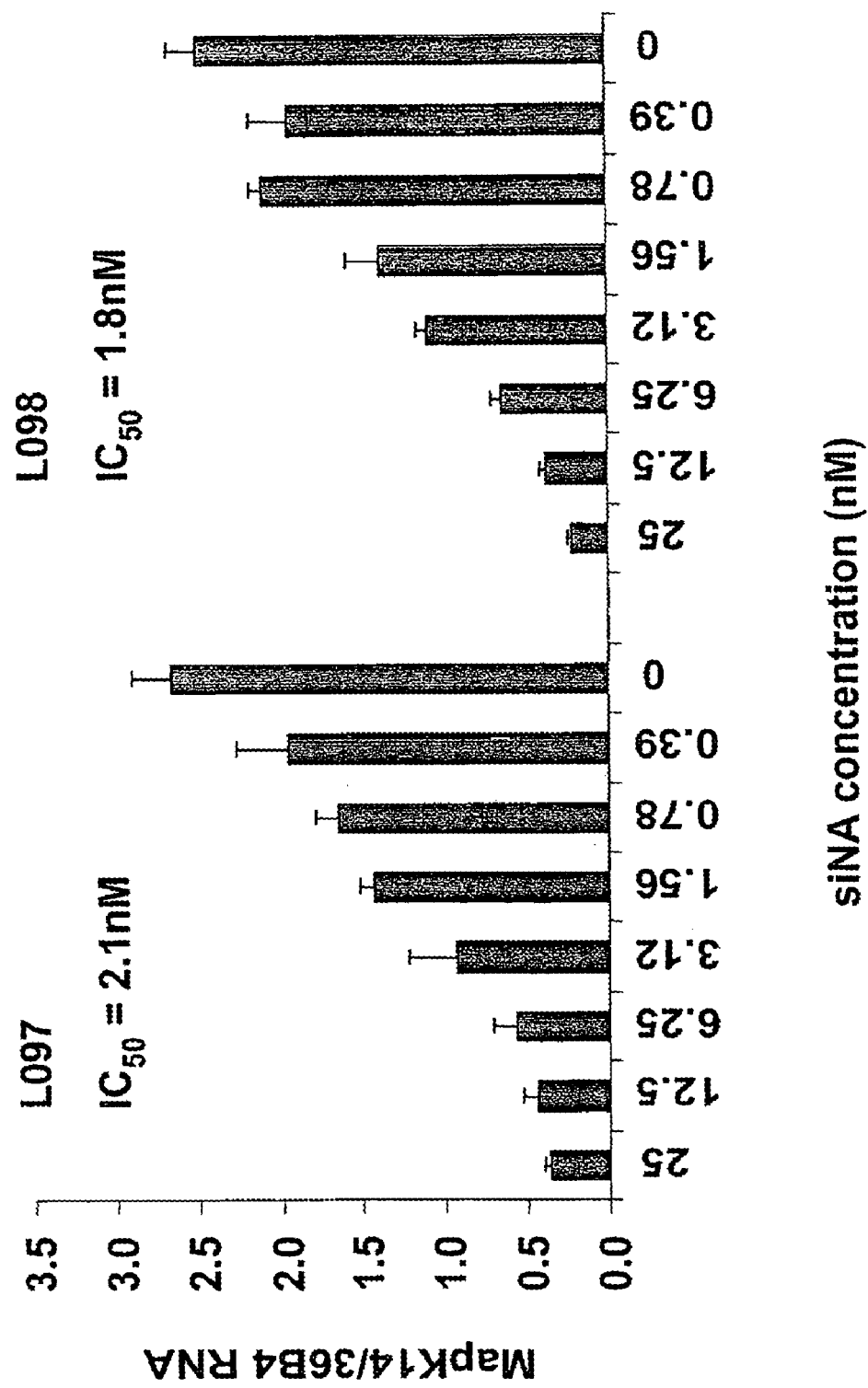
FIG. 41 shows the dose-dependent reduction of MapK14 RNA via MapK14 LNP 97 and LNP 98 formulated siNAs in 6.12 B cells.
Figure 42:
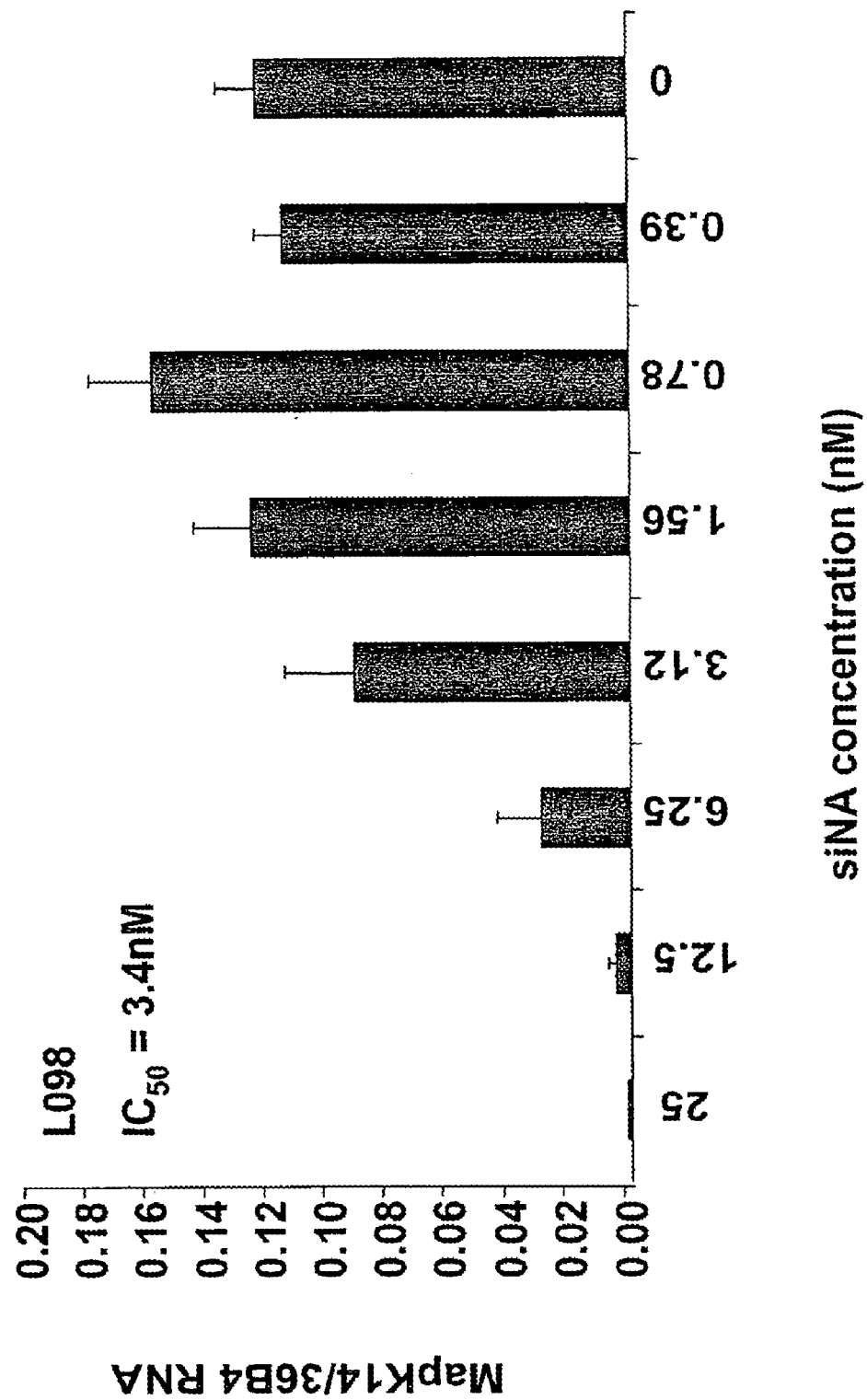
FIG. 42 shows the dose-dependent reduction of MapK14 RNA via MapK14 LNP 98 formulated siNAs in NIH 3T3 cells.

Proprietary MapK14 targeted LNPs were screened and compared to LF2K and a LNP control containing an inactive siNA in cultured cells. Furthermore, lead LNPs were tested in a dose response method to determine IC50 values. Results are summarized in Table V. FIG. 35 shows efficacy data for LNP 58 and LNP 98 formulations targeting MapK14 site 1033 in RAW 264.7 mouse macrophage cells. FIG. 36 shows efficacy data for LNP 98 formulations targeting MapK14 site 1033 in MM14.Lu normal mouse lung cells. FIG. 37 shows efficacy data for LNP 54, LNP 97, and LNP 98 formulations targeting MapK14 site 1033 in 6.12 B lymphocyte cells. FIG. 38 shows efficacy data for LNP 98 formulations targeting MapK14 site 1033 in NIH 3T3 cells. FIG. 39 shows the dose-dependent reduction of MapK14 RNA via MapK14 LNP 54 and LNP 98 formulated siNAs in RAW 264.7 cells. FIG. 40 shows the dose-dependent reduction of MapK14 RNA via MapK14 LNP 98 formulated siNAs in MM14.Lu cells. FIG. 41 shows the dose-dependent reduction of MapK14 RNA via MapK14 LNP 97 and LNP 98 formulated siNAs in 6.12 B cells. FIG. 42 shows the dose-dependent reduction of MapK14 RNA via MapK14 LNP 98 formulated siNAs in NIH 3T3 cells.

LF2K Transfection Method:

The following procedure was used for LF2K transfection. After 20-24 hours, cells were transfected using 0.25 or 0.35 uL Lipofectamine 2000/well and 0.15 or 0.25 uL/well, complexed with 25 nM siNA. Lipofectamine 2000 was mixed with OptiMEM and allowed to sit for at least 5 minutes. For 0.25 uL transfections, 1 uL of LF2K was mixed with 99 uL OptiMEM for each complex. For 0.35 uL transfections, 1.4 uL of LF2K was mixed with 98.6 uL OptiMEM for each complex. For 0.15 uL transfections, 0.60 uL of SilentFect was mixed with 99.4 uL OptiMEM for each complex. For 0.30 uL transfections, 1.2 uL of SilentFect was mixed with 98.2 uL OptiMEM for each complex. The siNA was added to a microtitre tube (BioRad #223-9395) and OptiMEM was then added to make 100 uL total volume to be used in 4 wells. 100 uL of the Lipofectamine 2000/OptiMEM mixture was added and the tube was vortexed on medium speed for 10 seconds and allowed to sit at room temperature for 20 minutes. The tube was vortexed quickly and 50 uL was added per well, which contained 100 uL media. RNA from treated cells was isolated at 24, 48, 72, and 96 hours.

LNP Transfection Method:

The following procedure was used for LF2K transfection. Cells were plated to the desired concentration in 100 uL of complete growth medium in 96-well plates, ranging from 5,000-30,000 cells/well. After 24 hours, the cells were transfected by diluting a 5× concentration of LNP in complete growth medium onto the cells, (25 uL of 5× results in a final concentration of 1×). RNA from treated cells was isolated at 24, 48, 72, and 96 hours.

Example 13

Reduction of Airway Hyper-responsiveness in a Mouse Model of Asthma

Figure 43:
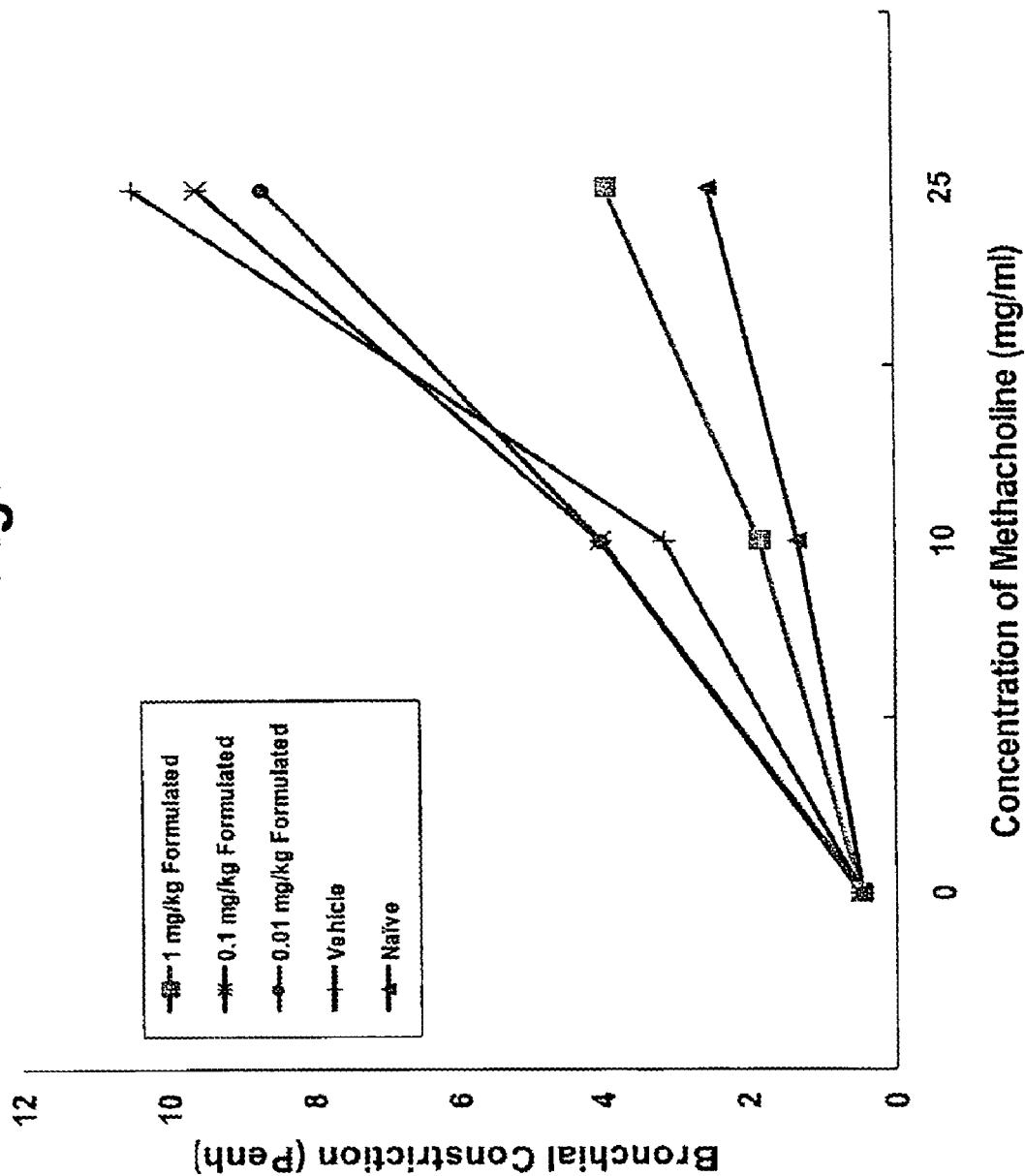
FIG. 43 shows a non-limiting example of reduced airway hyper-responsiveness from treatment with LNP-51 formulated siNAs targeting IL-4R in a mouse model of OVA challenge mediated airway hyper-responsiveness. Active formulated siNAs were tested at 0.01, 0.1, and 1.0 mg/kg and were compared to LNP vehicle along and untreated (naïve) animals.

An OVA induced airway hyper-responsiveness model was used to evaluate LNP formulated siNA molecules targeting interleukin 4R (IL-4R alpha) for efficacy in reducing airway hyper-responsiveness. The sense strand sequence of the active siNA targeting IL-4R alpha used in this study comprised 5'-B ucAGcAuuAccAAGAuuAATT B-3' (SEQ ID NO: 8) and the antisense strand sequence comprised 5'-UUA AucuuGGuAAuGcuGATsT-3' (SEQ ID NO: 9), where lower case=2'-deoxy-2'-fluoro; Upper Case italic=2'-deoxy; Upper Case underline=2'-O-methyl; Upper Case Bold=ribonucleotide; T=thymidine; B=inverted deoxyabasic; and s=phosphorothioate). On Day 0 and 7, the animals were immunized by intraperitoneal injection of 0.4 mg/mL OVA/saline solution mixed in an equal volume of Imject Alum for a final injection solution of 0.2 mg/mL (100 uL/mouse). LNP-51 formulated IL-4R-alpha Site 1111 siNA (see U.S. Ser. No. 11/001,347, incorporated by reference herein), prepared in PBS (w/o Ca2+, Mg2+), or irrelevant control was delivered by intratracheal dosing qd (once every day) beginning on Day 17 and ending on Day 26 for a total of 10 doses. Mice were aerosol challenged with OVA (1.5% in saline) for 30 minutes on days 24, 25 and 26 using the Pari LC aerosol nebulizer. Animals were allowed to rest for 24 hours prior to airway function analysis. On Day 28 airway responsiveness was assessed after challenge with aerosolized methacholine using the Buxco Whole Body Plethysmograph. After methacholine challenge, animals were euthanized. A tracheotomy was performed, and the lungs were lavaged with 0.5 mL of saline twice. Lung lavage was performed while massaging the animal's chest and all lavage fluid were collected and placed on ice. A cytospin preparation was performed to collect the cells from the BAL fluid for differential cell counts. Results are shown in FIG. 43, which clearly demonstrates the activity of the formulated siNA in a dose response (0.01, 0.1, and 1 mg/kg) compared to the LNP vehicle alone and untreated (naïve) animals.

Example 14

Efficient Reduction in Human Huntingtin (htt) Gene Expression in vivo Using LNP Formulated siNA Huntington's disease (HD) is a dominant neurodegenerative disorder caused by an expansion in the polyglutamine (polyQ) tract of the huntingtin (htt) protein. PolyQ expansion in htt induces cortical and striatal neuron cell less, and the formation of htt-containing aggregates within brain cells. HD patients have progressive psychiatric, cognitive and motor dysfunction and premature death. Early work in mouse models has demonstrated that reduction of mutant protein after the onset of disease phenotypes could improve motor dysfunction and reduce htt-aggregate burden. Thus, reduction of mutant htt in patient brain may improve the disease.

Recent work has shown that reduction of mutant htt in a mouse model of HD, using a viral vector expressing short interfering RNAs (siRNAs), protected the animal from the onset of behavioral and neuropathological hallmarks of the disease (see Harper et al., 2005, PNAS USA, 102: 5820-5). This study was utilized to determine whether delivery of synthetic siNAs directly to the brain by nonviral methods could be similarly effective. This approach has many advantages, including the ability to modify dosing regimines. Chemically modified siNA, sense strand having sequence 5'-B AccGuGuGAAucAuuGucuTT B-3' (SEQ ID NO:10) and antisense strand 5'-AGAcAAuGAuucAcAcGGuTsT-3' (SEQ ID NO:11) encapsulated in lipid nanoparticles (LNP) formulations LNP-061, LNP-098, and LNP-101 (see Table IV) were utilized in this study. In these sequences, lower case stands for 2'-deoxy-2'-fluoro, Upper Case stands for ribonucleotides, underline Upper Case stands for 2'-O-methyl nucleotides, T is thymidine, s is phosphorothioate, and B is inverted deoxy abasic. The siNA duplexes encapsulated in the various LNP formulations were screened for their ability to silence full-length htt in vitro, followed by testing in vivo. Using Alzet osmotic pumps, siNAs encapsulated in LNPs were infused into the lateral ventrical or striatum for 7 or 14 days, respectively, at concentrations ranging from 0.1 to 1 mg/ml (total dose ranging from 8.4 to 84 μg). An impressive 80% reduction in htt mRNA levels was observed in animals treated with LNP-061 and LNP-098 formulated siNA as determined by QPCR compared to scrambled control sequences, or naïve brain. Results are shown in FIG. 44.

Example 14

Figure 23A:
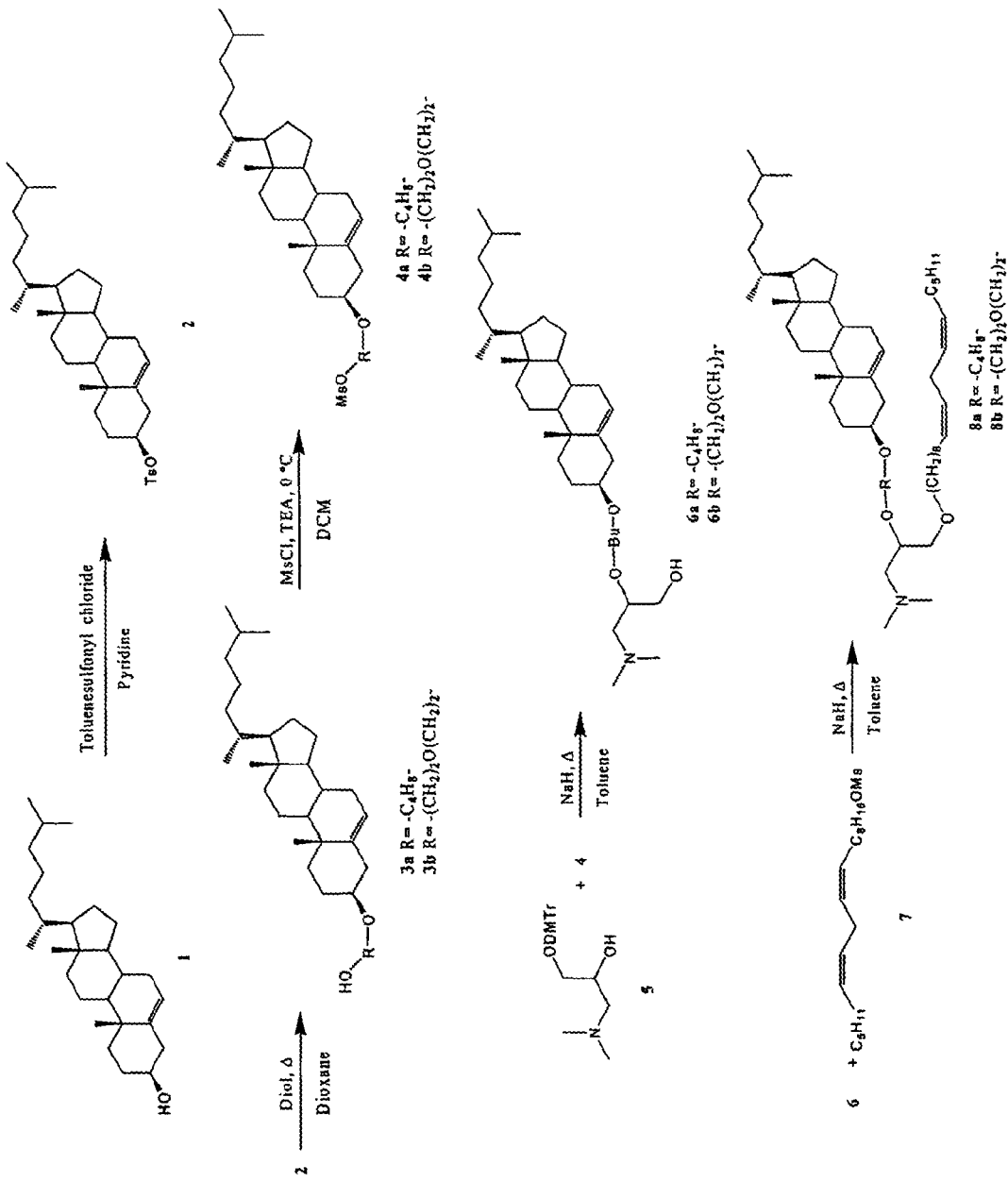
FIG. 23 shows a non-limiting example of a synthetic scheme used for the synthesis of 3-Dimethylamino-2-(Cholest-5-en-3β-oxybutan-4-oxy)-1-(cis,cis-9,12-octadecadienoxy)propane (CLinDMA).

Preparation of Cationic Lipids of the Invention (See Table III for Cationic Lipids and Intermediates, See FIG. 23A for Synthetic Scheme)

Cholest-5-en-3β-tosylate (2)

Cholesterol (1, 25.0 g, 64.7 mmol) was weighed into a 1 L round bottomed flask with a stir bar. The flask was charged with pyridine (250 mL), septum sealed and flushed with argon. Toluenesulfonyl chloride (25.0 g, 131 mmol) was weighed into a 100 mL round bottomed flask, which was then sealed and charged with pyridine. The toluenesulfonyl chloride solution was then transferred, via syringe, to the stirring cholesterol solution, which was allowed to stir overnight. The bulk of pyridine was removed in vacuo and the resulting solids were suspended in methanol (300 mL) and stirred for 3 hours, until the solids were broken up into a uniform suspension. The resultant suspension was filtered and the solids were washed with acetonitrile and dried under high vacuum to afford 31.8 g (91%) of a white powder (see for example Davis, S. C.; Szoka, F. C., Jr. Bioconjugate Chem. 1998, 9, 783).

Cholest-5-en-3β-oxybutan-4-ol (3a)

Cholest-5-ene-3β-tosylate (20.0 g, 37.0 mmol) was weighed into a 500 mL round bottomed flask with a stir bar. The flask was charged with dioxane (300 mL) and 1,4-butanediol (65.7 mL, 20 equiv.). The flask was fitted with a reflux condenser and the mixture was brought to reflux overnight. The reaction was cooled and concentrated in vacuo. The reaction mixture was suspended in water (400 mL). The solution was extracted with methylene chloride (3×200 mL). The organic phases were combined and washed with water (2×200), dried over magnesium sulfate, filtered and the solvent removed. The resultant oil/wax was further purified via column chromatography (15% Acetone/Hexanes) to afford 13.41 g (79%) of a colorless wax.

Cholest-5-en-3β-oxypent-3-oxa-an-5-ol (3b)

This compound was prepared similarly to cholest-5-en-3β-oxybutan-4-ol. Cholest-5-ene-3β-tosylate (5.0 g, 9.2 mmol)

was weighed into a 500 mL round bottomed flask with a stir bar. The flask was charged with dioxane (150 mL) and diethylene glycol (22 mL, 25 equiv.). The flask was fitted with a reflux condenser and the mixture was brought to reflux overnight. The reaction was cooled and concentrated. The reaction mixture was suspended in water (500 mL). The solution was extracted with methylene chloride (3×200 mL). The organic phases were combined and washed with water (2×200 mL), dried over magnesium sulfate, filtered and the solvent removed. The resultant oil/wax was further purified via column chromatography (25% EtOAc/Hexanes) to afford 3.60 g (82%) of colorless oil (see for example Davis, S. C.; Szoka, F. C., Jr. Bioconjugate Chem. 1998, 9, 783).

Cholest-5-en-3β-oxybutan-4-mesylate (4a)

Cholest-5-en-3β-oxybutan-4-ol (12.45 g, 27.14 mmol) was weighed into a 500 mL round bottomed flask with a stir bar. The flask was sealed, flushed with argon, charged with methylene chloride (100 mL) and triethylamine (5.67 mL, 1.5 equiv.) and cooled to 0° C. Methanesulfonyl chloride (3.15 mL, 1.5 equiv.) was measured in a PP syringe and added slowly to the stirring reaction mixture. The reaction was allowed to stir for 1 hr at 0° C. when TLC analysis (7.5% EtOAc/Hexanes) showed that the reaction was complete. The reaction mixture was diluted with methylene chloride (100 mL) and washed with saturated bicarbonate solution (2×200 mL) and brine (1×100 mL). The organic phase was dried over $MgSO_4$, filtered and concentrated to give 14.45 g (99%) of a colorless wax that was used without further purification.

Cholest-5-en-3β-oxypent-3-oxa-an-5-mesylate (4b)

This compound was prepared similarly to Cholest-5-en-3β-oxybutan-4-mesylate. Cholest-5-en-3β-oxypent-3-oxa-an-5-ol (3.60 g, 7.58 mmol) was weighed into a 500 mL round bottomed flask with a stir bar. The flask was sealed, flushed with argon, charged with methylene chloride (30 mL) and triethylamine (1.60 mL, 1.5 equiv.) and cooled to 0° C. Methanesulfonyl chloride (0.89 mL, 1.5 equiv.) was measured in a PP syringe and added slowly to the stirring reaction mixture. The reaction was allowed to stir for 1 hr at 0° C. when TLC analysis (10% EtOAc/Hexanes) showed that the reaction was complete. The reaction mixture was diluted with methylene chloride (150 mL) and washed with saturated bicarbonate solution (2×100 mL) and brine (1×100 mL). The organic phase was dried over $MgSO_4$, filtered and concentrated to give 4.15 g (99%) of a colorless wax that was used without further purification.

1-(4,4'-Dimethoxytrityloxy)-3-dimethylamino-2-propanol (5)

3-Dimethylamino-1,2-propanediol (6.0 g, 50 mmol) was weighed into a 1 L round bottomed flask with a stir bar. The flask was sealed, flushed with argon, charged with pyridine and cooled to 0° C. 4,4'-Dimethoxytrityl chloride (17.9 g, 1.05 equiv.) was weighed into a 100 mL round bottomed flask, sealed and then dissolved in pyridine (80 mL). The 4,4'-dimethoxytrityl chloride solution was transferred to the stirring reaction mixture slowly, using additional fresh pyridine (20 mL) to effect the transfer of residual 4,4'-dimethoxytrityl chloride. The reaction was allowed to come to room temperature while stirring overnight. The reaction was concentrated in vacuo and re-dissolved in dichloromethane (300 mL). The organic phase was washed with saturated bicarbonate (2×200 mL) and brine (1×200 mL), dried over $MgSO_4$, filtered, concentrated and dried under high vacuum to afford 22.19 g of a yellow gum that was used without further purification.

3-Dimethylamino-2-(cholest-5-en-3β-oxybutan-4-oxy)-1-propanol (6a)

1-(4,4'-Dimethoxytrityloxy)-3-Dimethylamino-2-propanol (7.50 g, 17.8 mmol) was weighed into a 200 mL round bottomed flask and co-evaporated with anhydrous toluene (2×50 mL). A stir bar was added to the flask which was septum sealed, flushed with argon and charged with toluene (60 mL). Sodium hydride (1.71 g, 4 equiv.) was added at once and the mixture was stirred at room temperature for 20 minutes. Cholest-5-en-3β-oxybutan-4-mesylate was dissolved in anhydrous toluene (20 mL) and added to the reaction mixture, via syringe. The flask was fitted with a reflux condenser with a continuous argon stream and the reaction was heated to reflux overnight. The reaction mixture was cooled to room temperature in a water bath and ethanol was added dropwise until gas evolution ceased. The reaction mixture was diluted with ethyl acetate (300 mL) and washed with aqueous 10% sodium carbonate (2×300 mL). The aqueous phases were combined and back extracted with ethyl acetate (2×100 mL). The organic phases were combined, dried over $MgSO_4$, filtered and concentrated to an oil in a 500 mL round bottomed flask.

The flask was fitted with a stir bar, sealed, purged with argon and charged with dichloroacetic acid solution (3% in DCM, 200 mL). Triethylsilane (14.2 mL, 89 mmol) was added to the mixture and the reaction was allowed to stir overnight. The reaction mixture was diluted with DCM (300 mL) and washed with saturated bicarbonate solution (2×200 mL). The aqueous phases were combined and back extracted with DCM (2×100 mL). The organic phases were combined and dried over $MgSO_4$, filtered and concentrated to an oil that was re-dissolved in ethanol (150 mL). Potassium fluoride (10.3 g, 178 mmol) was added to the solution, which was then brought to reflux for 1 hr. The mixture was cooled, concentrated in vacuo, re-dissolved in DCM (200 mL), filtered and concentrated to an oil/crystal mixture. The mixture was re-dissolved in a minimum of DCM and loaded onto a silica gel column which was pre-equilibrated and eluted with 25% EtOAc/Hexanes with 3% TEA to afford 4.89 g (49%) of a colorless wax.

3-Dimethylamino-2-(cholest-5-en-3β-oxypent-3-oxa-an-5-oxy)-1-propanol (6b)

This compound was prepared similarly to 3-Dimethylamino-2-(Cholest-5-en-3β-oxybutan-4-oxy)-1-propanol. 1-(4,4'-Dimethoxytrityloxy)-3-Dimethylamino-2-propanol (2.65 g, 6.31 mmol) was weighed into a 200 mL round bottomed flask and co-evaporated with anhydrous toluene (2×20 mL). A stir bar was added to the flask which was septum sealed, flushed with argon and charged with toluene (50 mL). Sodium hydride (0.61 g, 4 equiv.) was added at once and the mixture was stirred at room temperature for 20 minutes. Cholest-5-en-3β-oxypent-3-oxa-an-5-mesylate (4.15 g, 7.6 mmol) was dissolved in anhydrous toluene (10 mL) and added to the reaction mixture, via syringe. The flask was fitted with a reflux condenser with a continuous argon stream and the reaction was heated to reflux overnight. The reaction mixture was cooled to room temperature in a water bath and ethanol was added dropwise until gas evolution ceased. The reaction mixture was diluted with ethyl acetate (200 mL) and washed with aqueous 10% sodium carbonate (2×200 mL). The aqueous phases were combined and back extracted with ethyl acetate (2×100 mL). The organic phases were combined, dried over $MgSO_4$, filtered and concentrated to an oil in a 500 mL round bottomed flask.

The flask was fitted with a stir bar, sealed, purged with argon and charged with dichloroacetic acid solution (3% in DCM, 150 mL). Triethylsilane (4.03 mL, 25.2 mmol) was added to the mixture and the reaction was allowed to stir for 4 hours. The reaction mixture was diluted with DCM (100 mL) and washed with saturated bicarbonate solution (2×200 mL). The aqueous phases were combined and back extracted with DCM (2×100 mL). The organic phases were combined and dried over $MgSO_4$, filtered and concentrated to an oil that was re-dissolved in ethanol (100 mL). Potassium fluoride (3.6 g, 63 mmol) was added to the solution, which was then brought to reflux for 1 hr. The mixture was cooled, concentrated in vacuo, re-dissolved in DCM (200 mL), filtered and concentrated to an oil/crystal mixture. The mixture was re-dissolved in a minimum of DCM and loaded onto a silica gel column which was pre-equilibrated and eluted with 25% Acetone/Hexanes with 3% TEA to afford 2.70 g (74%) of a colorless wax.

Linoleyl mesylate (7)

Linoleyl alcohol (10.0 g, 37.5 mmol) was weighed into a 500 mL round bottomed flask with a stir bar. The flask was sealed, flushed with argon, charged with DCM (100 mL) and triethylamine (7.84 mL, 1.5 equiv.) and cooled to 0° C. Methanesulfonyl chloride (4.35 mL, 1.5 equiv.) was measured in a PP syringe and added slowly to the stirring reaction mixture. TLC analysis (7.5% EtOAc/Hexanes) showed the reaction was complete within 1 hr. The reaction was diluted with DCM (100 mL) and washed with saturated bicarbonate solution (2×200 mL). The organic phase was dried over $MgSO_4$, filtered and concentrated to give 12.53 g (97%) of colorless oil that was used without further purification.

3-Dimethylamino-2-(cholest-5-en-3β-oxybutan-4-oxy)-1-(cis,cis-9,12-octadecadienoxy)propane (8a)

3-Dimethylamino-2-(Cholest-5-en-3β-oxybutan-4-oxy)-1-propanol (2.6 g, 4.6 mmol) was weighed into a 200 mL round bottomed flask and co-evaporated with anhydrous toluene 2×20 mL). A stir bar was added to the flask, which was then sealed, flushed with argon and charged with anhydrous toluene (100 mL). Sodium hydride (0.7 g, 6 equiv) was added at once and the mixture was stirred, under argon, for 20 minutes. Linoleyl mesylate (4.6 g, 2.3 equiv.) was measured in a PP syringe and added slowly to the reaction mixture. The flask was fitted with a reflux condenser and the apparatus was flushed with argon. The reaction mixture was heated in an oil bath and allowed to stir at reflux overnight. The reaction mixture was then cooled to room temperature in a water bath and ethanol was added dropwise until gas evolution ceased. The reaction mixture was diluted with ethyl acetate (300 mL) and washed with aqueous 10% sodium carbonate (2×200 mL). The aqueous phases were combined and back extracted with ethyl acetate (2×100 mL). The organic phases were combined, dried over $MgSO_4$, filtered and concentrated. The resultant oil was purified via column chromatography (10% EtOAc/Hexanes, 3% TEA) to afford 3.0 g (81%) of a colorless oil.

3-Dimethylamino-2-(cholest-5-en-3β-oxypent-3-oxa-an-5-oxy)-1-(cis,cis-9,12-octadecadienoxy)propane (CLinDMA) (8b)

This compound was prepared similarly to 3-Dimethylamino-2-(Cholest-5-en-3β-oxybutan-4-oxy)-1-(cis,cis-9, 12-octadecadienoxy)propane. 3-Dimethylamino-2-(Cholest-5-en-3β-oxypent-3-oxa-an-5-oxy)-1-propanol (0.73 g, 1.3 mmol) was weighed into a 100 mL round bottomed flask and co-evaporated with anhydrous toluene. A stir bar was added to the flask, which was then sealed, flushed with argon and charged with anhydrous toluene. Sodium hydride (121 mg, 4 equiv.) was added at once and the mixture was stirred, under argon, for 20 minutes. Linoleyl mesylate (0.873 g, 2 equiv.) was measured in a PP syringe and added slowly to the reaction mixture. The flask was fitted with a reflux condenser and the apparatus was flushed with argon. The reaction mixture was heated in an oil bath and allowed to stir at reflux overnight. The reaction mixture was then cooled to room temperature in a water bath and ethanol was added dropwise until gas evolution ceased. The reaction mixture was diluted with ethyl acetate (150 mL) and washed with aqueous 10% sodium carbonate (2×100 mL). The aqueous phases were combined and back extracted with ethyl acetate (2×50 mL). The organic phases were combined, dried over $Na_2SO_4$, filtered and concentrated. The resultant oil was purified via column chromatography (15% EtOAc/Hexanes, 3% TEA) to afford 0.70 g (67%) of colorless oil.

Example 15

Figure 23B:
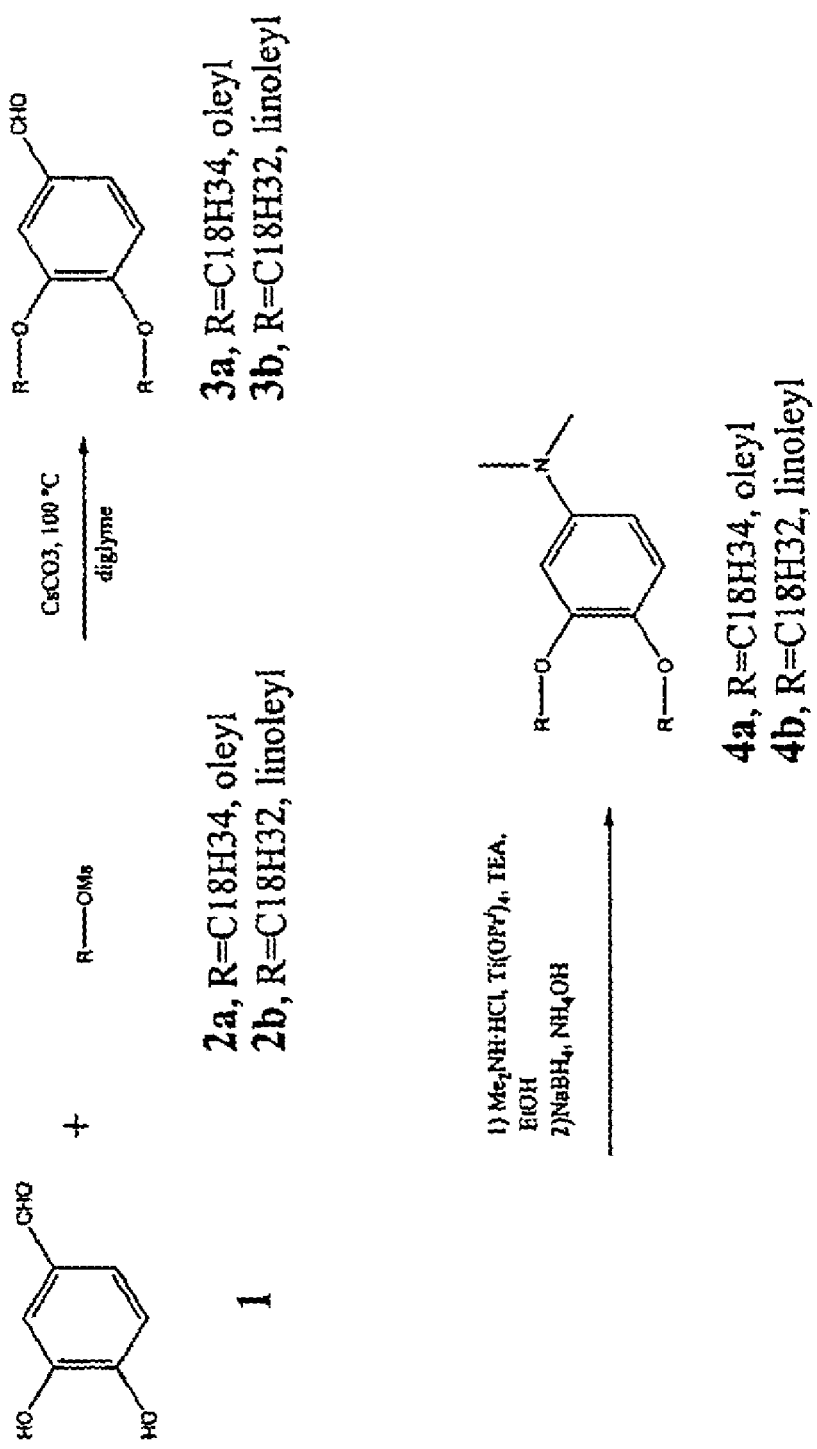

Preparation of Aromatic Lipids of the Invention (see FIG. 23B)

Dioleyloxybenzaldehyde, 3a 3,4-Dihydroxybenzaldehyde (2.76 g, 20.0 mmol) was weighed into a 200 mL round bottomed flask with a stir bar. The flask was charged with diglyme (100 mL), septum sealed and flushed with argon. Cesium carbonate (19.5 g, 60.0 mmol) was added to the solution slowly in portions. Oleyl mesylate (15.2 g, 44.0 mmol) was added via syringe. The reaction mixture was heated to 100° C. under slight positive pressure of argon. The reaction mixture was cooled to room temperature and filtered. The solids were washed with 1,2-dichloroethane. The combined filtrate and washes were concentrated and then dried under high vacuum at 65° C. to remove residual diglyme. The resultant yellow oil was purified via flash chromatography (5% ethyl acetate in hexanes) to afford 11.4 g (89%) of a yellow oil that turned to yellow wax upon standing at room temperature.

Dilinoleylbenzaldehyde, 3b 3,4-Dihydroxybenzaldehyde (2.76 g, 20.0 mmol) was weighed into a 200 mL round bottomed flask with a stir bar. The flask was charged with diglyme (100 mL), septum sealed and flushed with argon. Cesium carbonate (19.5 g, 60.0 mmol) was added to the solution slowly in portions. Linoleyl mesylate (15.2 g, 44.0 mmol) was added via syringe. The reaction mixture was heated to 100° C. under slight positive pressure of argon. The reaction mixture was cooled to room temperature and filtered. The solids were washed with 1,2-dichloroethane. The combined filtrate and washes were concentrated and then dried under high vacuum at 65° C. to remove residual diglyme. The resultant yellow oil was purified via flash chromatography (5% ethyl acetate in hexanes) to afford 11.9 g (94%) of a brown oil.

N,N-Dimethyl-3,4-dioleyloxybenzylamine, 4a

To a solution of triethylamineamine (2.0 mL, 14 mmol) in ethanol (20 mL) was added dimethylamine hydrochloride (1.63 g, 20 mmol), titanium tetraisopropoxide (5.96 mL, 20 mmol) and 3,4-dioleyloxybenzaldehyde (6.39 g, 10 mmol). The mixture was allowed to stir under argon for 10 h at room temperature. Sodium borohydride (0.57 g, 15 mmol) was added to the reaction mixture which was then allowed to stir at room temperature overnight. Concentrated aqueous ammonia (4 mL) was added slowly to the reaction mixture. The reaction mixture was filtered and the solids washed with dichloromethane. The filtrate was dried over $K_2CO_3$, filtered and concentrated. The resultant oil was purified via flash chromatography (2-10% acetone in dichloromethane, 0.5% TEA gradient) to afford 5.81 g (87-+%) of a yellow oil.

N,N-Dimethyl-3,4-dilinoleyloxybenzylamine, 4b

To a solution of triethylamineamine (2.0 mL, 14 mmol) in ethanol (20 mL) was added dimethylamine hydrochloride (1.63 g, 20 mmol), titanium tetraisopropoxide (5.96 mL, 20 mmol) and 3,4-dilinoleyloxybenzaldehyde (6.35 g, 10 mmol). The mixture was allowed to stir under argon for 10 h at room temperature. Sodium borohydride (0.57 g, 15 mmol) was added to the reaction mixture which was then allowed to stir at room temperature overnight. 6N Aqueous ammonia (30 mL), was added slowly to the reaction mixture followed by dichloromethane. The reaction mixture was filtered. The filtrate was dried over $K_2CO_3$, filtered and concentrated. The resultant oil was purified via flash chromatography (2-10% acetone in dichloromethane, 0.5% TEA gradient) to afford 4.94 g (74%) of a yellow oil.

Example 16

Figure 24:
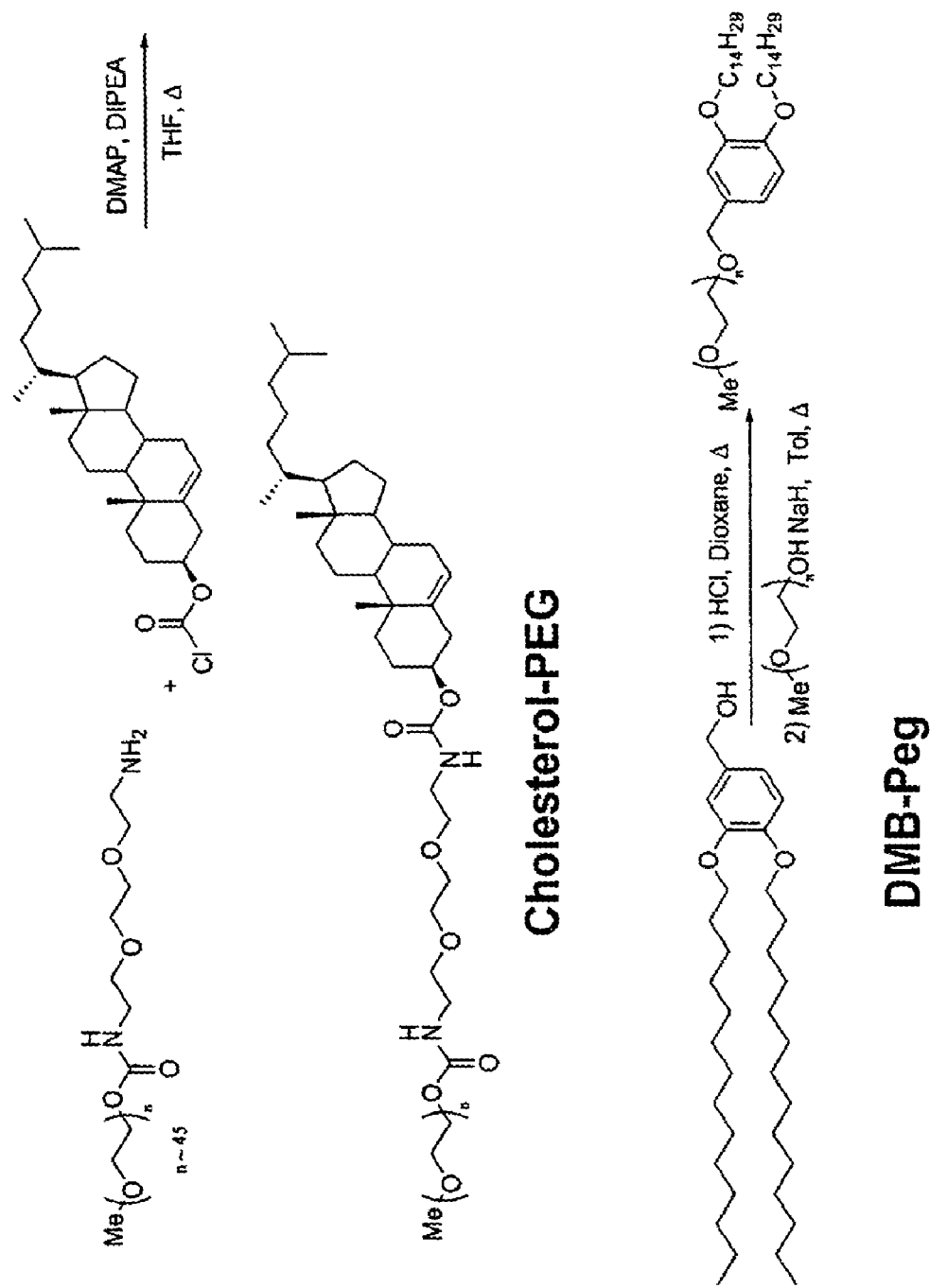
FIG. 24 shows a non-limiting example of a synthetic scheme used for the synthesis of 1-[8'-(Cholest-5-en-3β-oxy) carboxamido-3',6'-dioxaoctanyl]carbamoyl-ω-methyl-poly (ethylene glycol) (PEG-cholesterol) and 3,4-Ditetradecoxyylbenzyl-ω-methyl-poly(ethylene glycol)ether (PEG-DMB).
Figure 25:
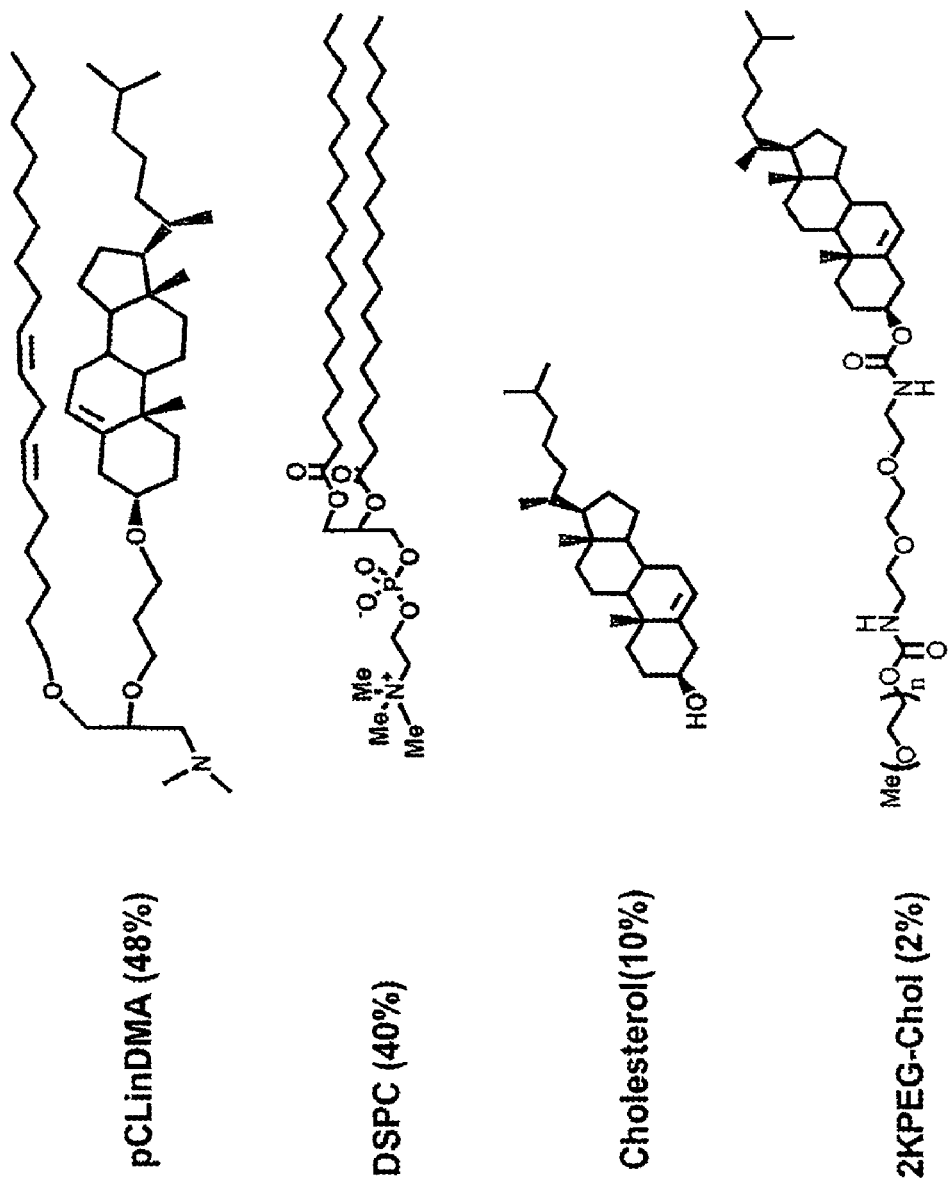
FIG. 25 shows the components of L083, a serum-stable formulated molecular composition that undergoes a rapid pH-dependent phase transition.
Figure 26:
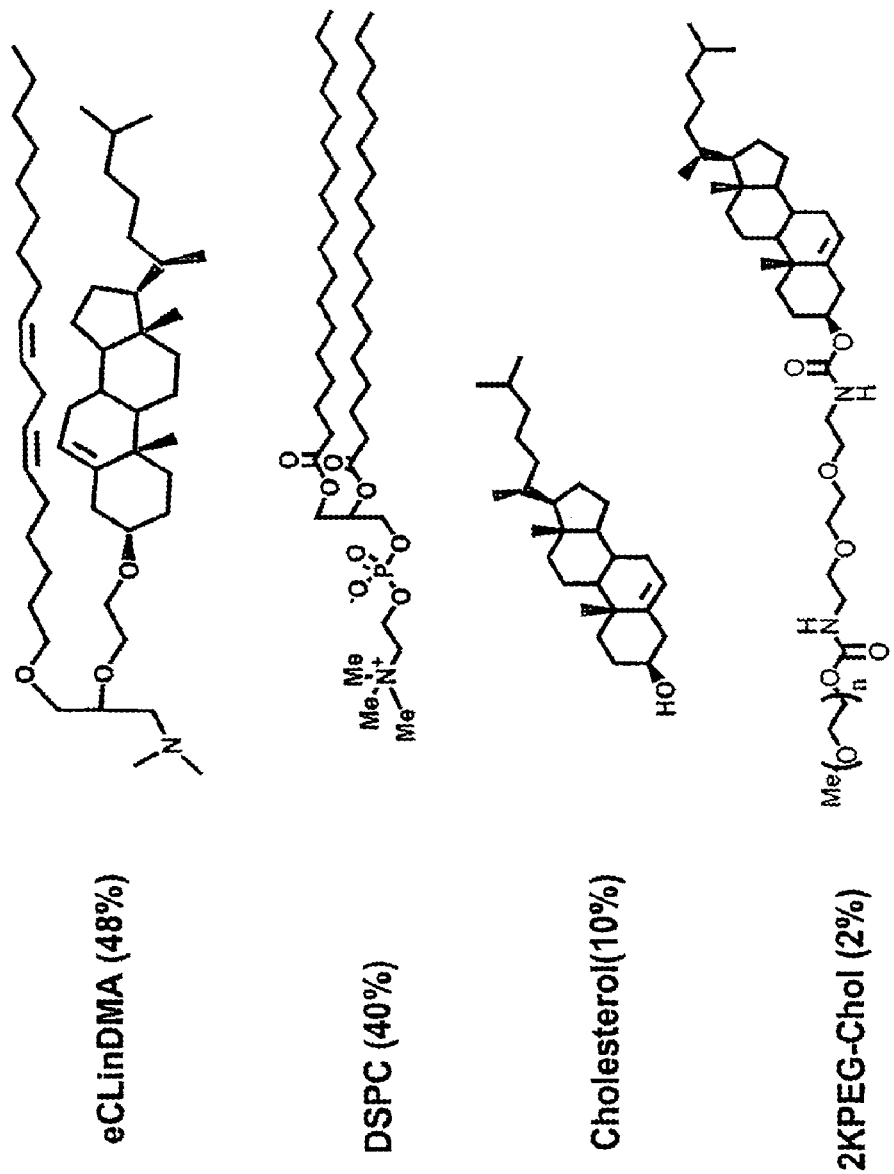
FIG. 26 shows the components of L077, a serum-stable formulated molecular composition that undergoes a rapid pH-dependent phase transition.
Figure 27:
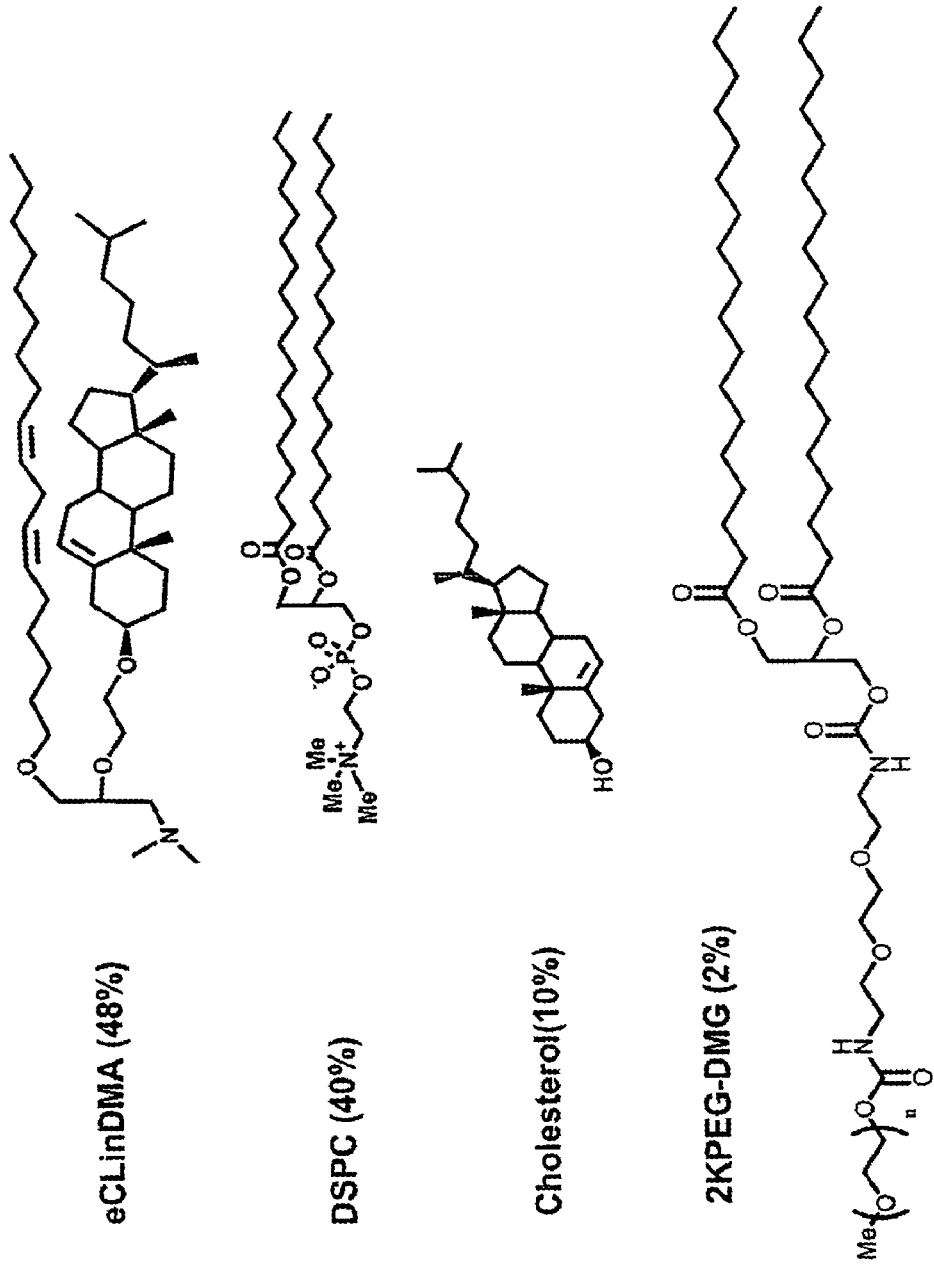
FIG. 27 shows the components of L080, a serum-stable formulated molecular composition that undergoes a rapid pH-dependent phase transition.
Figure 28:
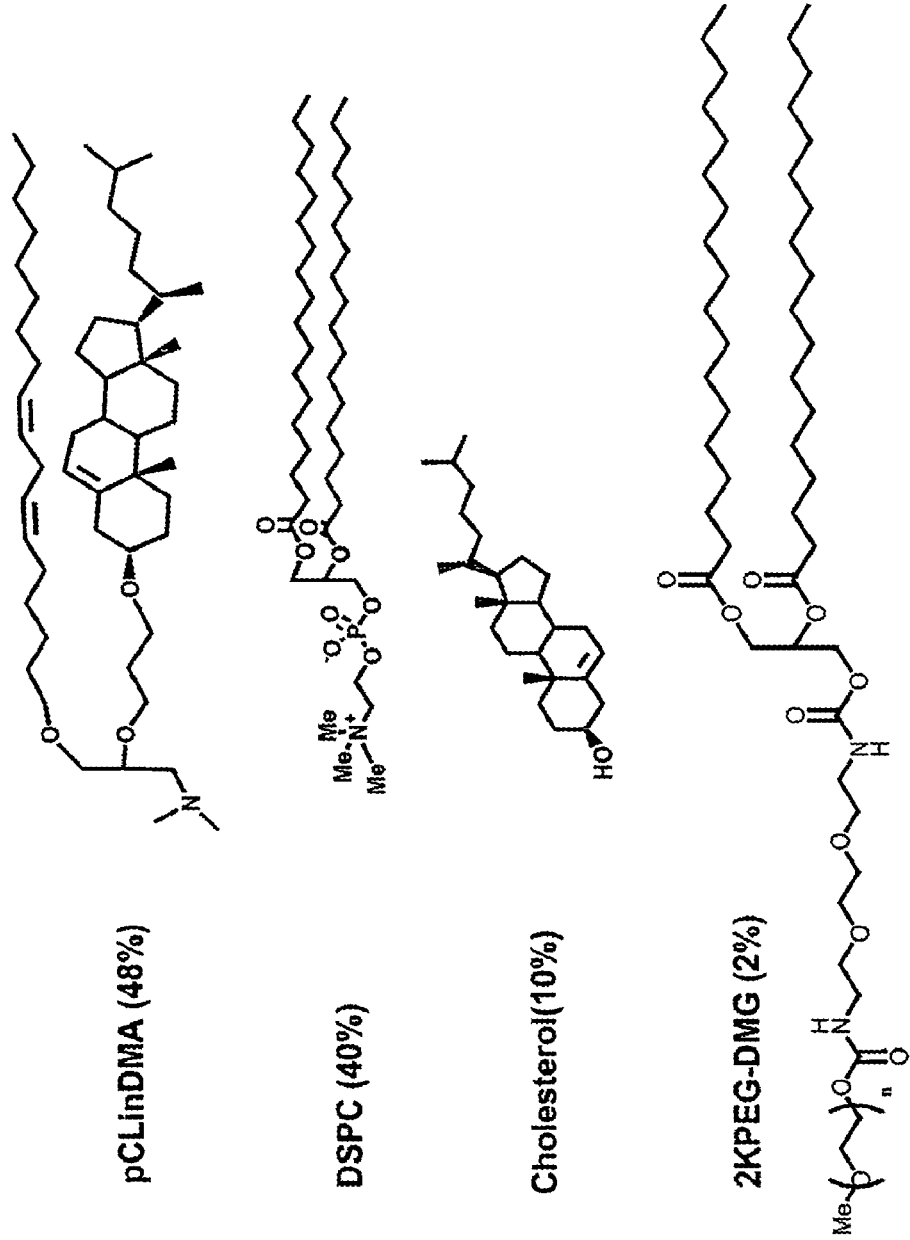
FIG. 28 shows the components of L082, a serum-stable formulated molecular composition that undergoes a rapid pH-dependent phase transition.

Preparation of PEG-conjugates of the Invention (See FIG. 24)

1-[8'-(Cholest-5-en-3β-oxy)carboxamido-3',6'-dioxaoctanyl]carbamoyl-ω-methyl-poly(ethylene glycol) (PEG-cholesterol)

To a 200-mL round-bottom flask charged with a solution of 2.0 g (0.89 mmol) of 1-[8'-amino-3',6'-dioxaoctanyl]carbamoyl-ω-methyl-poly(ethylene glycol), 22 mg (0.18 mmol) of 4-dimethylaminopyridine, and 0.93 mL (5.3 mmol) of diisopropylethylamine in 20 mL of anhydrous THF, was added with stirring a solution of 1.20 g (2.67 mmol) of cholesterol chloroformate in 20 mL of anhydrous THF. The resulting reaction mixture was heated to gentle reflux overnight. After cooled, the solvents were removed by rotary evaporation, and the resulting residue was applied onto a silica gel column for purification (methanol/dichloromethane 5:95 to 10:90). The chromatography yielded 2.43 g (91%) of white solid product.

3,4-Ditetradecoxylbenzyl-ω-methyl-poly(ethylene glycol) ether (PEG-DMB)

To a 100-mL round-bottom flask charged with a solution of 2.67 g (5.00 mmol) of ditetradecoxylbenzyl alcohol in 20 mL of 1,4-dioxane, was added 20 mL of 4.0 M HCl solution in 1,4-dioxane. The flask was then equipped with a refluxing condenser, which was connected to a sodium bicarbonate solution to absorb any evolved hydrogen chloride gas. After the reaction mixture was heated to 80 for 6 h, thin layer chromatography (dichloromethane as developing solvent) indicated the completion of the reaction. The solvent and the excessive reagent were completely removed under vacuum by rotary evaporation to afford 2.69 g (97%) of gray solid 3,4-ditetradecoxylbenzyl chloride. This crude material was employed directly for the next step reaction without further purification.

Poly(ethylene glycol) methyl ether (2.00 g, 1.00 mmol) was dried by co-evaporating with toluene (2×20 mL) under vacuum. To a solution of the dried poly(ethylene glycol) in 30 mL of anhydrous toluene, was added with stirring 0.17 g (7.2 mmol) of sodium hydride in portions. Gas evolvement took place instantly. The resulting mixture continued to be stirred at 60 for 2 h to ensure the complete formation of oxide. A solution of 0.668 g (1.20 mmol) 3,4-ditetradecoxylbenzyl chloride in 10 mL of anhydrous toluene was then introduced dropwise to the above mixture. The reaction mixture was allowed to stir at 80 overnight. After cooled, the reaction was quenched by the addition of 10 mL of saturated ammonium chloride solution. The resulting mixture was then taken into 300 mL of dichloromethane, washed with saturated ammonium chloride (3×100 mL), dried over anhydrous sodium sulfate, and evaporated to dryness. The residue was purified by flash chromatography (methanol/dichloromethane 2:98 to 5:95) to furnish 1.24 g (49%) of gray solid of the desired product.

Example 17

Preparation of Nanoparticle Encapsulated siNA Formulations siNA nanoparticle solutions were prepared by dissolving siNAs in 25 mM citrate buffer (pH 4.0) at a concentration of 0.9 mg/mL. Lipid solutions were prepared by dissolving a mixture of cationic lipid (e.g., CLinDMA or DOBMA, see structures and ratios for Formulations in Table IV), DSPC, Cholesterol, and PEG-DMG (ratios shown in Table IV) in absolute ethanol at a concentration of about 15 mg/mL. The nitrogen to phosphate ratio was approximate to 3:1.

Equal volume of siNA and lipid solutions was delivered with two FPLC pumps at the same flow rates to a mixing T connector. A back pressure valve was used to adjust to the desired particle size. The resulting milky mixture was collected in a sterile glass bottle. This mixture was then diluted slowly with an equal volume of citrate buffer, and filtered through an ion-exchange membrane to remove any free siRNA in the mixture. Ultra filtration against citrate buffer (pH 4.0) was employed to remove ethanol (test stick from ALCO screen), and against PBS (pH 7.4) to exchange buffer. The final liposome was obtained by concentrating to a desired volume and sterile filtered through a 0.2 μm filter.

The obtained liposomes were characterized in term of particle size, Zeta potential, alcohol content, total lipid content, nucleic acid encapsulated, and total nucleic acid concentration.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims. The present invention teaches one skilled in the art to test various combinations and/or substitutions of chemical modifications described herein toward generating nucleic acid constructs with improved activity for mediating RNAi activity. Such improved activity can comprise improved stability, improved bioavailability, and/or improved activation of cellular responses mediating RNAi. Therefore, the specific embodiments described herein are not limiting and one skilled in the art can readily appreciate that specific combinations of the modifications described herein can be tested without undue experimentation toward identifying siNA molecules with improved RNAi activity.

The invention illustratively described herein suitably can be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

TABLE I

Non-limiting examples of Stabilization Chemistries for chemically modified siNA constructs

| Chemistry | pyrimidine | Purine | cap | p = S | Strand |
|---|---|---|---|---|---|
| "Stab 00" | Ribo | Ribo | TT at 3'-ends | — | S/AS |
| "Stab 1" | Ribo | Ribo | — | 5 at 5'-end 1 at 3'-end | S/AS |
| "Stab 2" | Ribo | Ribo | — | All linkages | Usually AS |
| "Stab 3" | 2'-fluoro | Ribo | — | 4 at 5'-end 4 at 3'-end | Usually S |
| "Stab 4" | 2'-fluoro | Ribo | 5' and 3'-ends | — | Usually S |
| "Stab 5" | 2'-fluoro | Ribo | — | 1 at 3'-end | Usually AS |
| "Stab 6" | 2'-O-Methyl | Ribo | 5' and 3'-ends | — | Usually S |
| "Stab 7" | 2'-fluoro | 2'-deoxy | 5' and 3'-ends | — | Usually S |
| "Stab 8" | 2'-fluoro | 2'-O-Methyl | — | 1 at 3'-end | S/AS |
| "Stab 9" | Ribo | Ribo | 5' and 3'-ends | — | Usually S |
| "Stab 10" | Ribo | Ribo | — | 1 at 3'-end | Usually AS |
| "Stab 11" | 2'-fluoro | 2'-deoxy | — | 1 at 3'-end | Usually AS |
| "Stab 12" | 2'-fluoro | LNA | 5' and 3'-ends | — | Usually S |
| "Stab 13" | 2'-fluoro | LNA | — | 1 at 3'-end | Usually AS |
| "Stab 14" | 2'-fluoro | 2'-deoxy | — | 2 at 5'-end 1 at 3'-end | Usually AS |
| "Stab 15" | 2'-deoxy | 2'-deoxy | — | 2 at 5'-end 1 at 3'-end | Usually AS |
| "Stab 16" | Ribo | 2'-O-Methyl | 5' and 3'-ends | — | Usually S |
| "Stab 17" | 2'-O-Methyl | 2'-O-Methyl | 5' and 3'-ends | — | Usually S |
| "Stab 18" | 2'-fluoro | 2'-O-Methyl | 5' and 3'-ends | — | Usually S |
| "Stab 19" | 2'-fluoro | 2'-O-Methyl | 3'-end | — | S/AS |
| "Stab 20" | 2'-fluoro | 2'-deoxy | 3'-end | — | Usually AS |
| "Stab 21" | 2'-fluoro | Ribo | 3'-end | — | Usually AS |
| "Stab 22" | Ribo | Ribo | 3'-end | — | Usually AS |
| "Stab 23" | 2'-fluoro* | 2'-deoxy* | 5' and 3'-ends | — | Usually S |
| "Stab 24" | 2'-fluoro* | 2'-O-Methyl* | — | 1 at 3'-end | S/AS |
| "Stab 25" | 2'-fluoro* | 2'-O-Methyl* | — | 1 at 3'-end | S/AS |
| "Stab 26" | 2'-fluoro* | 2'-O-Methyl* | — | — | S/AS |
| "Stab 27" | 2'-fluoro* | 2'-O-Methyl* | 3'-end | — | S/AS |
| "Stab 28" | 2'-fluoro* | 2'-O-Methyl* | 3'-end | — | S/AS |
| "Stab 29" | 2'-fluoro* | 2'-O-Methyl* | — | 1 at 3'-end | S/AS |
| "Stab 30" | 2'-fluoro* | 2'-O-Methyl* | — | — | S/AS |
| "Stab 31" | 2'-fluoro* | 2'-O-Methyl* | 3'-end | — | S/AS |
| "Stab 32" | 2'-fluoro | 2'-O-Methyl | — | — | S/AS |
| "Stab 33" | 2'-fluoro | 2'-deoxy* | 5' and 3'-ends | — | Usually S |
| "Stab 34" | 2'-fluoro | 2'-O-Methyl* | 5' and 3'-ends | — | Usually S |
| "Stab 3F" | 2'-OCF3 | Ribo | — | 4 at 5'-end 4 at 3'-end | Usually S |
| "Stab 4F" | 2'-OCF3 | Ribo | 5' and 3'-ends | — | Usually S |
| "Stab 5F" | 2'-OCF3 | Ribo | — | 1 at 3'-end | Usually AS |

TABLE I-continued

Non-limiting examples of Stabilization Chemistries for chemically modified siNA constructs

| Chemistry | pyrimidine | Purine | cap | p = S | Strand |
|---|---|---|---|---|---|
| "Stab 7F" | 2'-OCF3 | 2'-deoxy | 5' and 3'-ends | — | Usually S |
| "Stab 8F" | 2'-OCF3 | 2'-O-Methyl | — | 1 at 3'-end | S/AS |
| "Stab 11F" | 2'-OCF3 | 2'-deoxy | — | 1 at 3'-end | Usually AS |
| "Stab 12F" | 2'-OCF3 | LNA | 5' and 3'-ends | | Usually S |
| "Stab 13F" | 2'-OCF3 | LNA | | 1 at 3'-end | Usually AS |
| "Stab 14F" | 2'-OCF3 | 2'-deoxy | | 2 at 5'-end 1 at 3'-end | Usually AS |
| "Stab 15F" | 2'-OCF3 | 2'-deoxy | | 2 at 5'-end 1 at 3'-end | Usually AS |
| "Stab 18F" | 2'-OCF3 | 2'-O-Methyl | 5' and 3'-ends | | Usually S |
| "Stab 19F" | 2'-OCF3 | 2'-O-Methyl | 3'-end | | S/AS |
| "Stab 20F" | 2'-OCF3 | 2'-deoxy | 3'-end | | Usually AS |
| "Stab 21F" | 2'-OCF3 | Ribo | 3'-end | | Usually AS |
| "Stab 23F" | 2'-OCF3* | 2'-deoxy* | 5' and 3'-ends | | Usually S |
| "Stab 24F" | 2'-OCF3* | 2'-O-Methyl* | — | 1 at 3'-end | S/AS |
| "Stab 25F" | 2'-OCF3* | 2'-O-Methyl* | — | 1 at 3'-end | S/AS |
| "Stab 26F" | 2'-OCF3* | 2'-O-Methyl* | — | | S/AS |
| "Stab 27F" | 2'-OCF3* | 2'-O-Methyl* | 3'-end | | S/AS |
| "Stab 28F" | 2'-OCF3* | 2'-O-Methyl* | 3'-end | | S/AS |
| "Stab 29F" | 2'-OCF3* | 2'-O-Methyl* | | 1 at 3'-end | S/AS |
| "Stab 30F" | 2'-OCF3* | 2'-O-Methyl* | | | S/AS |
| "Stab 31F" | 2'-OCF3* | 2'-O-Methyl* | 3'-end | | S/AS |
| "Stab 32F" | 2'-OCF3 | 2'-O-Methyl | | | S/AS |
| "Stab 33F" | 2'-OCF3 | 2'-deoxy* | 5' and 3'-ends | — | Usually S |
| "Stab 34F" | 2'-OCF3 | 2'-O-Methyl* | 5' and 3'-ends | | Usually S |

CAP = any terminal cap moiety.
All Stab 00-34 chemistries can comprise 3'-terminal thymidine (TT) residues
All Stab 00-34 chemistries typically comprise about 21 nucleotides, but can vary as described herein.
S = sense strand
AS = antisense strand
*Stab 23 has a single ribonucleotide adjacent to 3'-CAP
*Stab 24 and Stab 28 have a single ribonucleotide at 5'-terminus
*Stab 25, Stab 26, and Stab 27 have three ribonucleotides at 5'-terminus
*Stab 29, Stab 30, Stab 31, Stab 33, and Stab 34 any purine at first three nucleotide positions from 5'-terminus are ribonucleotides
p = phosphorothioate linkage

TABLE II

| Reagent | Equivalents | Amount | Wait Time* DNA | Wait Time* 2'-O-methyl | Wait Time* RNA |
|---|---|---|---|---|---|
| A. 2.5 μmol Synthesis Cycle ABI 394 Instrument | | | | | |
| Phosphoramidites | 6.5 | 163 μL | 45 sec | 2.5 min | 7.5 min |
| S-Ethyl Tetrazole | 23.8 | 238 μL | 45 sec | 2.5 min | 7.5 min |
| Acetic Anhydride | 100 | 233 μL | 5 sec | 5 sec | 5 sec |
| N-Methyl Imidazole | 186 | 233 μL | 5 sec | 5 sec | 5 sec |
| TCA | 176 | 2.3 mL | 21 sec | 21 sec | 21 sec |
| Iodine | 11.2 | 1.7 mL | 45 sec | 45 sec | 45 sec |
| Beaucage | 12.9 | 645 μL | 100 sec | 300 sec | 300 sec |
| Acetonitrile | NA | 6.67 mL | NA | NA | NA |
| B. 0.2 μmol Synthesis Cycle ABI 394 Instrument | | | | | |
| Phosphoramidites | 15 | 31 μL | 45 sec | 233 sec | 465 sec |
| S-Ethyl Tetrazole | 38.7 | 31 μL | 45 sec | 233 min | 465 sec |
| Acetic Anhydride | 655 | 124 μL | 5 sec | 5 sec | 5 sec |
| N-Methyl Imidazole | 1245 | 124 μL | 5 sec | 5 sec | 5 sec |
| TCA | 700 | 732 μL | 10 sec | 10 sec | 10 sec |
| Iodine | 20.6 | 244 μL | 15 sec | 15 sec | 15 sec |

TABLE II-continued

| Beaucage | 7.7 | 232 µL | 100 sec | 300 sec | 300 sec |
|---|---|---|---|---|---|
| Acetonitrile | NA | 2.64 mL | NA | NA | NA |

C. 0.2 µmol Synthesis Cycle 96 well Instrument

| Reagent | Equivalents: DNA/ 2'-O-methyl/Ribo | Amount: DNA/2'-O-methyl/Ribo | Wait Time* DNA | Wait Time* 2'-O-methyl | Wait Time* Ribo |
|---|---|---|---|---|---|
| Phosphoramidites | 22/33/66 | 40/60/120 µL | 60 sec | 180 sec | 360 sec |
| S-Ethyl Tetrazole | 70/105/210 | 40/60/120 µL | 60 sec | 180 min | 360 sec |
| Acetic Anhydride | 265/265/265 | 50/50/50 µL | 10 sec | 10 sec | 10 sec |
| N-Methyl Imidazole | 502/502/502 | 50/50/50 µL | 10 sec | 10 sec | 10 sec |
| TCA | 238/475/475 | 250/500/500 µL | 15 sec | 15 sec | 15 sec |
| Iodine | 6.8/6.8/6.8 | 80/80/80 µL | 30 sec | 30 sec | 30 sec |
| Beaucage | 34/51/51 | 80/120/120 | 100 sec | 200 sec | 200 sec |
| Acetonitrile | NA | 1150/1150/1150 µL | NA | NA | NA |

Wait time does not include contact time during delivery.
Tandem synthesis utilizes double coupling of linker molecule

TABLE III

| Structure | NAME | Abbrev. |
|---|---|---|
| 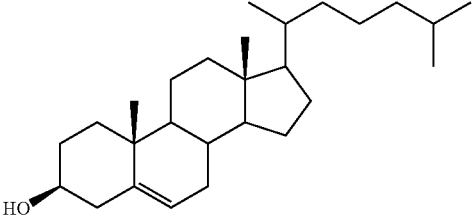 | Chloesterol | Chol |
| 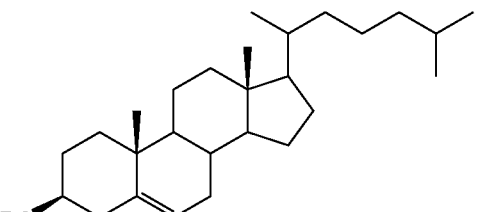 | Cholest-5-en-3β-tosylate | Chol-OTs |
| 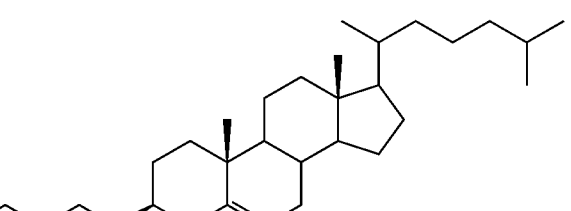 | Cholest-5-en-3β-oxybutan-4-ol | Chol-OBu-OH |
| 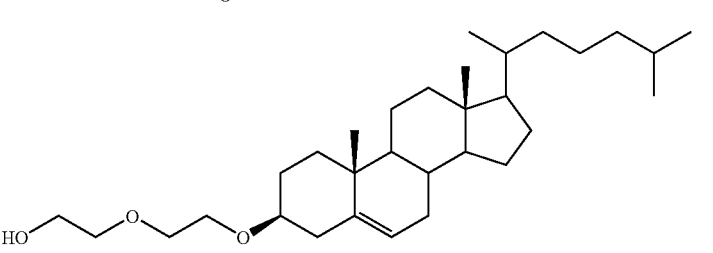 | Cholest-5-en-3β-oxypent-3-oxa-an-5-ol | Chol-DEG-OH |

TABLE III-continued

| Structure | NAME | Abbrev. |
|---|---|---|
| 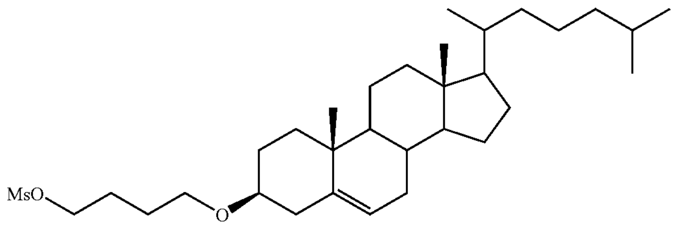 | Cholest-5-en-3β-oxybutan-4-mesylate | |
| 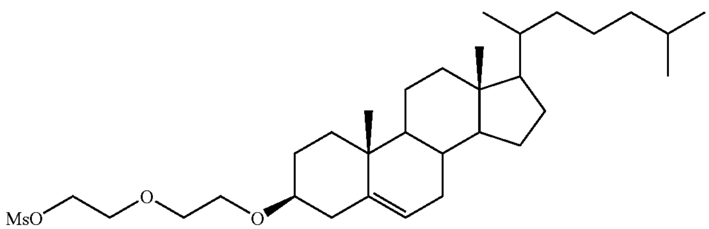 | Cholest-5-en-3β-oxypent-3-oxa-an-5-mesylate | |
| 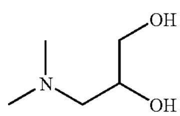 | 3-Dimethylamino-1,2-propanediol | |
| 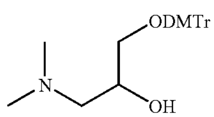 | 1-(4,4'-Dimethoxy-trityloxy)-3-Dimethylamino-2-propanol | |
| 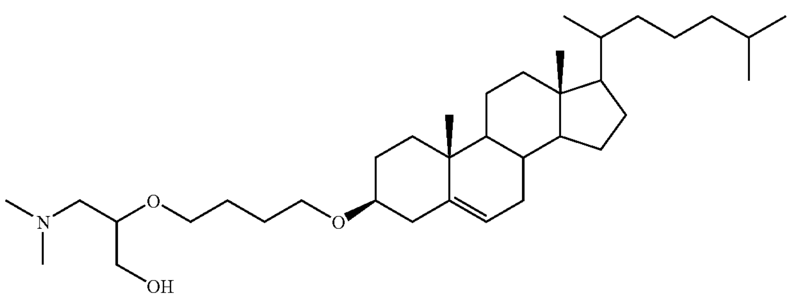 | 3-Dimethylamino-2-(Cholest-5-en-3β-oxybutan-4-oxy)-1-propanol | |
| 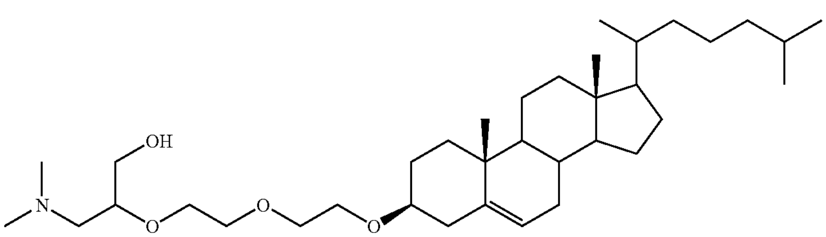 | 3-Dimethylamino-2-(Cholest-5-en-3β-oxypent-3-oxa-an-5-oxy)-1-propanol | |
| 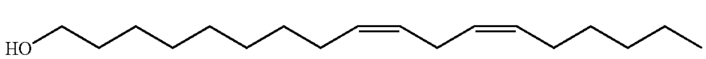 | cis,cis-9,12-octadecadiene-1-ol (linoleyl alcohol) | Lin-OH |

TABLE III-continued

| Structure | NAME | Abbrev. |
|---|---|---|
| MsO-(linoleyl chain) | cis,cis-9,12-octadecadiene-1-mesylate (linoleyl mesylate) | Lin-OMs |
| (dimethylamino-cholesteryl-linoleyl ether structure) | 3-Dimethylamino-2-(Cholest-5-en-3β-oxybutan-4-oxy)-1-(cis,cis-9,12-octadecadienoxy) propane | CLinDMA |
| (dimethylamino-diethyleneglycol-cholesteryl-linoleyl ether structure) | 3-Dimethylamino-2-(Cholest-5-en-3β-oxypent-3-oxa-an-5-oxy)-1-(cis,cis-9,12-octadecadienoxy) propane | DEG-CLinDMA |

TABLE IV

Lipid Nanoparticle (LNP) Formulations

| Formulation # | Composition | Molar Ratio |
|---|---|---|
| L051 | CLinDMA/DSPC/Chol/PEG-n-DMG | 48/40/10/2 |
| L053 | DMOBA/DSPC/Chol/PEG-n-DMG | 30/20/48/2 |
| L054 | DMOBA/DSPC/Chol/PEG-n-DMG | 50/20/28/2 |
| L069 | CLinDMA/DSPC/Cholesterol/PEG-Cholesterol | 48/40/10/2 |
| L073 | pCLinDMA or CLin DMA/DMOBA/DSPC/Chol/PEG-n-DMG | 25/25/20/28/2 |
| L077 | eCLinDMA/DSPC/Cholesterol/2KPEG-Chol | 48/40/10/2 |
| L080 | eCLinDMA/DSPC/Cholesterol/2KPEG-DMG | 48/40/10/2 |
| L082 | pCLinDMA/DSPC/Cholesterol/2KPEG-DMG | 48/40/10/2 |
| L083 | pCLinDMA/DSPC/Cholesterol/2KPEG-Chol | 48/40/10/2 |
| L086 | CLinDMA/DSPC/Cholesterol/2KPEG-DMG/Linoleyl alcohol | 43/38/10/2/7 |
| L061 | DMLBA/Cholesterol/2KPEG-DMG | 52/45/3 |
| L060 | DMOBA/Cholesterol/2KPEG-DMG N/P ratio of 5 | 52/45/3 |
| L097 | DMLBA/DSPC/Cholesterol/2KPEG-DMG | 50/20/28 |
| L098 | DMOBA/Cholesterol/2KPEG-DMG, N/P ratio of 3 | 52/45/3 |
| L099 | DMOBA/Cholesterol/2KPEG-DMG, N/P ratio of 4 | 52/45/3 |
| L100 | DMOBA/DOBA/3% PEG-DMG, N/P ratio of 3 | 52/45/3 |
| L101 | DMOBA/Cholesterol/2KPEG-Cholesterol | 52/45/3 |
| L102 | DMOBA/Cholesterol/2KPEG-Cholesterol, N/P ratio of 5 | 52/45/3 |
| L103 | DMLBA/Cholesterol/2KPEG- | 52/45/3 |
| | Cholesterol | |
| L104 | CLinDMA/DSPC/Cholesterol/2KPEG-cholesterol/Linoleyl alcohol | 43/38/10/2/7 |
| L105 | DMOBA/Cholesterol/2KPEG-Chol, N/P ratio of 2 | 52/45/3 |
| L106 | DMOBA/Cholesterol/2KPEG-Chol, N/P ratio of 3 | 67/30/3 |
| L107 | DMOBA/Cholesterol/2KPEG-Chol, N/P ratio of 1.5 | 52/45/3 |
| L108 | DMOBA/Cholesterol/2KPEG-Chol, N/P ratio of 2 | 67/30/3 |
| L109 | DMOBA/DSPC/Cholesterol/2KPEG-Chol, N/P ratio of 2 | 50/20/28/2 |
| L110 | DMOBA/Cholesterol/2KPEG-DMG, N/P ratio of 1.5 | 52/45/3 |
| L111 | DMOBA/Cholesterol/2KPEG-DMG, N/P ratio of 1.5 | 67/30/3 |
| L112 | DMLBA/Cholesterol/2KPEG-DMG, N/P ratio of 1.5 | 52/45/3 |
| L113 | DMLBA/Cholesterol/2KPEG-DMG, N/P ratio of 1.5 | 67/30/3 |
| L114 | DMLBA/Cholesterol/2KPEG-DMG, N/P ratio of 2 | 52/45/3 |
| L115 | DMOBA/Cholesterol/2KPEG-DMG, N/P ratio of 2 | 67/30/3 |
| L116 | DMLBA/Cholesterol/2KPEG-DMG, N/P ratio of 2 | 52/45/3 |
| L117 | DMLBA/Cholesterol/2KPEG-DMG, N/P ratio of 2 | 52/45/3 |

N/P ratio = Nitrogen:Phosphorous ratio between cationic lipid and nucleic acid

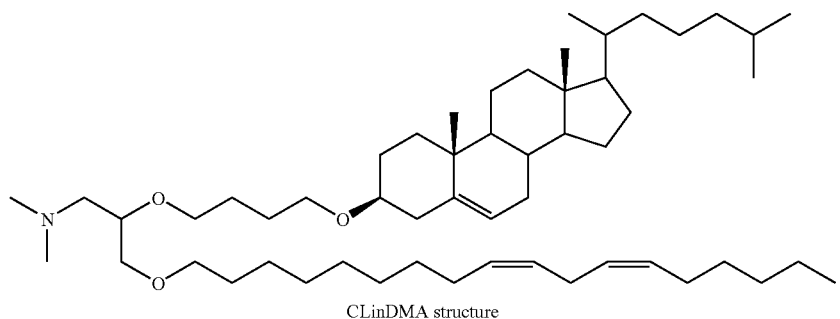
CLinDMA structure
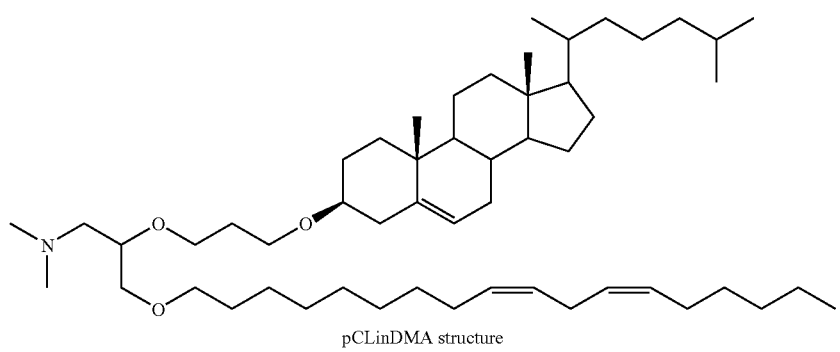
pCLinDMA structure
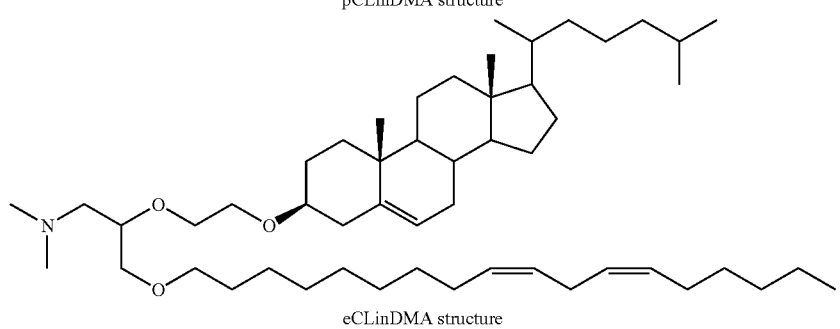
eCLinDMA structure
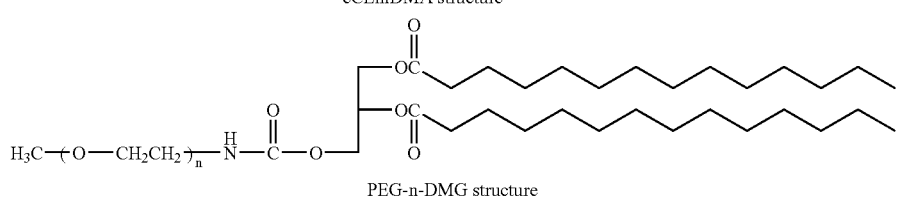
PEG-n-DMG structure
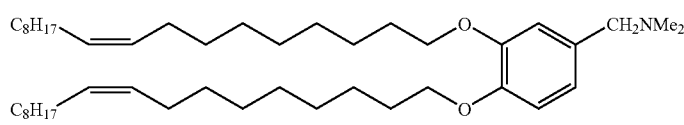
DMOBA structure
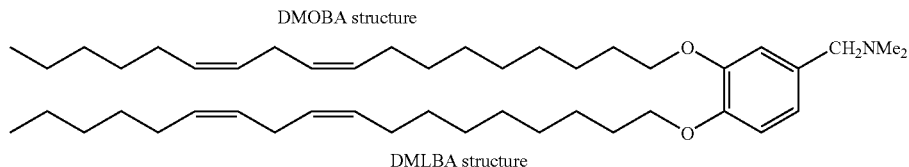
DMLBA structure
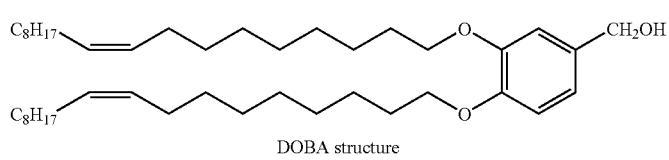
DOBA structure

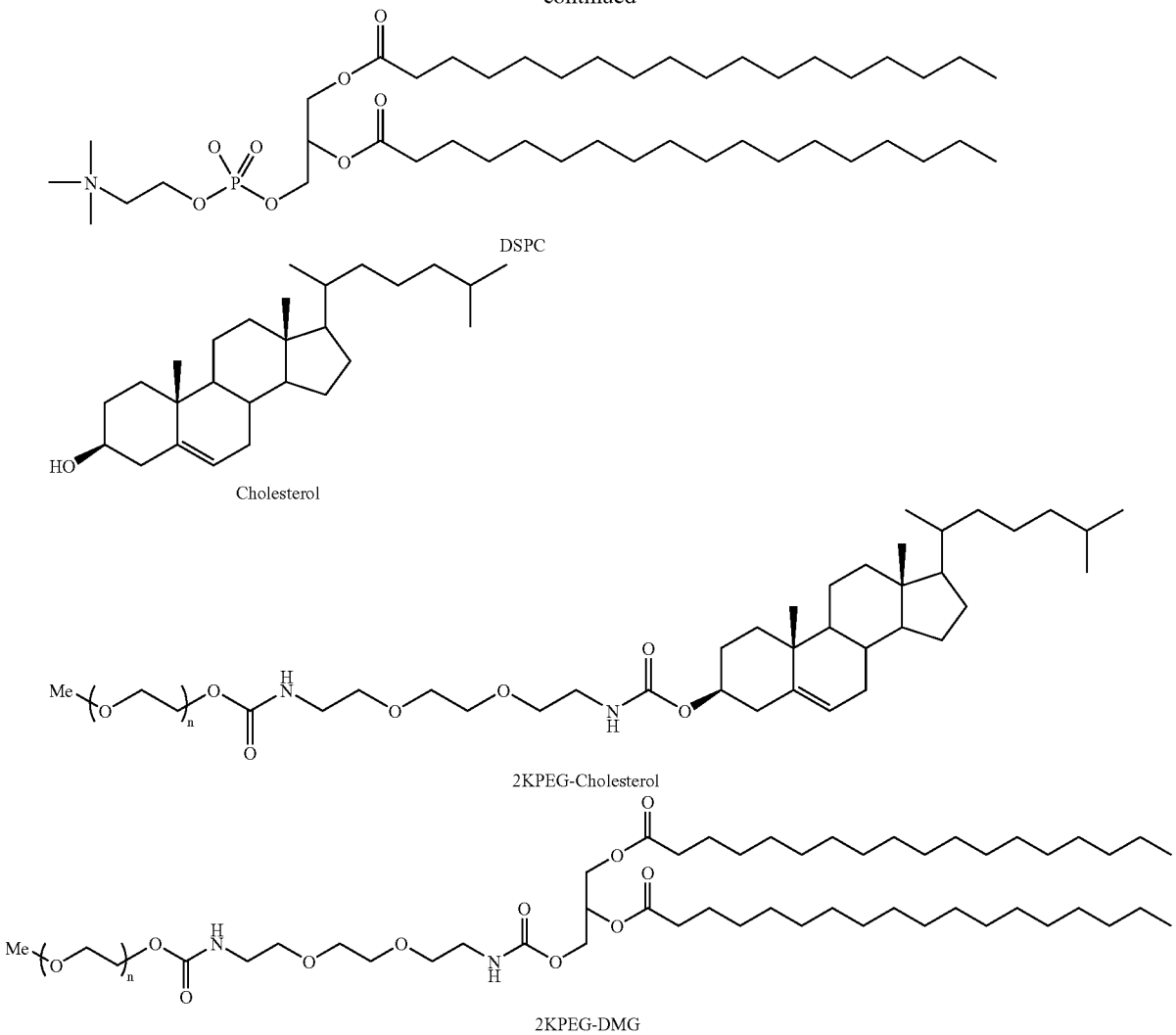

TABLE V

| Cell Line | Tissue | Cell Type | % RNA KD |
|---|---|---|---|
| 6.12 | spleen | B lymphocyte hybrid | LF2K = 50%<br>LNP97 = 90%<br>LNP98 = 92% |
| Raw 264.7 | tumor | macrophage/monocyte | LF2K = 85%<br>LNP54 = 75%<br>LPN98 = 75% |
| MM14.Lu | normal lung | endothelial/epithelial | LF2K = 90%<br>LNP98 = 98% |
| NIH 3T3 | embryo | fibroblast | LF2K = 95%<br>LNP51 = 65%<br>LPN54 = 65%<br>LPN98 = 85% |
| N/A | lung | primary macrophage | LF2K = 50%<br>LNP98 = 65% |

We claim:

1. A compound having Formula CLII:

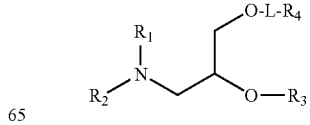

CLII wherein each R1 and R2 is independently a C1 to C10 alkyl, alkynyl, or aryl hydrocarbon; R3 is a C9-C24 aliphatic saturated or unsaturated hydrocarbon, L comprises a C1 to C10 alkyl, alkyl ether, polyether, polyethylene glycol, acetal, amide, carbonyl, carbamide, carbamate, carbonate, ester, or succinyl linker, and R4 comprises cholesterol.

* * * * *